US008765752B2

(12) United States Patent
Ohkouchi

(10) Patent No.: US 8,765,752 B2
(45) Date of Patent: Jul. 1, 2014

(54) 3-HYDROXYISOTHIAZOLE 1-OXIDE DERIVATIVES

(71) Applicant: Mochida Pharmaceutical Co., Ltd., Tokyo (JP)

(72) Inventor: Munetaka Ohkouchi, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/841,710

(22) Filed: Mar. 15, 2013

(65) Prior Publication Data

US 2013/0217690 A1    Aug. 22, 2013

Related U.S. Application Data

(63) Continuation of application No. 13/444,595, filed on Apr. 11, 2012.

(30) Foreign Application Priority Data

Apr. 27, 2011  (JP) ................... 2011-100203
Jun. 29, 2011  (JP) ................... 2011-144937
Aug. 26, 2011  (JP) ................... 2011-185337

(51) Int. Cl.
| A61K 31/535 | (2006.01) |
| A01N 43/58 | (2006.01) |
| A01N 43/60 | (2006.01) |
| A61K 31/50 | (2006.01) |
| A61K 31/495 | (2006.01) |
| A01N 43/42 | (2006.01) |
| A61K 31/44 | (2006.01) |
| A61K 31/47 | (2006.01) |
| A01N 43/40 | (2006.01) |
| A01N 43/78 | (2006.01) |
| A61K 31/425 | (2006.01) |
| A01N 43/80 | (2006.01) |

(52) U.S. Cl.
USPC ........ 514/236.8; 514/248; 514/249; 514/278; 514/312; 514/318; 514/326; 514/342; 514/369; 514/372; 544/133; 544/237; 546/17; 546/153; 546/194; 546/209; 546/271.1; 548/186; 548/213

(58) Field of Classification Search
None
See application file for complete search history.

(56) References Cited

U.S. PATENT DOCUMENTS

| 3,562,283 A | 2/1971 | Lewis et al. |
| 3,801,575 A | 4/1974 | Lewis et al. |
| 2003/0004193 A1 | 1/2003 | Barrett et al. |
| 2006/0100261 A1 | 5/2006 | Hamamura et al. |
| 2006/0258722 A1 | 11/2006 | Yasuma et al. |
| 2009/0170908 A1 | 7/2009 | Shimada et al. |
| 2009/0186909 A1 | 7/2009 | Negoro et al. |
| 2010/0130599 A1 | 5/2010 | Coty et al. |
| 2010/0261645 A1 | 10/2010 | Defossa et al. |
| 2010/0267775 A1 | 10/2010 | Negoro et al. |
| 2011/0065739 A1 | 3/2011 | Ishikawa et al. |
| 2012/0157459 A1 | 6/2012 | Okano et al. |

FOREIGN PATENT DOCUMENTS

| CN | 101781268 A | 7/2010 |
| JP | 2000-204077 A | 7/2000 |
| JP | 2005-15461 A | 1/2005 |
| WO | WO 00/42029 A1 | 7/2000 |
| WO | WO 2004/011446 A1 | 2/2004 |
| WO | WO 2004/022551 A1 | 3/2004 |
| WO | WO 2004/041266 A1 | 5/2004 |
| WO | WO 2005/035551 A2 | 4/2005 |
| WO | WO 2005/051890 A1 | 6/2005 |
| WO | WO 2005/063729 A1 | 7/2005 |

(Continued)

OTHER PUBLICATIONS

Chiasson et al., "Acarbose Treatment and the Risk of Cardiovascular Disease and Hypertension in Patients With Impaired Glucose Tolerance: The STOP-NIDDM Trial", Journal of the American Medical Association, vol. 290, No. 4, pp. 486-494, Jul. 23-30, 2003.

(Continued)

*Primary Examiner* — James H Alstrum Acevedo
*Assistant Examiner* — Zachary J Miknis
(74) *Attorney, Agent, or Firm* — Birch, Stewart, Kolasch & Birch, LLP

(57) ABSTRACT

[Object]
To provide a GPR40 activating agent containing, as an active ingredient, a novel compound having a GPR40 agonist action, a salt of the compound, a solvate of the compound or the salt, or the like, particularly, an insulin secretagogue and a prophylactic and/or therapeutic agent against diabetes, obesity, or other diseases.
[Means of Solving the Problem]
A compound of Formula (I):

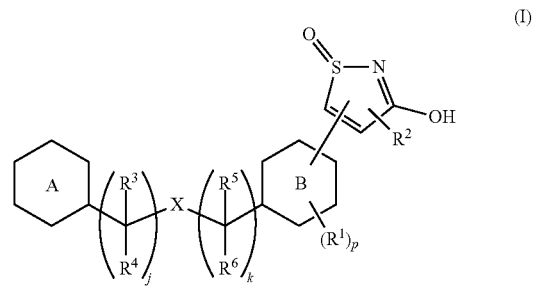

(where p is 0 to 4; j is 0 to 2; k is 0 to 1; a ring A is an aryl group, a heterocyclic group, a cycroalkyl group, a cycroalkenyl group, a spirocyclic group; a ring B is an aryl group, a heteroaryl group; X is O or —NR$^7$—; and R$^1$ to R$^7$ and L are specific groups), a salt of the compound, or a solvate of the compound or the salt.

15 Claims, No Drawings

(56) References Cited

FOREIGN PATENT DOCUMENTS

| | | |
|---|---|---|
| WO | WO 2005/086661 A2 | 9/2005 |
| WO | WO 2007/033002 A1 | 3/2007 |
| WO | WO 2007/123225 A1 | 11/2007 |
| WO | WO 2008/001931 A2 | 1/2008 |
| WO | WO 2008/030520 A1 | 3/2008 |
| WO | WO 2008/033931 A1 | 3/2008 |
| WO | WO 2008/066131 A1 | 6/2008 |
| WO | WO 2008/130514 A1 | 10/2008 |
| WO | WO 2009/039943 A1 | 4/2009 |
| WO | WO 2009/048527 A1 | 4/2009 |
| WO | WO 2009/054390 A1 | 4/2009 |
| WO | WO 2009/054423 A1 | 4/2009 |
| WO | WO 2009/054479 A1 | 4/2009 |
| WO | WO 2009/111056 A1 | 9/2009 |
| WO | WO 2009/147990 A1 | 12/2009 |
| WO | WO 2010/085525 A1 | 7/2010 |
| WO | WO 2010/091176 A1 | 8/2010 |
| WO | WO 2010/143733 A1 | 12/2010 |
| WO | WO 2011/046851 A1 | 4/2011 |
| WO | WO 2011/052756 A1 | 5/2011 |
| WO | WO 2011/066183 A1 | 6/2011 |
| WO | WO 2011/078371 A1 | 6/2011 |
| WO | WO 2012/046869 A1 | 4/2012 |

OTHER PUBLICATIONS

International Preliminary Report on Patentability for Application No. PCT/JP2010/073464 dated Dec. 2, 2011 (with English translation).
International Search Report and Written Opinion of the International Searching Authority in International Application No. PCT/JP2012/059933, mailed Jun. 19, 2012, with an English translation.
Itoh et al., "Free Fatty Acids Regulate Insulin Secretion from Pancreatic β cells through GPR40", Nature, vol. 422, pp. 173-176, Mar. 13, 2003.
Japanese Amendment for Application No. PCT/JP2010/073464 dated Nov. 10, 2011 (with English translation).
Japanese Demand for International Preliminary Examination for Application No.PCT/JP2010/073464 dated Sep. 30, 2011.
Japanese Reply for Application No. PCT/JP2010/073464 dated Nov. 10, 2011 (with English translation).
Kotarsky et al., "A Human Cell Surface Receptor Activated by Free Fatty Acids and Thiazolidinedione Drugs", Biochemical and Biophysical Research Communications, vol. 301, pp. 406-410, 2003.
Notification of Transmittal of Translation of the International Preliminary Report of Patentability (Chapter I or Chapter II) for International Application No. PCT/JP2010/073464 dated Aug. 9, 2012.
Technomics, Inc., "Saishin Soyaku Kagaku", The latest drug discovery chemistry, First Volume, Aug. 15, 1998, pp. 248-253 (with English translation).
Wermuth, "The Practice of Medicinal Chemistry", First Volume, Technomics, Inc., Table 13.8, pp. 248-253, Aug. 15, 1998.

3-HYDROXYISOTHIAZOLE 1-OXIDE DERIVATIVES

This application is a Continuation of co-pending application Ser. No. 13/444,595 filed on Apr. 11, 2012 and which claims priority to JP-2011-185337, filed on Aug. 26, 2011, JP-2011-144937, filed on Jun. 29, 2011 and JP-2011-100203, filed on Apr. 27, 2011. The entire content of all of the above applications is hereby incorporated by reference.

TECHNICAL FIELD

The present invention relates to a compound for modulationg the functions of G protein-coupled receptor 40 (GPR40). In particular, the present invention relates to a compound having a 3-hydroxyisothiazole 1-oxide group of Formula (I), a salt of the compound, a solvate of the compound or the salt, a pharmaceutical composition containing the compound as an active ingredient, prophylactic and/or therapeutic agents against GPR40-involving diseases, especially diabetes, and an insulin secretagogues.

BACKGROUND ART

Diabetes is categorized into Type 1 diabetes (insulin-dependent diabetes) and Type 2 diabetes (non-insulin-dependent diabetes), and borderline type diabetes (glucose tolerance disorders) has also attracted attention as a pre-diabetic condition in recent years. Type 1 diabetes is characterized by a partial or complete inability to produce insulin, which is a blood glucose regulating hormone. Type 2 diabetes is characterized by induced peripheral insulin resistance and impaired insulin secretion. Borderline type diabetes is a pathological condition exhibiting impaired glucose tolerance (IGT) or impaired fasting glucose (IFG), associated with a risk of developing Type 2 diabetes or diabetes complications.

Diabetes is caused by several predisposing factors. It is a disease characterized by high glucose levels in blood plasma in fasting and postprandial states or during an oral glucose tolerance test or by chronic hyperglycemia, in general. Controlling chronic hyperglycemia is essential in clinical management and treatment of diabetes. In particular, reduced insulin secretion from beta cells of the pancreas can induce an abrupt increase in postprandial blood glucose levels in Type 2 diabetes or borderline type diabetes. An international large-scale clinical trial has revealed that it is essential to control postprandial hyperglycemia in impaired glucose tolerance for suppressing the development and progress of not only diabetes but also hypertension and cardiovascular diseases (JAMA, 290, 486-494 (2003) (Non-Patent Document 1)). On the basis of these findings, the International Diabetes Federation published new guidelines for diabetes treatment (postprandial blood glucose control guidelines) in 2007, which recommend control of postprandial blood glucose levels as essential for Type 1 and 2 diabetic patients to alleviate diabetes and reduce risk of complications. As a practical step, an increased administration of an alpha-glucosidase inhibitor (voglibose) that is a drug for alleviating excessive postprandial blood glucose levels associated with diabetes, has been approved in Japan as a prophylactic agent against diabetes, aiming to "inhibit the development of Type 2 diabetes from impaired glucose tolerance". As described above, there has been increasing awareness of the needs of nonpharmacological and pharmacological treatments against diabetes and borderline type diabetes, targeting the control of postprandial blood glucose levels in recent years.

Diabetes is treated mainly through diet regulation and exercise. When these fail to alleviate symptoms, pharmacological treatment is needed. Various types of drugs are available as prophylactic or therapeutic agents against diabetes. Among them, examples of insulin secretagogues include sulfonylurea agents (e.g., glibenclamide, glimepiride) and rapid-acting insulin secretagogues (e.g., mitiglinide), all of which stimulate beta cells of the pancreas so as to accelerate insulin secretion. These drugs are, however, known for their ineffectiveness (primary failure, secondary failure) and side effects such as induced hypoglycemic effects. Analogs (e.g., exenatide, liraglutide) of glucagon-like peptide-1 (GLP-1), which are hormones accelerating glucose-responsive insulin secretion in beta cells of the pancreas, have become available as novel insulin secretagogues, but they are administered by injection and known for their side effects of transient gastrointestinal tract disorders. Other examples of insulin secretagogues include dipeptidyl peptidase IV (DPP-IV) inhibitors (e.g., sitagliptin, vildagliptin), which inhibit the degradation of intrinsic GLP-1, but they are known for their side effects of epipharyngitis, headache, and infections. Alpha-glucosidase inhibitors (e.g., acarbose, voglibose) inhibit the degradation and digestion of carbohydrate and thus limit an abrupt increase in postprandial blood glucose levels, but they need to be taken immediately before meals and are known for their side effects such as distension and diarrhea and serious liver disorders. Biguanides (e.g., metformin, buformin) are insulin resistance improving agents enhancing insulin sensitivity and thereby alleviating hyperglycemia, but are known to potentially induce side effects such as lactic acidosis, nausea, and vomiting. Thiazolidinedione derivatives (e.g., pioglitazone, rosiglitazone) are peroxisome proliferator-activated receptor (PPAR) gamma agonists. The derivatives increase insulin sensitivity in adipose tissue, the liver, and skeletal muscles and thereby alleviate chronic hyperglycemia, but are known to tend to cause edema, weight gain, and serious side effects of liver disorders. Side effects of these drugs do not always occur, but remain as a major obstacle to high satisfaction with treatment. Therefore, the demand has been increasing for insulin secretagogues, particularly orally administrable insulin secretagogues, entailing few problems and side effects caused by conventional prophylactic and therapeutic agents as described above and inhibiting postprandial hyperglycemia without inducing hypoglycemia.

Fatty acid plays an important role in insulin use in the liver and skeletal muscles, glucose-responsive insulin secretion from the pancreas, and inflammation associated with fat accumulation in adipose tissue. A strong correlation is known between increased levels of fatty acid in blood plasma and the development of diabetes, metabolic syndrome, obesity, and adiposity.

GPR40, one of the G-protein-coupled receptors, is categorized in the free fatty acid receptor (FFAR) family and activated by $C_{6-22}$ saturated or unsaturated fatty acid. It is reported that high expression of GPR40 is observed in beta cells of the pancreas where the receptor is involved in insulin secretion caused by fatty acid (Nature, 422, 173-176 (2003) (Non-Patent Document 2)). Non-fatty-acid low-molecular-weight compounds having a GPR40 agonist action have been found in recent years, and it is reported that thiazolidinediones, which are insulin sensitivity improving agents, and MEDICA 16, which is a hypolipidemic agent, also exhibit agonist actions (Biochem. Biophys. Res. Comm., 301, 406-410 (2003) (Non-Patent Document 3)).

In the pancreatic islets of Langerhans isolated from GPR40 knockout mice, the glucose-responsive insulin secretagogue action of fatty acid is lower than the case with normal mice. Accordingly, substances having a GPR40 agonist action like fatty acid are expected to have the effect of inhibiting postprandial hyperglycemia based on the glucose-responsive insulin secretagogue action in the pancreas. Therefore, substances having a GPR40 agonist action are considered to be effective as prophylactic and therapeutic agents against diabetes or borderline type diabetes.

In recent years, studies have been progressed on compounds having a GPR40 activating action as insulin secretagogues or therapeutic agents against diabetes.

Technologies related to compounds having a GPR40 agonist action are disclosed, for example, in WO 2004/041266 pamphlet (Patent Document 1), WO 2005/086661 pamphlet (Patent Document 2), WO 2007/123225 pamphlet (Patent Document 3), WO 2008/001931 pamphlet (Patent Document 4), WO 2009/054390 pamphlet (Patent Document 5), WO 2009/054423 pamphlet (Patent Document 6), WO 2009/054479 pamphlet (Patent Document 7), WO 2011/046851 pamphlet (Patent Document 8), WO 2010/143733 pamphlet (Patent Document 9), WO 2007/033002 pamphlet (Patent Document 10), WO 2009/048527 pamphlet (Patent Document 11), WO 2009/111056 pamphlet (Patent Document 12), WO 2005/051890 pamphlet (Patent Document 13), WO 2004/022551 pamphlet (Patent Document 14), WO 2004/011446 pamphlet (Patent Document 15), WO 2008/030520 pamphlet (Patent Document 16), WO 2011/066183 pamphlet (Patent Document 17), WO 2010/091176 pamphlet (Patent Document 18), WO 2010/085525 pamphlet (Patent Document 19), WO 2009/039943 pamphlet (Patent Document 20), WO 2005/063729 pamphlet (Patent Document 21), and WO 2008/130514 pamphlet (Patent Document 22). These documents, however, do not disclose or suggest any compounds having a 3-hydroxy-5-arylisothiazolyl 1-oxide group.

A technique related to a compound having a 3-hydroxy-5-arylisothiazolyl group is disclosed in WO 2005/035551 pamphlet (Patent Document 23). The compound disclosed in Patent Document 23, however, is a compound having an inhibitory effect on protein tyrosine phosphatase 1B (PTP1B), and its structure is fundamentally different from that of the compounds according to the present invention. Another compound having a 3-hydroxy-5-arylisothiazolyl group is disclosed in WO 2000/042029 pamphlet (Patent Document 24). The compound disclosed in Patent Document 24, however, is a compound having an inhibitory effect on MAP kinase (MEK) and containing a specific substituent on its side chain.

Quite recently, a compound with a GPR40 activating action having a 3-hydroxy-5-arylisoxazole group or a 3-hydroxy-5-arylisothiazole group is disclosed in WO 2011/052756 pamphlet (Patent Document 25) and WO 2011/078371 pamphlet (Patent Document 26).

In the development of drugs, various strict criteria must be met in terms of absorption, distribution, metabolism, excretion, and other factors as well as targeted pharmacological actions. There are various things to consider, for example, interaction with other drugs, desensitization or durability, digestive tract absorption after oral administration, speed to reach the small intestine, absorption speed and first pass effect, organ barriers, protein binding, drug metabolizing enzyme induction or inhibition, excretion route and clearance in the body, and application methods (application sites, methods, purposes). It is difficult to find a drug that meets all the criteria.

Several compounds are reported to have a GPR40 agonist action, but none of them has been marketed so far. Such agonists could also involve the above-mentioned general issues in the development phase of drugs. More specifically, they have problems in usefulness and safety, such as low metabolism stability and difficulty in systemic exposure by oral administration, unfavorable pharmacokinetic effects including absorption and persistence properties, an activity of inhibiting the human ether-a-go-go related gene (hERG) channel, possibly resulting in arrhythmia, and an activity of inducing, inhibiting drug metabolizing enzymes (e.g., cytochrome P450), or unwanted CNS-mediated side effects by brain penetration.

Therefore, required is a compound that solves these problems as much as possible and still has high efficacy.

In addition, required as a GPR40 agonist is a compound with fewer problems or side effects as described above than the aforementioned conventional drugs that have been used to prevent or treat diabetes (particularly Type 2 diabetes or borderline type diabetes).

RELATED-ART DOCUMENTS

Patent Documents

Patent Document 1: WO 2004/041266 pamphlet
Patent Document 2: WO 2005/086661 pamphlet
Patent Document 3: WO 2007/123225 pamphlet
Patent Document 4: WO 2008/001931 pamphlet
Patent Document 5: WO 2009/054390 pamphlet
Patent Document 6: WO 2009/054423 pamphlet
Patent Document 7: WO 2009/054479 pamphlet
Patent Document 8: WO 2011/046851 pamphlet
Patent Document 9: WO 2010/143733 pamphlet
Patent Document 10: WO 2007/033002 pamphlet
Patent Document 11: WO 2009/048527 pamphlet
Patent Document 12: WO 2009/111056 pamphlet
Patent Document 13: WO 2005/051890 pamphlet
Patent Document 14: WO 2004/022551 pamphlet
Patent Document 15: WO 2004/011446 pamphlet
Patent Document 16: WO 2008/030520 pamphlet
Patent Document 17: WO 2011/066183 pamphlet
Patent Document 18: WO 2010/091176 pamphlet
Patent Document 19: WO 2010/085525 pamphlet
Patent Document 20: WO 2009/039943 pamphlet
Patent Document 21: WO 2005/063729 pamphlet
Patent Document 22: WO 2008/130514 pamphlet
Patent Document 23: WO 2005/035551 pamphlet
Patent Document 24: WO 2000/042029 pamphlet
Patent Document 25: WO 2011/052756 pamphlet
Patent Document 26: WO 2011/078371 pamphlet Non-Patent Documents Non-Patent Document 1: JAMA, 290, 486-494 (2003)
Non-Patent Document 2: Nature, 422, 173-176 (2003)
Non-Patent Document 3: Biochem. Biophys. Res. Comm., 301, 406-410 (2003)

SUMMARY OF THE INVENTION

Problems to be Solved by the Invention

In view of such medical circumstances related to diabetes, prophylactic and therapeutic drugs are required that accelerate insulin secretion, particularly glucose-responsive insulin secretion, through activation of GPR40, and thus exhibit the action of lowering blood glucose levels, particularly inhibiting postprandial hyperglycemia.

Particularly required are orally administrable GPR40 activating agents, insulin secretagogues, prophylactic and/or therapeutic agents against GPR40-involving diseases (particularly prophylactic and/or therapeutic agents against diabetes or obesity) all of which have high safety, excellent efficacy, and high selectivity with respect to other members of the FFAR family or similar receptors.

In particular, there are issues to be addressed as problems with the conventional techniques described above. More specifically, there are the following issues to be addressed with prophylactic and therapeutic agents against diabetes: ineffectiveness (primary failure, secondary failure) and side effects such as induced hypoglycemic effects caused by sulfonylurea agents and rapid-acting insulin secretagogues; transient gastrointestinal tract disorders caused by GLP-1 analogs; side effects of epipharyngitis, headache, and infections caused by DPP-IV inhibitors; side effects such as distension and diarrhea and serious liver disorders caused by alpha-glucosidase inhibitors; side effects such as lactic acidosis, nausea, and vomiting caused by biguanides; edema, weight gain, and serious liver disorders caused by thiazolidinedione derivatives; and so on. Other issues to be addressed include solubility, improvement in metabolism stability, enhancement of absorption properties, improvement in pharmacokinetic effects, reduction in the activity of inhibiting hERG, reduction in the activity of inducing or inhibiting drug metabolizing enzymes (e.g., cytochrome P450), and reduction in the brain penetration. Consequently, there are the needs for insulin secretagogues and prophylactic and/or therapeutic agents against GPR40-involving diseases (particularly prophylactic and/or therapeutic agents against diabetes or obesity) all of which solve at least one of the issues, are orally administrable to mammals including human beings, and are clinically usable in particular.

Means for Solving the Problem

As a result of assiduous research for solving the above problems by obtaining a compound having high safety and/or excellent efficacy and modulationg the functions of GPR40, the inventors of the present invention have found that a 3-hydroxyisothiazole 1-oxide derivative of Formula (I) has a GPR40 agonist action. The compound of the present invention has an excellent glucose-responsive insulin secretagogue action and has a strong hyperglycemia-inhibiting action during glucose load.

Effects of the Invention

The present invention provides: a compound of Formula (I), characterized by having a 3-hydroxyisothiazole 1-oxide group, a salt of the compound, or a solvate of the compound or the salt; and a pharmaceutical composition, characterized by containing as an active ingredient, the compound, a pharmaceutically acceptable salt of the compound, or a solvate of the compound or the pharmaceutically acceptable salt.

The compound of the present invention is a compound having a GPR40 agonist action, or a compound having an action of lowering a blood glucose level, particularly an action of inhibiting postprandial hyperglycemia, by activating GPR40 to accelerate an insulin secretion, particularly a glucose-responsive insulin secretion. The pharmaceutical composition containing the compound of the present invention as an active ingredient can be orally administrated and is expected as an insulin secretagogues or a prophylactic agent and/or a therapeutic agent for a GPR40-involving disease, particularly diabetes (particularly Type 2 diabetes or borderline type diabetes) or obesity and adiposity.

The group of the compounds of the present invention has at least one of characteristics such as having advantageous solubility, having high metabolism stability, having excellent oral absorption properties, having a small activity of inhibiting the hERG channel, and having a lower brain penetration, and thus is highly useful.

MODES FOR CARRYING OUT THE INVENTION

The present invention provides: a compound of Formula (I) characterized by having a 3-hydroxyisothiazole 1-oxide group shown in the following aspects, a salt of the compound, or a solvate of the compound or the salt; and a pharmaceutical composition or GPR40 activating agent characterized by containing the compound, the salt, or the solvate as an active ingredient.

[Aspects of the Invention]
[1] Aspect [1] of the present invention
A first aspect of the present invention is a compound of Formula (I):

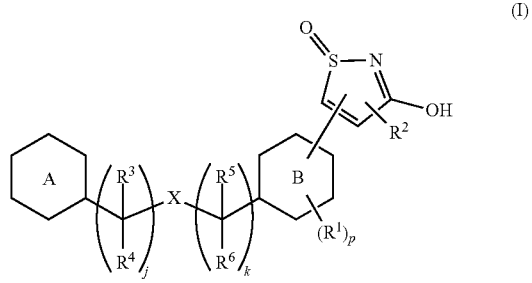

(where p is an integer of 0 to 4; j is an integer of 0 to 2; k is 0 or 1;

a ring A is a $C_{6-14}$ aryl group which is optionally substituted with 1 to 5 substituent(s) L, a 3- to 14-membered heterocyclic group which is optionally substituted with 1 to 5 substituent(s) L, a $C_{5-7}$ cycloalkyl group which is optionally substituted with 1 to 5 substituent(s) L, a $C_{5-7}$ cycloalkenyl group which is optionally substituted with 1 to 5 substituent(s) L, a 6- to 14-membered spirocyclic group which is optionally substituted with 1 to 5 substituent(s) L, or a 2-phenylamino-2-oxoacetyl group which is optionally substituted with 1 to 5 substituent(s) L;

a ring B is a $C_{6-14}$ aryl group or a 5- to 14-membered heteroaryl group;

X is an oxygen atom or —$NR^7$—;

$R^1$s are independently a group optionally selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group;

$R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group;

$R^3$, $R^4$, $R^5$, $R^6$, and $R^7$ are independently a hydrogen atom or a $C_{1-6}$ alkyl group; the substituents L are independently a group optionally selected from a halogen atom, —OH, an oxo group, a cyano group, a $C_{1-10}$ alkyl group which is optionally substituted with 1 to 5 substituent(s) RI, a $C_{2-10}$ alkenyl group which is optionally substituted with 1to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5substituent(s) RI, a $C_{2-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, —SF$_5$, a group: —S(O)$_i$R$^a$ (i is an integer of 0 to 2), a group: —NR$^b$R$^c$ and a substituted spiropiperidinylmethyl group:

R$^a$ is a group optionally selected from a $C_{1-6}$ alkyl group and a halogenated $C_{1-6}$ alkyl group;

R$^b$ and R$^c$ are independently a group optionally selected from a hydrogen atom, a $C_{1-6}$alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$alkoxy group), a $C_{1-6}$ alkylsulfonyl group, an arylcarbonyl group, and a heterocyclic carbonyl group, where R$^b$ and R$^c$ optionally form together with a nitrogen atom to which R$^b$ and R$^c$ are bonded, a 3- to 8-membered cyclic group, where in the cyclic group, one or two carbon atom(s) is (are) optionally substituted with an atom optionally selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

the substituents RI are the same as or different from each other and are each a group optionally selected from a halogen atom, —OH, a cyano group, a $C_{1-6}$ alkoxy group (the $C_{1-6}$ alkoxy group is optionally substituted with 1 to 5 halogen atom(s), 1 to 5—OH, 1 to 5$C_{1-6}$ alkoxy group(s), 1 to 5 aryl group(s) (the aryl group is optionally substituted with 1to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$), a group: —NR$^{b1}$R$^{c1}$ and a heterocyclic oxy group (the heterocyclic oxy group is optionally substituted with 1 to 3 $C_{1-6}$ alkyl group(s) or 1 to 3 oxo group(s));

the substituents RII are the same as or different from each other and are each a group optionally selected from the substituent RI, a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$ or 1 to 5 group(s): —NR$^{b1}$R$^{c1}$), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a group: —S(O)$_i$R$^a$ (i is an integer of 0 to 2), a group: —CONR$^d$R$^e$, and a group: —CONR$^d$R$^{e1}$ R$^d$ and R$^e$ are independently a hydrogen atom or a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s));

R$^{e1}$ is a $C_{1-6}$ alkyl group (the $C_{1-6}$ alkyl group is optionally substituted with 1 to 5 —OH, 1to 5 $C_{1-6}$ alkoxyl group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group or 1 to 3 oxo group(s)), 1 to 5 —S(O)$_i$R$^a$group(s) (i is an integer of 0 to 2), 1 to 5 —SO$_2$NR$^d$R$^e$ group(s), 1 to 5 —CONR$^d$R$^e$ group(s) or 1 to 5 —NR$^{b1}$R$^{c1}$ group(s);

R$^{b1}$ and R$^{c1}$ are independently a group optionally selected from a hydrogen atom, a $C_{1-6}$alkyl group, a $C_{2-7}$ alkanoyl group, and a $C_{1-6}$ alkylsulfonyl group, or R$^{b1}$ and R$^{c1}$ optionally form together with a nitrogen atom to which R$^{b1}$ and R$^{c1}$ are bonded, a 3-to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a $C_{1-6}$ alkyl group) or with a carbonyl group;

in an isothiazolyl group, in a case where the ring B is bonded at 5-position, R$^2$ is bonded at 4-position, and in a case where the ring B is bonded at 4-position, R$^2$ is bonded at 5-position)

or a pharmaceutically acceptable salt of the compound, or a pharmaceutically acceptable solvate of the salt or a pharmaceutically acceptable solvate of the compound.

Each group in Formula (I) according to Aspect [1] is specifically described below.

In the explanation of the compound according to the present invention, for example, "$C_{1-6}$" indicates that the number of constituent carbon atoms, which is the number of carbon atoms in a linear, branched, or cyclic group unless otherwise indicated, is 1 to 6. The number of constituent carbon atoms includes the total number of carbon atoms in a group having a linear or branched group substituted with a cyclic group or a cyclic group substituted with a linear or branched group. Therefore, as for an acyclic group, "$C_{1-6}$"means a "linear or branched chain with the number of constituent carbon atoms of 1 to 6". As for a cyclic group, "$C_{1-6}$" means a "cyclic group with the number of ring-constituting carbon atoms of 1 to 6". As for a group having an acyclic group and a cyclic group, "$C_{1-6}$" means a "group with the total number of carbon atoms of 1 to 6".

The "alkyl group" is a linear, branched, or cyclic alkyl group. For example, examples of the "$C_{1-6}$ alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, 1-cyclopropylethyl, 2-cyclopropylethyl, 2-cyclobutylethyl, and 2-methylcyclopropyl. Examples of the "$C_{1-10}$ alkyl group" include, in addition to the groups mentioned as the "$C_{1-6}$ alkyl group", heptyl, 1-methylhexyl, octyl, 2-ethylhexyl, 1,1-dimethylhexyl, nonyl, decyl, cycloheptyl, cyclohexylmethyl, 2-cyclohexylethyl, 4-methylcyclohexyl, 4,4-dimethylcyclohexyl, and 3,3,5,5-tetramethylcyclohexyl. In addition, a cyclic alkyl group is referred to also as "cycloalkyl group". "$C_{5-7}$ cycloalkyl group" includes cyclopentyl, cyclohexyl, and cycloheptyl.

The "alkenyl group" is a linear, branched, or cyclic alkenyl group. For example, examples of the "$C_{2-6}$ alkenyl group" include vinyl, allyl, isopropenyl, 2-methylallyl, butenyl, pentenyl, isopentenyl, hexenyl, 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, and 2,5-cyclohexadien-1-yl. Examples of the "$C_{2-10}$ alkenyl group" include, in addition to the groups mentioned as the "$C_{2-6}$ alkenyl group", heptenyl, octenyl, nonenyl, decenyl, 1-cyclohepten-1-yl, 1-cyclohexen-1-ylmethyl, 4-methyl-1-cyclohexen-1-yl, 4,4-dimethyl-1-cyclohexen-1-yl, and 3,3,5,5-tetramethyl-1-cyclohexen-1-yl. In addition, a cyclic alkenyl group is referred to also as "cycloalkenyl group". "$C_{5-7}$ cycloalkenyl group" includes 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 1-cyclohepten-1-yl, and the like.

The "alkynyl group" is a linear, branched, or cyclic alkynyl group. For example, examples of the "$C_{2-6}$ alkynyl group" include ethynyl, 1-propynyl, 2-propynyl, butynyl, pentynyl, and hexynyl. Examples of the "$C_{2-10}$ alkynyl group" include, in addition to the groups mentioned as the "$C_{2-6}$ alkynyl group", heptynyl, octynyl, nonynyl, and decynyl.

The "alkoxy group" is a linear, branched, or cyclic alkoxy group and comprehensively a group of RO— (as for the $C_{1-6}$ alkoxy group, R is the $C_{1-6}$ alkyl group listed above). For example, examples of the "$C_{1-6}$ alkoxy group" include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, cyclopropyloxy, cyclobutyloxy, cyclopentyloxy, cyclohexyloxy, cyclopropylmethoxy, cyclobutylmethoxy, cyclopentylmethoxy, 1-cyclopropylethoxy, 2-cyclopropylethoxy, 2-cyclobutylethoxy, and 2-methylcyclopropyloxy. Examples of the "$C_{1-10}$ alkoxy group" include, in addition to the groups mentioned as the "$C_{1-6}$ alkoxy group", heptyloxy, octyloxy, 2-ethylhexyloxy, nonyloxy, decyloxy, cycloheptyloxy, cyclohexylmethoxy, 2-cyclohexylethoxy, 4-methylcyclohexyloxy, 4,4-dimethylcyclohexyloxy, and 3,3,5,5-tetramethylcyclohexyloxy.

The "alkenyloxy group" is the "alkenyl group" which is substituted with an oxygen atom, denoting a linear, branched, or cyclic alkenyloxy group. For example, examples of the "$C_{2-6}$ alkenyloxy group" include vinyloxy, allyloxy, isopropenyloxy, 2-methylallyloxy, butenyloxy, pentenyloxy, isopentenyloxy, hexenyloxy, 1-cyclopropen-1-yloxy, 2-cyclopropen-1-yloxy, 1-cyclobuten-1-yloxy, 1-cyclopenten-1-yloxy, 2-cyclopenten-1-yloxy, 3-cyclopenten-1-yloxy, 1-cyclohexen-1-yloxy, 2-cyclohexen-1-yloxy, 3-cyclohexen-1-yloxy, 2,4-cyclopentadien-1-yloxy, and 2,5-cyclohexadien-1-yloxy. Examples of the "$C_{2-10}$ alkenyloxy group" include, in addition to the groups mentioned as the "$C_{2-6}$ alkenyloxy group", heptenyloxy, octenyloxy, nonenyloxy, decenyloxy, 1-cyclohepten-1-yloxy, 1-cyclohexen-1-ylmethoxy, 4-methyl-1-cyclohexen-1-yloxy, 4,4-dimethyl-1-cyclohexen-1-yloxy, and 3,3,5,5-tetramethyl-1-cyclohexen-1-yloxy.

The "alkynyloxy group" is the "alkynyl group" which is substituted with an oxygen atom, denoting a linear, branched, or cyclic alkynyloxy group. For example, examples of the "$C_{2-6}$ alkynyloxy group" include ethynyloxy, 1-propynyloxy, 2-propynyloxy, butynyloxy, pentynyloxy, and hexynyloxy. Examples of the "$C_{2-10}$ alkynyloxy group" include, in addition to the groups mentioned as the "$C_{2-6}$ alkynyloxy group", heptynyloxy, octynyloxy, nonynyloxy, and decynyloxy.

Examples of the "aryl group" include a monocyclic or ring-fused $C_{6-14}$ aryl group, for example, phenyl, 1-naphthyl, 2-naphthyl, anthryl, phenanthryl, acenaphthyl, and the like, or a fused aryl group which is partly hydrogenated such as (1-, 2-, 4-, or 5-)indanyl, indenyl, and tetrahydronaphthyl. The fused aryl group which is partly hydrogenated means a monovalent group obtained by removing any hydrogen atom from a fused ring which is partly hydrogenated, and the hydrogen atom to be removed is optionally a hydrogen atom in an aromatic ring moiety or a hydrogen atom in a hydrogenated moiety of the fused ring. For example, tetrahydronaphthyl includes 1,2,3,4-tetrahydronaphthalen(-1-yl, -2-yl, -3-yl, -4-yl, -5-yl, -6-yl, -7-yl, -8-yl), and the like.

Examples of the "heterocyclic group" include a "heteroaryl group", and a saturated or unsaturated "non-aromatic heterocyclic group". The term "cyclic" used for these groups means a monovalent group obtained by removing any hydrogen atom from a ring having a 3- to 14-membered, preferably a 3- to 12-membered, monocyclic ring or fused ring containing, in addition to carbon atoms, at least one (preferably 1 to 4) heteroatom(s) optionally selected from N, O, and S.

The "heteroaryl group" can be monocyclic or ring-fused, and the monocyclic heteroaryl group preferably has 5 to 7 ring members and includes, for example, pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, 1,4-oxazepinyl, and the like.

The ring-fused heteroaryl group preferably has 8 to 14 ring members and includes a monovalent group obtained by removing any hydrogen atom from a fused ring formed by fusing the 5- to 7-membered heterocyclic ring and a monocyclic aryl group or a monocyclic heteroaryl group, and the like. The hydrogen atom is optionally removed from any of the fused rings.

Specifically, indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo [1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, dibenzofuranyl, and the like are mentioned.

In addition, a ring-fused heteroaryl group, etc. which is partly hydrogenated, such as indolinyl, dihydrobenzofuranyl, dihydroisobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,3-benzodioxanyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl is mentioned. The ring-fused heteroaryl group, etc. which is partly hydrogenated is preferably one having 8 to 14 ring members, namely a monovalent group obtained by removing any hydrogen atom from a ring which is partly hydrogenated in the fused ring formed by fusing the 5- to 7-membered heterocyclic ring and a monocyclic aryl group or a monocyclic heteroaryl group. The hydrogen atom to be removed is optionally a hydrogen atom in the aryl group or in the heterocyclic moiety or a hydrogen atom in the hydrogenated moiety. In the case of tetrahydroquinolyl, examples of the partially hydrogenated ring-fused heteroaryl group include 5,6,7,8-tetrahydroquinolyl and 1,2,3,4-tetrahydroquinolyl. Depending on the position in these groups from which the hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" include a 3- to 8-membered saturated or unsaturated non-aromatic heterocyclic group, such as aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl (oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and oxepanyl, and the "non-aromatic heterocyclic group" means a monovalent group obtained by removing any hydrogen atom from the ring.

Examples of the "heterocyclic group (the heterocyclic group is optionally substituted with 1 to 3 substituent(s) with a $C_{1-6}$ alkyl group or oxo group)" include, in addition to the groups mentioned as the "heterocyclic group", a group in which the cyclic group is substituted with the 1- to 3 "$C_{1-6}$ alkyl group" or oxo group at any position. For example, methylpyrrolyl, methylfuryl, methylthienyl, methylimidazolyl, methylpyrazolyl, methyloxazolyl, methylisoxazolyl, methylthiazolyl, methylisothiazolyl, methylpyridyl, methylpyrimidinyl, methylaziridinyl, methylazetidinyl, methyloxiranyl, methyloxetanyl, methylthietanyl, methylpyrrolidinyl, methyltetrahydrofuryl, methylthiolanyl, methylpyrazolinyl, methylpyrazolidinyl, methylpiperidinyl, methyltetrahydropyranyl, methylpiperazinyl, methyloxazolinyl, methylisoxazolinyl, methyloxazolidinyl, methylisoxazolidinyl, methylthiazolinyl, methylisothiazolinyl, methylthiazolidinyl, methylisothiazolidinyl, methyloxadiazolinyl, methyloxadiazolidinyl, methylmorpholinyl, methylthiomorpholinyl, methylquinuclidinyl, methyloxepanyl, oxopyrrolidinyl, 1,1-dioxidetetrahydrothiopyranyl, and the like are mentioned.

The "aralkyl group" is a group in which a linear or branched alkyl group of the "$C_{1-6}$ alkyl group" is substituted with the "aryl group", and examples of the "aralkyl group" include benzyl, phenethyl, 3-phenylpropyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, and 1,2,3,4-tetrahydronaphthalen-2-ylmethyl.

The "heteroarylalkyl group" is a group in which a linear or branched alkyl group of the "$C_{1-6}$ alkyl group" is substituted with the "heteroaryl group", and examples of the "heteroarylalkyl group" include those substituted with the "monocyclic heteroaryl group", such as pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3-thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, 6H-1,3,4-thiadiazinylmethyl, 1,4-diazepinylmethyl, and 1,4-oxazepinylmethyl, and those substituted with the "ring-fused heteroaryl group", such as indolylmethyl, isoindolylmethyl, benzofuranylmethyl, isobenzofuranylmethyl, benzothienylmethyl, isobenzothienylmethyl, benzoxazolylmethyl, 1,2-benzisoxazolylmethyl, benzothiazolylmethyl, 1,2-benzisothiazolylmethyl, 1H-benzimidazolylmethyl, 1H-indazolylmethyl, 1H-benzotriazolylmethyl, 2,1,3-benzothiadiazinylmethyl, chromenylmethyl, isochromenylmethyl, 4H-1,4-benzoxazinylmethyl, 4H-1,4-benzothiazinylmethyl, quinolylmethyl, isoquinolylmethyl, cinnolinylmethyl, quinazolinylmethyl, quinoxalinylmethyl, phthalazinylmethyl, benzoxazepinylmethyl, benzoazepinylmethyl, benzodiazepinylmethyl, naphthyridinylmethyl, purinylmethyl, pteridinylmethyl, carbazolylmethyl, carbolinylmethyl, acridinylmethyl, phenoxazinylmethyl, phenothiazinylmethyl, phenazinylmethyl, phenoxathiinylmethyl, thianthrenylmethyl, phenanthridinylmethyl, phenanthrolinylmethyl, indolizinylmethyl, thieno[3,2-c]pyridylmethyl, thiazolo[5,4-c]pyridylmethyl, pyrrolo[1,2-b]pyridazinylmethyl, pyrazolo[1,5-a]pyridylmethyl, imidazo[1,2-a]pyridylmethyl, imidazo[1,5-a]pyridylmethyl, imidazo[1,2-b]pyridazinylmethyl, imidazo[1,5-a]pyrimidinylmethyl, 1,2,4-triazolo[4,3-a]pyridylmethyl, 1,2,4-triazolo[4,3-b]pyridazinylmethyl, 1H-pyrazolo[3,4-b]pyridylmethyl, 1,2,4-triazolo[1,5-a]pyrimidinylmethyl, indolinylmethyl, dihydrobenzofuranylmethyl, chromanylmethyl, tetrahydroquinolylmethyl, tetrahydroisoquinolylmethyl, 1,4-benzodioxanylmethyl, and 1,3-benzodioxolylmethyl.

The "non-aromatic heterocyclic alkyl group" is a linear or branched "$C_{1-6}$alkyl group" substituted with the "non-aromatic heterocyclic group", and for example includes aziridinylmethyl, azetidinylmethyl, oxiranylmethyl, oxetanylmethyl, thiethanylmethyl, pyrrolidinylmethyl, tetrahydrofurylmethyl, thioranylmethyl, pyrazolinylmethyl, pyrazolidinylmethyl, piperidinylmethyl, dihydropyranylmethyl, tetrahydropyranylmethyl, tetrahydrothiopyranylmethyl, piperadinylmethyl, dioxanylmethyl, oxazolinylmethyl, isoxazolinylmethyl, oxazolidinylmethyl, isoxazolidinylmethyl, thiazolinylmethyl, isothiazolinylmethyl, thiazolidinylmethyl, isothiazolidinylmethyl, oxadiazolinylmethyl, oxadiazolidinylmethyl, morpholinylmethyl, thiomorpholinylmethyl, quinuclidinylmethyl, oxepanylmethyl, and the like.

The "aryloxy group" is a group in which the "aryl group" is substituted with an oxygen atom and specifically, there can be mentioned a group in which a group exemplified as the "aryl group" above is substituted with an oxygen atom. Examples thereof include phenoxy, 1-naphthyloxy, 2-naphthyloxy, 2-anthryloxy, phenanthryloxy, 1-indanyloxy, 2-indanyloxy, 1,2,3,4-tetrahydronaphthalen-1-yloxy, 1,2,3,4-tetrahydronaphthalen-2-yloxy, and 1,2,3,4-tetrahydronaphthalen-8-yloxy.

The "heterocyclic oxy group" is a group in which the "heterocyclic group"is substituted with an oxygen atom, and includes "heteroaryloxy group" or "non-aromatic heterocyclic oxy group". Specific examples thereof include groups in which the "heterocyclic group" mentioned above is substituted with an oxygen atom. The "heteroaryloxy group" is a group in which the "heteroaryl group" is substituted with an oxygen atom and specifically, there can be mentioned a group in which a group exemplified as the "heteroaryl group" above is substituted with an oxygen atom. Examples thereof include pyrrolyloxy, furyloxy, thienyloxy, imidazolyloxy, pyrazolyloxy, oxazolyloxy, isoxazolyloxy, thiazolyloxy, isothiazolyloxy, (2-, 3-, or 4-)pyridyloxy, pyridazinyloxy, pyrimidinyloxy, pyrazinyloxy, indolyloxy, quinolyloxy, isoquinolyloxy, indolinyloxy, dihydrobenzofuranyloxy, chromanyloxy, tetrahydroquinolinyloxy, tetrahydroisoquinolyloxy, 1,4-benzodioxanyloxy, and 1,3-benzodioxolyloxy.

The "non-aromatic heterocyclic oxy group" is a group in which the "non-aromatic heterocyclic group" is substituted with an oxygen atom, and specific examples thereof include groups in which the "non-aromatic heterocyclic group"mentioned above is substituted with an oxygen atom. For example, they include 3- to 8-membered saturated or unsaturated non-aromatic heterocyclic oxy group, such as aziridinyloxy, azetidinyloxy, oxiranyloxy, oxetanyloxy, thiethanyloxy, pyrrolidinyloxy, tetrahydrofuryloxy, thioranyloxy, pyrazolinyloxy, pyrazolidinyloxy, (1-, 2-, 3- or 4-)piperidinyloxy, dihydropyranyloxy, (2-, 3- or 4-)tetrahydropyranyloxy ((2-, 3- or 4-)oxanyloxy), tetrahydrothiopyranyloxy, piperadinyloxy, dioxanyloxy, oxazolinyloxy, isoxazolinyloxy, oxazolidinyloxy, isoxazolidinyloxy, thiazolinyloxy, isothiazolinyloxy, thiazolidinyloxy, isothiazolidinyloxy, oxadiazolinyloxy, oxadiazolidinyloxy, morpholinyloxy, thiomorpholinyloxy, quinuclidinyloxy, oxetanyloxy, and the like.

The "heterocyclic oxy group (the heterocyclic oxy group is optionally substituted with 1-3 $C_{1-6}$ alkyl group(s) or 1 to 3 oxo group(s))" includes in addition to the above-mentioned "heterocyclic group", the "heterocyclic group" substituted with 1 to 3of the $C_{1-6}$ alkyl group(s) or 1 to 3 oxo group(s) at arbitrary position. In addition, the group can be referred to as the "heterocyclic group (the heterocyclic group is optionally substituted with 1-3 $C_{1-6}$ alkyl group(s) or 1 to 3 oxo group(s))" substituted with an oxygen atom. Specific examples thereof include the above-mentioned examples of the "heterocyclic group (the heterocyclic group is optionally substituted with 1-3 $C_{1-6}$ alkyl group(s) or 1 to 3 oxo group(s))" substituted with an oxygen atom.

The "aralkyloxy group" is a group in which the "aralkyl group" is substituted with an oxygen atom and specifically, there can be mentioned a group in which a group exemplified as the "aralkyl group" above is substituted with an oxygen atom. Examples thereof include benzyloxy, phenethyloxy, 3-phenylpropoxy, 1-naphthylmethoxy, 2-naphthylmethoxy, 2-(1-naphthyl)ethoxy, 2-(2-naphthyl)ethoxy, 1-indanylmethoxy, 2-indanylmethoxy, 1,2,3,4-tetrahydronaphthalen-1-ylmethoxy, and 1,2,3,4-tetrahydronaphthalen-2-ylmethoxy.

The "heteroarylalkyloxy group" is a group in which the "heteroarylalkyl group" is substituted with an oxygen atom and specifically, there can be mentioned a group in which a group exemplified as the "heteroarylalkyl group" above is substituted with an oxygen atom. Examples thereof include a "monocyclic heteroarylalkyl group"substituted with an oxygen atom, such as pyrrolylmethoxy, furylmethoxy, thienylmethoxy, imidazolylmethoxy, pyrazolylmethoxy, oxazolylmethoxy, isoxazolylmethoxy, thiazolylmethoxy, isothiazolylmethoxy, 1,2,3-triazolylmethoxy, 1,2,4-triazolylmethoxy, 1,2,3-oxadiazolylmethoxy, 1,2,4-oxadiazolylmethoxy, 1,3,4-oxadiazolylmethoxy, furazanylmethoxy, 1,2,3-thiadiazolylmethoxy, 1,2,4-thiadiazolylmethoxy, 1,3,4-thiadiazolylmethoxy, tetrazolylmethoxy, pyridylmethoxy, pyridazinylmethoxy, pyrimidinylmethoxy, pyrazinylmethoxy, 1,2,3-triazinylmethoxy, 1,2,4-triazinylmethoxy, 1,3,5-triazinylmethoxy, 2H-1,2,3-thiadiazinylmethoxy, 4H-1,2,4-thiadiazinylmethoxy, 6H-1,3,4-thiadiazinylmethoxy, 1,4-diazepinylmethoxy, and 1,4-oxazepinylmethoxy, and a "ring-fused heteroarylalkyl group" which is optionally partly hydrogenated and is substituted with an oxygen atom, such as indolylmethoxy, isoindolylmethoxy, benzofuranylmethoxy, isobenzofuranylmethoxy, benzothienylmethoxy, isobenzothienylmethoxy, benzoxazolylmethoxy, 1,2-benzisoxazolylmethoxy, benzothiazolylmethoxy, 1,2-benzisothiazolylmethoxy, 1H-benzimidazolylmethoxy, 1H-indazolylmethoxy, 1H-benzotriazolylmethoxy, 2,1,3-benzothiadiazinylmethoxy, chromenylmethoxy, isochromenylmethoxy, 4H-1,4-benzoxazinylmethoxy, 4H-1,4-benzothiazinylmethoxy, quinolylmethoxy, isoquinolylmethoxy, cinnolinylmethoxy, quinazolinylmethoxy, quinoxalinylmethoxy, phthalazinylmethoxy, benzoxazepinylmethoxy, benzoazepinylmethoxy, benzodiazepinylmethoxy, naphthyridinylmethoxy, purinylmethoxy, pteridinylmethoxy, carbazolylmethoxy, carbolinylmethoxy, acridinylmethoxy, phenoxazinylmethoxy, phenothiazinylmethoxy, phenazinylmethoxy, phenoxathiinylmethoxy, thianthrenylmethoxy, phenanthridinylmethoxy, phenanthrolinylmethoxy, indolizinylmethoxy, thieno[3,2-c]pyridylmethoxy, thiazolo[5,4-c]pyridylmethoxy, pyrrolo[1,2-b]pyridazinylmethoxy, pyrazolo[1,5-a]pyridylmethoxy, imidazo[1,2-a]pyridylmethoxy, imidazo[1,5-a]pyridylmethoxy, imidazo[1,2-b]pyridazinylmethoxy, imidazo[1,5-a]pyrimidinylmethoxy, 1,2,4-triazolo[4,3-a]pyridylmethoxy, 1,2,4-triazolo[4,3-b]pyridazinylmethoxy, 1H-pyrazolo[3,4-b]pyridylmethoxy, 1,2,4-triazolo[1,5-a]pyrimidinylmethoxy, indolinylmethoxy, dihydrobenzofuranylmethoxy, chromanylmethoxy, tetrahydroquinolylmethoxy, tetrahydroisoquinolylmethoxy, 1,4-benzodioxanylmethoxy, and 1,3-benzodioxolylmethoxy.

The "non-aromatic heterocyclic oxy group" is a group in which the "non-aromatic heterocyclic group" is substituted with an oxygen atom and specifically, there can be mentioned a group in which a group exemplified as the "non-aromatic heterocyclic group" above is substituted with an oxygen atom. Examples thereof include a 3- to 8-membered saturated or unsaturated non-aromatic heterocyclic oxy group, such as aziridinyloxy, azetidinyloxy, oxiranyloxy, oxetanyloxy, thietanyloxy, pyrrolidinyloxy, tetrahydrofuryloxy, thiolanyloxy, pyrazolinyloxy, pyrazolidinyloxy, (1-, 2-, 3-, or 4-)piperidinyloxy, dihydropyranyloxy, (2-, 3-, or 4-)tetrahydropyranyloxy ((2-, 3-, or 4-)oxanyloxy), tetrahydrothiopyranyloxy, piperazinyloxy, dioxanyloxy, oxazolinyloxy, isoxazolinyloxy, oxazolidinyloxy, isoxazolidinyloxy, thiazolinyloxy, isothiazolinyloxy, thiazolidinyloxy, isothiazolidinyloxy, oxadiazolinyloxy, oxadiazolidinyloxy, morpholinyloxy, thiomorpholinyloxy, quinuclidinyloxy, and oxepanyloxy.

The "spirocyclic group" is a mono spirocyclic-type cyclic group having 6 to 18 ring members in which two cyclic groups share one atom as a spiro atom and are spiro-fused. Each cyclic group forming a spirocyclic is a carbon ring group (such as a cyclic alkyl group and a fused aryl group which is partly hydrogenated) or a heterocyclic group (such as a non-aromatic heterocyclic group and a ring-fused heteroaryl group which is partly hydrogenated) and may be a monocycle or a fused cycle. The spirocyclic group has preferably 6 to 14 ring members and when each cyclic group forming the spirocyclic is a monocycle, each independently is preferably a 3- to 7-membered cyclic group. Each cyclic group forming the spirocyclic may independently have 1 to 3 double bond(s), preferably 1 double bond in the ring. For example, spiro[4,4]nona-(1- or 2-)ene-2-yl, spiro[4,5]dec-(1- or 2-)ene-2-yl, spiro[4,5]dec-(6- or 7-)ene-7-yl, spiro[5,5]undec-2-yl, spiro[5,5]undec-(1- or 2-)ene-2-yl, spiro[indene-1,4'-piperidin]-1'-yl, spiro[indoline-3,4'-piperidin]-1'-yl, spiro[isobenzofuran-1(3H),4'-piperidin]-1'-yl, and the like are mentioned. These spirocyclic are optionally substituted with 1 to 5 substituent(s) which may be the same as or different from each other such as a halogen atom, a —OH group, a $C_{1-6}$ alkyl group, a halogenated $C_{1-6}$ alkyl group, a $C_{1-6}$ alkoxy group, and an oxo group.

The "substituted spiropiperidinylmethyl group" is a methyl group to which a substituted spiropiperidinyl group defined by Formula (SP):

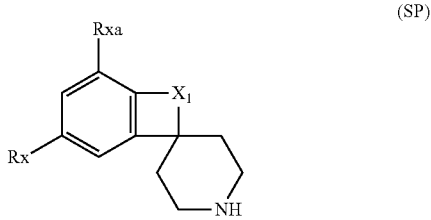

(SP)

(where Rx and Rxa are independently a group selected from a hydrogen atom, a fluorine atom, a chlorine atom, a $C_{1-3}$ alkyl group, a trifluoromethyl group, and a methoxy group; $X_1$ is —CH(Ry)CH$_2$—, —C(Ry)=CH—, —N(Rz)CH$_2$—, or —C(O)CH$_2$—;
Ry is a hydrogen atom or a $C_{1-3}$ alkyl group;
Rz is a hydrogen atom, a $C_{1-3}$ alkyl group, or a phenyl group) is bonded, or a methyl group to which a group of Formula (SP'):

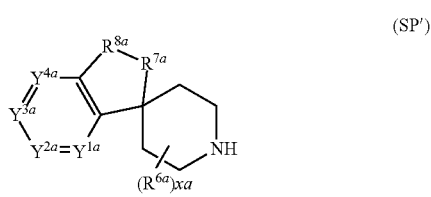

(SP')

(where $R^{6a}$s are independently a halogen atom or a $C_{1-3}$ alkyl group; xa is an integer of 0 to 8; $R^{7a}$ is an oxygen atom or —CH$_2$—, and $R^{8a}$ is an oxygen atom, —CH$_2$—, or —C(O)—, where $R^{7a}$ and $R^{8a}$ together optionally form —CH=CH— (with the proviso that $R^{7a}$ and $R^{8a}$ are not simultaneously an oxygen atom); $Y^{1a}$ is =CR$^{9a}$ or a nitrogen atom, $Y^{2a}$ is =CR$^{9b}$ or a nitrogen atom, $Y^{3a}$ is =CR$^{9c}$— or a nitrogen atom, and $Y^{4a}$ is =CR$^{9d}$— or a nitrogen atom; and $R^{9a}$, $R^{9b}$, $R^{9c}$, and $R^{9d}$ are independently a hydrogen atom, a halogen atom, or a $C_{1-6}$ alkyl group (with the proviso that two or more among $Y^{1a}$ to $Y^{4a}$ are not simultaneously a nitrogen atom)
is bonded, and
is specifically a group of (SP)—CH$_2$—:

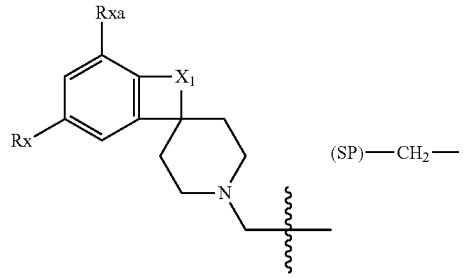

(SP)—CH$_2$—

(where each definition is the same as in the Formula (SP)), or a group of Formula (SP')—CH$_2$:

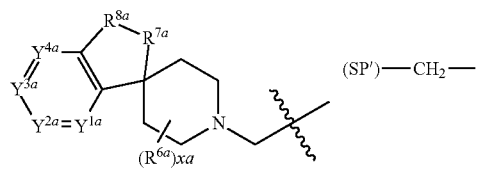

(SP')—CH$_2$—

(where each definition is the same as in the Formula (SP')).

More specifically, as Formula (SP)—CH$_2$—, spiro[indan-1,4'-piperidin]-1'-ylmethyl, (1'H-spiro[inden-1,4'-piperidin]-1'-yl)methyl, 1,2-dihydro-1'H-spiro[indol-3,4'-piperidin]-1'-ylmethyl, (1-methyl-1,2-dihydro-1'H-spiro[indol-3,4'-piperidin]-1'-yl)methyl, {1-(1-methylethyl)-1,2-dihydro-1'H-spiro[indol-3,4'-piperidin]-1'-yl}methyl, (1-phenyl-1,2-dihydro-1'H-spiro[indol-3,4'-piperidin]-1'-yl)methyl, (2,3-dihydro-1'H-spiro[inden-1,4'-piperidin]-1'-yl)methyl, (7-chloro-1-methyl-1,2-dihydro-1'H-spiro[indol-3,4'-piperidin]-1'-yl)methyl, (5-fluoro-1-methyl-1,2-dihydro-1'H-spiro[indol-3,4'-piperidin]-1'-yl)methyl, (5-methoxy-1-methyl-1,2-dihydro-1'H-spiro[indol-3,4'-piperidin]-1'-yl)methyl, (1,5-dimethyl-1,2-dihydro-1'H-spiro[indol-3,4'-piperidin]-1'-yl)methyl, [1-methyl-5-(trifluoromethyl)-1,2-dihydro-1'H-spiro[indol-3,4'-piperidin]-1'-yl]methyl, (3-oxo-2,3-dihydro-1'H-spiro[inden-1,4'-piperidin]-1'-yl)methyl, and the like are mentioned.

Here, as the description of a substituted spiropiperidinyl group or the example of a substituent in Formula (SP)-CH$_2$—, the description in WO 2011/046851 pamphlet, particularly Formula (3) on page 8 and the structural formulae and the chemical names in Example 1 to Example 39 can be referred to.

Or, as the example of Formula (SP')-CH$_2$—, (spiro[isobenzofuran-1(3H),4'-piperidin]-1-yl)methyl, (spiro[benzofuran-3(2H),4'-piperidin]-1-yl)methyl, (3-oxospiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, (spiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, (7-fluoro-1H-spiro[fluoro[3,4-c]pyridin-3,4'-piperidin]-1-yl)methyl, and the like are mentioned.

Here, as the description of a substituted spiropiperidinyl group or the example of a substituent in Formula (SP')-CH$_2$—, each definition, description, and Example of a spiropiperidine ring:

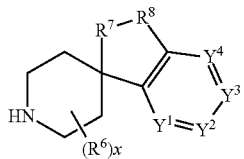

(where R$^6$s are the same as or different from each other and are a halogen atom or a C$_{1-3}$alkyl group; x is 0 or an integer of 1 to 8; R$^7$ is an oxygen atom or —CH$_2$—, or R$^7$ and R$^8$ together form —CH=CH—; R$^8$ is an oxygen atom, —CH$_2$—, or —C(O)—, or R$^7$ and R$^8$ together form —CH=CH—, with the proviso that R$^7$ and R$^8$ are not simultaneously an oxygen atom;
Y$^1$ is =CR$^{9a}$— or a nitrogen atom; Y$^2$ is =CR$^{9b}$— or a nitrogen atom; Y$^3$ is =CR$^{9c}$— or a nitrogen atom; Y$^4$ is =CR$^{9d}$— or a nitrogen atom; R$^{9a}$, R$^{9b}$, R$^{9c}$, and R$^{9d}$ are the same as or different from each other and are a hydrogen atom, a halogen atom, or a C$_{1-6}$ alkyl group, with the proviso that two or more among Y$^1$ to Y$^4$ are not simultaneously a nitrogen atom)
disclosed as Formula [II] in WO 2002/088989 pamphlet, page 9 (the definition of a substituent or the like refers to each definition in Formula [I] on pages 4 and 5), can be referred to.

As a specific example, spiropiperidine used in Examples described in WO 2002/088989 pamphlet is mentioned, and more specifically, for example, spiro[isobenzofuran-1(3H), 4'-piperidine], spiro[benzofuran-3(2H),4'-piperidine], spiro[6-azaisobenzofuran-1(3H),4'-piperidine], 3-oxospiro[4-azaisobenzofuran-1(3H), 4'-piperidine], 3-oxospiro[6-azaisobenzofuran-1(3H),4'-piperidine], and the like are mentioned.

Here, as a lower conception of spiropiperazine shown in WO 2002/088989 pamphlet, as specific examples of a halogenated spiropiperidine ring, further, Examples described in EP1595867 and WO 2011/037771 pamphlet can be referred to. More specifically, spiro[5-fluoroisobenzofuran-1(3H),4'-piperidine], spiro[6-fluoroisobenzofuran-1(3H),4'-piperidine], spiro[5-fluoro-6-azaisobenzofuran-1(3H),4'-piperidine], spiro[6-fluoro-5-azaisobenzofuran-1(3H),4'-piperidine], 7-fluoro-1H-spiro[fluoro[3, 4-c]pyridin-3,4'-piperidine, and the like are mentioned.

In a preferred aspect of various compounds having a substituted spiropiperidinyl group of Formula (SP') in a partial structure thereof in the present invention: xa is preferably 0; R$^{7a}$ and R$^{8a}$ are together, as —R$^{7a}$—R$^{8a}$—, any one of —OCH$_2$—, —CH$_2$O—, —CH$_2$—CH$_2$—, —CH=CH—, and —OC(O)—, more preferably —OCH$_2$— or —CH$_2$—CH$_2$—; Y$^{1a}$ is =CR$^{9a}$— or a nitrogen atom; Y$^{2a}$ is =CR$^{9b}$— or a nitrogen atom; Y$^{3a}$ is =CR$^{9c}$— or a nitrogen atom; Y$^{4a}$ is =CR$^{9d}$— or a nitrogen atom; and R$^{9a}$, R$^{9b}$, R$^{9c}$, and R$^{9d}$ are independently a hydrogen atom, a halogen atom, or a C$_{1-6}$ alkyl group (with the proviso that two or more of Y$^{1a}$ to Y$^{4a}$ are not simultaneously a nitrogen atom).

Examples of the "halogen atom" include a fluorine atom, a chlorine atom, a bromine atom, and an iodine atom.

The "halogenated C$_{1-6}$ alkyl group" is a group in which the "C$_{1-6}$ alkyl group" is optionally substituted with 1 to 5 halogen atom(s). For example, trifluoromethyl, trifluoroethyl, tetrafluoroethyl, pentafluoroethyl, and the like are mentioned.

The "C$_{2-7}$ alkanoyl group" means a "linear, branched, or cyclic C$_{2-7}$alkylcarbonyl group" and is referred to as R—CO— (R is the "C$_{1-6}$ alkyl group"), and includes, for example, acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, 2-methylcyclopropylcarbonyl, and the like.

The "C$_{2-7}$ alkanoyl group" (the alkanoyl group is optionally substituted with —OH or a C$_{1-6}$ alkoxy group) includes in addition to the above-mentioned "C$_{2-7}$ alkanoyl group", the alkanoyl group substituted with —OH or a C$_{1-6}$ alkoxy group at arbitrary position. Specific examples thereof include hydroxyacetyl, methoxyacetyl, and the like.

The "arylcarbonyl group" is a group in which a carbonyl group is bonded to the "aryl group", and examples thereof include, for example, C$_{6-14}$ arylcarbonyl such as benzoyl and naphthylcarbonyl.

The "heterocyclic carbonyl group" means a "heterocyclic carbonyl group", and examples thereof include the "heterocyclic group" (for example, a heteroaryl group, a saturated or unsaturated non-aromatic heterocyclic group, and the like) to which a carbonyl group is bonded, including a carbonyl group to which the "monocyclic heteroaryl group" is bonded, such as pyrrolylcarbonyl, furylcarbonyl, thienylcarbonyl, imidazolylcarbonyl, pyrazolylcarbonyl, oxazolylcarbonyl, isoxazolylcarbonyl, thiazolylcarbonyl, isothiazolylcarbonyl, 1,2,3-triazolylcarbonyl, 1,2,4-triazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, tetrazolylcarbonyl, pyridylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 2H-1,2,3-thiadiazinylcarbonyl, 4H-1,2,4-thiadiazinylcarbonyl, 6H-1,3,4-thiadiazinylcarbonyl, 1,4-diazepinylcarbonyl, and 1,4-oxazepinylcarbonyl; a carbonyl group to which the "ring-fused heteroaryl group" which is optionally partly hydrogenated is bonded, such as indolylcarbonyl, isoindolylcarbonyl, benzofuranylcarbonyl, isobenzofuranylcarbonyl, benzothienylcarbonyl, isobenzothienylcarbonyl, benzoxazolylcarbonyl, 1,2-benzisoxazolylcarbonyl, benzothiazolylcarbonyl, 1,2-benzisothiazolylcarbonyl, 1H-benzimidazolylcarbonyl, 1H-indazolylcarbonyl, 1H-benzotriazolylcarbonyl, 2,1,3-benzothiadiazinylcarbonyl, chromenylcarbonyl, isochromenylcarbonyl, 4H-1,4-benzoxazinylcarbonyl, 4H-1,4-benzothiazinylcarbonyl, quinolylcarbonyl, isoquinolylcarbonyl, cinnolinylcarbonyl, quinazolinylcarbonyl, quinoxalinylcarbonyl, phthalazinylcarbonyl, benzoxazepinylcarbonyl, benzoazepinylcarbonyl, benzodiazepinylcarbonyl, naphthyridinylcarbonyl, purinylcarbonyl, pteridinylcarbonyl, carbazolylcarbonyl, carbolinylcarbonyl, acridinylcarbonyl, phenoxazinylcarbonyl, phenothiazinylcarbonyl, phenazinylcarbonyl, phenoxathiinylcarbonyl, thianthrenylcarbonyl, phenanthridinylcarbonyl, phenanthrolinylcarbonyl, indolizinylcarbonyl, thieno[3,2-c]pyridylcarbonyl, thiazolo[5,4-c]pyridylcarbonyl, pyrrolo[1,2-b]pyridazinylcarbonyl, pyrazolo[1,5-a]pyridylcarbonyl, imidazo[1,2-a]pyridylcarbonyl, imidazo[1,5-a]pyridylcarbonyl, imidazo[1,2-b]pyridazinylcarbonyl, imidazo[1,5-a]pyrimidinylcarbonyl, 1,2,4-triazolo[4,3-a]pyridylcarbonyl, 1,2,4-triazolo[4,3-b]pyridazinylcarbonyl, 1H-pyrazolo[3,4-b]pyridylcarbonyl, 1,2,4-triazolo[1,5-a]pyrimidinylcarbonyl, indolinylcarbonyl, dihydrobenzofuranylcarbonyl, chromanylcarbonyl, tetrahydroquinolylcarbonyl, tetrahydroisoquinolylcarbonyl, 1,4-benzodioxanylcarbonyl, and 1,3-benzodioxolylcarbonyl, and a carbonyl group to which the "saturated or unsaturated non-aromatic heterocyclic group" is bonded, such as aziridinylcarbonyl, azetidinylcarbonyl, pyrrolidinylcarbonyl, tetrahydrofurylcarbonyl, piperidinylcarbonyl, tetrahydropyranylcarbonyl, piperazinylcarbonyl, and morpholinylcarbonyl.

The "non-aromatic heterocyclic carbonyl group" means the "heterocyclic carbonyl group" in which the "heterocyclic group" is replaced with "non-aromatic heterocyclic group". That is, the "non-aromatic heterocyclic carbonyl group" is a group in which a carbonyl group is bonded to the "non-aromatic heterocyclic group". Specific examples thereof include groups in which a carbonyl group is bonded to the "saturated or unsaturated non-aromatic heterocyclic group" described in the "heterocyclic carbonyl group".

In the "—COOR$^f$ group", R$^f$ is a hydrogen atom or a $C_{1-6}$ alkyl group and means a carboxy group or an alkoxycarbonyl group. Specifically, for example, carboxy, methoxycarbonyl, ethoxycarbonyl, and the like are mentioned.

In the "—S(O)$_i$R$^a$ group", i is an integer of 0 to 2, and R$^a$ is a group optionally selected from a $C_{1-6}$ alkyl group and a halogenated $C_{1-6}$ alkyl group. When i is 0, examples of the "—S(O)$_i$R$^a$ group" include a "$C_{1-6}$ alkylthio group" and a "halogenated $C_{1-6}$ alkylthio group", when i is 1, examples of the "—S(O)$_i$R$^a$ group" include a "$C_{1-6}$ alkylsulfinyl group" and a "halogenated $C_{1-6}$ alkylsulfinyl group", and when i is 2, examples of the "—S(O)$_i$R$^a$ group" include a "$C_{1-6}$ alkylsulfonyl group" and a "halogenated $C_{1-6}$ alkylsulfonyl group".

The "$C_{1-6}$ alkylthio group" means a linear, branched, or cyclic $C_{1-6}$ alkylthio group, and examples thereof include, for example, methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio, cyclopropylthio, cyclobutylthio, cyclopentylthio, cyclohexylthio, cyclopropylmethylthio, cyclobutylmethylthio, cyclopentylmethylthio, 1-cyclopropylethylthio, 2-cyclopropylethylthio, 2-cyclobutylethylthio, and 2-methylcyclopropylthio. The "halogenated $C_{1-6}$ alkylthio group" is a group in which the "$C_{1-6}$ alkylthio group" is optionally substituted with 1 to 5 halogen atom(s), and examples thereof include, for example, trifluoromethylthio.

The "$C_{1-6}$ alkylsulfinyl group" means a linear, branched, or cyclic $C_{1-6}$ alkylsulfinyl group, and examples thereof include, for example, methylsulfinyl, ethylsulfinyl, propylsulfinyl, isopropylsulfinyl, cyclopropylsulfinyl, cyclopropylmethylsulfinyl, and 2-methylcyclopropylsulfinyl. The "halogenated $C_{1-6}$ alkylsulfinyl group" is a group in which the "$C_{1-6}$ alkylsulfinyl group" is optionally substituted with 1 to 5 halogen atom(s), and examples thereof include, for example, trifluoromethylsulfinyl.

The "$C_{1-6}$ alkylsulfonyl group" means a linear, branched, or cyclic $C_{1-6}$ alkylsulfonyl group, and examples thereof include, for example, methylsulfonyl, ethylsulfonyl, propylsulfonyl, isopropylsulfonyl, cyclopropylsulfonyl, cyclopropylmethylsulfonyl, and 2-methylcyclopropylsulfonyl. The "halogenated $C_{1-6}$ alkylsulfonyl group" is a group in which the "$C_{1-6}$ alkylsulfonyl group" is optionally substituted with 1 to 5 halogen atom(s), and examples thereof include, for example, trifluoromethylsulfonyl.

The "—SO$_2$NR$^d$R$^e$ group", in which R$^d$ and R$^e$ are independently a hydrogen atom or a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)), means a sulfamoyl group in which 1 or 2 hydrogen atom(s) on a nitrogen atom of the sulfamoyl group is(are) optionally substituted with the "$C_{1-6}$ alkyl group", and further a sulfamoyl group substituted with a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)). Specifically, for example, a sulfamoyl group, a methylsulfamoyl group, an ethylsulfamoyl group, a propylsulfamoyl group, an isopropylsulfamoyl group, a cyclopropylsulfamoyl group, a butylsulfamoyl group, an isobutylsulfamoyl group, a pentylsulfamoyl group, an isopentylsulfamoyl group, a hexylsulfamoyl group, an isohexylsulfamoyl group, a dimethylsulfamoyl group, a diethylsulfamoyl group, a dipropylsulfamoyl group, a di-isopropylsulfamoyl group, a dibutylsulfamoyl group, a dipentylsulfamoyl group, an ethylmethylsulfamoyl group, a methylpropylsulfamoyl group, an ethylpropylsulfamoyl group, a butylmethylsulfamoyl group, a butylethylsulfamoyl group, a butylpropylsulfamoyl group, trifluoromethylsulfamoyl group, hydroxymethylsulfamoyl group, 2-hydroxyethylsulfamoyl group, 3-hydroxypropylsulfamoyl group, 3-hydroxybuthylsulfamoyl group, 3-hydroxy-3-methylbuthylsulfamoyl group, 2,3-dihydroxypropylsulfamoyl group, 3-hydroxy-2-hydroxymethylpropylsulfamoyl group, 3-hydroxy-2-hydroxymethyl-2-methylpropylsulfamoyl group, 2-methoxyethylsulfamoyl group, 2-ethoxyethylsulfamoyl group, 2-methoxy-3-hydroxypropylsulfamoyl group, and the like are mentioned.

The "—CONR$^d$R$^e$ group", in which R$^d$ and R$^e$ are independently a hydrogen atom or a $C_{1-6}$ alkyl group (the $C_{1-6}$ alkyl group is optionally substituted with 1 to 5halogen atom(s), 1 to 5 —OH or 1 to 5 $C_{1-6}$ alkoxyl group(s)), means a carbamoyl group in which 1 or 2 hydrogen atom(s) on a nitrogen atom of the carbamoyl group is(are) optionally substituted with the "$C_{1-6}$ alkyl group", and further a carbamoyl group substituted with a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)). Specifically, for example, a carbamoyl group, a methylcarbamoyl group, an ethylcarbamoyl group, a propylcarbamoyl group, an isopropylcarbamoyl group, a cyclopropylcarbamoyl group, a butylcarbamoyl group, an isobutylcarbamoyl group, a pentylcarbamoyl group, an isopentylcarbamoyl group, a hexylcarbamoyl group, an isohexylcarbamoyl group, a dimethylcarbamoyl group, a diethylcarbamoyl group, a dipropylcarbamoyl group, a diisopropylcarbamoyl group, a dibutylcarbamoyl group, a dipentylcarbamoyl group, an ethylmethylcarbamoyl group, a methylpropylcarbamoyl group, an ethylpropylcarbamoyl group, a butylmethylcarbamoyl group, a butylethylcarbamoyl group, a butylpropylcarbamoyl group, trifluoromethylcarbamoyl group, hydroxymethylcarbamoyl group, 2-hydroxyethylcarbamoyl group, 3-hydroxypropylcarbamoyl group, 3-hydroxybuthylcarbamoyl group, 3-hydroxy-3-methylbuthylcarbamoyl group, 2,3-dihydroxypropylcarbamoyl group, 3-hydroxy-2-hydroxymethylpropylcarbamoyl group, 3-hydroxy-2-hydroxymethyl-2-methylpropylcarbamoyl group, 2-methoxyethylcarbamoyl group, 2-ethoxyethylcarbamoyl group, 2-methoxy-3-hydroxypropylcarbamoyl group, and the like are mentioned.

In the "—$CONR^d R^{e1}$ group", $R^d$ is a hydrogen atom or a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)), and $R^{e1}$ is a $C_{1-6}$ alkyl group (the $C_{1-6}$ alkyl group is optionally substituted with 1 to 5 —OH, 1 to 5 $C_{1-6}$ alkoxyl group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_i R^a$ group(s) (i is an integer of 0 to 2), 1 to 5 —$SO_2 NR^d R^e$ group(s), 1 to 5 —$CO_2 NR^d R^e$ group(s), or 1 to 5 —$NR^{b1} R^{c1}$ group(s)). That is, the "—$CONR^d R^{e1}$ group" means a carbamoyl group in which one hydrogen atom on a nitrogen atom of the carbamoyl group is substituted with $R^{e1}$, and further a carbamoyl group in which another hydrogen atom on a nitrogen atom of the carbamoyl group is substituted with a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)). Specifically, for example, a hydroxymethylcarbamoyl group, a 2-hydroxyethylcarbamoyl group, a 3-hydroxy propylcarbamoyl group, a 3-hydroxybutylcarbamoyl group, a 3-hydroxy-3-methylbutylcarbamoyl group, a 2,3-dihyroxypropylcarbamoyl group, a 3-hydroxy-2-hydroxymethylpropylcarbamoyl group, a 3-hydroxy-2-hydroxymethyl-2-methylpropylcarbamoyl group, a 2-methoxyethylcarbamoyl group, a 2-ethoxyethylcarbamoyl group, a 2-methoxy-3-hydroxypropylcarbamoyl group, a 3-methylsulfonyl-propylcarbamoyl group, a 2-(morpholin-4-yl)ethylcarbamoyl group, a 2-(4-methylpiperazin-1-yl) ethylcarbamoyl group, a 2-(2-oxopyrrolidin-1-yl)ethylcarbamoyl group, a 3-(2-oxopyrrolidin-1-yl) propylcarbamoyl group, a (5-oxopyrrolidin-2-yl) methylcarbamoyl group, a 3-(2-oxooxazolidin-3-yl) propylcarbamoyl group, a (3-methyloxetan-3-yl) methylcarbamoyl group, a 3-(methylsulfonylamino) propylcarbamoyl group, and the like are mentioned.

In the "—$NR^b R^c$ group", $R^b$ and $R^c$ are independently a group optionally selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$ alkoxy group), a $C_{1-6}$ alkylsulfonyl group, an arylcarbonyl group, and a heterocyclic carbonyl group. $R^b$ and $R^c$ optionally form, together with a nitrogen atom to which they are bonded, a 3- to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII. Examples of the "—$NR^b R^c$ group" include, for example, amino, "mono/di $C_{1-6}$ alkylamino", "halogenated mono/di $C_{1-6}$ alkylamino", "mono/di $C_{2-6}$ alkenylamino", "mono/di $C_{2-6}$ alkynylamino", "$C_{2-7}$ alkanoylamino which is optionally substituted with —OH or $C_{1-6}$ alkoxy", "$C_{1-6}$ alkylsulfonylamino", "arylcarbonylamino", and "heterocyclic carbonylamino".

In the "—$NR^{b1} R^{c1}$ group", $R^{b1}$ and $R^{c1}$ are independently a group optionally selected from a hydrogen atom, a $C_{1-6}$ alkyl group, a $C_{2-7}$ alkanoyl group, and a $C_{1-6}$ alkylsulfonyl group. $R^{b1}$ and $R^{c1}$ optionally form, together with a nitrogen atom to which they are bonded, a 3- to 8-membered cyclic group, where in the cyclic group, one carbon atom is optionally substituted with an atom optionally selected from an oxygen atom, a sulfur atom, and a nitrogen atom (the nitrogen atom is optionally substituted with a $C_{1-6}$ alkyl group) or with a carbonyl group. Examples of the "—$NR^{b1} R^{c1}$ group" include, for example, amino, "mono/di $C_{1-6}$ alkylamino", "$C_{2-7}$ alkanoylamino", and "$C_{1-6}$ alkylsulfonylamino".

The "mono/di $C_{1-6}$ alkylamino" means an amino group, 1 or 2 hydrogen atom(s) of which is(are) substituted with a linear, branched, or cyclic "$C_{1-6}$ alkyl group". Specifically, methylamino, ethylamino, propylamino, isopropylamino, butylamino, isobutylamino, pentylamino, isopentylamino, hexylamino, isohexylamino, cyclopropylamino, cyclobutylamino, cyclopentylamino, cyclohexylamino, 1-cyclopropylmethylamino, 1-cyclobutylmethylamino, 1-cyclopentylmethylamino, 1-cyclohexylmethylamino, dimethylamino, diethylamino, dipropylamino, diisopropylamino, dibutylamino, dipentylamino, ethylmethylamino, propylmethylamino, propylethylamino, butylmethylamino, butylethylamino, butylpropylamino, N-cyclopropyl-N-methylamino, N-cyclobutyl-N-methylamino, N-cyclopentyl-N-methylamino, N-cyclohexyl-N-methylamino, and the like are mentioned.

The "halogenated mono/di $C_{1-6}$ alkylamino" is a group in which the "mono/di $C_{1-6}$ alkylamino" is optionally substituted with 1 to 5 halogen atom(s). For example, trifluoromethylamino is mentioned.

The "mono/di $C_{2-6}$ alkenylamino" means an amino group, 1 or 2 hydrogen atom(s) of which is(are) substituted with a linear, branched, or cyclic "$C_{2-6}$ alkenyl group". Specifically, vinylamino, allylamino, isopropenylamino, 2-methylallylamino, butenylamino, pentenylamino, hexenylamino, 1-cyclopropen-1-ylamino, 2-cyclopropen-1-ylamino, 1-cyclobuten-1-ylamino, 1-cyclopenten-1-ylamino, 2-cyclopenten-1-ylamino, 3-cyclopenten-1-ylamino, 1-cyclohexen-1-ylamino, 2-cyclohexen-1-ylamino, 3-cyclohexen-1-ylamino, 2,4-cyclopentadien-1-ylamino, 2,5-cyclohexadien-1-ylamino, divinylamino, diallylamino, diisopropenylamino, di(2-methylallyl)amino, dibutenylamino, dipentenylamino, dihexenylamino, di(1-cyclopropen-1-yl)amino, di(2-cyclopropen-1-yl)amino, di(1-cyclobuten-1-yl)amino, di(1-cyclopenten-1-yl)amino, di(2-cyclopenten-1-yl)amino, di(3-cyclopenten-1-yl)amino, di(1-cyclohexen-1-yl)amino, di(2-cyclohexen-1-yl)amino, di(3-cyclohexen-1-yl)amino, di(2,4-cyclopentadien-1-yl)amino, di(2,5-cyclohexadien-1-yl)amino, and the like are mentioned.

The "mono/di $C_{2-6}$ alkynylamino" means an amino group, 1 or 2 hydrogen atom(s) of which is(are) substituted with a linear, branched, or cyclic "$C_{2-6}$ alkynyl group". Specifically, ethynylamino, 1-propynylamino, 2-propynylamino, butynylamino, pentynylamino, hexynylamino, diethynylamino, di(1-propynyl)amino, di(2-propynyl)amino, dibutynylamino, dipentynylamino, dihexynylamino, and the like are mentioned.

The "$C_{2-7}$ alkanoylamino which is optionally substituted with —OH or $C_{1-6}$ alkoxy" means an amino group, a hydrogen atom of which is substituted with a linear, branched, or cyclic "$C_{2-7}$ alkanoyl group (the alkanoyl group is optionally substituted with —OH or a $C_{1-6}$ alkoxy group)". Specifically, acetamido, propionamide, butylamide, isobutylamide, valeramide, isovaleramide, pivalamide, hexanamide, heptanamide, cyclopropanecarboxamide, cyclobutanecarboxamide, cyclopentanecarboxamide, cyclohexanecarboxamide, 2-methylcyclopropanecarboxamide, hydroxyacetylamino, methoxyacetylamino, and the like are mentioned.

The "$C_{1-6}$ alkylsulfonylamino" means an amino group, a hydrogen atom of which is substituted with a linear, branched, or cyclic $C_{1-6}$ alkylsulfonyl group. Specifically, methylsulfonylamino, ethylsulfonylamino, propylsulfonylamino, isopropylsulfonylamino, cyclopropylsulfonylamino, cyclopropylmethylsulfonylamino, 2-methylcyclopropylsulfonylamino, and the like are mentioned.

The "arylcarbonylamino" means an amino group, a hydrogen atom of which is substituted with the "arylcarbonyl group". Specifically, $C_{6-14}$ arylcarbonylamino such as benzamide and naphthamide is mentioned.

The "heterocyclic carbonylamino" means an amino group, a hydrogen atom of which is substituted with the "heterocyclic carbonyl group". Specifically, pyrrolecarboxamide, furancarboxamide, thiophenecarboxamide, imidazolecarboxamide, pyrazolecarboxamide, pyridinecarboxamide, indolecarboxamide, quinolinecarboxamide, piperidinecarboxamide, and the like are mentioned.

With regard to "$R^b$ and $R^c$ optionally form, together with a nitrogen atom to which they are bonded, a 3- to 8-membered cyclic group" and "$R^{b1}$ and $R^{c1}$ optionally form, together with a nitrogen atom to which they are bonded, a 3- to 8-membered cyclic group", the 3- to 8-membered cyclic group specifically means, for example, a monovalent cyclic group obtained by removing a hydrogen atom which is bonded to a nitrogen atom from a ring that has a nitrogen atom in addition to carbon atoms in a 3- to 8-membered saturated or unsaturated non-aromatic heterocyclic group that is one of the "non-aromatic heterocyclic groups". For example, aziridinyl, azetidinyl, pyrrolidinyl, pyrazolinyl, pyrazolidinyl, piperidinyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, 2-oxopyrrolidinyl, and the like are mentioned. As for $R^b$ and $R^c$, and $R^{b1}$ and $R^{c1}$, with regard to "where in the cyclic group, one carbon atom is substituted with an oxygen atom, a sulfur atom, or a carbonyl group", examples of the cyclic group include, among the above-mentioned cyclic groups, for example, oxazolinyl, isoxazolinyl, oxazolidinyl, isoxazolidinyl, thiazolinyl, isothiazolinyl, thiazolidinyl, isothiazolidinyl, morpholinyl, thiomorpholinyl, and 2-oxopyrrolidinyl.

As for $R^b$ and $R^c$, with regard to "where the nitrogen atom is substituted with a $C_{1-6}$ alkyl group which is optionally substituted with 1 to 5 substituent(s) RI", examples of the cyclic group include, for example, 4-methylpiperazin-1-yl, 4-ethylpiperazin-1-yl, 4-propylpiperazin-1-yl, and 4-trifluoromethylpiperazin-1-yl.

As for $R^{b1}$ and $R^{c1}$, with regard to "where the nitrogen atom is substituted with a $C_{1-6}$ alkyl group", examples of the cyclic group include, for example, 4-methylpiperazin-1-yl, 4-ethylpiperazin-1-yl, and 4-propylpiperazin-1-yl.

As for $R^b$ and $R^c$, with regard to "where the cyclic group is further substituted with 1 to 5 substituent(s) RII", examples of the cyclic group include, for example, 4,4-difluoropiperidin-1-yl.

The "substituent RI" is a group optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5—SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)).

The "substituent RII" is a group optionally selected from the same groups as in the case of the above-mentioned "substituent RI", a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group.

In the meantime, $R^a$, $R^d$, $R^e$, $R^{b1}$, $R^{c1}$ and $R^{e1}$ are the same as the meaning of $R^a$, $R^d$, $R^e$, $R^{b1}$, $R^{c1}$ and $R^{e1}$ in the "—S(O)$_i$R$^a$ group", "—SO$_2$NR$^d$R$^e$ group", "—CONR$^d$R$^e$ group", "—CONR$^d$R$^{e1}$ group" and "—NR$^{b1}$R$^{c1}$ group".

The "$C_{1-6}$ alkyl group which is optionally substituted with 1 to 5 substituent(s) RI" is a "$C_{1-6}$ alkyl group which is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5—OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5—CONR$^d$R$^e$ group(s), or 1 to 5 —NR$^{b1}$R$^{c1}$ group(s)), a —NR$^{b1}$R$^{c1}$ group, and a heterocyclicoxy group (the heterocyclicoxy group is optionally substituted with 1 to 3 $C_{1-6}$ alkyl group(s) or 1 to 3 oxo group(s)), and specific examples thereof include the followings.

For example, a "$C_{1-6}$ alkyl group which is optionally substituted with 1 to 5 halogen atom(s)" includes, in addition to the "$C_{1-6}$ alkyl group", a group in which the alkyl group is optionally substituted with 1 to 5 halogen atom(s). Specifically, in addition to methyl, ethyl, propyl, isopropyl, butyl, isobutyl, sec-butyl, and tert-butyl, for example, trifluoromethyl, trifluoroethyl, tetrafluoroethyl, pentafluoroethyl, and the like are mentioned.

For example, a "$C_{1-6}$ alkyl group which is optionally substituted with 1 to 5 —OH" includes, in addition to the "$C_{1-6}$ alkyl group", a group in which the alkyl group is optionally substituted with 1 to 5 hydroxy, and there are many regioisomers depending on a substitution position. Specifically, in addition to methyl, ethyl, propyl, isopropyl, butyl, isobutyl, sec-butyl, and tert-butyl, for example, hydroxymethyl, 2-hydroxyethyl, 1-hydroxyethyl, 3-hydroxy-1-propyl, 2-hydroxy-1-propyl, 1-hydroxy-1-propyl, 2,3-dihydroxy-1-propyl, 1-hydroxy-1-methyl-1-ethyl, 2-hydroxy-1-methyl-1-ethyl, 4-hydroxy-1-butyl, 3-hydroxy-1-butyl, 2-hydroxy-1-butyl, 1-hydroxy-1-butyl, 3-hydroxy-2-methylpropyl, 2-hydroxy-2-methylpropyl, 3-hydroxy-2-hydroxymethylpropyl, 2-hydroxy-1,1-dimethyl-1-ethyl, 1-hydroxy-2-methylpropyl, 5-hydroxy-1-pentyl, 4-hydroxy-1-pentyl, 3-hydroxy-1-pentyl, 2-hydroxy-1-pentyl, 1-hydroxy-1-pentyl, 4-hydroxy-3-methylbutyl, 4-hydroxy-2-methylbutyl, 4-hydroxy-1-methylbutyl, 3-hydroxy-3-methylbutyl, 3-hydroxy-2-methylbutyl, 3-hydroxy-1-methylbutyl, 2-hydroxy-3-methylbutyl, 2-hydroxy-2-methylbutyl, 2-hydroxy-1-methylbutyl, 3-hydroxy-2,2-dimethylpropyl, 3-hydroxy-1,1-dimethylpropyl, 3-hydroxy-2-hydroxymethyl-2-methylpropyl, 6-hydroxy-1-hexyl, 4-hydroxy-1,1-dimethyl- 1-butyl, 4-hydroxy-3,3-dimethyl-1-butyl, 2-hydroxycyclopropyl, 4-hydroxycyclohexyl, and the like are mentioned.

For example, a "$C_{1-6}$ alkyl group which is optionally substituted with 1 to 5 $C_{1-6}$ alkoxy group(s)" includes, in addition to the "$C_{1-6}$ alkyl group", a group in which the alkyl group is optionally substituted with 1 to 5 of the "$C_{1-6}$ alkoxy group(s)". Specifically, in addition to methyl, ethyl, propyl, isopropyl, butyl, isobutyl, sec-butyl, and tert-butyl, for example, methoxymethyl, methoxyethyl, methoxypropyl, ethoxyethyl, and the like are mentioned.

For example, a "$C_{1-6}$ alkyl group which is optionally substituted with 1 to 5 $C_{1-6}$ alkoxy group(s) which is optionally substituted with 1 to 5 halogen atom(s)" includes, in addition to the "$C_{1-6}$ alkyl group" and the "$C_{1-6}$ alkyl group which is optionally substituted with 1 to 5 $C_{1-6}$ alkoxy group(s)", a group in which the alkyl group is optionally substituted with 1 to 5 of the "$C_{1-6}$ alkoxy group(s)" which is optionally substituted with 1 to 5 halogen atom(s). Specifically, in addition to methyl, ethyl, propyl, isopropyl, butyl, isobutyl, sec-butyl, tert-butyl, methoxymethyl, methoxyethyl, and methoxypropyl, for example, trifluoromethoxymethyl, trifluoromethoxyethyl, trifluoromethoxypropyl, and the like are mentioned.

Alternatively, the alkyl group is optionally substituted with 2 to 5 groups selected from two or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ group(s) (i is an integer of 0 to 2), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)). For example, a $C_{1-6}$ alkyl group which is substituted with a single —OH and a single $C_{1-6}$ alkoxy group, such as 2-hydroxy-3-methoxypropyl and 3-hydroxy-2-methoxypropyl, and the like are mentioned.

Similarly, the "$C_{2-6}$ alkenyl group which is optionally substituted with 1 to 5 substituents RI" includes, in addition to the "$C_{2-6}$ alkenyl group", a group in which the alkenyl group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$group(s)), a —NR$^{b1}$R$^{c1}$ group, and a heterocyclicoxy group (the heterocyclicoxy group is optionally substituted with 1 to 3 $C_{1-6}$ alkyl group(s) or 1 to 3 oxo group(s)). Specifically, in addition to vinyl, allyl, isopropenyl, 2-methylallyl, butenyl, pentenyl, and hexenyl, for example, trifluorovinyl, 2-hydroxyvinyl, 2-methoxyvinyl, 2-trifluoromethoxyvinyl, and the like are mentioned.

The "$C_{2-6}$ alkynyl group which is optionally substituted with 1 to 5 substituents RI" includes, in addition to the "$C_{2-6}$ alkynyl group", a group in which the alkynyl group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group (the aryl group is optionally substituted with 1 to 3 halogen atom(s)), 1to 5 heterocyclic group(s) (the heterocyclic group is optionally substituted with 1 to 3 $C_{1-6}$alkyl group(s) or 1 to 3 oxo group(s)), 1 to 5 —S(O)$_i$R$^a$ (i is an integer of 0 to 2) group(s), 1to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a heterocyclicoxy group (the heterocyclicoxy group is optionally substituted with 1 to 3 $C_{1-6}$ alkyl group(s) or 1 to 3 oxo group(s)). Specifically, in addition to ethynyl, 1-propynyl, 2-propynyl, butynyl, pentynyl, and hexynyl, for example, fluoroethynyl, 2-hydroxyethynyl, 2-methoxyethynyl, 2-trifluoromethoxyethynyl, and the like are mentioned.

The "$C_{1-6}$ alkoxy group which is optionally substituted with 1 to 5substituents RI" includes, in addition to the "$C_{1-6}$ alkoxy group", a group in which the alkoxy group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group (the aryl group is optionally substituted with 1 to 3 halogen atom(s)), 1 to 5 heterocyclic group(s) (the heterocyclic group is optionally substituted with 1 to 3 $C_{1-6}$ alkyl group or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$group(s)), a —NR$^{b1}$R$^{c1}$ group, and a heterocyclicoxy group (the heterocyclicoxy group is optionally substituted with 1 to 3 $C_{1-6}$ alkyl group(s) or 1 to 3 oxo group(s)). Specifically, in addition to methoxy, ethoxy, propoxy, isopropoxy, butoxy, isobutoxy, sec-butoxy, and tert-butoxy, for example, trifluoromethoxy, hydroxymethoxy, 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2 methylpropoxy, 2-methoxyethoxy, 2-ethoxyethoxy, 2-trifluoromethoxyethoxy, 2-methoxy-3-hydroxypropoxy, 2-hydroxy-3-methoxypropoxy, and the like are mentioned.

The "aryl group which is optionally substituted with 1 to 5 substituents RII" is a group in which any hydrogen atom in the "aryl group" is optionally substituted with 1 to 5 substituent(s) RII. That is to say, the "aryl group which is optionally substituted with 1 to 5 substituents RII" includes, in addition to the "aryl group", an "aryl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), —NR$^{b1}$R$^{c1}$ group(s), a heterocyclic oxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1to 5 —CONR$^d$R$^e$ group(s), or 1 to 5 —NR$^{b1}$R$^{c1}$ group(s)), a $C_{2-6}$ alkenyl group, a $C_{2-7}$alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkoxy group(s) or 1 to 3 oxo group(s)), a —S(O)$_r$R$^a$ (i is an integer of 0 to 2) group, a —CONR$^d$R$^e$ group, and a —CONR$^d$R$^{e1}$ group.

Specifically, in addition to the "aryl group", for example, an "aryl group which is substituted with 1 to 5 halogen atom(s)", an "aryl group which is substituted with 1 to 5 group(s) optionally selected from the "$C_{1-6}$ alkoxy group" (the $C_{1-6}$ alkoxy group is optionally substituted with 1 to 5 group(s) optionally selected from a halogen atom, —OH, a $C_{1-6}$ alkoxy group, an aryl group (the aryl group is optionally substituted with 1 to 3 halogen atom(s)), a heterocyclic group (the heterocyclic group is optionally substituted with 1 to 3 $C_{1-6}$ alkyl group(s) or 1 to 3 oxo group(s)), a —S(O)$_r$R$^a$ (i is an integer of 0 to 2) group, a —SO$_2$NR$^d$R$^e$ group, a —CONR$^d$R$^e$ group, or a —NR$^{b1}$R$^{c1}$ group)", an "aryl group which is substituted with 1 to 5 group(s) optionally selected from the "$C_{1-6}$alkyl group" (the $C_{1-6}$ alkyl group is optionally substituted with 1 to 5 group(s) optionally selected from a halogen atom, —OH, a $C_{1-6}$ alkoxy group, a —S(O)$_r$R$^a$ (i is an integer of 0 to 2) group, a —SO$_2$NR$^d$R$^e$ group, a —CONR$^d$R$^e$ group, or a —NR$^{b1}$R$^{c1}$ group)", and the like are mentioned.

Alternatively, the aryl group is optionally substituted with 2 to 5 groups optionally selected from two or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_r$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_r$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$alkyl group(s) or 1 to 3 oxo group(s)), a heterocyclic carbonyl group (the heterocyclic carbonyl group is optionally substituted with 1 to 3 $C_{1-6}$ alkoxy group(s) or 1 to 3 oxo group(s)), a —S(O)$_r$R$^a$ (i is an integer of 0 to 2) group, a —CONR$^d$R$^e$ group, and a —CONR$^d$R$^{e1}$ group. Specifically, for example, an "aryl group which is optionally substituted with 1 or 2 of the "$C_{1-6}$ alkyl group(s)" and 1 or 2 of the "$C_{1-6}$ alkoxy group(s)" (the $C_{1-6}$ alkoxy group is optionally substituted with 1 to 5 halogen atom(s), 1to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_r$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))" and the like are mentioned. More preferably, for example, an "aryl group which is optionally substituted with 1 or 2 of the "$C_{1-6}$ alkyl group(s)" and one of the "$C_{1-6}$ alkoxy groups" (the $C_{1-6}$ alkoxy group is optionally substituted with 1 or 2 —OH, 1 or 2 $C_{1-6}$ alkoxy group(s), 1 or 2 non-aromatic heterocyclic group(s) (the heterocyclic group is optionally substituted with a $C_{1-6}$ alkyl group), 1 or 2 —S(O)$_r$R$^a$ (i is an integer of 0 to 2) group(s), or 1 or 2 —NR$^{b1}$R$^{c1}$ group(s))", and the like are mentioned.

Examples of the "aryl group which is optionally substituted with 1 to 5 substituents RII" more specifically include, in addition to phenyl, (1- or 2-)naphthyl, indanyl, and tetrahydronaphthyl, for example, (2-, 3-, or 4-)fluorophenyl, (2-, 3-, or 4-)chlorophenyl, (2,6-, 2,5-, 2,4-, 2,3-, or 3,5-)difluorophenyl, 4-chloro-2-fluorophenyl, (2-, 3-, or 4-)hydroxyphenyl, (2-, 3-, or 4-)cyanophenyl, (2,6- 2,5-, 2,4-, 2,3-, 3,4- or 3,5-)dicyanophenyl, (2-, 3-, or 4-)methoxyphenyl, (2-, 3-, or 4-)ethoxyphenyl, (2-, 3-, or 4-)propoxyphenyl, (2-, 3-, or 4-)isopropoxyphenyl, (2-, 3-, or 4-)trifluoromethoxyphenyl, (2-, 3-, or 4-)methylphenyl, (2-, 3-, or 4-)ethylphenyl, (2-, 3-, or 4-)propylphenyl, (2-, 3-, or 4-)isopropylphenyl, (2-, 3-, or 4-)isobutylphenyl, (2-, 3-, or 4-)tert-butylphenyl, (2-, 3-, or 4-)trifluoromethylphenyl, (2,6-, 2,5-, 2,4-, 2,3-, or 3,5-)dimethoxyphenyl, (2,6-, 2,5-, 2,4-, or 2,3-)dimethylphenyl, 3,5-ditrifluoromethylphenyl, (4- or 5-)fluoro-(2-, or 3-)methylphenyl, 3-fluoro-4-methylphenyl, 2-chloro-(4- or 5-)methylphenyl, (4- or 5-)fluoro-2-trifluoromethylphenyl, (4- or 5-)chloro-2-trifluoromethylphenyl, 2-(fluoro- or chloro-)5-trifluoromethylphenyl, (4- or 5-)fluoro-(2-, or 3-)methoxy phenyl, 2-fluoro-(3-, 4-, or 5-)methoxyphenyl, (4- or 5-)chloro-(2-, or 3-)methoxyphenyl, 2-chloro-(3-, 4-, or 5-)methoxyphenyl, (4- or 5-)fluoro-2-ethoxyphenyl, (4- or 5-)chloro-2-ethoxyphenyl, 3-(fluoro- or chloro-)4-ethoxyphenyl, 2-methoxy-5-methylphenyl, 4-methoxy-2-methylphenyl, 4-methoxy-(2,6-, 2,5-, or 2,3-)dimethylphenyl, (2-, 3- or 4-)hydroxymethylphenyl, 4-cyano-3-hydroxymethylphenyl, (3-, or 4-)(2-hydroxyethyl)phenyl, (3-, or 4-)(3-hydroxy-3-methylbutoxy)phenyl, 4-(2-hydroyethoxy)-2-methylphenyl, 4-(2,3-dihydroxypropoxy)-2-methylphenyl, 4-(3-hydroxy-3-methylbutoxy)-2-methylphenyl, 3-(3-hydroxy-3-methylbutoxy)-2-methylphenyl, 4-(2-hydroxyethoxy)-(2,6-, 2,5-, or 2,3-)dimethylphenyl, 4-(3-hydroxypropoxy)-2-methylphenyl, 4-(3-hydroxypropoxy)-(2,6-, 2,5-, or 2,3-)dimethylphenyl, 4-(2,3-dihydroxypropoxy)-(2, 6-, 2,5-, or 2,3-)dimethylphenyl, 4-((2R)-2,3-dihydroxypropoxy)-(2,6-, 2,5-, or 2,3-)dimethylphenyl, 4-((2S)-2,3-dihydroxypropoxy)-(2,6-, 2,5-, or 2,3-)dimethylphenyl, 4-(3-hydroxy-2-hydroxymethylpropoxy)-2-methylphenyl, 4-(3-hydroxy-2-hydroxymethyl-2-methylpropoxy)-2-methylphenyl, 4-(3-hydroxybutoxy)-2-methylphenyl, 4-((3S)-3-hydroxybutoxy)-2-methylphenyl, 4-((3R)-3-hydroxybutoxy)-2-methylphenyl, 4-(3-hydroxy-2-hydroxymethylpropoxy)-(2,6-, 2,5-, or 2,3-)dimethylphenyl, 4-(3-hydroxy-2-hydroxymethyl-2-methylpropoxy)-(2,6-, 2,5-, or 2,3-)dimethylphenyl, 4-(3-hydroxybutoxy)-(2,6-, 2,5-, or 2,3-)dimethylphenyl, 4-((3S)-3-hydroxybutoxy)-(2,6-, 2,5-, or 2,3-)dimethylphenyl, 4-((3R)-3-hydroxybutoxy)-(2,6-, 2,5-, or 2,3-)dimethylphenyl, 4-(3-hydroxy-3-methylbutoxy)-(2,6-, 2,5-, or 2,3-)dimethylphenyl, 4-(3-aminopropoxy)-2-methylphenyl, 4-(3-aminopropoxy)-(2,6-, 2,5-, or 2,3-)dimethylphenyl, 4-(2-(2-oxo-1-pyrrolidinyl)ethoxy)-2-methylphenyl, 4-(2-(2-oxo-1-pyrrolidinyl)ethoxy)-(2,6-, 2,5-, or 2,3-)dimethylphenyl, 4-(3-(2-oxo-1-pyrrolidinyl) propoxy)-2-methylphenyl, 4-(3-(2-oxo-1-pyrrolidinyl)propoxy)-(2,6-, 2,5-, or 2,3-)dimethylphenyl, 4-(5-oxo-2-pyrrolidinyl)methoxy-2-methylphenyl, 4-(5-oxo-2-pyrrolidinyl) methoxy-(2,6-, 2,5-, or 2,3-)dimethylphenyl, 4-(2-ethoxy-ethoxy)-2-methylphenyl, 4-(2-ethoxy-ethoxy)-(2,6-, 2,5-, or 2,3-)dimethylphenyl, 4-(2-methylsulfonyl-ethoxy)-2-methylphenyl, 4-(2-methylsulfonyl-ethoxy)-(2,6-, 2,5-, or 2,3-)dimethylphenyl, 4-(3-methylsulfonyl-propoxy)phenyl, 4-(3-methylsulfonyl-propoxy)-2-methylphenyl, 4-(3-methylsulfonyl-propoxy)-(2,6-, 2,5-, or 2,3-)dimethylphenyl, 4-((1,1-dioxidetetrahydro-2H-thiopyran-4-yl)oxy)-2-methylphenyl, 4-((1,1-dioxidetetrahydro-2H-thiopyran-4-yl)oxy)-(2,6-, 2,5-, or 2,3-)dimethylphenyl, 4-((4-hydroxy-1,1-dioxidetetrahydro-2H-thiopyran-4-yl) methoxy)-2-methylphenyl, 4-((4-hydroxy-1,1-dioxidetetrahydro-2H-thiopyran-4-yl)methoxy)-(2,6-, 2,5-, or 2,3-)dimethylphenyl, 4-((3-methyloxetan-3-yl)methoxy)-2-methylphenyl, 4-((3-methyloxetan-3-yl)methoxy)-(2,6-, 2,5-, or 2,3-)dimethylphenyl, 4-(2-acetylamino-ethoxy)-2-methylphenyl, 4-(2-acetylamino-ethoxy)-(2,6-, 2,5-, or 2,3-)dimethylphenyl, 4-(3-acetylamino-propoxy)-2-methylphenyl, 4-(3-acetylamino-propoxy)-(2,6-, 2,5-, or 2,3-)dimethylphenyl, 4-(2-methylsulfonylamino-ethoxy)-2-methylphenyl, 4-(2-methylsulfonylamino-ethoxy)-(2,6-, 2,5-, or 2,3-)dimethylphenyl, 4-(3-methylsulfonylamino-propoxy)-2-methylphenyl, 4-(3-methylsulfonylamino-propoxy)-(2,6-, 2,5-, or 2,3-)dimethylphenyl, 4-(2-carbamoyl-ethoxy)-2-methylphenyl, 4-(2-carbamoyl-ethoxy)-(2,6-, 2,5-, or 2,3-)dimethylphenyl, 4-(3-carbamoyl-propoxy)-2-methylphenyl, 4-(3-carbamoyl-propoxy)-(2,6-, 2,5-, or 2,3-)dimethylphenyl, 4-(2-methylcarbamoyl-ethoxy)-2-methylphenyl, 4-(2-methylcarbamoyl-ethoxy)-(2,6-, 2,5-, or 2,3-)dimethylphenyl, 4-(3-methylcarbamoyl-propoxy)-2-methylphenyl, 4-(3-methylcarbamoyl-propoxy)-(2,6-, 2,5-, or 2,3-)dimethylphenyl, 4-(2-dimethylcarbamoyl-ethoxy)-2-methylphenyl, 4-(2-dimethylcarbamoyl-ethoxy)-(2,6-, 2,5-, or 2,3-)dimethylphenyl, 4-(3-dimethylcarbamoyl-propoxy)-2-methylphenyl, 4-(3-dimethylcarbamoyl-propoxy)-(2,6-, 2,5-, or 2,3-)dimethylphenyl, 4-(2-sulfamoyl-ethoxy)-2-methylphenyl, 4-(2-sulfamoyl-ethoxy)-(2,6-, 2,5-, or 2,3-)dimethylphenyl, 4-(3-sulfamoyl-propoxy)-2-methylphenyl, 4-(3-sulfamoyl-propoxy)-(2,6-, 2,5-, or 2,3-)dimethylphenyl, 4-(2-methylsulfamoyl-ethoxy)-2-methylphenyl, 4-(2-methylsulfamoyl-ethoxy)-(2,6-, 2,5-, or 2,3-)dimethylphenyl, 4-(3-methylsulfamoyl-propoxy)-2-methylphenyl, 4-(3-methylsulfamoyl-propoxy)-(2,6-, 2,5-, or 2,3-)dimethylphenyl, 4-(2-dimethylsulfamoyl-ethoxy)-2-methylphenyl, 4-(2-dimethylsulfamoyl-ethoxy)-(2,6-, 2,5-, or 2,3-)dimethylphenyl, 4-(3-dimethylsulfamoyl-propoxy)-2-methylphenyl, 4-(3-dimethylsulfamoyl-propoxy)-(2,6-, 2,5-, or 2,3-)dimethylphenyl, 3-fluoro-4-(3-hydroxy-3-methylbutoxy)-2-methylphenyl, 3-fluoro-4-(3-hydroxy-3-methylbutoxy)-(2,6- or 2,5-)dimethylphenyl, 3-fluoro-4-(3-methylsulfonyl-propoxy)-2-methylphenyl, 3-fluoro-4-(3-methylsulfonyl-propoxy)-(2,6- or 2,5-)dimethylphenyl, 4-(3-hydroxy-3-methylbutoxy)-2-hydroxymethylphenyl, 4-(3-hydroxy-3-methylbutoxy)-6-methyl-2-hydroxymethylphenyl, 4-(3-methylsulfonyl-propoxy)-2-hydroxymethylphenyl, 4-(3-methylsulfonyl-propoxy)-6-methyl-2-hydroxymethylphenyl, (2-, 3-, or 4-)vinylphenyl, (2-, 3-, or 4-)acetylphenyl, (2-, 3-, or 4-)benzyloxyphenyl, 2-benzyloxy(3-, 4-, 5-, or 6-)fluorophenyl, 4-benzyloxy-(2-, or 3-)fluorophenyl, 4-benzyloxy-(2-, or 3-)methylphenyl, (2-, 3-, or 4-)methylsulfonylphenyl, (2-, 3-, or 4-)carbamoylphenyl, (2-, 3- or 4-)N-methylcarbamoylphenyl, (2-, 3- or 4-)N,N-dimethylcarbamoylphenyl, (2-, 3- or 4-)(N-(2-hydroxyethyl)carbamoyl)phenyl, (2-, 3- or 4-)(N-(2-methoxyethyl) carbamoyl)phenyl, (2-, 3- or 4-)(N-(2-hydroxyethyl)-N-methylcarbamoyl)phenyl, (2-, 3- or 4-)(N-(2-methoxyethyl)-N-methylcarbamoyl)phenyl, (2-, 3- or 4-)(N-(2-methylsulfonyl-ethyl)carbamoyl)phenyl, (2-, 3- or 4-)(N-(2-methylsulfonyl-ethyl)-N-methylcarbamoyl)phenyl, 4-cyano-3-carbamoylphenyl, 3-cyano-4-carbamoylphenyl, (2-, 3- or 4-)(pyrrolidine-1-yl)carbonylphenyl, (2-, 3- or 4-)morpholinophenyl, 4-cyano-3-morpholinophenyl, (2-, 3- or 4-)(2-oxooxazolidin-3-yl)phenyl, 4-cyano-3-(2-oxooxazolidin-3-yl)phenyl, (4-, 5-, 6-, or 7-)fluoro-1-indanyl, (4-, 5-, 6-, or 7-)chloro-1-indanyl, (4-, 5-, 6-, or 7-)bromo-1-indanyl, (4-, 5-, 6-, or 7-)trifluoromethyl-1-indanyl, (4-, 5-, 6-, or 7-)fluoro-2-indanyl, (4-, 5-, 6-, or 7-)chloro-2-indanyl, (4-, 5-, 6-, or 7-)bromo-2-indanyl, (4-, 5-, 6-, or 7-)trifluoromethyl-2-indanyl, (2-, 3-, 4-, 5-, 6-, 7-, or 8-)fluoro-naphthalene-1-yl, (2-, 3-, 4-, 5-, 6-, 7-, or 8-)chloro-naphthalene-1-yl, (2-, 3-, 4-, 5-, 6-, 7-, or 8-)methyl-naphthalene-1-yl, and the like.

The "heterocyclic group which is optionally substituted with 1 to 5 substituent(s) RII" is a group in which any hydrogen atom in the "heterocyclic group" is optionally substituted with 1 to 5 substituent(s) RII. Namely, the "heterocyclic group which is optionally substituted with 1 to 5 substituent(s) RII" is, in addition to the unsubstituted "heteroaryl group" and the "non-aromatic heterocyclic group" both exemplified above as a "heterocyclic group" (these rings are each a monovalent group obtained by removing any hydrogen atom from a ring having a monocycle or a fused ring that is a 3- to 14-membered ring, or preferably, a 3- to 12-membered ring, containing, in addition to carbon atoms, at least one hetero atom (preferably 1 to 4 atom(s)) optionally selected from N, O, and S): a "heterocyclic group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1to 5 —NR$^{b1}$R$^{c1}$ group(s)), a C$_{2-6}$ alkenyl group, a C$_{2-7}$ alkanoyl group, an aralkyloxy group, a heterocyclic group (the heterocyclic group is optionally substituted with 1 to 3 $C_{1-6}$alkyl group(s) or 1 to 3 oxo group(s)), heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group".

Specific examples of the "heterocyclic group which is optionally substituted with 1 to 5 substituent(s) RII" include, in addition to the "heterocyclic group", the "heterocyclic group optionally substituted with 1 to 5 halogen atom(s)", the "heterocyclic group substituted with 1 to 5 group(s) optionally selected from a "C$_{1-6}$alkoxy group" (the C$_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$)" and the "heterocyclic group substituted with 1 to 5 group(s) optionally selected from a "C$_{1-6}$ alkyl group" (the C$_{1-6}$alkyl group is optionally substituted with 1 to 5 halogen atom(s), 1 to 5 —OH, 1 to 5 C$_{1-6}$alkoxy group(s), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5 group(s): —NR$^{b1}$R$^{c1}$)". More specific examples thereof include a "heteroaryl group substituted with 1 to 5 group(s) optionally selected from a "C$_{1-6}$ alkyl group" (the C$_{1-6}$ alkyl group is optionally substituted 1 to 5halogen atom(s), 1 to 5 —OH, 1 to 5 C$_{1-6}$ alkoxy group(s), 1 to 5 group(s): —S(O)$_i$R$^a$ (i is an integer of 0 to 2), 1 to 5 group(s): —SO$_2$NR$^d$R$^e$, 1 to 5 group(s): —CONR$^d$R$^e$, or 1 to 5group(s): —NR$^{b1}$R$^{c1}$)" and a "heteroaryl group substituted with 1 to 5 groups(s) optionally selected from a "C$_{1-6}$ alkoxy group" (the C$_{1-6}$ alkoxy group is optionally substituted with 1 to 5 halogen atom(s), 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl group(s) or 1 to 3 oxo group(s)), 1 to 5 group(s): —S(O)$_i$R$^a$ (i is an integer of 0 to 2), 1 to 5group(s): —SO$_2$NR$^d$R$^e$, 1 to 5 group(s): —CONR$^d$R$^e$, or 1 to 5 group(s): —NR$^{b1}$R$^{c1}$)".

Furthermore, the heterocyclic group is optionally substituted at 2 to 5positions with a group optionally selected from 2 or more types of a halogen atom, —OH, a cyano group, a C$_{1-6}$ alkoxy group (the C$_{1-6}$ alkoxy group is optionally substituted with 1to 5 halogen atom(s), 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl group(s) or 1 to 3 oxo group(s)), 1 to 5 —S(O)$_i$R$^a$ (i is an integer of 0 to 2) group(s), 1 to 5—SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$group, a heterocyclicoxy group (the heterocyclicoxy group is optionally substituted with 1 to 3 C$_{1-6}$ alkyl group(s) or 1 to 3 oxo group(s)), a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a C$_{2-6}$ alkenyl group, a C$_{2-7}$alkanoyl group, an aralkyloxy group, a heterocyclic group (the heterocyclic group is optionally substituted with 1 to 3 C$_{1-6}$ alkyl group(s) or 1 to 3 oxo group(s)), heterocyclic carbonyl group (the heterocyclic carbonyl group is optionally substituted with 1 to 3 C$_{1-6}$alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group. Specific examples thereof include a "heterocyclic group optionally substituted with 1 or 2 "C$_{1-6}$ alkyl group(s)" and 1 or 2"C$_{1-6}$ alkoxy group(s)" (the C$_{1-6}$ alkoxy group is optionally substituted with 1 to 5 halogen atom(s), 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))". More preferred examples thereof include a "heteroaryl group optionally substituted with 1 or 2 "C$_{1-6}$ alkyl group(s)" and one "C$_{1-6}$ alkoxy group" (the C$_{1-6}$ alkoxy group is optionally substituted with 1 or 2 —OH, 1 or 2 C$_{1-6}$ alkoxy group(s), 1 or 2 non-aromatic heterocyclic group(s) (the heterocyclic group is optionally substituted with a C$_{1-6}$ alkyl group), 1 or 2 —S(O)$_i$R$^a$(i is an integer of 0 to 2) group(s), or 1 or 2 —NR$^{b1}$R$^{c1}$ group(s))".

The "heteroaryl group" in the "heterocyclic group which is optionally substituted with 1 to 5 substituent(s) RII" may be monocyclic or ring-fused. The monocyclic heteroaryl group preferably has a 5- to 7-membered ring, and examples thereof include those groups described in the definition of the "heteroaryl group", such as pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, and 1,4-oxazepinyl. The ring-fused heteroaryl group preferably has an 8- to 14-membered ring, and examples thereof include a monovalent group obtained by removing any hydrogen atom from a fused ring formed by fusing the 5- to 7-membered heterocyclic ring and a monocyclic aryl group (such as a benzene ring) or a monocyclic heteroaryl group. The hydrogen atom is optionally removed from any of the fused rings. Specific examples include those groups described in the definition of the "heteroaryl group", such as indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, and dibenzofuranyl. Specific examples thereof also include a ring-fused heteroaryl group which is partly hydrogenated, such as indolinyl, dihydrobenzofuranyl, dihydroisobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl. The ring-fused heteroaryl group which is partly hydrogenated preferably has an 8- to 12-membered ring, namely a monovalent group obtained by removing any hydrogen atom from a fused ring which is partly hydrogenated and formed by fusing the 5- to 7-membered heterocyclic ring and a monocyclic aryl group (such as a benzene ring) or a monocyclic heteroaryl group. Any of the hydrogen atom in the aryl group or in the heterocyclic moiety and of the hydrogen atom in the hydrogenated moiety is optionally removed. In the case of tetrahydroquinolyl, examples of the partially hydrogenated ring-fused heteroaryl group include 5,6,7,8-tetrahydroquinolyl and 1,2,3,4-tetrahydroquinolyl. Depending on the position in these groups from which any hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" in the "heterocyclic group which is optionally substituted with 1 to 5 substituent(s) RII" include a 3- to 8-membered saturated or unsaturated non-aromatic heterocyclic group. Specific examples thereof include aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl (oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and oxepanyl. The "non-aromatic heterocyclic group" means a monovalent group obtained by removing any hydrogen atom from the ring.

Specific examples of the "heterocyclic group which is optionally substituted with 1 to 5 substituent(s) RII" include pyrrolyl, furyl, thienyl, pyrazolyl, isoxazolyl, pyridyl, pyrimidinyl, indolyl, 1H-benzimidazolyl, quinolyl, dibenzofuranyl, dihydrobenzofuranyl, dihydroisobenzofuranyl, chromanyl, 1,3-benzodioxanyl, 1,4-benzodioxanyl, piperidinyl, dihydropyranyl, and tetrahydropyranyl (oxanyl). Specific examples thereof include 2-pyrrolyl, 3-pyrrolyl, 2-furyl, 3-furyl, 2-thienyl, 3-thienyl, 1-pyrazolyl, 3-pyrazolyl, 4-pyrazolyl, 5-pyrazolyl, 3-isoxazolyl, 4-isoxazolyl, 5-isoxazolyl, 2-pyridyl, 3-pyridyl, 4-pyridyl, 2-pyrimidinyl, 4-pyrimidinyl, 5-pyrimidinyl, 1-indolyl, 2-indolyl, 3-indolyl, 4-indolyl, 5-indolyl, 6-indolyl, 7-indolyl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 2-quinolyl, 3-quinolyl, 4-quinolyl, 5-quinolyl, 6-quinolyl, 7-quinolyl, 8-quinolyl, 1-dibenzofuranyl, 2-dibenzofuranyl, 3-dibenzofuranyl, 4-dibenzofuranyl, 1,4-benzodioxazin-2-yl, 1,4-benzodioxazin-3-yl, 1,4-benzodioxazin-5-yl, 1,4-benzodioxazin-6-yl, piperidin-1-yl, piperidin-2-yl, piperidin-3-yl, piperidin-4-yl, 3,6-dihydro-2H-pyran-4-yl, and 4-tetrahydropyranyl (4-oxanyl). Any hydrogen atom of the groups is optionally substituted with 1 to 5 substituent(s) RII. Specific examples thereof include (3-, 4-, or 5-)chlorothiophen-2-yl, (2-, 4-, or 5-)chlorothiophene-2-yl, (3-, 4-, or 5-)acetylthiophene-2-yl, 1-methylpyrazol-4-yl, 3,5-dimethylisoxazol-4-yl, (2-, 4-, 5-, or 6-)fluoropyridin-3-yl, (2-, 4-, 5-, or 6-)chloropyridin-3-yl, (2-, 4-, 5-, or 6-)hydroxypyridin-3-yl, (3-, 4-, 5-, or 6-)cyanopyridin-2-yl, (2-, 4-, 5-, or 6-)cyanopyridin-3-yl, (2-, or 3-)cyanopyridin-4-yl, (3-, 4-, 5-, or 6-)methoxypyridin-2-yl, (2-, 4-, 5-, or 6-)methoxypyridin-3-yl, (2-, or 3-)methoxypyridin-4-yl, (2-, 4-, 5-, or 6-)ethoxypyridin-3-yl, (2-, 4-, 5-, or 6-)cyclopropylmethoxypyridin-3-yl, (3-, 4-, 5-, or 6-)methylpyridin-2-yl, (2-, 4-, 5-, or 6-)methylpyridin-3-yl, (2-, or 3-)methylpyridin-4-yl, (2-, 4-, 5-, or 6-)trifluoromethylpyridin-3-yl, 6-(3-hydroxybutoxy)pyridin-3-yl, 6-(3-hydroxy-3-methylbutoxy)pyridin-3-yl, 6-(2-ethoxyethoxy)pyridin-3-yl, 6-(3-methylsulfonyl-propoxy)pyridin-3-yl, (2,4-, 2,5-, 2,6-, 4,5-, 4,6-, or 5,6-)dimethylpyridin-3-yl, (2,4-, 2,5-, 2,6-, 4,5-, 4,6-, or 5,6-)dimethoxypyridin-3-yl, 6-isopropyl-(2-, 4-, or 5-)chloropyridin-3-yl, 6-methoxy-(2-, 4-, or 5-)methylpyridin-3-yl, 6-(2-hydroxyethoxy)-(2-, or 4-)methylpyridin-3-yl, 6-(3-hydroxypropoxy)-(2-, or 4-)methylpyridin-3-yl, 6-(2,3-dihydroxypropoxy)-(2-, or 4-)methylpyridin-3-yl, 6-((2R)-2,3-dihydroxypropoxy)-(2-, or 4-)methylpyridin-3-yl, 6-((2S)-2,3-dihydroxypropoxy)-(2-, or 4-)methylpyridyl-3-yl, 6-((3S)-3-hydroxybutoxy)-(2-, or 4-)methylpyridyl-3-yl, 6-((3R)-3-hydroxybutoxy)-(2-, or 4-)methylpyridyl-3-yl, 6-(3-hydroxy-3-methylbutoxy)-(2-, or 4-)methylpyridin-3-yl, 6-(3-hydroxy-2-hydroxymethylpropoxy)-(2-, or 4-)methylpyridin-3-yl, 6-(3-hydroxy-2-hydroxymethyl-2-methylpropoxy)-(2-, or 4-)methylpyridin-3-yl, 6-(3-hydroxybutoxy)-(2-, or 4-)methylpyridin-3-yl, 6-(2-ethoxyethoxy)-(2-, or 4-)methylpyridin-3-yl, 6-(2-methylsulfonylethoxy)-(2-, or 4-)methylpyridin-3-yl, 6-(3-methylsulfonyl-propoxy)-(2-, or 4-)methylpyridin-3-yl, 6-((1,1-dioxidetetrahydro-2H-thiopyran-4-yl)oxy)-(2-, or 4-)methylpyridin-3-yl, 6-((4-hydroxy-1,1-dioxidetetrahydro-2H-thiopyran-4-yl)methoxy)-(2-, or 4-)methylpyridin-3-yl, 6-((3-methyloxetane-3-yl)methoxy)-(2-, or 4-)methylpyridin-3-yl, 6-(2-hydroxyethoxy)-(2,4-, 2,5-, or 4,5-)dimethylpyridin-3-yl, 6-(3-hydroxypropoxy)-(2,4-, 2,5-, or 4,5-)dimethylpyridin-3-yl, 6-(2,3-dihydroxypropoxy)-(2,4-, 2,5-, or 4,5-)dimethylpyridin-3-yl, 6-(3-hydroxy-2-hydroxymethylpropoxy)-(2,4-, 2,5-, or 4,5-)dimethylpyridin-3-yl, 6-(3-hydroxy-2-hydroxymethyl-2-methylpropoxy)-(2,4-, 2,5-, or 4,5-)dimethylpyridin-3-yl, 6-(3-hydroxybutoxy)-(2,4-, 2,5-, or 4,5-)dimethylpyridin-3-yl, 6-(3-hydroxy-3-methylbutoxy)-(2,4-, 2,5-, or 4,5-)dimethylpyridin-3-yl, 6-(2-ethoxyethoxy)-(2,4-, 2,5-, or 4,5-)dimethylpyridin-3-yl, 6-(2-methylsulfonylethoxy)-(2,4-, 2,5-, or 4,5-)dimethylpyridin-3-yl, 6-(3-methylsulfonyl-propoxy)-(2,4-, 2,5-, or 4,5-)dimethylpyridin-3-yl, 6-((1,1-dioxidetetrahydro-2H-thiopyran-4-yl)oxy)-(2,4-, 2,5-, or 4,5-)dimethylpyridin-3-yl, 6-((4-hydroxy-1,1-dioxidetetrahydro-2H-thiopyran-4-yl)methoxy)-(2,4-, 2,5-, or 4,5-)dimethylpyridin-3-yl, 6-((3-methyloxetane-3-yl)methoxy)-(2,4-, 2,5-, or 4,5-)dimethylpyridin-3-yl, 6-(3-hydroxy-3-methylbutoxy)-(2-, or 4-)methoxypyridin-3-yl, 6-(2-aminoethoxy)-(2-, or 4-)methylpyridin-3-yl, 6-(2-aminoethoxy)-(2,4-, 2,5-, or 4,5-)dimethylpyridin-3-yl, 6-(3-aminopropoxy)-(2-, or 4-)methylpyridin-3-yl, 6-(3-aminopropoxy)-(2,4-, 2,5-, or 4,5-)dimethylpyridin-3-yl, 6-(2-acetylamino-ethoxy)-(2-, or 4-)methylpyridin-3-yl, 6-(2-acetylamino-ethoxy)-(2,4-, 2,5-, or 4,5-)dimethylpyridin-3-yl, 6-(3-acetylamino-propoxy)-(2-, or 4-)methylpyridin-3-yl, 6-(3-acetylamino-propoxy)-(2,4-, 2,5-, or 4,5-)dimethylpyridin-3-yl, 6-(2-methylsulfonylamino-ethoxy)-(2-, or 4-)methylpyridin-3-yl, 6-(2-methylsulfonylamino-ethoxy)-(2,4-, 2,5-, or 4,5-)dimethylpyridin-3-yl, 6-(3-methylsulfonylamino-propoxy)-(2-, or 4-)methylpyridin-3-yl, 6-(3-methylsulfonylamino-propoxy)-(2,4-, 2,5-, or 4,5-)dimethylpyridin-3-yl, 6-(2-carbamoyl-ethoxy)-(2-, or 4-)methylpyridin-3-yl, 6-(2-carbamoyl-ethoxy)-(2,4-, 2,5-, or 4,5-)dimethylpyridin-3-yl, 6-(3-carbamoyl-propoxy)-(2-, or 4-)methylpyridin-3-yl, 6-(3-carbamoyl-propoxy)-(2,4-, 2,5-, or 4,5-)dimethylpyridin-3-yl, 6-(2-methylcarbamoyl-ethoxy)-(2-, or 4-)methylpyridin-3-yl, 6-(2-methylcarbamoyl-ethoxy)-(2,4-, 2,5-, or 4,5-)dimethylpyridin-3-yl, 6-(3-methylcarbamoyl-propoxy)-(2-, or 4-)methylpyridin-3-yl, 6-(3-methylcarbamoyl-propoxy)-(2,4-, 2,5-, or 4,5-)dimethylpyridin-3-yl, 6-(2-dimethylcarbamoyl-ethoxy)-(2-, or 4-)methylpyridin-3-yl, 6-(2-dimethylcarbamoyl-ethoxy)-(2,4-, 2,5-, or 4,5-)dimethylpyridin-3-yl, 6-(3-dimethylcarbamoyl-propoxy)-(2-, or 4-)methylpyridin-3-yl, 6-(3-dimethylcarbamoyl-propoxy)-(2,4-, 2,5-, or 4,5-)dimethylpyridin-3-yl, 6-(2-sulfamoyl-ethoxy)-(2-, or 4-)methylpyridin-3-yl, 6-(2-sulfamoyl-ethoxy)-(2,4-, 2,5-, or 4,5-)dimethylpyridin-3-yl, 6-(3-sulfamoyl-propoxy)-(2-, or 4-)methylpyridin-3-yl, 6-(3-sulfamoyl-propoxy)-(2,4-, 2,5-, or 4,5-)dimethylpyridin-3-yl, 6-(2-methylsulfamoyl-ethoxy)-(2-, or 4-)methylpyridin-3-yl, 6-(2-methylsulfamoyl-ethoxy)-(2,4-, 2,5-, or 4,5-)dimethylpyridin-3-yl, 6-(3-methylsulfamoyl-propoxy)-(2-, or 4-)methylpyridin-3-yl, 6-(3-methylsulfamoyl-propoxy)-(2,4-, 2,5-, or 4,5-)dimethylpyridin-3-yl, 6-(2-dimethylsulfamoyl-ethoxy)-(2-, or 4-)methylpyridin-3-yl, 6-(2-dimethylsulfamoyl-ethoxy)-(2,4-, 2,5-, or 4,5-)dimethylpyridin-3-yl, 6-(3-dimethylsulfamoyl-propoxy)-(2-, or 4-)methylpyridin-3-yl, 6-(3-dimethylsulfamoyl-propoxy)-(2,4-, 2,5-, or 4,5-)dimethylpyridin-3-yl, 6-(2-(2-oxo-1-pyrrolidinyl)ethoxy)-(2-, or 4-)methylpyridin-3-yl, 6-(2-(2-oxo-1-pyrrolidinyl)ethoxy)-(2,4-, 2,5-, or 4,5-)dimethylpyridin-3-yl, 6-(3-(2-oxo-1-pyrrolidinyl)propoxy)-(2-, or 4-)methylpyridin-3-yl, 6-(3-(2-oxo-1-pyrrolidinyl)propoxy)-(2,4-, 2,5-, or 4,5-)dimethylpyridin-3-yl, 6-(1-piperidinyl)pyridin-3-yl, 6-(4-morpholino)pyridin-3-yl, 6-(4-morpholino)-(2,4-, 2,5-, or 4,5-)dimethylpyridin-3-yl, 6-acetylpyridin-3-yl, 6-benzyloxypyridin-3-yl, 6-methylsulfonylpyridin-3-yl, 6-carbamoylpyridin-3-yl, (2- or 4-)methoxypyrimidin-5-yl, 2-(3-hydroxy-3-methylbutoxy)-4-methylpyrimidin-5-yl, 2-(3-methylsulfonyl-propoxy)-4-methylpyrimidin-5-yl, 2-(3-hydroxy-3-methylbutoxy)-4,6-dimethylpyrimidin-5-yl, 2-(3-methylsulfonyl-propoxy)-4,6-dimethylpyrimidin-5-yl, 2-(4-morpholino)-4,6-dimethylpyrimidin-5-yl, 2-ethyl-6,7-difluoro-1H-benzimidazol-1-yl, 2-ethoxy-6,7-difluoro-1H-benzimidazol-1-yl, (2-, 4-, 5-, 6-, 7-, or 8-)methylquinolin-3-yl, 6-(1-piperidinyl)pyridin-3-yl, 1-methylpiperidin-4-yl, and 4,4-difluoropiperidin-1-yl.

The "aralkyl group which is optionally substituted with 1 to 5 substituent(s) RII" is the "aralkyl group" in which any hydrogen atom is optionally substituted with 1 to 5 substituent(s) RII. That is to say, the "aralkyl group which is optionally substituted with 1 to 5 substituent(s) RII" includes, in addition to the unsubstituted groups exemplified as the "aralkyl group": "an aralkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3oxo group(s)), 1 to 5 —S(O)$_i$R$^a$ (i is an integer of 0 to 2) group(s), 1 to 5 —SO$_2$NR$^d$R$^e$group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$group, and a —CONR$^d$R$^{e1}$ group". The substituent(s) of the aralkyl group is(are) optionally substituted with either the aryl moiety or the alkyl moiety. Specific examples thereof include, in addition to unsubstituted benzyl, phenethyl, 1-naphthylmethyl, or 2-naphthylmethyl: (2-, 3-, or 4-)fluorobenzyl, (2-, 3-, or 4-)chlorobenzyl, (2-, 3-, or 4-)hydroxybenzyl, (2-, 3-, or 4-)methoxybenzyl, (2-, 3-, or 4-)trifluoromethoxybenzyl, (2-, 3-, or 4-)methylbenzyl, (2-, 3-, or 4-)trifluoromethylbenzyl, (2,6-, 2,5-, 2,4-, or 2,3-)dimethylbenzyl, 3,5-ditrifluoromethylbenzyl, 4-(2-hydroxyethoxy)-2,6-dimethylbenzyl, 4-(2,3-dihydroxypropoxy)-2,6-dimethylbenzyl, and 4-(3-hydroxy-3-methylbutoxy)-2,6-dimethylbenzyl.

The "heteroarylalkyl group which is optionally substituted with 1 to 5substituent(s) RII" is the "heteroarylalkyl group" in which any hydrogen atom is optionally substituted with 1 to 5 substituent(s) RII. That is to say, the "heteroarylalkyl group which is optionally substituted with 1 to 5 substituent(s) RII" includes, in addition to the unsubstituted groups exemplified as the "heteroarylalkyl group": "a heteroarylalkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5—SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the heteroarylalkyl group is(are) optionally substituted with either the heteroaryl moiety or the alkyl moiety. Specific examples thereof include, in addition to unsubstituted pyrrolylmethyl, furylmethyl, pyridylmethyl, or quinolylmethyl: (2-, 4-, 5-, or 6-)chloropyridin-3-ylmethyl, (2-, 4-, 5-, or 6-)hydroxypyridin-3-ylmethyl, (2-, 4-, 5-, or 6-)methoxypyridin-3-ylmethyl, (2-, 4-, 5-, or 6-)methylpyridin-3-ylmethyl, (2,4-, 2,5-, 2,6-, 4,5-, or 4,6-)dimethylpyridin-3-ylmethyl, 6-(2-hydroxyethoxy)-2,4-dimethylpyridin-3-ylmethyl, 6-(2,3-dihydroxypropoxy)-2,4-dimethylpyridin-3-ylmethyl, and 6-(3-hydroxy-3-methylbutoxy)-2,4-dimethylpyridin-3-ylmethyl.

The "non-aromatic heterocyclic alkyl group which is optionally substituted with 1 to 5 substituent(s) RII" is the "non-aromatic heterocyclic alkyl group"in which any hydrogen atom is optionally substituted with 1 to 5 substituent(s) RII. That is to say, the "non-aromatic heterocyclic alkyl group which is optionally substituted with 1 to 5 substituent(s) RII" includes, in addition to the unsubstituted groups exemplified as the "non-aromatic heterocyclic alkyl group": "a non-aromatic heterocyclic alkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5heterocyclic group(s) (the heterocyclic group is optionally substituted with 1 to 3 $C_{1-6}$alkyl group(s) or 1 to 3 oxo group(s)), 1 to 5 —S(O)$_i$R$^a$ (i is an integer of 0 to 2) group(s), 1to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5$C_{1-6}$ alkoxy group(s), 1 to 5 —S(O)$_i$R$^a$ (i is an integer of 0 to 2) group(s), 1 to 5 —SO$_2$NR$^d$R$^e$group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^e$ group", and the substituents of the non-aromatic heterocyclic alkyl group may be present on the non-aromatic heterocyclic moiety or the alkyl moiety. Examples thereof include, in addition to pyrrolidinylmethyl, tetrahydrofurylmethyl, piperidinylmethyl, and tetrahydropyranylmethyl that are unsubstituted, (2-, 3- or 4-)chloropiperidin-1-yl methyl, (2-, 3- or 4-)hydroxypiperidin-1-yl methyl, (2-, 3- or 4-)cyanopiperidin-1-yl methyl, (2-, 3- or 4-)methoxypiperidin-1-yl methyl, (2-, 3- or 4-)methylpiperidin-1-yl methyl, (2,3-, 2,4-, 2,5-, 2,6-, 3,4- or 3,5-)dimethylpiperidin-1-yl methyl, 4-(2-hydroxyethoxy)-2,6-dimethylpiperidin-1-yl methyl, 4-(2,3-dihydrorxypropoxy)-2,6-dimethylpiperidin-1-yl methyl, 4-(3-hydroxy-3-methylbutoxy)-2,6-dimethylpiperidin-1-yl methyl, and the like.

The "aryloxy group which is optionally substituted with 1 to 5 substituent(s) RII" is the "aryloxy group" in which any hydrogen atom is optionally substituted with 1 to 5 substituent(s) RII. The "aryloxy group which is optionally substituted with 1 to 5 substituent(s) RII" may be also a group in which the "aryl group which is optionally substituted with 1 to 5 substituent(s) RII" is substituted with an oxygen atom. That is to say, the "aryloxy group which is optionally substituted with 1to 5 substituent(s) RII" includes, in addition to the unsubstituted groups exemplified as the "aryloxy group": "an aryloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5$C_{1-6}$ alkoxy group(s), 1 to 5 aryl group(s) (the aryl group is optionally substituted with 1to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a —$NR^{b1}R^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —$S(O)_iR^a$ (i is an integer of 0 to 2) group, a —$CONR^dR^e$ group, and a —$CONR^dR^{e1}$ group". Specifically, there can be mentioned a group in which the group specifically exemplified above as the "aryl group which is optionally substituted with 1 to 5 substituent(s) RII" is substituted with an oxygen atom. Specific examples thereof include, in addition to unsubstituted phenoxy, 1-naphthyloxy, 2-naphthyloxy, 1-indanyloxy, or 2-indanyloxy: (2-, 3-, or 4-)fluorophenoxy, (2-, 3-, or 4-)chlorophenoxy, (2-, 3-, or 4-)hydroxyphenoxy, (2-, 3-, or 4-)cyanophenoxy, (2-, 3-, or 4-)methoxyphenoxy, (2-, 3-, or 4-)trifluoromethoxyphenoxy, (2-, 3-, or 4-)methylphenoxy, (2-, 3-, or 4-)trifluoromethylphenoxy, (2,6-, 2,5-, 2,4-, or 2,3-)dimethylphenoxy, (3-, or 4-)(2-hydroxyethyl)phenoxy, 4-(2-hydroxyethoxy)phenoxy, 4-(2,3-dihydroxypropoxy)phenoxy, (3-, or 4-)(3-hydroxy-3-methylbutoxy)phenoxy, (3-, or 4-)(2-ethoxy-ethoxy)phenoxy, (3-, or 4-)(3-methylsulfonyl-propoxy)phenoxy, 4-(3-hydroxy-3-methylbutoxy)-2-methylphenoxy, 4-(2-ethoxyethoxy)-2-methylphenoxy, 4-(3-methylsulfonyl-propoxy)-2-methylphenoxy, 4-(2-hydroxyethoxy)-2,6-dimethylphenoxy, 4-(2,3-dihydroxypropoxy)-2,6-dimethylphenoxy, 4-(3-hydroxy-3-methylbutoxy)-2,6-dimethylphenoxy, 4-(2-ethoxy-ethoxy)-2,6-dimethylphenoxy, 4-(3-methylsulfonyl-propoxy)-2,6-dimethylphenoxy, 4-methylsulfonylphenoxy, and 4-(4-morpholino)phenoxy.

The "heteroaryloxy group which is optionally substituted with 1 to 5substituent(s) RII" is the "heteroaryloxy group" in which any hydrogen atom is optionally substituted with 1 to 5 substituent(s) RII. The "heteroaryloxy group which is optionally substituted with 1 to 5 substituent(s) RII" may be also a group in which a group having the "heteroaryl group" among the "heterocyclic groups which is optionally substituted with 1 to 5 substituent(s) RII" is substituted with an oxygen atom. That is to say, the "heteroaryloxy group which is optionally substituted with 1 to 5 substituent(s) RII"includes, in addition to the unsubstituted groups exemplified as the "heteroaryloxy group": "a heteroaryloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0to 2) group(s), 1 to 5 —$SO_2NR^dR^e$ group(s), 1 to 5 —$CONR^dR^e$ group(s), or 1 to 5 —$NR^{b1}R^{c1}$group(s)), a —$NR^{b1}R^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5—OH, 1 to 5 $C_{1-6}$ alkoxy group(s), 1 to 5 —$S(O)_iR^a$ (i is an integer of 0 to 2) group(s), 1 to 5—$SO_2NR^dR^e$ group(s), 1 to 5 —$CONR^dR^e$ group(s), or 1 to 5 —$NR^{b1}R^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —$S(O)_iR^a$ (i is an integer of 0 to 2) group, a —$CONR^dR^e$ group, and a —$CONR^dR^{e1}$ group". Specifically, there can be mentioned a group in which a group having the "heteroaryl group" among the groups specifically exemplified above as the "heterocyclic group which is optionally substituted with 1 to 5 substituent(s) RII" is substituted with an oxygen atom. Specific examples thereof include, in addition to pyrrolyloxy, furyloxy, thienyloxy, (2-, 3-, or 4-)pyridyloxy, pyrimidinyloxy, or quinolyloxy: (2-, 4-, 5-, or 6-)chloropyridin-3-yloxy, (2-, or 3-)chloropyridin-4-yloxy, (2-, 4-, 5-, or 6-)hydroxypyridin-3-yloxy, (2-, or 3-)hydroxypyridin-4-yloxy, (3-, 4-, 5-, or 6-)cyanopyridin-2-yloxy, (2-, 4-, 5-, or 6-)cyanopyridin-3-yloxy, (2-, or 3-)cyanopyridin-4-yloxy, (2-, 4-, 5-, or 6-)methoxypyridin-3-yloxy, (2-, or 3-)methoxypyridin-4-yloxy, (2-, 4-, 5-, or 6-)methylpyridin-3-yloxy, (2-, or 3-)methylpyridin-4-yloxy, (2,4-, 2,5-, 2,6-, 4,5-, or 4,6-)dimethylpyridin-3-yloxy, (2,3-, 2,5-, 2,6-, or 3,5-)dimethylpyridin-4-yloxy, 6-methoxy-(2,4-, or 5-)methylpyridin-3-yloxy, 6-(2-hydroxyethoxy)pyridin-3-yloxy, 6-(2,3-dihydroxypropoxy)pyridin-3-yloxy, 6-(3-hydroxy-3-methylbutoxy)pyridin-3-yloxy, 6-(2-ethoxyethoxy)pyridin-3-yloxy, 6-(3-methylsulfonyl-propoxy)pyridin-3-yloxy, 6-(3-hydroxy-3-methylbutoxy)-(2- or 4-)methylpyridin-3-yloxy, 6-(2-ethoxyethoxy)-(2-, or 4-)methylpyridin-3-yloxy, 6-(3-methylsulfonyl-propoxy)-(2-, or 4-)methylpyridin-3-yloxy, 6-(2-hydroxyethoxy)-2,4-dimethylpyridin-3-yloxy, 6-(2,3-dihydroxypropoxy)-2,4-dimethylpyridin-3-yloxy, 6-(3-hydroxy-3-methylbutoxy)-2,4-dimethylpyridin-3-yloxy, 6-(2-ethoxyethoxy)-2,4-dimethylpyridin-3-yloxy, 6-(3- methylsulfonyl-propoxy)-2,4-dimethylpyridin-3-yloxy, and 6-(4-morpholino)pyridin-3-yloxy.

The "non-aromatic heterocyclicoxy group which is optionally substituted with 1 to 5 substituent(s) RII" is the "non-aromatic heterocyclicoxy group" in which any hydrogen atom is optionally substituted with 1 to 5 substituent(s) RII. That is to say, the "non-aromatic heterocyclicoxy group which is optionally substituted with 1 to 5substituent(s) RII" includes, in addition to the unsubstituted groups exemplified as the "non-aromatic heterocyclicoxy group": "a non-aromatic heterocyclicoxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3oxo group(s)), 1 to 5 —S(O)$_i$R$^a$ (i is an integer of 0 to 2) group(s), 1 to 5 —SO$_2$NR$^d$R$^e$group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5—CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". For example, a 3- to 8-membered saturated or unsaturated non-aromatic heterocyclicoxy group optionally substituted with 1 to 5 substituent(s) RII is included. Examples thereof include, in addition to pyrrolidinyloxy, tetrahydrofuryloxy, piperidinyloxy, dihydropyranyloxy, or tetrahydropyranyloxy(oxanyloxy): (2-, or 3-)fluorooxan-4-yloxy, (2-, or 3-)chlorooxan-4-yloxy, (2-, or 3-)hydroxyoxan-4-yloxy, (2-, or 3-)methoxyoxan-4-yloxy, (2-, or 3-)trifluoromethoxyoxan-4-yloxy, (2-, or 3-)methyloxan-4-yloxy, (2-, or 3-)trifluoromethyloxan-4-yloxy, (2,3-, 2,5-, 2,6-, or 3,5-)dimethyloxan-4-yloxy, 1-methylpiperidin-4-yloxy, and (1,2-, or 1,3-)dimethylpiperidin-4-yloxy.

The "aralkyloxy group which is optionally substituted with 1 to 5substituent(s) RII" is the "aralkyloxy group" in which any hydrogen atom is optionally substituted with 1 to 5 substituent(s) RII. That is to say, the "aralkyloxy group which is optionally substituted with 1 to 5 substituent(s) RII"includes, in addition to the unsubstituted groups exemplified as the "aralkyloxy group": "an aralkyloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3oxo group(s)), 1 to 5 —S(O)$_i$R$^a$ (i is an integer of 0 to 2) group(s), 1 to 5 —SO$_2$NR$^d$R$^e$group(s), 1 to 5 —CONR$^d$R$^e$ group(s), or 1 to 5 —NR$^{b1}$R$^{c1}$ group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the aralkyloxy group is(are) optionally substituted with the aryl moiety or the alkyl moiety. Specific examples thereof include, in addition to benzyloxy, phenethyloxy, 1-naphthylmethoxy, or 2-naphthylmethoxy: (2-, 3-, or 4-)fluorobenzyloxy, (2-, 3-, or 4-)chlorobenzyloxy, (2-, 3-, or 4-)hydroxybenzyloxy, (2-, 3-, or 4-)methoxybenzyloxy, (2-, 3-, or 4-)trifluoromethoxybenzyloxy, (2-, 3-, or 4-)methylbenzyloxy, (2-, 3-, or 4-)trifluoromethylbenzyloxy, (2-, 3-, or 4-)methoxyphenethyloxy, (2,6-, 2,5-, 2,4-, or 2,3-)dimethylbenzyloxy, 4-(2-hydroxyethoxy)-2,6-dimethylbenzyloxy, 4-(2,3-dihydroxypropoxy)-2,6-dimethylbenzyloxy, and 4-(3-hydroxy-3-methylbutoxy)-2,6-dimethylbenzyloxy.

The "heteroarylalkyloxy group which is optionally substituted with 1 to 5substituent(s) RII" is the "heteroarylalkyloxy group" in which any hydrogen atom is optionally substituted with 1 to 5 substituent(s) RII. That is to say, the "heteroarylalkyloxy group which is optionally substituted with 1 to 5 substituent(s) RII"includes, in addition to the unsubstituted groups exemplified as the "heteroarylalkyloxy group": "a heteroarylalkyloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0to 2) group(s), 1 to 5 —SO$_2$NR$^d$R$^e$ group(s), 1 to 5 —CONR$^d$R$^e$ group(s), or 1 to 5 —NR$^{b1}$R$^{c1}$group(s)), a —NR$^{b1}$R$^{c1}$ group, a heterocyclicoxy group (the heterocyclicoxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5—OH, 1 to 5 $C_{1-6}$ alkoxy group(s), 1 to 5 —S(O)$_i$R$^a$ (i is an integer of 0 to 2) group(s), 1 to 5—SO$_2$NR$^d$R$^e$ group(s), 1 to 5 —CONR$^d$R$^e$ group(s), or 1 to 5 —NR$^{b1}$R$^{c1}$ group(s)), a $C_{2-6}$alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the heteroarylalkyloxy group is(are) optionally substituted with either the heteroaryl moiety or the alkyl moiety. Specific examples thereof include, in addition to pyrrolylmethoxy, furylmethoxy, pyridylmethoxy, or quinolylmethoxy: (2-, 4-, 5-, or 6-)chloropyridin-3-ylmethoxy, (2-, 4-, 5-, or 6-)hydroxypyridin-3-ylmethoxy, (2-, 4-, 5-, or 6-)methoxypyridin-3-ylmethoxy, (2-, 4-, 5-, or 6-)methylpyridin-3-ylmethoxy, (2,4-, 2,5-, 2,6-, 4,5-, or 4,6-)dimethylpyridin-3-ylmethoxy, 6-(2-hydroxyethoxy)-2,4-dimethylpyridin-3-ylmethoxy, 6-(2,3-dihydroxypropoxy)-2, 4-dimethylpyridin-3-ylmethoxy, and 6-(3-hydroxy-3-methylbutoxy)-2,4-dimethylpyridin-3-ylmethoxy.

In the compound of Formula (I), the 3-hydroxy-isothiazolyl group is a group that can be a 3(2H)-isothiazolonyl group by proton tautomerism, and the resultant tautomer is included in Formula (I). The abundance ratio of this structure can vary depending on whether the compound of Formula (I) is in the solid state or in the dissolved state in a liquid.

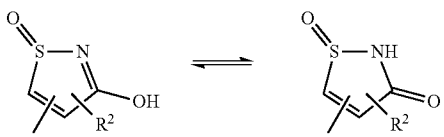

The description of any specific types of tautomers in any structural formulae of the present specification is not intended to limit the present invention, but is intended to represent the whole set of tautomers that are applicable.

Specifically, for example, a tautomer, namely, 5-(4-(5-bromo-2,3-dihydro-1H-inden-1-yloxy)phenyl)-3(2H)-isothiazolone 1-oxide, of the compounds described as 5-(4-(5-bromo-2,3-dihydro-1H-inden-1-yloxy)phenyl)isothiazol-3-ole 1-oxide among compounds of Example 1 is also categorized as a compound of Example 1.

[1-1] In the compound of Formula (I) according to Aspect [1], Ls are independently a group optionally selected from a halogen atom, —OH, an oxo group, a cyano group, a $C_{1-10}$ alkyl group which is optionally substituted with 1 to 5substituent(s) RI, a $C_{2-10}$ alkenyl group which is optionally substituted with 1 to 5substituent(s) RI, a $C_{2-10}$ alkynyl group which is optionally substituted with 1 to 5substituent(s) RI, a $C_{1-10}$ alkoxy group which is optionally substituted with 1 to 5substituent(s) RI, a $C_{2-10}$ alkenyloxy group which is optionally substituted with 1 to 5substituent(s) RI, a $C_{2-10}$ alkynyloxy group which is optionally substituted with 1 to 5substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5substituent(s) RII, an aryloxy group which is optionally substituted with 1 to 5substituent(s) RII, a heteroaryloxy group which is optionally substituted with 1 to 5substituent(s) RII, a non-aromatic heterocyclicoxy group which is optionally substituted with 1 to 5 substituent(s) RII, an aralkyloxy group which is optionally substituted with 1to 5 substituent(s) RII, a heteroarylalkyloxy group which is optionally substituted with 1to 5 substituent(s) RII, —SH, —SF$_5$, a —S(O)$_i$R$^a$ (i is an integer of 0 to 2) group, a —NR$^b$R$^c$group, and a substituted spiropiperidinylmethyl group; and the substituent(s) RI, the substituent(s) RII, i, R$^a$, R$^b$, R$^c$ are the same as defined in Aspect [1].

[1-1-a] Preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1to 5 substituent(s) RI, a $C_{2-10}$ alkynyl group which is optionally substituted with 1 to 5substituent(s) RI, a $C_{1-10}$ alkoxy group which is optionally substituted with 1 to 5substituent(s) RI, a $C_{2-10}$ alkenyloxy group which is optionally substituted with 1 to 5substituent(s) RI, a $C_{2-10}$ alkynyloxy group which is optionally substituted with 1 to 5substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5substituent(s) RII, an aryloxy group which is optionally substituted with 1 to 5substituent(s) RII, a heteroaryloxy group which is optionally substituted with 1 to 5substituent(s) RII, a non-aromatic heterocyclicoxy group which is optionally substituted with 1 to 5 substituent(s) RII, an aralkyloxy group which is optionally substituted with 1to 5 substituent(s) RII, a heteroarylalkyloxy group which is optionally substituted with 1to 5 substituent(s) RII, a —NR$^b$R$^c$ group, and a substituted spiropiperidinylmethyl group (the substituent(s) RI and the substituent(s) RII are the same as defined in Aspect [1]).

[1-1-b] More preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, an aryl group which is optionally substituted with 1 to 5 substituent(s) RII, a heterocyclic group which is optionally substituted with 1to 5substituent(s) RII, an aralkyl group which is optionally substituted with 1 to 5substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5substituent(s) RII, a heteroaryloxy group which is optionally substituted with 1 to 5substituent(s) RII, a non-aromatic heterocyclicoxy group which is optionally substituted with 1 to 5 substituent(s) RII, an aralkyloxy group which is optionally substituted with 1to 5 substituent(s) RII, a heteroarylalkyloxy group which is optionally substituted with 1to 5 substituent(s) RII, a —NR$^b$R$^c$ group, and a substituted spiropiperidinylmethyl group (the substituent(s) RI and the substituent(s) RII are the same as defined in Aspect [1]).

[1-1-c] Further preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, an aryl group which is optionally substituted with 1 to 5 substituent(s) RII, a heterocyclic group which is optionally substituted with 1to 5substituent(s) RII, an aralkyl group which is optionally substituted with 1 to 5substituent(s) RII, a non-aromatic heterocyclic alkyl group which is optionally substituted with 1 to 5 substituent(s) RII, an aryloxy group which is optionally substituted with 1 to 5substituent(s) RII, a heteroaryloxy group which is optionally substituted with 1 to 5substituent(s) RII, a non-aromatic heterocyclicoxy group which is optionally substituted with 1 to 5 substituent(s) RII, an aralkyloxy group which is optionally substituted with 1to 5 substituent(s) RII, and a substituted spiropiperidinylmethyl group (the substituent(s) RI and the substituent(s) RII are the same as defined in Aspect [1]).

[1-1-d] Most preferable examples of Ls include a group optionally selected from a halogen atom, a cyano group, a $C_{1-10}$ alkyl group (the $C_{1-10}$ alkyl group is optionally substituted with 1 to 5 halogen atom(s), 1 to 5 —OH, or 1 to 5 $C_{1-4}$ alkoxy group(s)), a $C_{2-10}$ alkenyl group (the $C_{2-10}$ alkenyl group is optionally substituted with 1 to 5 halogen atom(s), 1 to 5 —OH, or 1 to 5 $C_{1-4}$ alkoxy group(s)), a $C_{1-10}$ alkoxy group (the $C_{1-10}$ alkoxy group is optionally substituted with 1 to 5 halogen atom(s), 1 to 5 —OH, or 1to 5 $C_{1-4}$ alkoxy group(s)), a $C_{2-10}$ alkenyloxy group (the $C_{2-10}$ alkenyloxy group is optionally substituted with 1 to 5 halogen atom(s), 1 to 5 —OH, or 1 to 5 $C_{1-4}$ alkoxy group(s)), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, a non-aromatic heterocyclic alkyl group which is optionally substituted with 1 to 5substituent(s) RIIa, an aryloxy group which is optionally substituted with 1 to 5substituent(s) RIIa, a heteroaryloxy group which is optionally substituted with 1 to 5 substituent(s) RIIa, a non-aromatic heterocyclicoxy group which is optionally substituted with 1 to 5 substituent(s) RIIa, an aralkyloxy group which is optionally substituted with 1to 5 substituent(s) RIIa, and a substituted spiropiperidinylmethyl group (the substituent(s) RIIa are the same as or different from each other and are each a group optionally selected from a halogen atom, a cyano group, a $C_{1-6}$ alkoxy group (the $C_{1-6}$ alkoxy group is optionally substituted with 1 to 5 halogen atom(s), 1 to 5 —OH, 1 to 5 $C_{1-4}$ alkoxy group(s), 1 to 5 a non-aromatic heterocyclic group (the non-aromatic heterocyclic group which is optionally substituted with 1 to 2 $C_{1-4}$ alkoxy group(s) or 1 to 2 oxo group(s)), or 1 to 5—$S(O)_iR^a$ (i is an integer of 0 to 2)), a —$NR^{b1}R^{c1}$ group, a non-aromatic heterocyclicoxy group (the non-aromatic heterocyclicoxy group which is optionally substituted with 1 to 2oxo group(s)), a $C_{1-6}$ alkyl group (the $C_{1-6}$ alkyl group is optionally substituted with 1 to 5halogen atom(s), 1 to 5 —OH, or 1 to 5 $C_{1-4}$ alkoxy group(s)), a $C_{2-6}$ alkenyl group, a $C_{2-7}$alkanoyl group, an aralkyloxy group, a non-aromatic heterocyclic carbonyl group (the non-aromatic heterocyclic carbonyl group which is optionally substituted with 1 to 2 oxo group(s)), a —$S(O)_iR^a$ (i is an integer of 0 to 2) group, a —$CONR^dR^e$ group, and —$CONR^{d3}R^{e3}$ group ($R^{d3}$ is a hydrogen atom or a $C_{1-4}$ alkyl group, and $R^{e3}$ is a $C_{1-6}$ alkyl group (the $C_{1-6}$ alkyl group is optionally substituted with 1 to 5 substituent(s) arbitrarily selected from —OH, $C_{1-6}$ alkoxyl group, non-aromatic heterocyclic group (the heterocyclic group is optionally substituted with 1 to 2 $C_{1-4}$ alkyl group(s) or 1 to 2 oxo group(s)), and —$S(O)_iR^a$ group(s) (i is an integer of 0 to 2))). Substitution with one to three substituent(s) RIM is preferable.

More specifically, examples of L include groups specifically exemplified as the "halogen atom", the "$C_{1-6}$ alkyl group which is optionally substituted with 1 to 5substituent(s) RI", the "$C_{1-6}$ alkoxy group which is optionally substituted with 1 to 5substituent(s) RI", the "aryl group which is optionally substituted with 1 to 5 substituent(s) RII", the "heterocyclic group which is optionally substituted with 1 to 5substituent(s) RII", the "aralkyl group which is optionally substituted with 1 to 5substituent(s) RII", the "heteroarylalkyl group which is optionally substituted with 1 to 5substituent(s) RII", the "non-aromatic heterocyclic alkyl group which is optionally substituted with 1 to 5 substituent(s) RII", the "aryloxy group which is optionally substituted with 1 to 5 substituent(s) RII", the "heteroaryloxy group which is optionally substituted with 1 to 5 substituent(s) RII", the "non-aromatic heterocyclicoxy group which is optionally substituted with 1 to 5 substituent(s) RII", the "aralkyloxy group which is optionally substituted with 1 to 5 substituent(s) RII", the "heteroarylalkyloxy group which is optionally substituted with 1 to 5 substituent(s) RII", the "substituted spiropiperidinylmethyl group", and the like.

[1-2] In the compound of Formula (I) according to Aspect [1], $R^1$s are independently a group optionally selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group (the substituent(s) RI are the same as or different from each other and are the same as defined as the substituent(s) RI above).

[1-2-a] Preferable examples of $R^1$s include a halogen atom, a $C_{1-4}$ alkyl group which is optionally substituted with 1 to 5 halogen atom(s), a $C_{1-4}$ alkoxy group which is optionally substituted with 1 to 5 halogen atom(s), and a cyano group, and more specifically, $R^1$ is a fluorine atom, a chlorine atom, a bromine atom, methyl, ethyl, propyl, isopropyl, trifluoromethyl, methoxy, cyano, and the like.

[1-3] In the compound of Formula (I) according to Aspect [1], $R^2$ is a hydrogen atom, a halogen atom, a $C_{1-6}$ alkyl group, a $C_{2-6}$ alkenyl group, a $C_{2-6}$ alkynyl group, a $C_{1-6}$ alkoxy group, or a cyano group.

[1-3-a] Preferable examples of $R^2$ include a hydrogen atom and a halogen atom, and specific examples thereof include a hydrogen atom, a fluorine atom, a chlorine atom, and a bromine atom. More preferably, $R^2$ is a hydrogen atom.

[1-4] In the compound of Formula (I) according to Aspect [1], $R^3$, $R^4$, $R^5$, $R^6$, and $R^7$ are independently a hydrogen atom or a $C_{1-6}$ alkyl group. Preferably, $R^3$, $R^4$, $R^5$, $R^6$, and $R^7$ are a hydrogen atom.

[1-5] In the compound of Formula (I) according to Aspect [1], X is an oxygen atom or —$NR^7$— ($R^7$ is the same as defined as $R^7$ above).

[1-5-a] Preferably, X is an oxygen atom or —NH—.

[1-5-b] More preferably, X is an oxygen atom.

[1-6] In the compound of Formula (I) according to Aspect [1], j is an integer of 0 to 2. Preferably, when the ring A is a monocycle or a spiro ring, j is 0 or 1, and when the ring A is a fused ring, j is 0. More preferably, when the ring A is a monocycle or a spiro ring, j is 1.

[1-7] In the compound of Formula (I) according to Aspect [1], k is 0 or 1, preferably 0.

[1-8] In the compound of Formula (I) according to Aspect [1], p is an integer of 0 to 4, preferably 0 or 1, more preferably 0.

[1-9] In the compound of Formula (I) according to Aspect [1], the ring A is a $C_{6-14}$ aryl group which is optionally substituted with 1 to 5 substituent(s) L, a 3- to 14-membered heterocyclic group which is optionally substituted with 1 to 5 substituent(s) L, a $C_{5-7}$ cycroalkyl group which is optionally substituted with 1 to 5 substituent(s) L, a $C_{5-7}$ cycroalkenyl group which is optionally substituted with 1 to 5 substituent(s) L, a 6- to 14-membered spiro ring group which is optionally substituted with 1 to 5 substituent(s) L, or a 2-phenylamino-2-oxoacetyl group which is optionally substituted with 1 to 5substituent(s) L.

[1-9-a] Preferably, the ring A is phenyl which is optionally substituted with 1 to 5substituent(s) L, a fused $C_{6-14}$ aryl group which is optionally substituted with 1 to 5substituent(s) L and partially hydrogenated, a 5- to 7-membered monocyclic heteroaryl group which is optionally substituted with 1 to 5 substituent(s) L, an 8- to 14-membered ring-fused heteroaryl group which is optionally substituted with 1 to 5 substituent(s) L, a 8- to 14-membered ring-fused heteroaryl group which is optionally substituted with 1 to 5 substituent(s) L and partially hydrogenated, a 3- to 8-membered non-aromatic heterocyclic group which is optionally substituted with 1 to 5 substituent(s) L, a $C_{5-7}$cycroalkenyl group which is optionally substituted with 1 to 5 substituent(s) L, or a 7- to 13-membered spiro ring group which is optionally substituted with 1 to 5 substituent(s) L.

[1-9-b] More preferably, the ring A is phenyl which is optionally substituted with 1 to 5 substituent(s) L, indanyl which is optionally substituted with 1 to 5 substituent(s) L, thienyl which is optionally substituted with 1 to 5 substituent(s) L, thiazolyl which is optionally substituted with 1 to 5 substituent(s) L, phthaladinyl which is optionally substituted with 1 to 5 substituent(s) L, 1,2,3,4-tetrahydro-4-isoquinolyl which is optionally substituted with 1 to 5 substituent(s) L, 1,2,3,4-tetrahydro-4-quinolyl which is optionally substituted with 1 to 5 substituent(s) L, dihydrobenzofuranyl which is optionally substituted with 1 to 5 substituent(s) L, pyrrolidinyl which is optionally substituted with 1 to 5 substituent(s) L, piperidinyl which is optionally substituted with 1to 5 substituent(s) L, cyclohexenyl which is optionally substituted with 1 to 5substituent(s) L, or a 7- to 13-membered spiro ring group which is optionally substituted with 1 to 5 substituent(s) L.

[1-9-c] The ring A in Formula (I) is preferably the Partial Structural Formula (A):

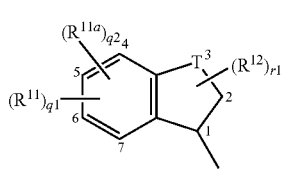

(A)

(where q1 is an integer of 0 to 3; q2 is 0 or 1; r1 is an integer of 0 to 2 (with the proviso that q1+q2+r1 is an integer of 0 to 5;

T is —$CH_2$— or an oxygen atom;

$R^{11}$ and $R^{12}$ are independently a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a —S(O)$_i$R$^a$ (i is an integer of 0 to 2) group, or a —NR$^{b1}$R$^{c1}$ group;

$R^{11a}$ is a group optionally selected from an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclicoxy group which is optionally substituted with 1 to 5 substituent(s) RII, an aralkyloxy group which is optionally substituted with 1 to 5 substituent(s) RII, a heteroarylalkyloxy group which is optionally substituted with 1to 5 substituent(s) RII, and a substituted spiropiperidinylmethyl group), where the definitions of $R^a$, $R^b$, $R^c$, the substituent RI, and the substituent RII are the same as in Formula (I)).

The bonding positions of $R^{11}$, $R^{12}$, and $R^{11a}$ in Formula (A) are any position which can be taken in the ring.

[1-9-c-1] As Formula (A), more preferably, there can be mentioned Formula (A1):

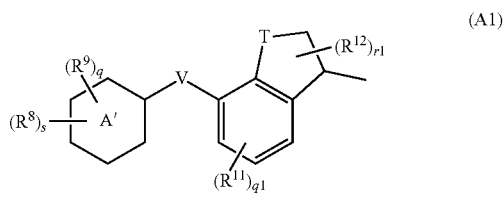

(A1)

(where each definition of q1, r1, T, $R^{11}$, and $R^{12}$ is the same as in Formula (A) (with the proviso that q1+r1 is an integer of 0 to 4);

q is an integer of 0 to 4; s is an integer of 0 to 2 (with the proviso that q+s is an integer of 0 to 5);

the ring A' is an aryl group or a heteroaryl group; V is a bonding hand or an oxygen atom;

$R^8$s are independently a $C_{1-6}$ alkoxy group which is optionally substituted with 1 to 5 substituent(s) RIII, a —CONR$^d$R$^{e1}$ group, an aralkyloxy group, a heterocyclicoxy group (the heterocyclicoxy group is optionally substituted with 1 to 3 $C_{1-6}$ alkyl group(s) or 1 to 3 oxo group(s)), a heterocyclic group (the heterocyclic group is optionally substituted with 1 to 3 $C_{1-6}$ alkyl group(s) or 1 to 3 oxo group(s)), or a heterocyclic carbonyl group (the heterocyclic carbonyl group is optionally substituted with 1 to 3 $C_{1-6}$ alkyl group(s) or 1 to 3 oxo group(s)); the substituent RIII is a group optionally selected from —OH, a $C_{1-6}$ alkoxy group, an aryl group (the aryl group is optionally substituted with 1 to 3 halogen atom(s)), a heterocyclic group (the heterocyclic group is optionally substituted with 1 to 3 $C_{1-6}$ alkyl group or 1 to 3 oxo group), a —S(O)$_i$R$^a$ (i is an integer of 0 to 2) group, a —SO$_2$NR$^d$R$^e$ group, a —CONR$^d$R$^e$ group, and a —NR$^{b1}$R$^{c1}$ group;

$R^9$s are independently a group optionally substituted from a halogen atom, a cyano group, a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s)), a $C_{1-6}$ alkoxy group (the $C_{1-6}$ alkoxy group is optionally substituted with 1 to 5 halogen atom(s)), a $C_{2-6}$ alkenyl group, a $C_{2-7}$ alkanoyl group, a —S(O)$_i$R$^a$ (i is an integer of 0 to 2) group, a —CONR$^d$R$^e$ group, and a —NR$^{b1}$R$^{c1}$ group, where the definitions of $R^a$, $R^d$, $R^e$, $R^{b1}$, $R^{c1}$, and $R^{e1}$ are the same as in Formula (I)).

The bonding positions of $R^{11}$ and $R^{12}$ in Formula (A1) each are any position which can be taken in the ring, and the bonding positions of $R^8$ and $R^9$ are any position which can be taken in the ring A'.

[1-9-c-1-1] As Formula (A) or Formula (A1), specifically, Formula (A1)-1:

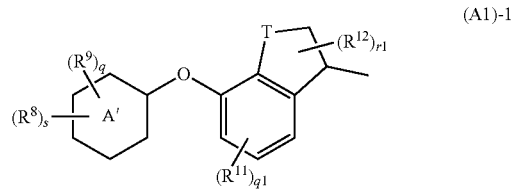

(A1)-1

(where each definition of q1, r1, T, R$^{11}$, and R$^{12}$ is the same as in Formula (A) (with the proviso that q1+r1 is an integer of 0 to 4); and each definition of q, s, the ring A', R$^8$ and R$^9$ is the same as in Formula (A1) (with the proviso that q+s is an integer of 0 to 5)) is mentioned.

[1-9-c-2] As the ring A in the Formula (I) or the Formula (A1), more preferably, the Partial Structural Formula (AA1):

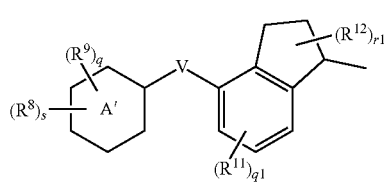

(AA1)

(where each definition of q1, r1, R$^{11}$, and R$^{12}$ is the same as in Formula (A) (with the proviso that q1+r1 is an integer of 0 to 4); and each definition of q, s, the ring A', V, R$^8$ and R$^9$ is the same as in Formula (A1))
is mentioned.

[1-9-c-2-1] As Formula (A1)-1 or Formula (AA1), specifically, Formula (AA1)-1:

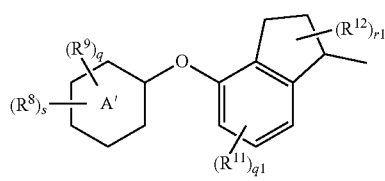

(AA1)-1

(each definition of q1, r1, R$^{11}$, and R$^{12}$ is the same as in Formula (A) (with the proviso that q1+r1 is an integer of 0 to 4); and each definition of q, s, the ring A', R$^8$ and R$^9$ is the same as in Formula (A1))
is mentioned.

[1-9-c-3] As the ring A in the Formula (I) or the Formula (A), more preferably, the Partial Structural Formula (AB):

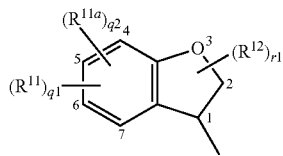

(AB)

(where each definition of q1, q2, r1, R$^{11}$, R$^{12}$, and R$^{11a}$ is the same as in Formula (A))
is mentioned.

[1-9-c-3-1] As Formula (A1) or Formula (AB), further preferably, Formula (AB1):

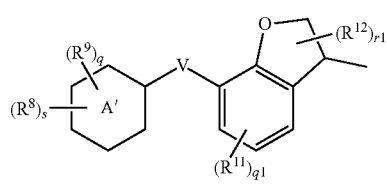

(AB1)

(where each definition of q1, r1, R$^{11}$, and R$^{12}$ is the same as in Formula (A) (with the proviso that q1+r1 is an integer of 0 to 4); and each definition of q, s, the ring A', V, R$^8$ and R$^9$ is the same as in Formula (A1))
is mentioned.

[1-9-c-3-2] As Formula (A), Formula (A1)-1, or Formula (AB1), specifically, Formula (AB1)-1 and Formula (AB1)-2:

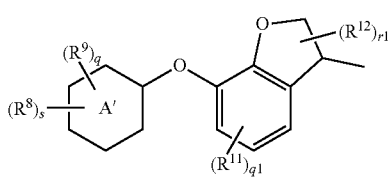

(AB1)-1

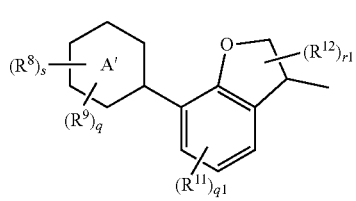

(AB1)-2

(where each definition of q1, r1, R$^{11}$, and R$^{12}$ is the same as in Formula (A) (with the proviso that q1+r1 is an integer of 0 to 4); and each definition of q, s, the ring A', R$^8$ and R$^9$ is the same as in Formula (A1))
are mentioned.

[1-9-c-4] In Formula (A1), Formula (A1)-1, Formula (AA1), Formula (AA1)-1, Formula (AB1), Formula (AB1)-1, or Formula (AB1)-2, more specifically, the ring A' is preferably benzene, naphthalene, pyridine, pyrimidine, thiophene, quinoline, benzimidazole, or dibenzofuran. The ring A' is more preferably benzene, pyridine, pyrimidine, thiophene, or quinoline, further preferably benzene, pyridine, or pyrimidine, the most preferably benzene or pyridine.

[1-9-c-5] In Formula (A1), Formula (A1)-1, Formula (AA1), Formula (AA1)-1, Formula (AB1), Formula (AB1)-1, or Formula (AB1)-2, q is preferably an integer of 0 to 3, more preferably an integer of 0 to 2. s is preferably 0 or 1. More preferably, any one of q and s is 1 or more.

[1-9-c-6] In Formula (A1), Formula (A1)-1, Formula (AA1), Formula (AA1)-1, Formula (AB1), Formula (AB1)-1, or Formula (AB1)-2, R$^8$s are preferably independently a C$_{1-6}$ alkoxy group which is optionally substituted with 1 to 5 substituent(s) RIII$_a$, a —CONR$^d$R$^{e2}$ group, an aralkyloxy group, a non-aromatic heterocyclicoxy group (the heterocyclicoxy group is optionally substituted with 1 to 2 oxo group(s)), or a non-aromatic heterocyclic carbonyl group (the heterocyclic carbonyl group is optionally substituted with 1 to 2 oxo group(s)); and examples of the substituent RIIIa include —OH, a C$_{1-6}$ alkoxy group, a non-aromatic heterocyclicoxy group (the heterocyclicoxy group is optionally substituted with 1 to 3 C$_{1-6}$ alkyl group(s) or 1 to 3 oxo group(s)), a —S(O)$_i$R$^a$ (i is an integer of 0 to 2) group, a —SO$_2$NR$^d$R$^e$ group, a —CONR$^d$R$^e$ group, and a —NR$^{b1}$R$^{c1}$ group; R$^{e2}$ is a C$_{1-6}$ alkyl group (the C$_{1-6}$ alkyl group is optionally substituted with 1 to 5 substituent(s) arbitrarily selected from —OH, C$_{1-6}$ alkoxyl group, non-aromatic heterocyclic group (the heterocyclic group is optionally substituted with 1 to 3 C$_{1-6}$ alkyl group(s) or 1 to 3 oxo group(s)), —S(O)$_i$R$^a$ group(s) (i is an integer of 0 to 2, —SO$_2$NR$^d$R$^e$ group, —CONR$^d$R$^e$ group or —NR$^{b1}$R$^{c1}$).

More preferable examples of $R^8$ include a $C_{1-6}$ alkoxy group (the $C_{1-6}$ alkoxy group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group), —CONR$^{d3}$R$^{e3}$ group (R$^{d3}$ is a hydrogen atom or a $C_{1-4}$ alkyl group, and R$^{ea}$ is a $C_{1-6}$ alkyl group (the $C_{1-6}$ alkyl group is optionally substituted with 1 to 5 substituent(s) arbitrarily selected from —OH, $C_{1-6}$ alkoxyl group, non-aromatic heterocyclic group (the heterocyclic group is optionally substituted with 1 to 2 $C_{1-4}$ alkyl group(s) or 1 to 2 oxo group(s)), and —S(O)$_i$R$^a$ group(s) (i is an integer of 0 to 2))), an aralkyloxy group, a non-aromatic heterocyclicoxy group (the heterocyclicoxy group is optionally substituted with 1 to 2 oxo group(s), and a non-aromatic heterocyclic carbonyl group (the heterocyclic carbonyl group is optionally substituted with 1 to 2 oxo group(s)).

Further preferable examples of $R^8$ include a $C_{1-6}$ alkoxy group which is substituted with 1 to 5 —OH, 1 to 5 methoxy, 1 to 5 ethoxy, 1 to 5 2-oxo-1-pyrrolidinyl, 1to 5 5-oxo-2-pyrrolidinyl, 1 to 5 3-methyoxetane-3-yl or 1 to 5 methylsulfonyl, —CONR$^{d4}$R$^{e4}$ group (R$^{d4}$ is a hydrogen atom or a $C_{1-4}$ alkyl group, and R$^{e4}$ is a $C_{1-6}$ alkyl group (the $C_{1-6}$ alkyl group is substituted with 1 to 5 substituent(s) selected from —OH, methoxy, 2-oxo-1-pyrrolidinyl, 5-oxo-2-pyrrolidinyl, 3-methyloxetan-3-yl or methylsulfonyl)), an aralkyloxy group, (1,1-dioxidetetrahydro-2H-thiopyran-4-yl)oxy, and (pyrrolidine-1-yl)carbonyl. In the $C_{1-6}$ alkoxy group or the $C_{1-6}$ alkyl group as R$^{e4}$, the substitution number of —OH, methoxy, ethoxy, 2-oxo-1-pyrrolidinyl, 5-oxo-2-pyrrolidinyl, 3-methyloxetane-3-yl, or methylsulfonyl is particularly preferably 1to 2.

More specific examples of $R^8$ include 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-ethoxyethoxy, 2-methylsulfonylethoxy, 3-methylsulfonyl-propoxy, 2-(2-oxo-1-pyrrolidinyl)ethoxy, 3-(2-oxo-1-pyrrolidinyl)propoxy, (5-oxo-2-pyrrolidinyl)methoxy, N-(2-hydroxyethyl)carbamoyl, N-(2-methoxyethyl)carbamoyl, N-(2-hydroxyethyl)-N-methylcarbamoyl, N-(2-methoxyethyl)-N-methylcarbamoyl, N-(2-methylsulfonyl-ethyl)carbamoyl, N-(2-methylsulfonyl-ethyl)-N-methylcarbamoyl, benzyloxy, (1,1-dioxytetrahydro-2H-thiopyran-4-yl)oxy, and (pyrrolidine-1-yl)carbonyl.

A $C_{1-6}$ alkoxy group or a heterocyclicoxy group which is substituted with a group of A in Formula (I) in WO 2010/143733 pamphlet, particularly a $C_{1-6}$ alkoxy group substituted with (2) to (8) which is shown in [9] (c) on pages 25 to 26 or a heterocyclicoxy group which is shown in [9] (e), and the corresponding groups shown by Examples can also be referred to as specific examples of $R^8$ of the present specification. The corresponding groups shown by Formulae and Examples in the pamphlets below can also be referred to as specific examples of $R^8$ of the present specification.
WO 2008/001931 pamphlet: a group of R$^1$—X—O— in Formula (I);
WO 2010/123017 pamphlet: a group of R$^7$ in Formula (I);
WO 2010/123016 pamphlet: a group of R$^{10}$ in Formula (I);
WO 2009/054423 pamphlet: groups of A and B in Formula (II);

[1-9-c-7] In Formula (A1), Formula (A1)-1, Formula (AA1), Formula (AA1)-1, Formula (AB1), Formula (AB1)-1, or Formula (AB1)-2, preferable examples of $R^9$ include, independently, a halogen atom, a cyano group, a $C_{1-4}$ alkyl group (the $C_{1-4}$ alkyl group is optionally substituted with 1 to 5 halogen atom(s) or 1 to 5 —OH), a $C_{1-4}$alkoxy group (the $C_{1-4}$ alkoxy group is optionally substituted with 1 to 5 halogen atom(s)), a $C_{2-4}$ alkenyl group, a $C_{2-5}$ alkanoyl group, a —S(O)$_i$R$^a$ (R$^a$ is a $C_{1-4}$ alkyl group) group, a —CONR$^d$R$^e$ group (R$^d$ and R$^e$ are independently a hydrogen atom or a $C_{1-4}$ alkyl group), or a —NR$^{b1}$R$^{c1}$ group (R$^{b1}$ and R$^{c1}$ form together with a nitrogen atom to which they are bonded a 3- to 8-membered cyclic group and in the cyclic group, one or two carbon atom in the ring is optionally substituted with an atom optionally selected from an oxygen atom, a sulfur atom, and a nitrogen atom or with a carbonyl group).

More preferable examples of $R^9$ independently include a halogen atom, a cyano group, a $C_{1-4}$ alkyl group (the $C_{1-4}$ alkyl group is optionally substituted with 1 to 5fluorine atom(s) or 1 to 5 —OH), a $C_{1-4}$ alkoxy group (the $C_{1-4}$ alkoxy group is optionally substituted with 1 to 5 fluorine atom(s)), a $C_{2-4}$ alkenyl group, a $C_{2-5}$ alkanoyl group, a —S(O)$_i$R$^a$ (i is 2 and R$^a$ is a $C_{1-4}$ alkyl group) group, a —CONR$^d$R$^e$ (R$^d$ and R$^e$ are independently a hydrogen atom or a $C_{1-4}$ alkyl group) group, or a —NR$^{b1}$R$^{c1}$ group (R$^{b1}$ and R$^{c1}$ form together with a nitrogen atom to which they are bonded a 3- to 8-membered cyclic group, and in the cyclic group, one or two carbon atom of the ring is optionally substituted with an oxygen atom, a nitrogen atom or a carbonyl group).

More specific examples of $R^9$ include a fluorine atom, a chlorine atom, a bromine atom, cyano, methyl, ethyl, propyl, isopropyl, butyl, isobutyl, sec-butyl, tert-butyl, trifluoromethyl, hydroxymethyl, 2-hydroxyethyl, methoxy, ethoxy, isopropoxy, cyclopropylmethoxy, trifluoromethoxy, trifluoroethoxy, vinyl, acetyl, methylsulfonyl, carbamoyl, methylcarbamoyl, dimethylcarbamoyl, 1-piperidinyl, 4-morpholinyl, and 2-Oxazolidinedione-3-yl.

An amino group, a $C_{1-6}$ alkylthio group, a $C_{1-6}$ alkyl group, a $C_{3-10}$cycloalkyl group and a $C_{1-6}$ alkoxy group which are substituted with a group of A in Formula (I) of WO 2010/143733 pamphlet, particularly a $C_{1-6}$ alkyl group and a halogenated $C_{1-6}$ alkyl group shown on pages 25 to 26, [9] (b), or a $C_{1-6}$ alkoxy group optionally substituted with (1) shown in [9] (c), and the corresponding groups shown by Examples can also be referred to as the specific examples of R$^9$ of the present specification. The corresponding groups shown by Formulae or Examples in pamphlets below can also be referred to as the specific examples of R$^9$ of the present specification.
WO 2008/001931 pamphlet: groups of R$^2$, R$^3$, R$^4$, and R$^5$ in Formula (I)
WO 2010/123017 pamphlet: groups of R$^5$, R$^6$, R$^7$, and e in Formula (I)
WO 2010/123016 pamphlet: groups of R$^8$, R$^9$, R$^{10}$, and R$^Y$ in Formula (I)
WO 2009/054423 pamphlet: groups of R$^3$, R$^4$, A, and B in Formula (II) and Formula (III)

[1-9-c-8] In Formula (A1)-1 or Formula (AA1)-1, preferably, any one of q and s is 1 or more and R$^9$ is a group optionally selected from a halogen atom, a cyano group, a $C_{1-6}$ alkyl group (the $C_{1-6}$ alkyl group is optionally substituted with 1 to 5halogen atom(s), 1 to 5 —OH, or 1 to 5 $C_{1-6}$ alkoxy group(s)), a $C_{1-6}$ alkoxy group (the $C_{1-6}$alkoxy group is optionally substituted with 1 to 5 halogen atom(s)), a $C_{2-6}$ alkenyl group, a $C_{2-7}$ alkanoyl group, a —S(O)$_i$R$^a$ (i is an integer of 0 to 2) group, a —CONR$^d$R$^e$ group, and a —NR$^{b1}$R$^{c1}$ group.

In Formula (A1)-1 or Formula (AA1)-1, more preferably, any one of q and s is 1 or more; R$^8$ is a $C_{1-6}$ alkoxy group (the $C_{1-6}$ alkoxy group is optionally substituted with 1 to 5 —OH, 1 to 5 $C_{1-6}$ alkoxy group(s), or 1 to 5 —S(O)$_i$R$^a$ (i is an integer of 0 to 2) group(s)); and $R^9$ is a group optionally selected from a halogen atom, a cyano group, a $C_{1-6}$ alkyl group (the $C_{1-6}$ alkyl group is optionally substituted with 1 to 5 halogen atom(s) or 1 to 5—OH), a $C_{1-6}$ alkoxy group (the $C_{1-6}$ alkoxy group is optionally substituted with 1 to 5 halogen atom(s)), a —S(O)$_i$R$^a$ (i is an integer of 0 to 2) group, and a —NR$^{b1}$R$^{c1}$ group.

[1-9-c-9] In Formula (A1), Formula (A1)-1, Formula (AA1), Formula (AA1)-1, Formula (AB1), Formula (AB1)-1, or Formula (AB1)-2, when the ring A' is a 6-membered ring and s is 1, the substitution position of $R^8$ is preferably an m-position or a p-position, more preferably a p-position relative to a substitution position in a fused-ring side such as indan-V— and indan-O—.

[1-9-c-10] In Formula (A1)-1 or Formula (AA1)-1, when the ring A' is a 6-membered ring; q is 1; s is 0; and $R^9$ is a $C_{1-6}$ alkyl group or a $C_{1-6}$ alkoxy group, the substitution position of $R^9$ is preferably a p-position relative to a substitution position in a fused-ring side such as indan-O—.

[1-9-c-11] In Formula (A1), Formula (A1)-1, Formula (AA1), Formula (AA1)-1, Formula (AB1), Formula (AB1)-1, or Formula (AB1)-2, as a preferred aspect of the ring A' moiety having $(R^8)_s$ and $(R^9)_q$, there can be mentioned the same group as the group having an aryl group or a heteroaryl group among preferred aspects of L described in Aspect [1-1-d], the preferable aspect of q, s, ring A', $R^8$ and $R^9$ is the same as the preferable aspect of the above-mentioned aspect [1-9-c-4], [1-9-c-5], [1-9-c-6] or [1-9-c-7]. As specific examples of the ring A' moiety having $(R^8)_s$ and $(R^9)_q$, there can be mentioned the same group as the group having a heteroaryl group among specific examples of the "aryl group optionally substituted with 1 to 5 substituent(s) RII" and specific examples of the "heterocyclic group optionally substituted with 1 to 5 substituent(s) RII" which are described Aspect [1]. More specifically, there can be mentioned specific examples the same as those of the group having benzene, naphthalene, pyridine, pyrimidine, thiophene, quinoline, benzimidazole, or dibenzofuran.

The groups of A in Formula (I) of WO 2010/143733 pamphlet or the groups of Q in Formula (V) of WO 2007/033002 pamphlet, particularly, among the corresponding groups shown by Examples of each pamphlet, the groups having a cyclic group can be mentioned as the specific examples of the ring A' moiety having $(R^8)_s$ and $(R^9)_q$ of the present specification. The corresponding groups shown by Formulae or Examples of the pamphlets below can also be referred to as the specific examples of the ring A' moiety having $(R^8)_s$ and $(R^9)_q$ of the present specification.

WO 2008/001931 pamphlet: a phenyl group having $R^1$—X—O—, $R^2$, $R^3$, $R^4$, and $R^5$ in Formula (I)

WO 2010/123017 pamphlet: a 6-membered ring group having $R^5$, $R^6$, and $R^7$ in Formula (I)

WO 2010/123016 pamphlet: a 6-membered ring group having $R^8$, $R^9$, and $R^{16}$ in Formula (I)

WO 2009/054423 pamphlet: a group of Formula (II) and a group of Formula (III)

Namely, 4-(3-methylsulfonyl-propoxy)-2,6-dimethylphenyl, 4-((1,1-dioxidetetrahydro-2H-thiopyran-4-yl)oxy)-2,6-dimethylphenyl, 2-(4-morpholino)-4,6-dimethylpyrimidin-5-yl, 2-ethyl-6,7-difluoro-1H-benzimidazole-1-yl, 2-ethoxy-6,7-difluoro-1H-benzimidazole-1-yl, and the like are mentioned.

[1-9-c-12] In Formula (A), Formula (A1), Formula (A1)-1, Formula (AA1), Formula (AA1)-1, Formula (AB), Formula (AB1), Formula (AB1)-1, or Formula (AB1)-2, preferable examples of $R^{11}$ and $R^{12}$ include, independently, a halogen atom, a $C_{1-4}$ alkyl group which is optionally substituted with 1 to 5 halogen atom(s), and a $C_{1-4}$ alkoxy group which is optionally substituted with 1 to 5 halogen atom(s). More specific examples of $R^{12}$ include a fluorine atom, a chlorine atom, a bromine atom, methyl, ethyl, propyl, isopropyl, butyl, isobutyl, sec-butyl, tert-butyl, cyclopropyl, difluoromethyl, trifluoromethyl, methoxy, and trifluoromethoxy.

The groups of $R^3$ in Formula (II) of WO 2010/143733 pamphlet, the groups of $R^6$ in Formula (II) or the groups of $R^7$ in Formula (III) in WO 2009/157418 pamphlet, or the groups of Q and $R^4$ in Formula (V) of WO 2007/033002 pamphlet, particularly, among the corresponding groups shown by Examples of each pamphlet, groups other than the cyclic groups can also be mentioned as the specific examples of $R^{11}$ of the present specification.

[1-9-c-13] In Formula (A) or Formula (AB), preferable examples of $R^{11a}$ include a group optionally selected from an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIM, a non-aromatic heterocyclic alkyl group which is optionally substituted with 1 to 5 substituent(s) RIIa, an aryloxy group which is optionally substituted with 1 to 5 substituent(s) RIIa, a heteroaryloxy group which is optionally substituted with 1 to 5 substituent(s) RIIa, a non-aromatic heterocyclicoxy group which is optionally substituted with 1 to 5 substituent(s) RIM, an aralkyloxy group which is optionally substituted with 1 to 5 substituent(s) RIM, and a substituted spiropiperidinylmethyl group (the definition of the above substituent RIIa is the same as the definition described in Aspect [1-1-d]). The number of substitutions by the substituent RIIa is preferably 1 to 3.

More specifically, examples of $R^{11a}$ include groups exemplified specifically above as the "aryl group which is optionally substituted with 1 to 5 substituent(s) RII", the "heterocyclic group which is optionally substituted with 1 to 5 substituent(s) RII", the "aralkyl group which is optionally substituted with 1 to 5 substituent(s) RII", the "heteroarylalkyl group which is optionally substituted with 1 to 5 substituent(s) RII", the "non-aromatic heterocyclic alkyl group which is optionally substituted with 1 to 5 substituent(s) RII", the "aryloxy group which is optionally substituted with 1 to 5 substituent(s) RII", the "heteroaryloxy group which is optionally substituted with 1 to 5 substituent(s) RII", the "non-aromatic heterocyclicoxy group which is optionally substituted with 1 to 5 substituent(s) RII", the "aralkyloxy group which is optionally substituted with 1 to 5 substituent(s) RII", the "heteroarylalkyloxy group which is optionally substituted with 1 to 5 substituent(s) RII", the "substituted spiropiperidinylmethyl group", and the like.

The groups of A in Formula (II) of WO 2010/143733 pamphlet or the groups of Q in Formula (V) of WO 2007/033002 pamphlet, particularly, among the corresponding groups shown by Examples of each pamphlet, the groups having a cyclic group can also be mentioned as the specific examples of $R^{11a}$ of the present specification.

[1-9-c-14] In Formula (A), Formula (A1), Formula (A1)-1, Formula (AA1), Formula (AA1)-1, Formula (AB), Formula (AB1), Formula (AB1)-1, or Formula (AB1)-2, q1 is preferably 0 or 1, more preferably 0.

[1-9-c-15] In Formula (A), Formula (A1), Formula (A1)-1, Formula (AA1), Formula (AA1)-1, Formula (AB), Formula (AB1), Formula (AB1)-1, or Formula (AB1)-2, r1 is preferably 0 or 1, more preferably 0.

[1-9-c-16] By appropriately combining preferable aspects or preferable specific examples of Aspects [1-9-c-1] to [1-9-c-15], preferable aspects or preferable specific examples of the Partial Structural Formula of Formula (A), Formula (A1), Formula (A1)-1, Formula (AA1), Formula (AA1)-1, Formula (AB), Formula (AB1), Formula (AB1)-1, or Formula (AB1)-2 can be optionally formed.

A dihydrobenzofuran group having A and $R^3$ in Formula (II) of WO 2010/143733 pamphlet, an indan group having Q and $R^4$ in Formula (V) in WO 2007/033002 pamphlet, or a dihydrobenzofuran group having $R^6$ and an indan group having $R^7$ in Formula (II) of WO 2009/157418 pamphlet, particularly, the corresponding groups shown by Examples of each pamphlet can also be mentioned as the specific examples of the ring A of the present specification.

Namely, 4-methyl-2,3-dihydro-1H-inden-1-yl, 6-fluoro-4-trifluoromethyl-2,3-dihydro-1H-inden-1-yl, 4-trifluoromethoxy-2,3-dihydro-1H-inden-1-yl, 7-trifluoromethoxy-2,3-dihydro-1-benzofuran-3-yl, 7-(4-(3-methylsulfonylpropoxy)-2,6-dimethylphenyl)-2,3-dihydro-1-benzofuran-3-yl, 7-(4-((1,1-dioxidetetrahydro-2H-thiopyran-4-yl)oxy)-2,6-dimethylphenyl)-2,3-dihydro-1-benzofuran-3-yl, 7-(2-(4-morpholino)-4,6-dimethylpyrimidin-5-yl)-2,3-dihydro-1-benzofuran-3-yl, 7-(2-ethyl-6,7-difluoro-1H-benzimidazol-1-yl)-2,3-dihydro-1-benzofuran-3-yl, 7-(2-ethoxy-6,7-difluoro-1H-benzimidazol-1-yl)-2,3-dihydro-1-benzofuran-3-yl, and the like are mentioned.

[1-9-d] The ring A in Formula (I) is preferably the Partial Structural Formula (A)-III:

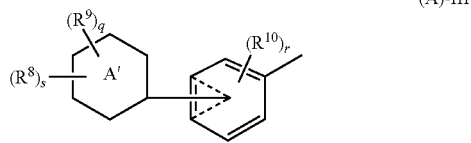

(where the definitions of q, s, the ring A', V, $R^8$, and $R^9$ are the same as in Formula (A1) described in Aspect [1-9-c-1]; r is an integer of 0 to 4; $R^{10}$s are independently a halogen atom, a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s)), or a $C_{1-6}$ alkoxy group (the $C_{1-6}$ alkoxy group is optionally substituted with 1 to 5 halogen atom(s)); and the broken line indicates a bonding position of the ring A'-V-). The bonding position of $R^{10}$ in Formula (A)-III is any position which can be taken in the benzene ring and the bonding positions of $R^8$ and $R^9$ are any position which can be taken in the ring A'. Formula (A)-III is concretely Formula (A)-III-1 or Formula (A)-III-2:

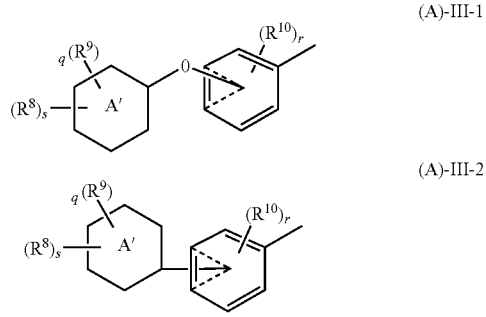

(where the definition of q, s, ring A', $R^8$ and $R^9$ is the same of the definition in Formula (A1) described in the above-mentioned aspect [1-9-c-1]; the definition of r, $R^{10}$ and broken line is the same of the definition in Formula (A)-III described in the above-mentioned aspect [1-9-d]).

[1-9-d-1] More preferable example of Formula (A)-III or Formula (A)-III-1 includes Formula (A1)-III-1:

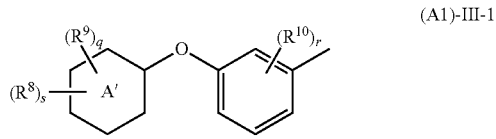

(where the definition of q, s, ring A', $R^8$ and $R^9$ is the same of the definition in Formula (A1) described in the above-mentioned aspect [1-9-c-1]; the definition of r and $R^{10}$ is the same of the definition in Formula (A)-III described in the above-mentioned aspect [1-9-d]).

[1-9-d-2] In Formula (A)-III, Formula (A)-III-1, Formula (A)-III-2 or Formula (A1)-III, more specifically, it is preferable that ring A' is benzene, pyridine, pyrimidine, thiophene or benzimidazole. More preferably, ring A' is benzene, pyridine or pyrimidine, and further preferably benzene or pyridine, and it is particularly preferable that ring A' is benzene.

[1-9-d-3] In Formula (A)-III, Formula (A)-III-1, Formula (A)-III-2 or Formula (A1)-III, more specifically, s is 0 or 1, and when s is 1 and the ring A' is a 6-membered ring, the substitution position of $R^8$ is preferably a p-position. q is more preferably an integer of 0 to 2, and further preferably 1 or 2.

[1-9-d-4] In Formula (A)-III, Formula (A)-III-1, Formula (A)-III-2 or Formula (A1)-III more specifically, r is preferably 0 or 1.

[1-9-d-5] In Formula (A)-III or Formula (A)-III-2, more preferably, Formula (A1)-III-2:

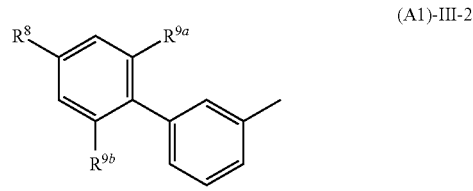

(where the definition of $R^8$ is the same as in Formula (A1) described in Aspect [1-9-c-1], and $R^{9a}$ and $R^{9b}$ independently are a hydrogen atom or mean the same as $R^9$ in Formula (A1)), is mentioned.

[1-9-d-6] In Formula (A)-III, Formula (A)-III-1, Formula (A)-III-2, Formula (A1)-III-1 or Formula (A1)-III-2, more preferably, $R^8$ is a $C_{1-6}$ alkoxy group substituted with 1 to 5 substituent(s) of —OH, methoxy, ethoxy, methylsulfonyl, sulfamoyl, methylsulfamoyl, dimethylsulfamoyl, carbamoyl, methylcarbamoyl, dimethylcarbamoyl, —NH$_2$, acetylamino, methylsulfonylamino, 2-oxo-1-pyrrolidinyl, 5-oxo-2-pyrrolidinyl, or 3-methyloxetane-3-yl, or —CONR$^{d4}$R$^{e4}$ (R$^{d4}$ is hydrogen atom or $C_{1-4}$ alkyl group, R$^{e4}$ is $C_{1-6}$ alkyl group (the $C_{1-6}$ alkyl group is substituted with 1 to 5 substituent(s) of —OH, methoxy, ethoxy, methylsulfonyl, sulfamoyl, methylsulfamoyl, dimethylsulfamoyl, carbamoyl, methylcarbamoyl, dimethylcarbamoyl, —NH$_2$, acetylamino, methylsulfonylamino, 2-oxo-1-pyrrolidinyl, 5-oxo-2-pyrrolidinyl, or 3-methyloxetane-3-yl)), an aralkyloxy group, (1,1-dioxidetetrahydro-2H-thiopyran-4-yl-oxy, or (pyrrolidin-1-yl)carbonyl. In the $C_{1-6}$ alkoxy group or $C_{1-6}$ alkyl group as R$^{e4}$, the substitution number of —OH, ethoxy, methylsulfonyl, sulfamoyl, methylsulfamoyl, dimethylsulfamoyl, carbamoyl, methylcarbamoyl, dimethylcarbamoyl, —NH₂, acetylamino, methylsulfonylamino, 2-oxo-1-pyrrolidinyl, or 3-methyloxetane-3-yl is preferably 1 to 2.

More specifically, $R^8$ is 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-aminoethoxy, 3-aminopropoxy, 2-(2-oxo-1-pyrrolidinyl)ethoxy, 3-(2-oxo-1-pyrrolidinyl)propoxy, (5-oxo-2-pyrrolidinyl)methoxy, 2-ethoxyethoxy, 2-methylsulfonylethoxy, 3-methylsulfonyl-propoxy, (1,1-dioxidetetrahydro-2H-thiopyran-4-yl)oxy, (4-hydroxy-1,1-dioxidetetrahydro-2H-thiopyran-4-yl)methoxy, (3-methyloxetane-3-yl)methoxy, 2-acetylamino-ethoxy, 2-acetylamino-ethoxy, 3-acetylamino-propoxy, 2-methylsulfonylamino-ethoxy, 3-methylsulfonylamino-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, 3-dimethylsulfamoyl-propoxy, N-(2-hydroxyethyl)carbamoyl, N-(2-methoxyethyl)carbamoyl, N-(2-hydroxyethyl)-N-methylcarbamoyl, N-(2-methoxyethyl)-N-methylcarbamoyl, N-(2-methylsulfonyl-ethyl)carbamoyl, N-(2-methylsulfonyl-ethyl)-N-methylcarbamoyl, benzyloxy, (pyrrolidine-1-yl)carbonyl and the like.

[1-9-d-7] In Formula (A)-III, Formula (A)-III-1, Formula (A)-III-2, Formula (A1)-III-1 or Formula (A1)-III-2, $R^9$, $R^{9a}$, $R^{9b}$, and $R^{10}$ are preferably independently a halogen atom, a $C_{1-4}$ alkyl group which is optionally substituted with 1 to 5 halogen atom(s), or a $C_{1-4}$ alkoxy group which is optionally substituted with 1 to 5 halogen atom(s). More specifically, $R^9$, $R^{9a}$, $R^{9b}$, and $R^{10}$ are a fluorine atom, a chlorine atom, a bromine atom, methyl, ethyl, propyl, isopropyl, butyl, isobutyl, sec-butyl, tert-butyl, trifluoromethyl, methoxy, ethoxy, trifluoromethoxy, trifluoroethoxy, or the like. More preferably, $R^9$, $R^{9a}$, and $R^{9b}$ are a fluorine atom, methyl, or methoxy, and more preferably, $R^{10}$ is methyl.

[1-9-d-8] As a preferable aspect of the ring A' moiety having $(R^8)_s$ and $(R^9)_q$ in Formula (A)-III, Formula (A)-III-1, Formula (A)-III-2 or Formula (A1)-III-1, among preferable aspects of L described in Aspect [1-1-d], the same group as that having an aryl group or a heteroaryl group is mentioned. As a specific example of the ring A' moiety having $(R^8)_s$ and $(R^9)_q$, among specific examples of the "aryl group which is optionally substituted with 1 to 5 substituent(s) RII" or specific examples of the "heterocyclic group which is optionally substituted with 1 to 5 substituent(s) RII" which are described in Aspect [1], the same group as that having a heteroaryl group is mentioned. More specifically, the same group as that having benzene, naphthalene, pyridine, pyrimidine, thiophene, quinoline, or dibenzofuran is mentioned. As a specific example of the benzene ring moiety having $R^8$, $R^{9a}$, and $R^{9b}$ in Formula (A1)-III-2, among specific examples of the "aryl group which is optionally substituted with 1 to 5 substituent(s) RII"described in Aspect [1], the same group as the benzene ring group having a substituent corresponding to 2-position, 4-position, or 6-position is mentioned.

[1-9-d-9] As the ring A in Formula (I), Formula (A)-III or Formula (A)-III-2, preferably, Formula (A2)-III-2:

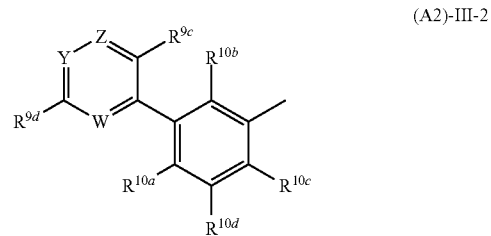

(A2)-III-2

(where W, Y, and Z are =CH— or a nitrogen atom (with the proviso that 0 or 1 of W, Y, and Z is nitrogen atom and when $R^{9c}$ is a fluorine atom, Z is =CH—);
$R^{9c}$ is a hydrogen atom, a fluorine atom, a chlorine atom, a trifluoromethyl group, or a $C_{1-6}$ alkoxy group; $R^{9d}$ is a hydrogen atom, a fluorine atom, a chlorine atom, —OH, a $C_{1-4}$alkyl group, a $C_{1-3}$ alkoxy group, or a $C_{1-2}$ alkylthio group;
$R^{10a}$ is a $C_{1-10}$ alkyl group (the $C_{1-10}$ alkyl group is optionally substituted with 1 to 4 halogen atom(s), 1 to 4 —OH, or 1 to 4 $C_{1-4}$ alkoxy group(s) (the $C_{1-4}$ alkoxy group is optionally substituted with 1 to 4 halogen atom(s), 1 to 4 —OH, or 1 to 4 $C_{1-2}$ alkoxy group(s))), a $C_{2-10}$ alkenyl group (the $C_{2-10}$ alkenyl group is optionally substituted with 1 to 4 halogen atom(s), 1 to 4 —OH, or 1 to 4 $C_{1-4}$ alkoxy group(s) (the $C_{1-4}$ alkoxy group is optionally substituted with 1 to 4 halogen atom(s), 1 to 4 —OH, or 1 to 4 $C_{1-2}$ alkoxy group(s))), a $C_{1-10}$ alkoxy group (the $C_{1-10}$ alkoxy group is optionally substituted with 1 to 4 halogen atom(s), 1 to 4 —OH, or 1 to 4 $C_{1-2}$ alkoxy group(s)), or a $C_{2-10}$ alkenyloxy group (the $C_{2-10}$ alkenyloxy group is optionally substituted with 1 to 4 halogen atom(s), 1 to 4 —OH, or 1 to 4 $C_{1-2}$ alkoxy group);
$R^{10b}$, $R^{10c}$, and $R^{10d}$ are independently a hydrogen atom, a fluorine atom, a chlorine atom, a $C_{1-4}$ alkyl group, or a $C_{1-4}$ alkoxy group)
is mentioned.

In Formula (A2)-III-2, as $R^{10a}$, preferably Formula ($R^{10a'}$):

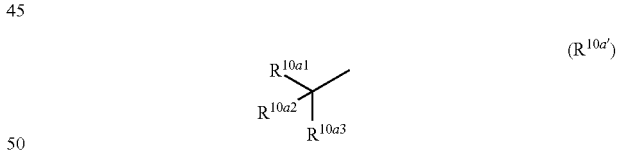

($R^{10a'}$)

(where $R^{10a1}$, $R^{10a2}$, and $R^{10a3}$ are independently a hydrogen atom, a fluorine atom, or a $C_{1-4}$ alkyl group; at least two of $R^{10a1}$, $R^{10a2}$ and $R^{10a3}$ are a group other than a hydrogen atom and $R^{10a1}$, $R^{10a2}$, and $R^{10a3}$ form optionally together with a carbon atom to which they are bonded a 3- to 8-membered cyclic group)
is mentioned. It is preferred that all of $R^{10a1}$, $R^{10a2}$, and $R^{10a3}$ be a methyl group or form a cyclopropyl group.

In Formula (A2)-III-2, W, Y, and Z are preferably =CH—; $R^{9c}$ is preferably a fluorine atom or a butoxy group; $R^{9d}$ is preferably a methoxy group; $R^{10b}$, $R^{10c}$, and $R^{10d}$ are preferably a hydrogen atom.

As Formula (A2)-III-2, specifically, 6-(1,1-dimethylethyl)-2'-fluoro-5'-methoxy-1,1'-biphenyl-3-yl, 2'-butoxy-6-(1,1-dimethylethyl)-5'-methoxy-1,1'-biphenyl-3-yl, and the like are mentioned.

[1-9-d-10] As the ring A in Formula (I), Formula (A)-III or Formula (A)-III-2, preferably, Formula (A3)-III-2:

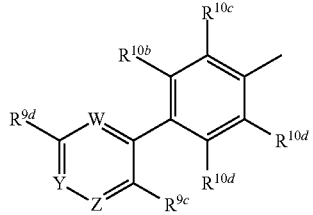

(A3)-III-2

(where the definitions of W, Y, Z, $R^{9c}$, $R^{9d}$, $R^{10a}$, $R^{10b}$, $R^{10c}$ and $R^{10d}$ are the same as in Formula (A2)-III-2 described in Aspect [1-9-d-9]) is mentioned.

In Formula (A3)-III-2, the alkyl chain or the alkenyl chain of $R^{10a}$ is a linear, branched, or cyclic chain and includes a linear or branched chain group substituted with a cyclic group or a cyclic group substituted with a linear or branched chain group. When $R^{10a}$ is a $C_{1-10}$ alkyl group, specifically, Formula ($R^{10a'}$) described in Aspect [1-9-d-9] or the like is mentioned. As $R^{10a}$, more specifically, 1,1-dimethylethyl(tert-butyl), 2,2-dimethylcyclopentyl, 5,5-dimethylcyclopent-1-enyl, 2,2-dimethyl-1-hydroxypropyl, 2,2-dimethyl-1-methoxypropyl, and the like are mentioned. The group of A in Formula I of WO 2009/048527 pamphlet, the group of A in Formula I and Formula III of WO 2009/111056 pamphlet, and the group of A in Formula I'A of WO 2010/045258 pamphlet, particularly the corresponding groups shown by Examples are mentioned as the specific examples of $R^{10a}$ of the present specification.

In Formula (A3)-III-2, W and Z are preferably =CH—; $R^{9c}$ is preferably a fluorine atom; $R^{9d}$ is preferably a methoxy group; $R^{10b}$ and $R^{10d}$ are preferably a hydrogen atom; and $R^{10c}$ is preferably a hydrogen atom or a fluorine atom.

As Formula (A3)-III-2, specifically, 2-(1,1-dimethylethyl)-2'-fluoro-5'-methoxy-1,1'-biphenyl-4-yl, 2-(2,2-dimethylcyclopentyl)-2'-fluoro-5'-methoxy-1,1'-biphenyl-4-yl, 2-(2,2-dimethyl-1-methoxypropyl)-2'-fluoro-5'-methoxy-1,1'-biphenyl-4-yl, and the like are mentioned.

[1-9-e] As the ring A in Formula (I), preferably, Partial Structural Formula (A)-IV:

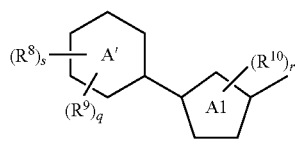

(A)-IV (where the definitions of q, s, the ring A', $R^8$, and $R^9$ are the same as in Formula (A1) described in Aspect [1-9-c-1]; the definitions of r and $R^{10}$ are the same as in Formula (A)-III described in Aspect [1-9-d]; and the ring A1 is a 5-membered heterocyclic group) is mentioned. The bonding position of $R^{10}$ in Formula (A)-IV is any position which can be taken in the ring A1 and the bonding positions of $R^8$ and $R^9$ are any position which can be taken in the ring A'.

[1-9-e-1] In Formula (A)-IV, the ring A1 is a 5-membered non-aromatic heterocyclic group or a 5-membered heteroaryl group and specifically, the ring A1 is preferably pyrrolidine, furan, thiophene, imidazole, oxazole, thiazole, pyrazole, isoxazole, 1,2,3-triazole, or 1,2,4-oxadiazole. The ring A1 is more preferably pyrrolidine, furan, thiophene, oxazole, or thiazole, further preferably pyrrolidine, thiophene, or thiazole.

[1-9-e-2] The ring A in Formula (I) or Formula (A)-IV is preferably Partial Structural Formula (A1)-IV:

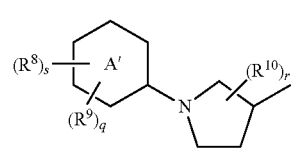

(A1)-IV (where the definitions of q, s, the ring A', $R^8$, and $R^9$ are the same as in Formula (A1) described in Aspect [1-9-c-1]; and the definitions of r and $R^{10}$ are the same as in Formula (A)-III described in Aspect [1-9-d]). The bonding position of $R^{10}$ in Formula (A1)-IV is any position which can be taken in the pyrrolidine ring and the bonding positions of $R^8$ and $R^9$ are any position which can be taken in the ring A'.

[1-9-e-3] As the ring A in Formula (I) or Formula (A)-IV, preferably Partial Structural Formula (A2)-IV:

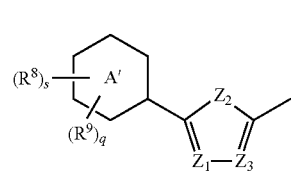

(A2)-IV (where the definitions of q, s, the ring A', $R^8$, and $R^9$ are the same as in Formula (A1) described in Aspect [1-9-c-1]; $Z_1$ is —$CR^{10e}$— or a nitrogen atom; $Z_2$ is a sulfur atom or an oxygen atom; $Z_3$ is —$CR^{10f}$— or a nitrogen atom; and $R^{10e}$ and $R^{10f}$ are independently a hydrogen atom, a $C_{1-6}$ alkyl group, or a methoxy group (with the proviso that at least one of $Z_1$ and $Z_3$ is —$CR^{10e}$— or —$CR^{10f}$—) is mentioned. The bonding positions of $R^8$ and $R^9$ in Formula (A2)-IV is any position which can be taken in the ring A'. Here, in Formula (A2)-IV, as the ring A', in addition to the above description, a substituted spiropiperidinylmethyl group may also be mentioned.

As Formula (A2)-IV, specifically, Formula (A4)-IV described in Aspect [1-9-e-8]below or Formula (A5)-IV described in Aspect [1-9-e-9] below is mentioned.

The groups corresponding to Formula (A2)-IV of the present specification in WO 2005/086661 pamphlet, WO 2005/051890 pamphlet, WO 2004/022551 pamphlet, and WO 2004/011446 pamphlet (for example, a 5-membered ring group as an example for W in [0195], page 25 of WO 2005/086661 pamphlet, or the like), particularly the corresponding groups shown by Examples are also mentioned as specific examples of Formula (A2)-IV of the present specification.

[1-9-e-4] In Formula (A)-IV, Formula (A1)-IV, or Formula (A2)-IV, more specifically, the ring A' is preferably benzene, pyridine, or pyrimidine, more preferably benzene or pyrimidine, and further preferably benzene.

[1-9-e-5] In Formula (A)-IV, Formula (A1)-IV, or Formula (A2)-IV, more specifically, s is preferably 0 or 1 and when s is 1 and the ring A' is a 6-membered ring, the substitution position of $R^8$ is preferably a p-position. q is more preferably an integer of 0 to 2, and further preferably 1 or 2. Particularly preferably, s is 0 or 1 and q is 2.

[1-9-e-6] In Formula (A)-IV or Formula (A1)-IV, more specifically, r is preferably 0.

[1-9-e-7] In Formula (A)-IV or Formula (A1)-IV, more preferably, Formula (A3)-IV:

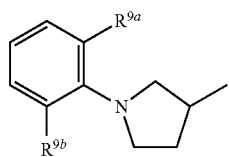

(A3)-IV (where $R^{9a}$ and $R^{9b}$ independently are a hydrogen atom or mean the same as $R^9$ in Formula (A)-IV) is mentioned.

[1-9-e-8] The ring A in Formula (I) and Formula (A)-IV or Formula (A2)-IV are preferably Partial Structural Formula (A4)-IV:

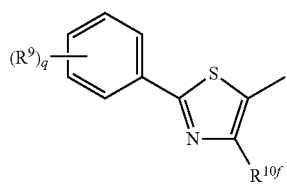

(A4)-IV (where the definitions of q and $R^9$ are the same as in Formula (A1) described in Aspect [1-9-c-1]; and the definition of $R^{10f}$ is the same as in Formula (A2)-IV described in Aspect [1-9-e-3]).

In Formula (A4)-IV, $R^9$ is preferably a group optionally selected from a halogen atom, a cyano group, a $C_{1-6}$ alkyl group (the $C_{1-6}$ alkyl group is optionally substituted with 1 to 5 halogen atom(s)), and a $C_{1-6}$ alkoxy group (the $C_{1-6}$ alkoxy group is optionally substituted with 1 to 5 halogen atom(s)). q is preferably an integer of 0 to 2. $R^{10f}$ is preferably a hydrogen atom or a $C_{1-6}$ alkyl group, more preferably a hydrogen atom or a methyl group.

As Formula (A4)-IV, specifically, 4-methyl-2-(4-trifluoromethylphenyl)thiazole-5-yl, 4-methyl-2-(4-butoxy-3-chlorophenyl)thiazole-5-yl, and the like are mentioned. The groups of a formula the same as Formula (A4)-IV of the present specification in WO 2008/030520 pamphlet, namely, the corresponding groups among groups of Formula VIIC on page 8, particularly the corresponding groups shown by Examples are also mentioned as specific examples of Formula (A4)-IV of the present specification.

[1-9-e-9] The ring A in Formula (I) and Formula (A)-IV or Formula (A2)-IV is preferably Partial Structural Formula (A5)-IV:

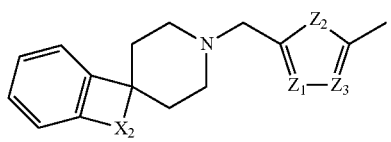

(A5)-IV (where the definitions of $Z_1$, $Z_2$, and $Z_3$ are the same as in Formula (A2)-IV described in Aspect [1-9-e-3] (with the proviso that $R^{10e}$ and $R^{10f}$ are independently a hydrogen atom, a methyl group, or a methoxy group); $X_2$ is —$CH_2CH_2$—, —CH=CH—, or —N($Rz_1$)$CH_2$—; and $Rz_1$ is a hydrogen atom or a $C_{1-3}$ alkyl group).

In Formula (A5)-IV, preferably, $Z_1$ is —$CR^{10e}$—; $R^{10e}$ is a hydrogen atom or a methyl group; $Z_2$ is a sulfur atom; $Z_3$ is —$CR^{10f}$—; and $R^{10f}$ is a hydrogen atom. $X_2$ is —CH=CH— or —N($Rz_1$)$CH_2$— and $Rz_1$ is a methyl group.

As Formula (A5)-IV, specifically, 5-(spiro[inden-1,4'-piperidin]-1'-ylmethyl)-2-thienyl, 4-methyl-5-(spiro[inden-1,4'-piperidin]-1'-ylmethyl)-2-thienyl, 5-(1-methylspiro[indoline-3,4'-piperidin]-1'-ylmethyl)-2-thienyl, and the like are mentioned. In WO 2011/066183 pamphlet, the groups of a formula the same as Formula (A5)-IV of the present specification, particularly the corresponding groups shown by Examples are also mentioned as specific examples of Formula (A5)-IV of the present specification.

[1-9-e-10] In Formula (A)-IV, Formula (A1)-IV, or Formula (A2)-IV, more preferably, $R^8$ is $C_{1-6}$ alcoxyl group (the $C_{1-6}$ alcoxyl group substituted with 1 to 5 substituent(s) of —OH, methoxy, ethoxy, methylsulfonyl, sulfamoyl, methylsulfamoyl, dimethylsulfamoyl, carbamoyl, methylcarbamoyl, dimethylcarbamoyl, —$NH_2$, acetylamino, methylsulfonylamino, 2-oxo-1-pyrrolidinyl, 5-oxo-2-pyrrolidinyl, or 3-methyloxetane-3-yl), —$CONR^{d4}R^{e4}$ ($R^{d4}$ is hydrogen atom or $C_{1-4}$ alkyl group, $R^{e4}$ is $C_{1-6}$ alkyl group (the $C_{1-6}$ alkyl group is substituted with 1 to 5 substituent(s) of —OH, methoxy, ethoxy, methylsulfonyl, sulfamoyl, methylsulfamoyl, dimethylsulfamoyl, carbamoyl, methylcarbamoyl, dimethylcarbamoyl, —$NH_2$, acetylamino, methylsulfonylamino, 2-oxo-1-pyrrolidinyl, 5-oxo-2-pyrrolidinyl, or 3-methyloxetane-3-yl)), (1,1-dioxidetetrahydro-2H-thiopyran-4-yl-oxy, or (pyrrolidin-1-yl)carbonyl. The substitution number of —OH, ethoxy, methylsulfonyl, sulfamoyl, methylsulfamoyl, dimethylsulfamoyl, carbamoyl, methylcarbamoyl, dimethylcarbamoyl, —$NH_2$, acetylamino, methylsulfonylamino, 2-oxo-1-pyrrolidinyl, 5-oxo-2-pyrrolidinyl, or 3-methyloxetane-3-yl is preferably 1 to 2.

More specifically, $R^8$ is 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-aminoethoxy, 3-aminopropoxy, 2-(2-oxo-1-pyrrolidinyl)ethoxy, 3-(2-oxo-1-pyrrolidinyl)propoxy, (5-oxo-2-pyrrolidinyl) methoxy, 2-ethoxyethoxy, 2-methylsulfonylethoxy, 3-methylsulfonyl-propoxy, (1,1-dioxidetetrahydro-2H-thiopyran-4-yl)oxy, (4-hydroxy-1,1-dioxidetetrahydro-2H-thiopyran-4-yl)methoxy, (3-methyloxetane-3-yl)methoxy, 2-acetylamino-ethoxy, 2-acetylamino-ethoxy, 3-acetylamino-propoxy, 2-methylsulfonylamino-ethoxy, 3-methylsulfonylamino-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, and 3-dimethylsulfamoyl-propoxy, N-(2-hydroxyethyl)carbamoyl, N-(2-methoxyethyl)carbamoyl, N-(2-hydroxyethyl)-N-methylcarbamoyl, N-(2-methoxyethyl)-N-methylcarbamoyl, N-(2-methylsulfonyl-ethyl)carbamoyl, N-(2-methylsulfonyl-ethyl)-N-methylcarbamoyl, (pyrrolidine-1-yl)carbonyl.

[1-9-e-11] In Formula (A)-IV, Formula (A1)-IV, Formula (A2)-IV, Formula (A3)-IV, or Formula (A4)-IV, it is preferable that $R^9$, $R^{9a}$, $R^{9b}$ and $R^{10}$ are independently a halogen atom, a cyano group, a $C_{1-4}$ alkyl group (the $C_{1-4}$ alkyl group is optionally substituted with 1 to 5 halogen atom(s) or —OH), a $C_{1-4}$ alkoxy group which is optionally substituted with 1 to 5 halogen atom(s), a $C_{2-4}$ alkenyl group, a $C_{2-5}$ alkanoyl group, —S(O)$_i$R$^a$ (i is 2, and R$^a$ is a $C_{1-4}$ alkyl group), —CONR$^d$R$^e$ group (R$^d$ and R$^e$ are independently a hydrogen atom or a $C_{1-4}$ alkyl group), or —NR$^{b1}$R$^{c1}$ group (R$^{b1}$ and R$^{c1}$ form a 3- to 8-membered cyclic group together with the nitrogen atom to which R$^{b1}$ and R$^{c1}$ are bonded, and one or two carbon atom(s) in the cyclic group is(are) optionally substituted with an oxygen atom, and a sulfur atom or with a carbonyl group.

More specifical examples include a fluorine atom, a chlorine atom, a bromine atom, cyano, methyl, ethyl, propyl, isopropyl, butyl, isobutyl, sec-butyl, tert-butyl, trifluoromethyl, hydroxymethyl, 2-hydroxyethyl, methoxy, ethoxy, trifluoromethoxy, trifluoroethoxy, vinyl, acetyl, methylsulfonyl, carbamoyl, methylcarbamoyl, dimethylcarbamoyl, 1-piperidinyl, 4-morpholinyl, 2-oxooxazolidin-3-yl, and the like. More preferably, that R$^9$, R$^{9a}$ and R$^{9b}$ are a fluorine atom methyl or methoxy, and R$^{10}$ is methyl.

[1-9-e-12] As a preferable aspect of the ring A' moiety having (R$^8$)$_s$ and (R$^9$)$_q$ in Formula (A)-IV, Formula (A1)-IV, or Formula (A2)-IV, among preferable aspects of L described in Aspect [1-1-d], the same group as that having an aryl group or a heteroaryl group is mentioned. As a specific example for the ring A' moiety having (R$^8$)$_s$ and (R$^9$)$_q$, among specific examples of the "aryl group which is optionally substituted with 1 to 5 substituent(s) RII" or specific examples of the "heterocyclic group which is optionally substituted with 1 to 5 substituent(s) RII", which are described in Aspect [1], the same group as that having a heteroaryl group is mentioned. More specifically, the same group as that having benzene, naphthalene, pyridine, pyrimidine, thiophene, quinoline, or dibenzofuran is mentioned. As a specific example of the benzene ring moiety having R$^{9a}$ and R$^{9b}$ in Formula (A3)-IV, among specific examples of the "aryl group which is optionally substituted with 1 to 5 substituent(s) RII" described in Aspect [1], the same group as the benzene ring group having a substituent corresponding to a 2-position or a 6-position, is mentioned.

[1-9-f] The ring A in Formula (I) is preferably Partial Structural Formula (A)-V:

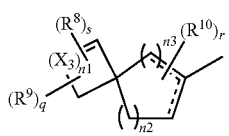

(A)-V (where the definitions of q, s, R$^8$, and R$^9$ are the same as in Formula (A1) described in Aspect [1-9-c-1]; the definitions of r and R$^{10}$ are the same as in Formula (A)-III described in Aspect [1-9-d]; n1 is an integer of 0 to 4; n2 is an integer of 1 to 4, n3 is an integer of 0 to 2 (with the proviso that n2+n3 is an integer of 2 to 4); X$_3$s are independently —CR$_{V1}$R$_{V2}$— or —NR$_{V3}$—; R$_{V1}$, R$_{V2}$, and R$_{V3}$ are independently a hydrogen atom, R$^8$, or R$^9$; and the broken line in the ring is a single bond or a double bond). The bonding positions of R$^8$, R$^9$, and R$^{10}$ in Formula (A)-V is any position which can be taken in the ring. Here, in Formula (A)-V, R$^9$ and R$^{10}$ may also be an —OH group or an oxo group in addition to the above description, and R$^8$ may also be, in addition to the above description, —NHR$_{V4}$ (R$_{V4}$ is a $C_{1-6}$ alkyl group (the $C_{1-6}$ alkyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group) or a $C_{2-7}$ alkanoyl group (the $C_{2-7}$ alkanoyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2oxo group(s)), and a —S(O)$_i$R$^a$ (i is an integer of 0 to 2) group), and the spiro ring is optionally substituted with 1 to 5 group(s) of these substituents which are the same as or different from each other.

[1-9-f-1] Formula (A)-V is more preferably Formula (A1)-V:

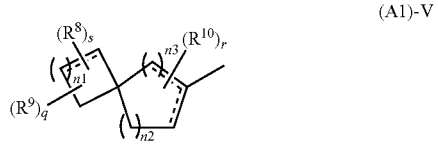

(A1)-V (where the definitions of q and s are the same as in Formula (A1) described in Aspect [1-9-c-1]; the definition of r is the same as in Formula (A)-III described in Aspect [1-9-d]; and the definitions of R$^8$, R$^9$, R$^{10}$, n1, n2, n3, and the broken line are the same as in Formula (A)-V). Here, in Formula (A1)-V, the spiro ring is optionally substituted with 1 to 5 groups of the substituents R$^8$, R$^9$, and R$^{10}$ which are the same as or different from each other.

[1-9-f-2] Formula (A)-V or Formula (A1)-V is more preferably Formula (A2)-V:

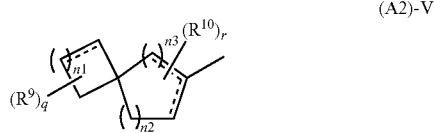

(A2)-V (where the definition of q is the same as in Formula (A1) described in Aspect [1-9-c-1]; the definition of r is the same as in Formula (A)-III described in Aspect [1-9-d]; and the definitions of R$^9$, R$^{10}$, n1, n2, n3, and the broken line are the same as in Formula (A)-V). Here, in Formula (A2)-V, the spiro ring is optionally substituted with 1 to 5 groups of the substituents R$^9$ and R$^{10}$ which are the same as or different from each other.

[1-9-f-3] In Formula (A)-V, Formula (A1)-V, or Formula (A2)-V, it is preferred that n1 be an integer of 0 to 4, n2 be an integer of 1 to 3, and n3 be 1 or 2. More preferably, n1 is 2 or 3, n2 is 1 or 2, and n3 is 1.

[1-9-f-4] In Formula (A)-V, Formula (A1)-V, or Formula (A2)-V, it is preferred that q be an integer of 0 to 2 and r be an integer of 0 to 2. More preferably, q and r are 0.

[1-9-f-5] In Formula (A)-V or Formula (A1)-V, s is preferably 0 or 1, and more preferably 0.

[1-9-f-6] As Formula (A2)-V, further preferably, Formula (A3)-V:

(A3)-V (where n1, n2, and the broken line mean the same as in Formula (A)-V) is mentioned. In Formula (A3)-V, it is particularly preferred that n1 be 2 or 3 and n2 be 1 or 2.

As Formula (A)-V, Formula (A1)-V, Formula (A2)-V, or Formula (A3)-V, specifically, spiro[4,5]dec-6-ene-7-yl, spiro[5,5]undec-2-yl, spiro[5,5]undec-1-ene-2-yl, spiro[5,5]undec-2-ene-2-yl, and the like are mentioned.

The groups of a formula the same as Formula (A2)-V or Formula (A3)-V of the present specification in WO 2009/054479 pamphlet, namely, the groups as the spiro ring AB in an item 2 in 4 to 5 pages, particularly the corresponding groups shown by Examples are also mentioned as specific examples of Formula (A)-V, Formula (A1)-V, Formula (A2)-V, or Formula (A3)-V of the present specification.

[1-9-f-7] In Formula (A)-V, Formula (A1)-V, or Formula (A2)-V, $R^9$ and $R^{10}$ are preferably independently a halogen atom, a $C_{1-4}$ alkyl group which is optionally substituted with 1 to 5 halogen atom(s), a $C_{1-4}$ alkoxy group which is optionally substituted with 1 to 5 halogen atom(s), an —OH group, or an oxo group. More specifically, $R^9$ and $R^{10}$ are a fluorine atom, a chlorine atom, a bromine atom, methyl, ethyl, propyl, isopropyl, butyl, isobutyl, sec-butyl, tert-butyl, trifluoromethyl, methoxy, ethoxy, trifluoromethoxy, trifluoroethoxy, —OH, and the like. More preferably, $R^9$ is a fluorine atom, methyl, methoxy, or —OH, and $R^{10}$ is methyl or —OH.

As the group substituted with $R^9$ or $R^{10}$ in Formula (A)-V, Formula (A1)-V, or Formula (A2)-V, in the formula as Formula [Ia] in WO 2009/054479 pamphlet, the corresponding groups as a spiro ring AB substituted with a substituent (an —OH group, a $C_{1-6}$ alkyl group, a $C_{1-6}$ alkoxy group, or an oxo group), particularly the corresponding groups shown by Examples are also mentioned as specific examples of Formula (A)-V, Formula (A1)-V, or Formula (A2)-V of the present specification.

[1-9-f-8] In Formula (A)-V, Formula (A1)-V, or Formula (A2)-V, $R^8$s are preferably independently a $C_{1-6}$ alkoxy group (the $C_{1-6}$ alkoxy group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group), —CONR$^{d3}$R$^{e3}$ (R$^{d3}$ is hydrogen atom or $C_{1-4}$ alkyl group, R$^{e3}$ is $C_{1-6}$ alkyl group (the $C_{1-6}$ alkyl group is optionally substituted with 1 to 5 group(s) optionally selected from —OH, a $C_{1-6}$ alkoxyl group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2)), an aralkyloxy group, a non-aromatic heterocyclic oxy group (the heterocyclic oxy group is optionally substituted with 1 to 2 oxo group(s)), a non-aromatic heterocyclic carbonyl group (the heterocyclic carbonyl group is optionally substituted with 1 to 2 oxo group(s)) or —NHR$_{V4}$ (R$_{V4}$ is a $C_{1-6}$ alkyl group (the $C_{1-6}$ alkyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group or 1 to 2 oxo group(s)), and a —S(O)$_i$R$^a$ (i is an integer of 0 to 2) group) or a $C_{2-7}$ alkanoyl group (the $C_{2-7}$ alkanoyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group)). More specifically, $R^8$ is a $C_{1-6}$ alkoxy group which is substituted with 1 to 2 —OH, 1 to 2 methoxy, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl, —CONR$^{d4}$R$^{e4}$ (R$^{d4}$ is hydrogen atom or $C_{1-4}$ alkyl group, R$^{e4}$ is $C_{1-6}$ alkyl group (the $C_{1-6}$ alkyl group is substituted with 1 to 5 —OH, 1 to 5 methoxy, 1 to 5 ethoxy, 1 to 5 2-oxo-1-pyrrolidinyl, 1 to 5 5-oxo-2-pyrrolidinyl, 1 to 5 3-methyloxetane-3-yl or 1 to 5 methylsulfonyl)), an aralkyloxy group, (1,1-dioxidetetrahydro-2H-thiopyran-4-yl)oxy, (pyrrolidine-1-yl)carbonyl, or NHR$_{V4}$ (R$_{V4}$ is a $C_{1-6}$ alkyl group (the $C_{1-6}$ alkyl group is optionally substituted with 1 to 2-OH, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl) or a $C_{2-7}$ alkanoyl group (the $C_{2-7}$ alkanoyl group is optionally substituted with 1 to 2 —OH, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl)).

[1-9-f-9] The ring A in Formula (I) is preferably Partial Structural Formula (AA)-V:

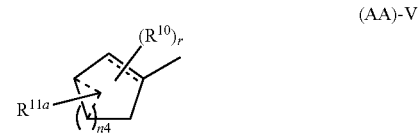

(AA)-V (where the definition of $R^{11a}$ is the same as the definition in Formula (A) described in Aspect [1-9-c]; the definition of r is the same as the definition in Formula (A)-III described in Aspect [1-9-d]; the definition of $R^{10}$ is the same as the definition in Formula (A)-V described in Aspect [1-9-f]; n4 is an integer of 1 to 3, a broken line is a single bond or a double bond, or the bonding position of $R^{11a}$).

[1-9-f-10] The ring A in Formula (I) or Formula (AA)-V is preferably Formula (AA1)-V:

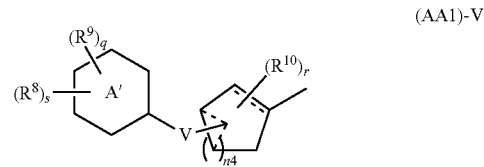

(AA1)-V (where the definition of q, s, ring A', V, $R^8$ and $R^9$ is the same as the definition in Formula (A1) described in Aspect [1-9-c-1]; the definition of r is the same as the definition in Formula (A)-III described in Aspect [1-9-d]; the definition of $R^{10}$ is the same as the definition in Formula (A)-V described in Aspect [1-9-f]; the definition of n4 and a broken line is the same as the definition in Formula (AA)-V).

[1-9-f-11] The Formula (AA1)-V is more preferably Formula (AA1)-V-1:

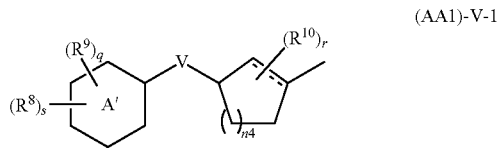

(AA1)-V-1

(where the definition of q, s, ring A', V, $R^8$ and $R^9$ is the same as the definition in Formula (A1) described in Aspect [1-9-c-1]; the definition of r is the same as the definition in Formula (A)-III described in Aspect [1-9-d]; the definition of $R^{10}$ and a broken line is the same as the definition in Formula (A)-V described in Aspect [1-9-f]; the definition of n4 is the same as the definition in Formula (AA)-V).

[1-9-f-12] In Formula (AA)-V, Formula (AA1)-V, or Formula (AA1)-V-1, n4 is preferably 1 or 2, and more preferably 2.

[1-9-f-13] In Formula (AA)-V, Formula (AA1)-V, or Formula (AA1)-V-1, r is preferably an integer of 0 to 2. In Formula (AA1)-V, or Formula (AA1)-V-1, q is preferably an integer of 0 to 3, and more preferably an integer of 0 to 2, s is preferably 0 or 1. It is more preferable that either q or s is an integer of 1 or more.

[1-9-f-14] In Formula (AA)-V, the preferable aspect of $R^{11a}$ is the same as the preferable aspect described in Aspect [1-9-c-13].

In Formula (AA1)-V, or Formula (AA1)-V-1, the preferable aspect of ring A', $R^8$ and $R^9$ is the same as the preferable aspect described in Aspect [1-9-c-4], [1-9-c-6], or [1-9-c-7]. In addition, the preferable aspect of the ring A' moiety having $(R^8)_s$ and $(R^9)_q$ is the same as the preferable aspect described in [1-9-c-11].

In Formula (AA)-V, Formula (AA1)-V, or Formula (AA1)-V-1, the preferable aspect of $R^{10}$ is the same as the preferable aspect described in Aspect [1-9-f-7]

[1-9-g] The ring A in Formula (I) is preferably Partial Structural Formula (A)-VI:

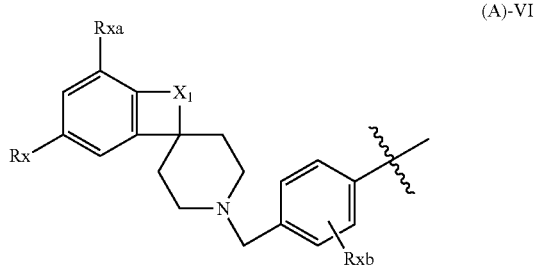

(where the definitions of Rx, Rxa, and $X_1$ are the same as Formula (SP) described as the "substituted spiropiperidinyl group" in Aspect [1]; and Rxb is a group selected from a hydrogen atom, a fluorine atom, a chlorine atom, $C_{1-3}$ alkyl, trifluoromethyl, and methoxy).

[1-9-g-1] In Formula (A)-VI, preferably, at least one of Rx and Rxa is a hydrogen atom. More preferably, Rxa is a hydrogen atom and Rx is a group selected from a hydrogen atom, a fluorine atom, methyl, trifluoromethyl, and methoxy, or Rxa is a hydrogen atom or a chlorine atom and Rx is a hydrogen atom, or both of Rx and Rxa are a hydrogen atom.

In Formula (A)-VI, Rxb is preferably a group selected from a hydrogen atom, methyl, trifluoromethyl, and methoxy, and more preferably a hydrogen atom.

In Formula (A)-VI, $X_1$ is preferably —CH(Ry)CH$_2$—, —C(Ry)=CH—, or —N(Rz)CH$_2$, and more preferably —C(Ry)=CH— or —N(Rz)CH$_2$.

In Formula (A)-VI, Ry is preferably a hydrogen atom or methyl, and more preferably a hydrogen atom.

In Formula (A)-VI, Rz is preferably a hydrogen atom or $C_{1-3}$ alkyl, more preferably methyl.

Specifically, in Aspect [1-9-g], Partial Structural Formula (SP)-CH$_2$—:

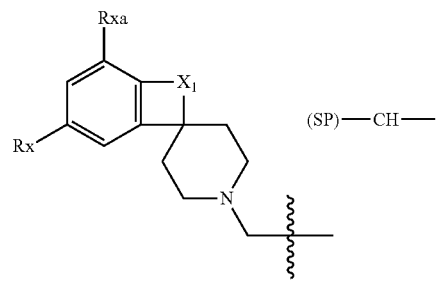

in Formula (A)-VI, is a group selected from spiro[indan-1,4'-piperidin]-1'-ylmethyl, (1'H-spiro[inden-1,4'-piperidin]-1'-yl)methyl, 1,2-dihydro-1'H-spiro[indol-3,4'-piperidin]-1'-ylmethyl, (1-methyl-1,2-dihydro-1'H-spiro[indol-3,4'-piperidin]-1'-yl)methyl, {1-(1-methylethyl)-1,2-dihydro-1'H-spiro[indol-3,4'-piperidin]-1'-yl}methyl, (1-phenyl-1,2-dihydro-1'H-spiro[-3,4'-piperidine]-1'-yl)methyl, (2,3-dihydro-1'H-spiro[inden-1,4'-piperidin]-1'-ylmethyl, (7-chloro-1-methyl-1,2-dihydro-1'H-spiro[indol-3,4'-piperidin]-1'-yl)methyl, (5-fluoro-1-methyl-1,2-dihydro-1'H-spiro[indol-3,4'-piperidin]-1'-yl)methyl, (5-methoxy-1-methyl-1,2-dihydro-1'H-spiro[indol-3,4'-piperidin]-1'-yl)methyl, (1,5-dimethyl-1,2-dihydro-1'H-spiro[indol-3,4'-piperidin]-1'-yl)methyl, [1-methyl-5-(trifluoromethyl)-1,2-dihydro-1'H-spiro[indol-3,4'-]-1'-yl]methyl, and (3-oxo-2,3-dihydro-1'H-spiro[indene-1,4'-piperidine]-1'-yl)methyl.

[1-9-g-2] The ring A in Formula (I) is preferably Partial Structural Formula (AA)-VI:

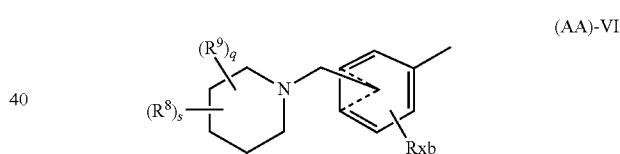

(where the definition of q, s, $R^8$ and $R^9$ is the same as the definition in Formula (A1) described in Aspect [1-9-c-1]; the definition of Rxb is the same as the definition in Formula (A)-VI described in Aspect [1-9-g]; a broken line is the bonding position of piperidinylmethyl group).

In Formula (AA)-VI, the preferable aspect of q, s, $R^8$ and $R^9$ is the same as the preferable aspect described in Aspect [1-9-c-5], [1-9-c-6], or [1-9-c-7].

[1-9-h] The ring A in Formula (I) is preferably Partial Structural Formula (A)-VII:

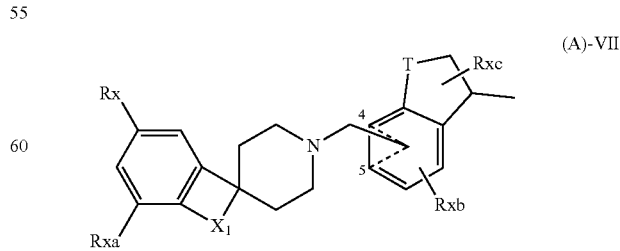

(where the definition of T is the same as in Formula (A) described in Aspect [1-9-c]; the definitions of Rx, Rxa, and $X_1$ are the same as in Formula (SP) described as the "substituted spiropiperidinyl group" in Aspect [1]; the definition of Rxb is the same as in Formula (A)-VI described in Aspect [1-9-g]; Rxc is a group selected from a hydrogen atom, a fluorine atom, a chlorine atom, a $C_{1-3}$ alkyl, trifluoromethyl, and methoxy; and the broken line and the numbers "4" and "5" indicate the bonding positions of the substituted spiropiperidinylmethyl group).

[1-9-h-1] The ring A in Formula (I) is preferably Partial Structural Formula (AA)-VII:

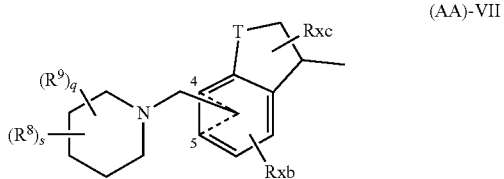

(AA)-VII (where the definition of T is the same as the definition in Formula (A) described in Aspect [1-9-c]; the definition of q, s, $R^8$ and $R^9$ is the same as the definition in Formula (A1) described in Aspect [1-9-c-1]; the definition of Rxb is the same as the definition in Formula (A)-VI described in Aspect [1-9-g]; the definition of Rxc is the same as the definition in Formula (A)-VII described in Aspect [1-9-h]; a broken line is the bonding position of piperidinylmethyl group).

In Formula (AA)-VII, the preferable aspect of q, s, $R^8$ and $R^9$ is the same as the preferable aspect described in Aspect [1-9-c-5], [1-9-c-6], or [1-9-c-7].

[1-9-i] As the ring A in Formula (I), preferably, phthalazinyl which is optionally substituted with 1 to 5 substituent(s) L is mentioned.

Specific examples of phthalazinyl which is optionally substituted with 1 to 5 substituent(s) L include 4-chloro-1-phthalazinyl, 4-trifluoromethyl-1-phthalazinyl, 4-cyano-1-phthalazinyl, and 4-cyclopropylmethoxy-1-phthalazinyl.

The groups of G in Formula (I) in WO 2010/091176 pamphlet, particularly the corresponding groups shown by Examples are mentioned as specific examples of the ring A of the present specification.

[1-9-j] As the ring A in Formula (I), preferably, Partial Structural Formula (A)-VIII:

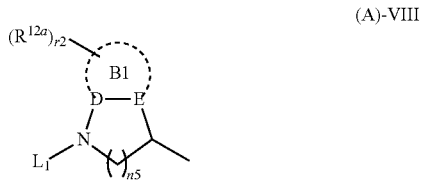

(A)-VIII (where r2 is an integer of 0 to 4; n5 is 1 or 2;
D is —CO—C $R^{12b}R^{12c}$— or —$(CR^{12b}R^{12c})_m$ (m is 1 or 2)-;
E is —$CR^{12d}R^{12e}$—;
$L_1$ is a group optionally selected from a $C_{1-10}$ alkyl group (the $C_{1-10}$ alkyl group is optionally substituted with 1 to 5 halogen atom(s)), an aryl group (the aryl group is optionally substituted with 1 to 5 halogen atom(s), 1 to 5 $C_{1-6}$ alkyl group(s), or 1 to 5 halogenated $C_{1-6}$ alkyl group(s)), a heterocyclic group (the heterocyclic group is optionally substituted with 1 to 5 halogen atom(s), 1 to 5 $C_{1-6}$ alkyl group(s), or 1 to 5 halogenated $C_{1-6}$ alkyl group(s)), an aralkyl group (the aralkyl group is optionally substituted with 1 to 5 halogen atom(s), 1 to 5 $C_{1-6}$ alkyl group(s), or 1 to 5 halogenated $C_{1-6}$ alkyl group(s)), a heteroarylalkyl group (the heteroarylalkyl group is optionally substituted with 1 to 5 halogen atom(s), 1 to 5 $C_{1-6}$ alkyl group(s), or 1 to 5 halogenated $C_{1-6}$ alkyl group(s)), a $C_{2-7}$ alkanoyl group, and a —$S(O)_iR^a$ (i is an integer of 0 to 2), and the definition of $R^a$ is the same as in Formula (I)) group);
$R^{12a}$s are independently a halogen atom, a $C_{1-6}$ alkyl group (the $C_{1-6}$ alkyl group is optionally substituted with 1 to 5 halogen atom(s)), or a $C_{1-6}$ alkoxy group (the $C_{1-6}$ alkoxy group is optionally substituted with 1 to 5 halogen atom(s)));
$R^{12b}$, $R^{12c}$, $R^{12d}$, and $R^{12e}$ are independently a hydrogen atom, a halogen atom, or a $C_{1-6}$ alkyl group (the $C_{1-6}$ alkyl group is optionally substituted with 1 to 5 halogen atom(s)), where $R^{12c}$ and $R^{12e}$ form optionally together with a carbon atom to which they are bonded a 5- to 6-membered aryl group or heteroaryl group (ring B 1) is mentioned.

In Formula (A)-VIII, $L_1$ is preferably a group optionally selected from a $C_{1-4}$ alkyl group (the $C_{1-4}$ alkyl group is optionally substituted with 1 to 5 halogen atom(s)), a heteroaryl group (the heteroaryl group is optionally substituted with 1 to 5 halogen atom(s), 1 to 5 $C_{1-4}$ alkyl group(s), or 1 to 5 halogenated $C_{1-4}$ alkyl group(s)), and a —$S(O)_iR^a$ (i is an integer of 0 to 2 and the definition of $R^a$ is the same as in Formula (I) group).

Specific examples of Formula (A)-VIII include 1,2,3,4-tetrahydro-1-oxo-2-(2,2,2-trifluoroethyl)-4-isoquinolyl, 2-cyclopropylmethyl-1,2,3,4-tetrahydro-1-oxo-4-isoquinolyl, 1,2,3,4-tetrahydro-2-(2-methylpropyl)-1-oxo-4-isoquinolyl, 1-(5-fluoro-2-pyridinyl)-3-piperidinyl, 1-(5-trifluoromethyl-2-pyridinyl)-3-piperidinyl, 1,2,3,4-tetrahydro-1-methylsulfonyl-4-quinolyl, 8-fluoro-1,2,3,4-tetrahydro-1-methylsulfonyl-4-quinolyl, 1,2,3,4-tetrahydro-1-(2,2,2-trifluoroethyl)-4-quinolyl, and 8-fluoro-1,2,3,4-tetrahydro-1-(2,2,2-trifluoroethyl)-4-quinolyl.

The cyclic groups containing D and E in Formula (I) or the like in WO 2010/085525 pamphlet, particularly the corresponding groups shown by Examples are also mentioned as specific examples for the ring A and Formula (A)-V of the present specification.

[1-9-k] As the ring A in Formula (I), preferably, a 2-phenylamino-2-oxoacetyl group optionally substituted with 1 to 5 substituent(s) L is mentioned, more preferably, Partial Structural Formula (A)-IX:

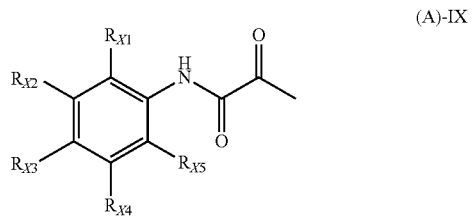

(A)-IX (where $R_{X3}$ is a group optionally selected from a hydrogen atom, a halogen atom, a $C_{1-8}$ alkyl group (the $C_{1-8}$ alkyl group is optionally substituted with 1 to 5 halogen atom(s)), a trifluoromethoxy group, a phenyl group, and a —$COOR^f$ group;
$R_{X1}$ and $R_{X5}$ are independently a group optionally selected from a hydrogen atom, a halogen atom, a $C_{1-6}$ alkyl group (the $C_{1-6}$ alkyl group is optionally substituted with 1 to 5 halogen atom(s)), a phenyl group, and a —$COOR^f$ group;

$R_{X2}$ and $R_{X4}$ are independently a group optionally selected from a hydrogen atom, a halogen atom, a $C_{1-6}$ alkyl group (the $C_{1-6}$ alkyl group is optionally substituted with 1 to 5 halogen atom(s)), and a —COOR$^f$ group; and R$^f$ is a hydrogen atom or a $C_{1-6}$ alkyl group) is mentioned.

In Formula (A)-IX, $R_{X3}$ is preferably a hydrogen atom, a halogen atom, a $C_{1-6}$ alkyl group, a trifluoromethyl group, a methoxycarbonyl group, or a phenyl group. $R_{X1}$ and $R_{X5}$ are preferably independently a hydrogen atom, a halogen atom, a methyl group, a trifluoromethyl group, a methoxycarbonyl group, or a phenyl group. $R_{X2}$ and $R_{X4}$ are preferably independently a hydrogen atom, a halogen atom, or a trifluoromethyl group.

Specific examples of Formula (A)-IX include 2-((2-bromo-4-isopropylphenyl)amino)-2-oxoacetyl, 2-((4-isopropyl-2-(trifluoromethyl)phenyl)amino)-2-oxoacetyl, 2-((2,4-bis(trifluoromethyl)phenyl)amino)-2-oxoacetyl, and 2-((4-bromo-3-chlorophenyl)amino)-2-oxoacetyl.

The groups of a formula the same as Formula (A)-IX of the present specification in Formula (I) in WO 2009/039943 pamphlet, particularly the corresponding groups shown by Examples are also mentioned as specific examples for the ring A and the ring of Formula (A)-IX of the present specification.

[1-9-l] An aspect in which each spiropiperidine ring (SP) of the preferred Aspects [1-9-e-9], [1-9-g], and [1-9-h] of the ring A in Formula (I) is replaced by the above spiropiperidine ring (SP') is also a preferred aspect.

Accordingly, it can be understood that in addition to the preferred Aspects [1-9-e-9], [1-9-g], and [1-9-h] of the ring A in Formula (I) of the present invention, Aspects [1-9-e-9a], [1-9-ga], and [1-9-ha] below can be anew mentioned.

[1-9-e-9a] The ring A in Formula (I) is preferably Partial Structural Formula (A5)-IVa:

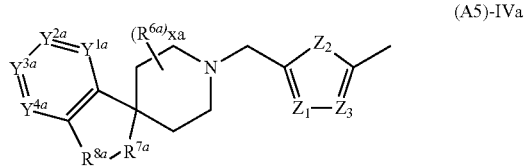

(where the definitions of $Z_1$, $Z_2$, and $Z_3$ are the same as in Formula (A2)-IV described in Aspect [1-9-e-3], and the definitions of R$^{6a}$, R$^{7a}$, R$^{8a}$, xa, and Y$^{1a}$ to Y$^{4a}$ are the same as in Formula (SP')).

In Formula (A5)-IVa, preferably, $Z_1$ is —CR$^{10e}$—, R$^{10e}$ is a hydrogen atom or a methyl group, $Z_2$ is a sulfur atom, $Z_3$ is —CR$^{10f}$—, and R$^{10f}$ is a hydrogen atom. $X_2$ is —CH=CH— or —N(R$_{Z1}$)CH$_2$— and R$_{Z1}$ is a methyl group.

Specific examples of Formula (A5)-IVa include 5-(spiro[isobenzofuran-1(3H),4'-piperidine]-1'-ylmethyl)-2-thienyl, 5-(spiro[benzofuran-3(2H),4'-piperidine]-1'-ylmethyl)-2-thienyl, 5-(spiro[6-azaisobenzofuran-1(3H),4'-piperidine]-1'-ylmethyl)-2-thienyl, 5-(3-oxospiro[4-azaisobenzofuran-1(3H),4'-piperidine]-1'-ylmethyl)-2-thienyl, 5-(3-oxospiro[6-azaisobenzofuran-1(3H),4'-piperidine]-1'-ylmethyl)-2-thienyl, 5-(spiro[5-fluoroisobenzofuran-1(3H),4'-piperidine]-1'-ylmethyl)-2-thienyl, 5-(spiro[6-fluoroisobenzofuran-1(3H),4'-piperidine]-1'-ylmethyl)-2-thienyl, 5-(spiro[5-fluoro-6-azaisobenzofuran-1(3H),4'-piperidinepiperidin]-1'-ylmethyl)-2-thien yl, 5-(spiro[6-fluoro-5-azaisobenzofuran-1(3H),4'-piperidin]-1'-ylmethyl)-2-thienyl, and 5-(7-fluoro-1H-spiro[fluoro[3,4-c]pyridin-3,4'-piperidin]-1'-ylmethyl)-2-thienyl.

[1-9-ga] The ring A in Formula (I) is preferably Formula (A)-VIa:

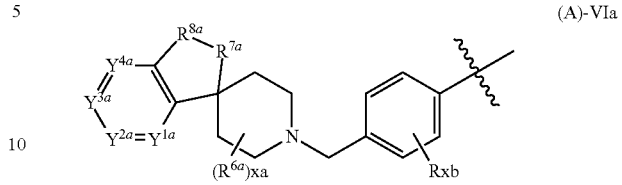

(where R$_{Xb}$ is a group selected from a hydrogen atom, a fluorine atom, a chlorine atom, $C_{1-3}$ alkyl, trifluoromethyl, and methoxy, and more preferably a hydrogen atom; and the definitions of R$^{6a}$, R$^{7a}$, R$^{8a}$, xa, and Y$^{1a}$ to Y$^{4a}$ are the same as in Formula (SP')).

Specific examples thereof include Partial Structural Formula (SP')-CH$_2$—:

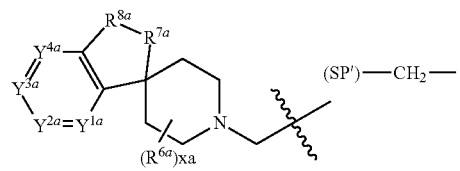

in Formula (A)-VIa which is (spiro[isobenzofuran-1(3H),4'-piperidin]-1-yl)methyl, (spiro[benzofuran-3(2H),4'-piperidin]-1-yl)methyl, (3-oxospiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, (spiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, or (7-fluoro-1H-spiro[fluoro[3,4-c]pyridin-3,4'-piperidin]-1-yl)methyl.

[1-9-ha] The ring A in Formula (I) is preferably Partial Structural Formula (A)-VIIa:

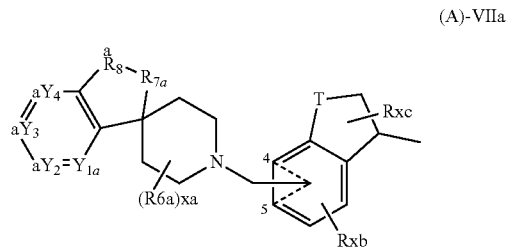

(where the definition of T is the same as in Formula (A) described in Aspect [1-9-c]; the descriptions of R$^{6a}$, R$^{7a}$, R$^{8a}$, xa, and Y$^{1a}$ to Y$^{4a}$ correspond to the definitions of R$^6$, R$^7$, R$^8$, x, and Y$^1$ to Y$^4$ respectively in Formula [II] in WO 2002/088989 pamphlet; R$_{xb}$ is a group selected from a hydrogen atom, a fluorine atom, a chlorine atom, $C_{1-3}$ alkyl, trifluoromethyl, and methoxy, and preferably a hydrogen atom; R$_{Xc}$ is a group selected from a hydrogen atom, a fluorine atom, a chlorine atom, $C_{1-3}$ alkyl, trifluoromethyl, and methoxy, and preferably a hydrogen atom;

and the broken line and the numbers "4" and "5" indicate the bonding position of a substituted spiropiperidinylmethyl group).

Specific examples thereof include Partial Structural Formula (SP')-CH$_2$—:

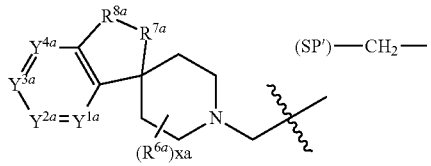

in Formula (A)-VIIa which is (spiro[isobenzofuran-1(3H),4'-piperidin]-1-yl)methyl, (spiro[benzofuran-3(2H),4'-piperidin]-1-yl)methyl, (3-oxospiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, (spiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, or (7-fluoro-1H-spiro[fluoro[3,4-c]pyridin-3,4'-piperidin]-1-yl)methyl.

[1-10] In the linker moiety containing X which is bonded to the ring A and the ring B the benzene ring in Formula (I), preferably, k is 0 and $R^3$ and $R^4$ are a hydrogen atom. More preferably, $R^7$ is a hydrogen atom.

Preferred specific examples of the linker moiety containing X which is bonded to the ring A and the ring B and the benzene ring include Formula (c1) to Formula (c4):

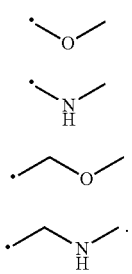

[1-10-a] When the ring A is a monocycle or a spiro ring, namely, when the ring A is a phenyl group, a monocyclic heterocyclic group, a cycroalkyl group, a cycroalkenyl group, or a spirocyclic group, specifically, when the ring A is Formula (A)-III, Formula (A)-III-1, Formula (A)-III-2, Formula (A1)-III-1, Formula (A1)-III-2, formula (A2)-III-2 or Formula (A3)-III-2, which are described in Aspects [1-9-d] to [1-9-d-10]; Formula (A)-IV, Formula (A1)-IV, Formula (A2)-IV, Formula (A3)-IV, Formula (A4)-IV, or Formula (A5)-IV which are described in Aspects [1-9-e] to [1-9-e-9]; Formula (A)-V, Formula (A1)-V, Formula (A2)-V, Formula (A3)-V, Formula (AA)-V, Formula (AA1)-V or Formula (AA1)-V-1 which are described in Aspects [1-9-f] to [1-9-f-11]; or Formula (A)-VI or Formula (AA)-VI which is described in Aspect [1-9-g] to [1-9-g-2], or Formula (A5)-IVa or Formula (A)-VIa which is described in Aspect [1-9-e-9a] or [1-9-ga], the linker moiety is more preferably Formula (c3) or Formula (c4), and further preferably Formula (c3).

[1-10-b] When the ring A is a fused-ring, namely, when the ring A is a fused-ring aryl group, a partly hydrogenated fused-ring aryl group, a fused-ring heteroaryl group, a partly hydrogenated fused-ring heteroaryl group, or a fused-ring non-aromatic heterocyclic group, specifically, when the ring A is Formula (A), Formula (A1), Formula (A1)-1, Formula (AA1), Formula (AA1)-1, Formula (AB), Formula (AB1), Formula (AB1)-1, or Formula (AB1)-2 which are described in Aspects [1-9-c] to [1-9-c-3-2]; Formula (A)-VII or Formula (AA)-VII described in Aspect [1-9-h] or [1-9-h-1]; a phthalazinyl group described in Aspect [1-9-i]; or Formula (A)-VIII described in Aspect [1-9-j], or Formula (A)-VIIa described in Aspect [1-9-ha]; the linker moiety is more preferably Formula (c1) or Formula (c2), and further preferably Formula (c1).

[1-10-c] When the ring A is a 2-phenylamino-2-oxoacetyl group, specifically, when the ring A is a Formula (A)-IX described in Aspect [1-9-k], the linker moiety is preferably —NR$^7$—, and more preferably Formula (c2).

[1-11] As the compound of Formula (I) in Aspect [1], a preferable compound is Formula (I)-A:

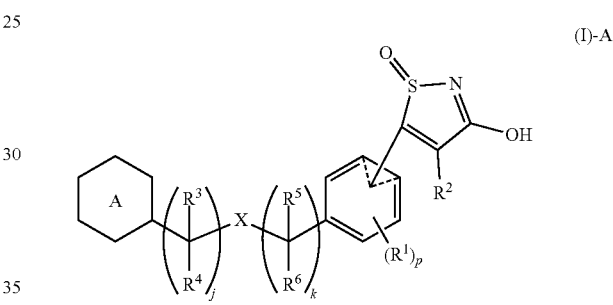

(where the definition of p, j, k, ring A, X, $R^1$, $R^2$, $R^3$, $R^4$, $R^5$ and $R^6$ is the same as the definition in Formula (I) described in Aspect [1]; a broken line is the bonding position of isothiazolyl group).

More specifically, the preferred aspect of p, j, k, ring A, X, $R^1$, $R^2$, $R^3$, $R^4$, $R^5$ and $R^6$ is the same as the preferred aspect described in any one of Aspect [1-1] to [1-10].

The Formula (I)-A is more preferably Formula (I)-1:

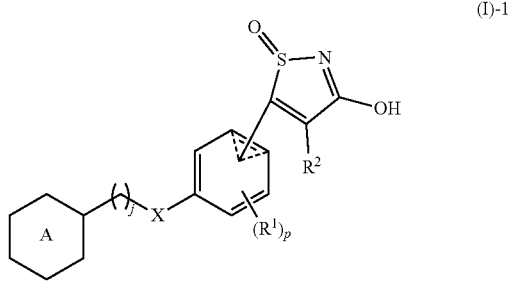

(where the descriptions of p, j, the ring A, X, $R^1$, and $R^2$ are the same as in Formula (I) described in Aspect [1], a broken line is the bonding position of isothiazolyl group).

More specifically, the preferred aspects of p, j, the ring A, X, $R^1$, and $R^2$ are the same as the preferred aspects described in any one of Aspects [1-1] to [1-10].

[1-12] As the compound of Formula (I)-1 of Aspect [1-11], a preferable compound is Formula (II):

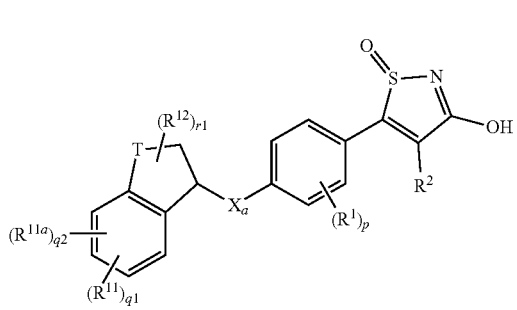

(II)

(where the definitions of p, R$^1$, and R$^2$ are the same as in Formula (I) described in Aspect [1]; the definitions of q1, q2, r1, T, R$^{11}$, R$^{12}$, and R$^{11a}$ are the same as in Formula (A) described in Aspect [1-9-c]; and X$_a$ is an oxygen atom or —NH—).

More specifically, preferable aspects of p, q1, q2, r1, T, R$^1$, R$^2$, R$^{11}$, R$^{12}$, and R$^{11a}$ are the same as the preferable aspects described in any one of Aspects [1-1] to [1-11]. X$_a$ is preferably an oxygen atom.

[1-12-a] The compound of Formula (II) of Aspect [1-12] is more preferably Formula (II)-1:

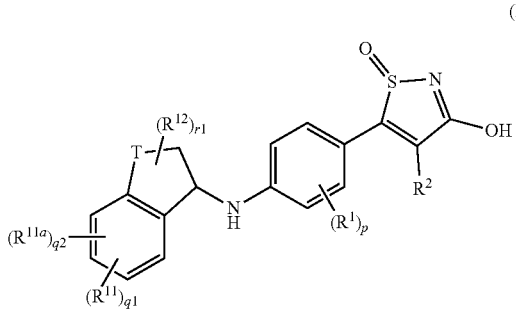

(II)-1

(where the definitions of p, R$^1$, and R$^2$ are the same as in Formula (I) described in Aspect [1]; and the definitions of q1, q2, r1, T, R$^{11}$, R$^{12}$, and R$^{11a}$ are the same as in Formula (A) described in Aspect [1-9-c]).

More specifically, preferable aspects of p, q1, q2, r1, T, R$^{11}$, R$^{12}$, and R$^{11a}$ are the same as the preferable aspects described in any one of Aspects [1-1] to [1-11].

[1-12-b] The compound described in Formula (II) described in Aspect [1-12] is more preferably Formula (II)-2:

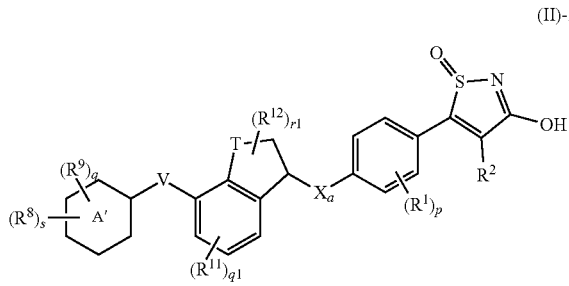

(II)-2

(where the definitions of p, R$^1$, and R$^2$ are the same as in Formula (I) described in Aspect [1]; the definitions of q1, r1, T, R$^{11}$ and R$^{12}$ are the same as in Formula (A) described in Aspect [1-9-c]; the definitions of q, s, the ring A', V, R$^8$, and R$^9$ are the same as in Formula (A1) described in Aspect [1-9-c-1]; and the definition of X$_a$ is the same as in Formula (II) described in Aspect [1-12]).

More specifically, preferable aspects of p, q, s, q1, r1, the ring A', V, T, R$^1$, R$^2$, R$^8$, R$^9$, R$^{11}$, R$^{12}$, and X$_a$ are the same as the preferable aspects described in any one of Aspects [1-1] to [1-12].

[1-12-b-1] The compound of Formula (II)-2 of Aspect [1-12-b] is more preferably Formula (II)-2a:

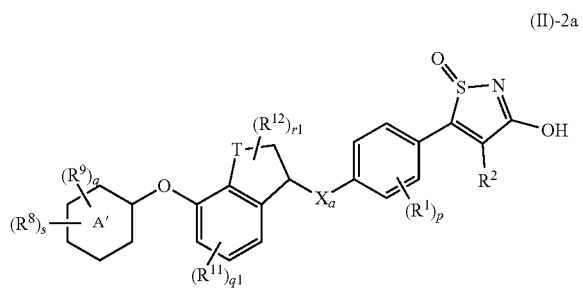

(II)-2a (where the definitions of p, R$^1$, and R$^2$ are the same as in Formula (I) described in Aspect [1]; the definitions of q1, r1, T, R$^{11}$ and R$^{12}$ are the same as in Formula (A) described in Aspect [1-9-c]; the definitions of q, s, the ring A', R$^8$, and R$^9$ are the same as in Formula (A1) described in Aspect [1-9-c-1]; and the definition of X$_a$ is the same as in Formula (II) described in Aspect [1-12] (with the proviso that compounds of 3-hydroxy-5-[4-[(4-phenoxy-2,3-dihydro-1H-inden-1-yl)oxy]phenyl]isothiazole 1-oxide, 3-hydroxy-5-[4-[[4-(2-methylpyridin-3-yl)oxy-2,3-dihydro-1H-inden-1-yl]oxy]phenyl]isothiazole 1-oxide, 3-hydroxy-5-[4-[[4-(2-methoxypyridin-4-yl)oxy-2,3-dihydro-1H-inden-1-yl]oxy]phenyl]isothiazole 1-oxide, and 3-hydroxy-5-[4-[(4-pyridin-4-yloxy-2,3-dihydro-1H-inden-1-yl)oxy]phenyl]isothiazole 1-oxide, are excluded)).

More specifically, preferable aspects of p, q, s, q1, r1, the ring A', T, R$^1$, R$^2$, R$^8$, R$^9$, R$^{11}$, R$^{12}$, and X$_a$ are the same as the preferable aspects described in any one of Aspects [1-1] to [1-12].

[1-12-c] The compound described in Formula (II) described in Aspect [1-12] is more preferably Formula (II)-3:

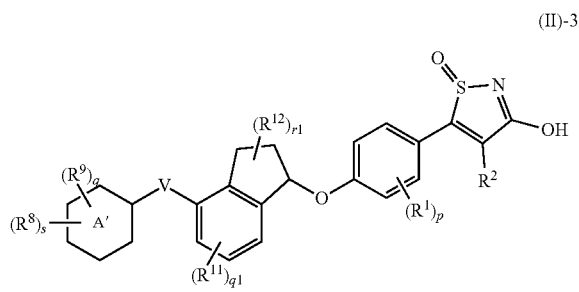

(II)-3

(where the definitions of p, R$^1$, and R$^2$ are the same as in Formula (I) described in Aspect [1]; the definitions of q1, r1, R$^{11}$ and R$^{12}$ are the same as in Formula (A) described in Aspect [1-9-c]; and the definitions of q, s, the ring A', V, R$^8$, and R$^9$ are the same as in Formula (A1) described in Aspect [1-9-c-1]).

More specifically, preferable aspects of p, q, s, q1, r1, the ring A', V, $R^1$, $R^2$, $R^8$, $R^9$, $R^{11}$, and $R^{12}$ are the same as the preferable aspects described in any one of Aspects [1-1] to [1-11].

As a preferable aspect of the ring A' moiety having $(R^8)_s$ and $(R^9)_q$, among preferable aspects of L described in Aspect [1-1-d], the same group as that having an aryl group or a heteroaryl group is mentioned and as a specific example thereof, among specific examples of the "aryl group which is optionally substituted with 1 to 5 substituent(s) RII" or specific examples of the "heterocyclic group which is optionally substituted with 1 to 5 substituent(s) RII" which are described in Aspect [1], the same group as that having a heteroaryl group is mentioned. More specifically, the same group as that having benzene, naphthalene, pyridine, pyrimidine, thiophene, benzimidazole, quinoline, or dibenzofuran is mentioned.

[1-12-c-1] The compound of Formula (II)-3 of Aspect [1-12-c] is further preferably Formula (II)-3a:

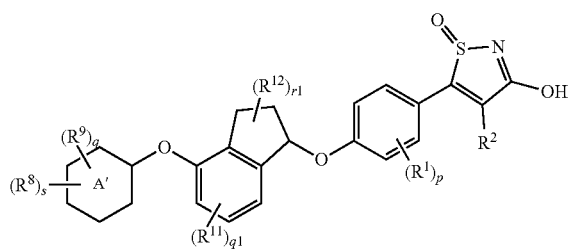

(II)-3a (where the definitions of p, $R^1$, and $R^2$ are the same as in Formula (I) described in Aspect [1]; the definitions of q1, r1, $R^{11}$, and $R^{12}$ are the same as in Formula (A) described in Aspect [1-9-c]; and the definitions of q, s, the ring A', $R^8$, and $R^9$ are the same as in Formula (A1) described in Aspect [1-9-c-1] (with the proviso that compounds of 3-hydroxy-5-[4-[(4-phenoxy-2,3-dihydro-1H-inden-1-yl)oxy]phenyl]isothiazole 1-oxide, 3-hydroxy-5-[4-[[4-(2-methylpyridin-3-yl)oxy-2,3-dihydro-1H-inden-1-yl]oxy]phenyl] isothiazole 1-oxide, 3-hydroxy-5-[4-[[4-(2-methoxypyridin-4-yl)oxy-2,3-dihydro-1H-inden-1-yl] oxy]phenyl]isothiazole 1-oxide, and 3-hydroxy-5-[4-[(4-pyridin-4-yloxy-2,3-dihydro-1H-inden-1-yl)oxy]phenyl] isothiazole 1-oxide, are excluded)).

More specifically, preferable aspects of p, q, s, q1, r1, the ring A', $R^1$, $R^2$, $R^8$, $R^9$, $R^{11}$, and $R^{12}$ are the same as the preferable aspects described in any one of Aspects [1-1] to [1-11].

As a preferable aspect of the ring A' moiety having $(R^8)_s$ and $(R^9)_q$, among preferable aspects of L described in Aspect [1-1-d], the same group as that having an aryl group or a heteroaryl group is mentioned, and as a specific example thereof, among specific examples of the "aryl group which is optionally substituted with 1 to 5 substituent(s) RII" or specific examples of the "heterocyclic group which is optionally substituted with 1 to 5 substituent(s) RII" which are described in Aspect [1], the same group as that having a heteroaryl group is mentioned. More specifically, the same group as that having benzene, pyridine, pyrimidine, thiophene, or quinoline is mentioned.

[1-12-c-1-1] As a preferable aspect of Formula (II)-3a, Formula (II)-3a in which any one of q and s is 1 or more, is mentioned.

[1-12-c-1-2] As a more preferable aspect of Formula (II)-3a, Formula (II)-3a in which any one of q and s is 1 or more and $R^9$ is a group optionally selected from a halogen atom, a cyano group, a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s)), a $C_{1-6}$ alkoxy group (the $C_{1-6}$ alkoxy group is optionally substituted with 1 to 5 halogen atom(s)), a $C_{2-6}$ alkenyl group, a $C_{2-7}$ alkanoyl group, a —$S(O)_iR^a$ (i is an integer of 0 to 2) group, a —$CONR^dR^e$ group, and a —$NR^{b1}R^{c1}$ group, is mentioned.

[1-12-c-1-3] Further preferably, Formula (II)-3a in which: any one of q and s is 1 or more; $R^8$ is a $C_{1-6}$ alkoxy group (the $C_{1-6}$ alkoxy group is optionally substituted with 1 to 5 —OH, 1 to 5 $C_{1-6}$ alkoxy group(s), or 1 to 5 —$S(O)_iR^a$ (i is an integer of 0 to 2) group(s)); and $R^9$ is a group optionally selected from a halogen atom, a cyano group, a $C_{1-6}$ alkyl group (the $C_{1-6}$ alkyl group is optionally substituted with 1 to 5 halogen atom(s) or 1 to 5 —OH), a $C_{1-6}$ alkoxy group (the $C_{1-6}$ alkoxy group is optionally substituted with 1 to 5 halogen atom(s)), a —$S(O)_iR^a$ (i is an integer of 0 to 2) group, and a —$NR^{b1}R^{c1}$ group, is mentioned.

[1-12-c-2] As the compound of Formula (II)-3a of Aspect [1-12-c-1], preferably, Formula (II)-3a-1:

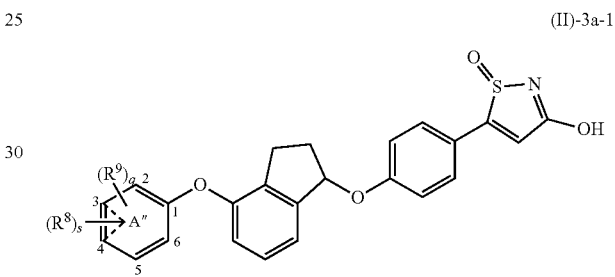

(II)-3a-1

(where the definitions of q, s, $R^8$, and $R^9$ are the same as in Formula (A1) described in Aspect [1-9-c-1]; the ring A" is a benzene ring, a pyridine ring, or a pyrimidine ring; and the broken line indicates the bonding position of $R^8$, and the numbers of "1" to "6" indicate the bonding position of the substituents (with the proviso that compounds of 3-hydroxy-5-[4-[(4-phenoxy-2,3-dihydro-1H-inden-1-yl)oxy] phenyl]isothiazole 1-oxide, 3-hydroxy-5-[4-[[4-(2-methylpyridin-3-yl)oxy-2,3-dihydro-1H-inden-1-yl]oxy] phenyl]isothiazole 1-oxide, 3-hydroxy-5-[4-[[4-(2-methoxypyridin-4-yl)oxy-2,3-dihydro-1H-inden-1-yl] oxy]phenyl]isothiazole 1-oxide, and 3-hydroxy-5-[4-[(4-pyridin-4-yloxy-2,3-dihydro-1H-inden-1-yl)oxy]phenyl] isothiazole 1-oxide, are excluded)), is mentioned.

More specifically, preferable aspects of q, s, $R^8$, and $R^9$ are the same as the preferable aspects described in any one of Aspects [1-1] to [1-11] and [1-12-c-1].

[1-12-c-2-1] As a preferable aspect of Formula (II)-3a-1, Formula (II)-3a-1 in which any one of q and s is 1 or more, is mentioned.

[1-12-c-2-2] As a more preferable aspect of Formula (II)-3a-1, Formula (II)-3a-1 in which any one of q and s is 1 or more and $R^9$ is a group optionally selected from a halogen atom, a cyano group, a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s)), a $C_{1-6}$ alkoxy group (the $C_{1-6}$ alkoxy group is optionally substituted with 1 to 5 halogen atom(s)), a $C_{2-6}$ alkenyl group, a $C_{2-7}$ alkanoyl group, a —$S(O)_iR^a$ (i is an integer of 0 to 2) group, a —$CONR^dR^e$ group, and a —$NR^{b1}R^{c1}$ group, is mentioned.

[1-12-c-2-3] Further preferably, Formula (II)-3a-1 in which: any one of q and s is 1 or more; $R^8$ is a $C_{1-6}$ alkoxy group (the $C_{1-6}$ alkoxy group is optionally substituted with 1 to 5 —OH, 1 to 5 $C_{1-6}$ alkoxy group(s), or 1 to 5 —S(O)$_i$R$^a$ (i is an integer of 0 to 2) group(s)); and R$^9$ is a group optionally selected from a halogen atom, a cyano group, a $C_{1-6}$ alkyl group (the $C_{1-6}$ alkyl group is optionally substituted with 1 to 5 halogen atom(s) or 1 to 5 —OH), a $C_{1-6}$ alkoxy group (the $C_{1-6}$ alkoxy group is optionally substituted with 1 to 5 halogen atom(s)), a —S(O)$_i$R$^a$ (i is an integer of 0 to 2) group, and a —NR$^{b1}$R$^{c1}$ group, is mentioned.

[1-12-c-2-4] As another preferable aspect of Formula (II)-3a-1, Formula (II)-3a-1 in which any one of q and s is 1 or more (with the proviso that when q is 1, s is 0, and R$^9$ is a $C_{1-6}$ alkyl group or a $C_{1-6}$ alkoxy group, R$^9$ is substituted at a 4-position), is mentioned.

[1-12-c-3] As the compound of Formula (II)-3 in Aspect [1-12-c], preferably, Formula (II)-3b:

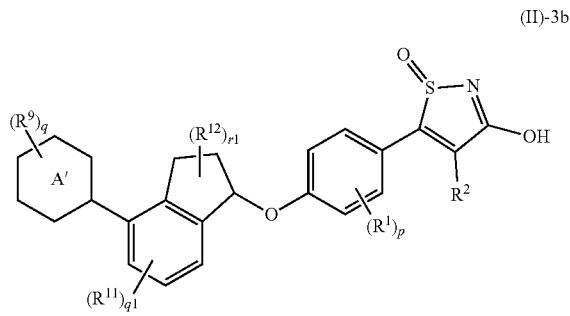

(II)-3b (where the definitions of p, R$^1$, and R$^2$ are the same as in Formula (I) described in Aspect [1]; the definitions of q1, r1, R$^{11}$ and R$^{12}$ are the same as in Formula (A) described in Aspect [1-9-c]; and the definitions of q, the ring A', and R$^9$ are the same as in Formula (A1) described in Aspect [1-9-c-1]), is mentioned.

More specifically, preferable aspects of p, q, q1, r1, the ring A', R$^1$, R$^2$, R$^9$, R$^{11}$, and R$^{12}$ are the same as the preferable aspects described in any one of Aspects [1-1] to [1-11].

Here, as a preferable aspect of the ring A' moiety having (R$^9$)$_q$, among preferable aspects of L described in Aspect [1-1-d], the group the same as an aryl group or heteroaryl group having the corresponding substituent is mentioned, and as a specific example thereof, among specific examples of the "aryl group which is optionally substituted with 1 to 5 substituent(s) RII" or specific examples of the "heterocyclic group which is optionally substituted with 1 to 5 substituent(s) RII" which are described in Aspect [1], the same group as an aryl group or heteroaryl group having the corresponding substituent is mentioned. More specifically, the same group as that having benzene, naphthalene, pyridine, thiophene, or dibenzofuran is mentioned.

[1-12-d] The compound of Formula (II) in Aspect [1-12] is more preferably Formula (II)-4:

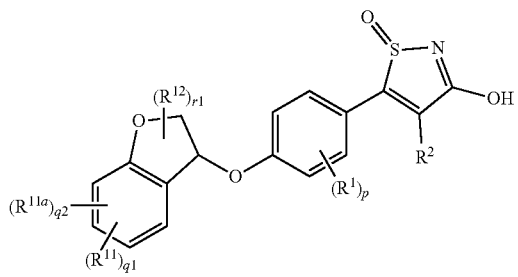

(II)-4

(where the definitions of p, R$^1$, and R$^2$ are the same as in Formula (I) described in Aspect [1]; and the definitions of q1, q2, r1, R$^{11}$, R$^{12}$, and R$^{11a}$ are the same as in Formula (A) described in Aspect [1-9-c] (with the proviso that compound of 3-hydroxy-5-[4-[[7-(trifluoromethyl)-2,3-dihydro-1-benzofuran-3-yl]oxy]phenyl]isothiazole 1-oxide is excluded)).

More specifically, preferable aspects of p, q1, q2, r1, R$^1$, R$^2$, R$^{11}$, R$^{12}$, and R$^{11a}$ are the same as the preferable aspects described in any one of Aspects [1-1] to [1-11].

[1-12-d-1] The compound of Formula (II)-4 of Aspect [1-12-d] is more preferably Formula (II)-4a:

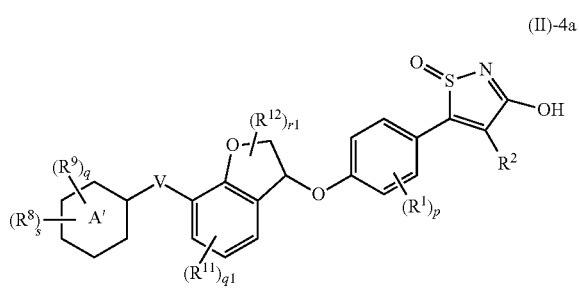

(II)-4a (where the definitions of p, R$^1$, and R$^2$ are the same as in Formula (I) described in Aspect [1]; the definitions of q1, r1, R$^{11}$ and R$^{12}$ are the same as in Formula (A) described in Aspect [1-9-c]; and the definitions of q, s, the ring A', V, R$^8$, and R$^9$ are the same as in Formula (A1) described in Aspect [1-9-c-1]).

More specifically, preferable aspects of p, q, s, q1, r1, the ring A', R$^1$, R$^2$, R$^8$, R$^9$, R$^{11}$, and R$^{12}$ are the same as the preferable aspects described in any one of Aspects [1-1] to [1-11].

[1-13] As the compound of Formula (I)-1 of Aspect [1-11], a preferable compound is Formula (III):

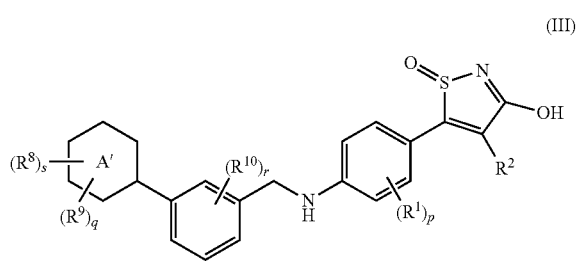

(III)

(where the definitions of p, R$^1$, and R$^2$ are the same as in Formula (I) described in Aspect [1]; the definitions of q, s, the ring A', R$^8$, and R$^9$ are the same as in Formula (A1) described in Aspect [1-9-c-1]; and the definitions of r and R$^{10}$ are the same as in Formula (A)-III described in Aspect [1-9-d] (with the proviso that compound of 3-hydroxy-5-[4-[(3-phenoxyphenyl)methoxy]phenyl]isothiazole 1-oxide is excluded)).

More specifically, preferable aspects of p, q, r, s, the ring A', R$^1$, R$^2$, R$^8$, R$^9$, and R$^{10}$ are the same as the preferable aspects described in any one of Aspects [1-1] to [1-11].

Here, as a preferable aspect of the ring A' moiety having (R$^8$)$_s$ and (R$^9$)$_q$, among preferable aspects of L described in Aspect [1-1-d], the same group as that having an aryl group or a heteroaryl group is mentioned, and as a specific example thereof, among specific examples of the "aryl group which is optionally substituted with 1 to 5 substituent(s) RII" or specific examples of the "heterocyclic group which is optionally substituted with 1 to 5 substituent(s) RII" which are described in Aspect [1], the same group as that having a heteroaryl group is mentioned. More specifically, the same group as that having benzene, naphthalene, pyridine, pyrimidine, thiophene, quinoline, or dibenzofuran is mentioned.

[1-13-a] The compound of Formula (III) in Aspect [1-13] is more preferably Formula (III)-1:

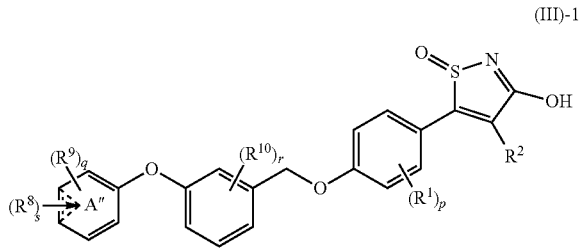

(III)-1

(where the definitions of p, $R^1$, and $R^2$ are the same as in Formula (I) described in Aspect [1]; the definitions of q, s, $R^8$, and $R^9$ are the same as in Formula (A1) described in Aspect [1-9-c-1]; the definitions of r and $R^{10}$ are the same as in Formula (A)-III described in Aspect [1-9-d]; the definitions of the ring A" and broken line are the same as in Formula (II)-3a-1 described in Aspect [1-12-c-2] (with the proviso that compound of 3-hydroxy-5-[4-[(3-phenoxyphenyl)methoxy]phenyl]isothiazole 1-oxide is excluded)).

More specifically, preferable aspects of p, q, r, s, the ring A", $R^1$, $R^2$, $R^8$, $R^9$, and $R^{10}$ are the same as the preferable aspects described in any one of Aspects [1-1] to [1-11].

[1-13-a-1] The preferable aspect of Formula (III)-1 includes those in which either q or s is an integer of 1 or more.

[1-13-a-2] The preferable aspect of Formula (III)-1 includes those in which either q or s is an integer of 1 or more, and $R^9$ is a group arbitrarily selected from a halogen atom, a cyano group, a $C_{1-6}$ alkyl group (the $C_{1-6}$ alkyl group is optionally substituted with 1 to 5 substituent(s) arbitrarily selected from halogen atom, —OH or $C_{1-6}$ alkoxyl group), a $C_{1-6}$ alkoxyl group (the $C_{1-6}$ alkoxyl group is optionally substituted with 1 to 5 halogen atom(s)), a $C_{2-6}$ alkenyl group, a $C_{2-7}$ alkanoyl group, —S(O)$_i$R$^a$ group (i is an integer of 0 to 2), —CONR$^d$R$^e$ group, and —NR$^{b1}$R$^{c1}$ group.

[1-13-a-3] More preferably, either q or s is an integer of 1 or more, $R^8$ is a $C_{1-6}$ alkoxyl group (the $C_{1-6}$ alkoxyl group is optionally substituted with 1 to 5 group(s) of —OH, $C_{1-6}$ alkyl group or —S(O)$_i$R$^a$ group (i is an integer of 0 to 2)), and $R^9$ is a group arbitrarily selected from a halogen atom, a cyano group, a $C_{1-6}$ alkyl group (the $C_{1-6}$ alkyl group is optionally substituted with 1 to 5 substituent(s) arbitrarily selected from halogen atom or —OH), —S(O)$_i$R$^a$ group (i is an integer of 0 to 2), and —NR$^{b1}$R$^{c1}$ group.

[1-13-b] The preferable compound in the compound of Formula (I)-1 in Aspect [1-11] is the compound of Formula (III-A):

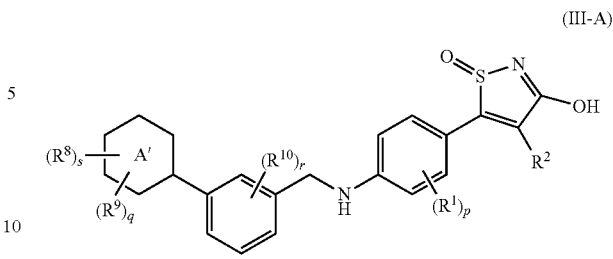

(III-A)

(where the definitions of p, $R^1$, and $R^2$ are the same as in Formula (I) described in Aspect [1]; the definitions of q, s, ring A', $R^8$, and $R^9$ are the same as in Formula (A1) described in Aspect [1-9-c-1]; the definitions of r and $R^{10}$ are the same as in Formula (A)-III described in Aspect [1-9-d]).

More specifically, preferable aspects of p, q, r, s, the ring A', $R^1$, $R^2$, $R^8$, $R^9$, and $R^{10}$ are the same as the preferable aspects described in any one of Aspects [1-1] to [1-11].

In the meantime, the preferable aspect of the ring A' moiety having $(R^8)_s$ and $(R^9)_q$ includes the same groups as those having an aryl group or a heteroaryl group in the preferable aspect of L described in [1-1-d]. Specific examples include the same groups as those having a heteroaryl group in the specific examples of "aryl group optionally substituted with 1 to 5 substituent(s) RII" or "heterocyclic group optionally substituted with 1 to 5 substituents) RII" described in Aspect [1]. More specifically, the same groups as those having benzene, naphthalene, pyridine, pyrimidine, thiophene, quinoline or dibenzofuran can be mentioned.

[1-13-b-1] The preferable compound in the compounds of Formula (III-A) in Aspect [1-13-b] is a compound of Formula (III-A)-1:

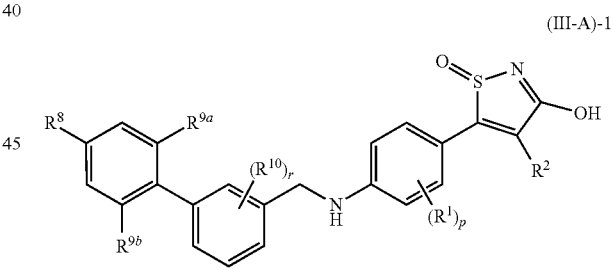

(III-A)-1

(where the definitions of p, $R^1$, and $R^2$ are the same as in Formula (I) described in Aspect [1]; the definition of $R^8$ is the same as in Formula (A1) described in Aspect [1-9-c-1]; the definitions of r and $R^{10}$ are the same as in Formula (A)-III described in Aspect [1-9-d]; and the definitions of $R^{9a}$ and $R^{9b}$ are the same as in Formula (A1)-III-2 described in Aspect [1-9-d-5]).

More specifically, preferable aspects of p, r, $R^1$, $R^2$, $R^8$, $R^{9a}$, $R^{9b}$, and $R^{10}$ are the same as the preferable aspects described in any one of Aspects [1-1] to [1-11].

[1-13-c] As the compound of Formula (I)-1 of Aspect [1-11], a preferable compound is a compound of Formula (III-B):

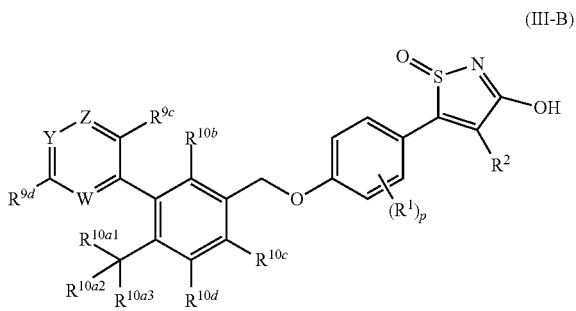

(III-B)

(where the definitions of p, $R^1$, and $R^2$ are the same as in Formula (I) described in Aspect [1]; and the definitions of W, Y, Z, $R^{9c}$, $R^{9d}$, $R^{10a1}$, $R^{10a2}$, $R^{10a3}$, $R^{10b}$, $R^{10c}$, and $R^{10d}$ are the same as in Formula (A2)-III-2 or Formula ($R^{10a'}$) described in Aspect [1-9-d-9]).

More specifically, preferable aspects of p, $R^1$, $R^2$, W, Y, Z, $R^{9c}$, $R^{9d}$, $R^{10a1}$, $R^{10a2}$, $R^{10a3}$, $R^{10b}$, $R^{10c}$, and $R^{10d}$ are the same as the preferable aspects described in any one of Aspects [1-1] to [1-11].

[1-13-d] As the compound of Formula (I)-1 of Aspect [1-11], a preferable compound is Formula (III-C):

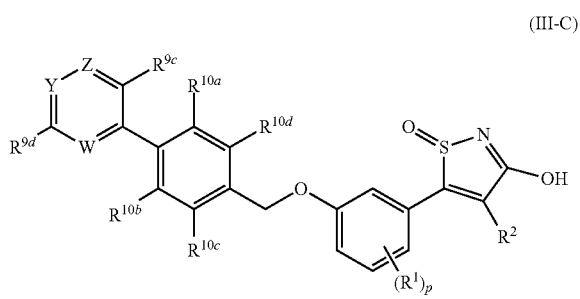

(III-C)

(where the definitions of p, $R^1$, and $R^2$ are the same as in Formula (I) described in Aspect [1]; and the definitions of W, Y, Z, $R^{9c}$, $R^{9d}$, $R^{10a}$, $R^{10b}$, $R^{10c}$, and $R^{10d}$ are the same as in Formula (A2)-III-2 described in Aspect [1-9-d-9]).

More specifically, preferable aspects of p, $R^1$, $R^2$, W, Y, Z, $R^{9c}$, $R^{9d}$, $R^{10a}$, $R^{10b}$, $R^{10c}$, and $R^{10d}$ are the same as the preferable aspects described in any one of Aspects [1-1] to [1-11].

[1-14] As the compound of Formula (I)-1 of Aspect [1-11], a preferable compound is Formula (IV):

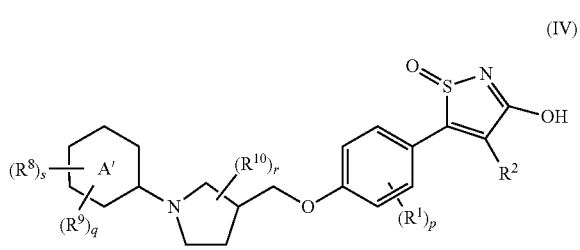

(IV)

(where the definitions of p, $R^1$, and $R^2$ are the same as in Formula (I) described in Aspect [1]; the definitions of q, s, the ring A', $R^8$, and $R^9$ are the same as in Formula (A1) described in Aspect [1-9-c-1]; and the definitions of r and $R^{10}$ are the same as in Formula (A)-III described in Aspect [1-9-d]).

More specifically, preferable aspects of p, q, r, s, the ring A', $R^1$, $R^2$, $R^8$, $R^9$, and $R^{10}$ are the same as the preferable aspects described in any one of Aspects [1-1] to [1-11].

[1-14-a] The compound of Formula (IV) of Aspect [1-14] is more preferably Formula (IV)-1:

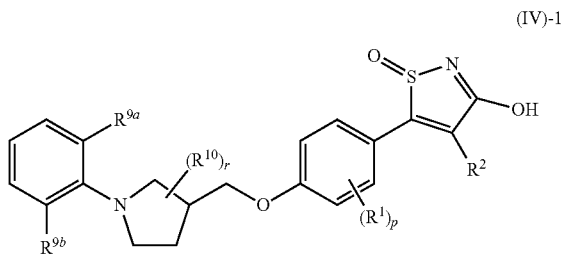

(IV)-1

(where the definitions of p, $R^1$, and $R^2$ are the same as in Formula (I) described in Aspect [1]; the definitions of r and $R^{10}$ are the same as in Formula (A)-III described in Aspect [1-9-d]; and the definitions of $R^{9a}$ and $R^{9b}$ are the same as in Formula (A1)-III-2 described in Aspect [1-9-d-5]).

More specifically, preferable aspects of p, r, $R^1$, $R^2$, $R^{9a}$, $R^{9b}$, and $R^{10}$ are the same as the preferable aspects described in any one of Aspects [1-1] to [1-11].

[1-14-b] As the compound of Formula (I)-1 of Aspect [1-11], a preferable compound is Formula (IV-A):

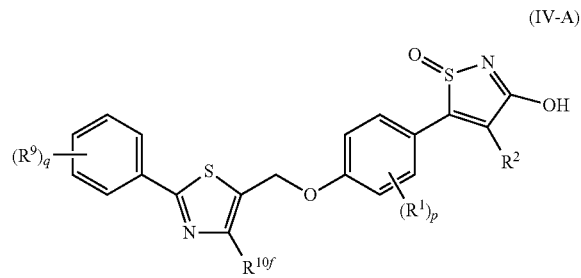

(IV-A)

(where the definitions of p, $R^1$, and $R^2$ are the same as in Formula (I) described in Aspect [1]; the definitions of q and $R^9$ are the same as in Formula (A1) described in Aspect [1-9-c-1]; and the definition of $R^{10f}$ is the same as in Formula (A2)-IV described in Aspect [1-9-e-3]).

More specifically, preferable aspects of p, q, $R^1$, $R^2$, $R^9$, and $R^{10f}$ are the same as the preferable aspects described in any one of Aspects [1-1] to [1-11].

[1-14-c] As the compound of Formula (I)-1 of Aspect [1-11], a preferable compound is Formula (IV-B):

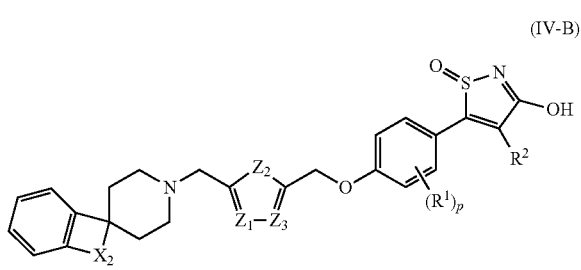

(IV-B)

(where the definitions of p, $R^1$, and $R^2$ are the same as in Formula (I) described in Aspect [1]; and the definitions of $Z_1$, $Z_2$, $Z_3$, and $X_2$ are the same as in Formula (A5)-IV described in Aspect [1-9-e-9]).

More specifically, preferable aspects of p, $R^1$, $R^2$, $Z_1$, $Z_2$, $Z_3$, and $X_2$ are the same as the preferable aspects described in any one of Aspects [1-1] to [1-11].

[1-15] As the compound of Formula (I)-1 of Aspect [1-11], a preferable compound is Formula (V):

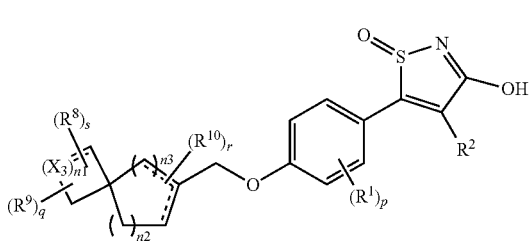

(V)

(where the definitions of p, $R^1$, and $R^2$ are the same as in Formula (I) described in Aspect [1]; the definitions of q and s are the same as in Formula (A1) described in Aspect [1-9-c-1]; the definitions of r is the same as in Formula (A)-III described in Aspect [1-9-d]; and the definitions of $R^8$, $R^9$, $R^{10}$, n1, n2, n3, $X_3$, and the broken line are the same as in Formula (A)-V described in Aspect [1-9-f]).

More specifically, preferable aspects of p, q, r, s, $R^1$, $R^2$, $R^8$, $R^9$, $R^{10}$, n1, n2, n3, and $X_3$ are the same as the preferable aspects described in any one of Aspects [1-1] to [1-11].

[1-15-a] The compound described in Formula (V) described in Aspect [1-15] is more preferably Formula (V)-1:

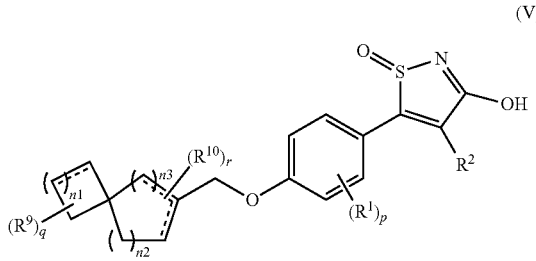

(V)-1

(where the definitions of p, $R^1$, and $R^2$ are the same as in Formula (I) described in Aspect [1]; the definitions of q is the same as in Formula (A1) described in Aspect [1-9-c-1]; the definitions of r is the same as in Formula (A)-III described in Aspect [1-9-d]; and the definitions of $R^9$, $R^{10}$, n1, n2, n3, and the broken line are the same as in Formula (A)-V described in Aspect [1-9-f]).

More specifically, preferable aspects of p, q, r, $R^1$, $R^2$, $R^9$, $R^{10}$, n1, n2, and n3 are the same as the preferable aspects described in any one of Aspects [1-1] to [1-11].

[1-15-b] The compound of Formula (V)-1 in Aspect [1-15-a] is further preferably Formula (V)-2:

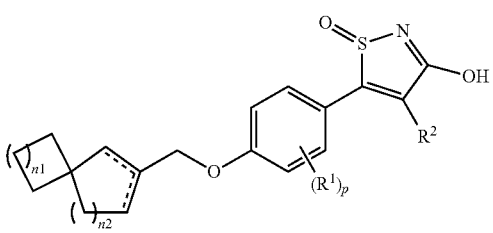

(V)-2

(where the definitions of p, $R^1$, and $R^2$ are the same as in Formula (I) described in Aspect [1]; and the definitions of n1 and n2 are the same as in Formula (A)-V described in Aspect [1-9-f]).

More specifically, preferable aspects of p, n1, n2, $R^1$, and $R^2$ are the same as the preferable aspects described in any one of Aspects [1-1] to [1-11].

The preferable compound in the compounds of Formula (I)-1 in Aspect [1-11] is a compound of Formula (V-A):

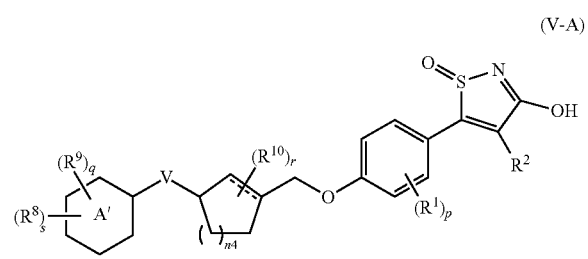

(V-A)

(where the definition of p, $R^1$ and $R^2$ is the same of the definition in Formula (1) described in the above-mentioned aspect [1]; the definition of q, s, ring A', $R^8$ and $R^9$ is the same of the definition in Formula (A1) described in the above-mentioned aspect [1-9-c-1]; the definition of r is the same of the definition in Formula (A)-III described in the above-mentioned aspect [1-9-d], $R^{10}$ and broken line is the same of the definition in Formula (A)-V described in the above-mentioned aspect [1-9-f]; the definition of n4 is the same of the definition in Formula (AA)-V described in the above-mentioned aspect [1-9-f-9]).

More specifically, the preferred aspect of p, q, r, s, ring A', V, $R^1$, $R^2$, $R^8$, $R^9$, $R^{10}$ and n4 is the same as the preferred aspect described any one of Aspect [1-1] to [1-11].

[1-16] As the compound of Formula (I)-1 of Aspect [1-11], a preferable compound is Formula (VI):

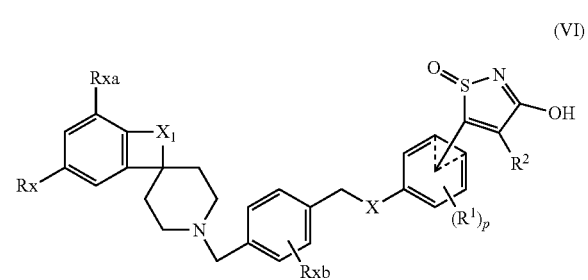

(VI)

(where the definitions of X, p, $R^1$, $R^2$, and the broken line are the same as in Formula (I) described in Aspect [1]; and the definitions of Rx, Rxa, Rxb, and $X_1$ (including Ry and Rz) are the same as in Formula (A)-VI described in Aspect [1-9-g]). Preferable aspects of X, p, $R^1$, $R^2$, Rx, Rxa, Rxb, and $X_1$ are the same as the preferable aspects described in any one of Aspects [1-1] to [1-11].

Here, as preferable aspects and specific examples of the Partial Structural Formula (A)-VI moiety having a substituted spiropiperidinylmethyl group described in Aspect [1-9-g], the same compounds as in the preferable aspects and the specific examples described in Aspects [1-9-g] and [1-9-g-1] are mentioned.

[1-16-a] The preferable compound in the compound of Formula (I)-1 of Aspect [1-11] is a compound of Formula (VIa):

(VIa)

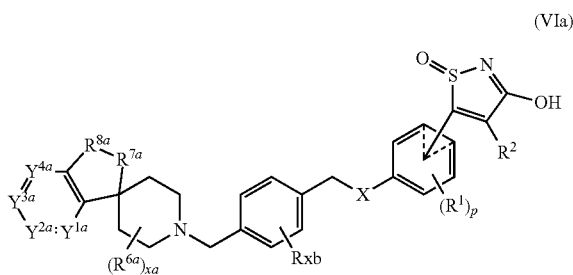

(where the definitions of X, p, $R^1$, $R^2$, and the broken line are the same as in Formula (I) described in Aspect [1]; the definition of Rxb is the same as in Formula (A)-VI described in Aspect [1-9-g]; and the definitions including the preferable aspects of $Y^{1a}$ to $Y^{4a}$, $R_{6a}$ to $R^{8a}$, and xa are the same as the definitions including the preferable aspects in Formula (SP')).

[1-16-b] The preferable compound in the compounds of Formula (I)-1 in Aspect [1-11] is a compound of Formula (VI-A):

(VI-A)

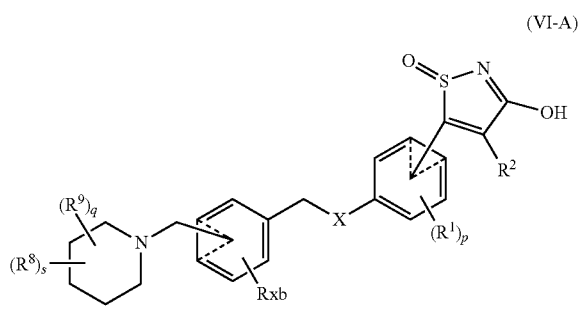

(where the definition of X, p, $R^1$ and $R^2$ is the same of the definition in Formula (1) described in the above-mentioned aspect [1]; the definition of q, s, $R^8$ and $R^9$ is the same of the definition in Formula (A1) described in the above-mentioned aspect [1-9-c-1]; the definition of Rxb is the same of the definition in Formula (A)-VI described in the above-mentioned aspect [1-9-g]; the broken line is the bonding position of isothiazolyl group or piperidinylmethyl group).

More specifically, the preferred aspect of X, p, q, s, $R^1$, $R^2$, $R^8$, $R^9$ and Rxb is the same as the preferred aspect described any one of Aspect [1-1] to [1-11].

[1-17] The ring B in the compounds of Formula (I) in Aspect [1] is preferably a benzene ring, a pyridine ring, a pyrimidine ring of Formula (BB1) or Formula (BB2):

(BB1)

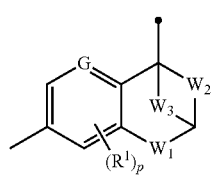

(BB2)

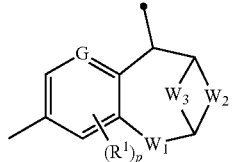

(where the definition of p and $R^1$ is the same of the definition in Formula (1); G is carbon atom or nitrogen atom; $W_1$ is a single bond, oxygen atom, sulfur atom, —$CH_2$—, —$CF_2$—, —CO—, —SO— or —$SO_2$—; $W_2$ is a single bond or —$CH_2$—; $W_3$ is not present or is —$CH_2$—; ● is a bond to isothiazolyl group). More preferably, the ring B is a benzene ring, Formula (BB1) or Formula (BB2), and further preferably is a benzene ring.

The preferable aspect of p and $R^1$ in Formula (BB1) or Formula (BB2) is the same as the preferable aspect described in Aspect [1-8] and [1-2-a].

[1-17-a] It is preferable that G is carbon atom in Formula (BB1) or Formula (BB2).

[1-17-b] It is preferable that $W_1$ is oxygen atom, sulfur atom or —$CH_2$— in Formula (BB1). When $W_3$ is —$CH_2$—, $W_2$ is preferably —$CH_2$—.

[1-17-c] It is preferable that $W_1$ is a single bond, oxygen atom, sulfur atom or —$CH_2$— in Formula (BB2). When $W_3$ is —$CH_2$—, $W_2$ is preferably —$CH_2$—.

[1-18] The ring B and the isothiazolyl group in Formula (I) of Aspect [1] is represented by Partial Structural Formula (B):

(B)

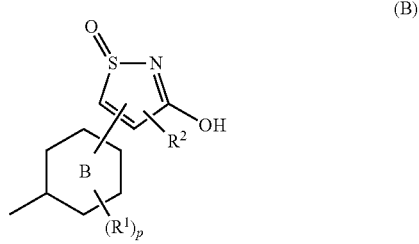

(where the definition of p, ring B, $R^1$ and $R^2$ is the same of the definition in Formula (1) described in Aspect [1]; in the isothiazoyl group, when ring B is bonded at 5-position, $R^2$ is bonded at 4-position, when ring B is bonded at 4-position, $R^2$ is bonded at 5-position).

In Formula (B), in a case where the ring B is a single ring, it is preferable that the ring B is bonded at 5-position of the isothiazolyl group and $R^2$ is bonded at 4-position thereof.

In a case where the ring B is a benzene ring, Formula (B) is preferably Formula (B)-1:

(B)-1

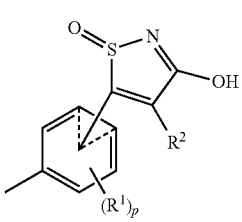

(where the definition of p, $R^1$ and $R^2$ is the same of the definition in Formula (1) described in the above-mentioned aspect [1]; the broken line is the bonding position of isothiazolyl group).

In a case where the ring B is Formula (BB1) or Formula (BB2), Formula (B) includes Formula (BB1)-1 or (BB2)-1:

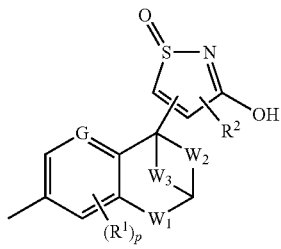
(BB1)-1

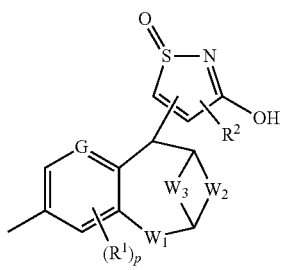
(BB2)-1

(where the definition of p, $R^1$ and $R^2$ is the same of the definition in Formula (1) described in the above-mentioned aspect [1]; G, $W_1$, $W_2$ and $W_3$ are the same of the definition in Formula (BB1) or Formula (BB2) described in the above-mentioned aspect [1-17]). Specifically, it includes Formula (BB1)-1a, Formula (BB1)-1b, Formula (BB2)-1a or Formula (BB2)-1b:

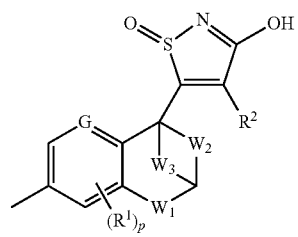
(BB1)-1a

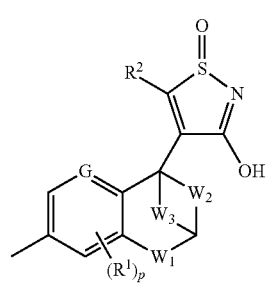
(BB1)-1b

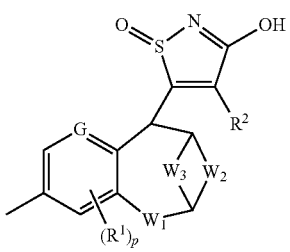
(BB2)-1a

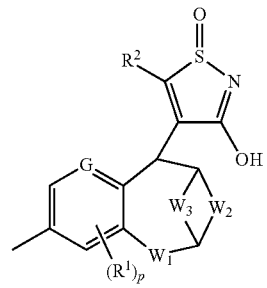
(BB2)-1b (where the definition of p, $R^1$ and $R^2$ is the same of the definition in Formula (1) described in the above-mentioned aspect [1]; G, $W_1$, $W_2$ and $W_3$ are the same of the definition in Formula (BB1) or Formula (BB2) described in the above-mentioned aspect [1-17]).

[1-18-a] When the ring A is Formula (A)-III described in Aspect [1-9-d] and the ring A'-V- is bonded to an m-position relative to a bonding position with a linker moiety containing X, specifically, the ring A' is Formula (A1)-III-1, Formula (A1)-III-2 or Formula (A2)-III-2 described in Aspect [1-9-d-1], Aspect [1-9-d-5] or Aspect [1-9-d-9], in Formula (B)-1, the isothiazole group is preferably bonded to a p-position relative to a bonding position with the linker moiety containing X. Also when the ring A is Formula (A1), Formula (A1)-1, Formula (AA1), Formula (AA1)-1, Formula (AB1), Formula (AB1)-1, or Formula (AB1)-2 which are described in Aspects [1-9-c-1] to [1-9-c-3-2]; Formula (A)-IV, Formula (A1)-IV, Formula (A2)-IV, Formula (A3)-IV, Formula (A4)$_4$V, or Formula (A5)-IV which are described in Aspects [1-9-e] to [1-9-e-9]; Formula (A)-V, Formula (A1)-V, Formula (A2)-V, Formula (A3)-V, Formula (AA)-V, Formula (AA1)-V or Formula (AA1)-V-1 which are described in Aspects [1-9-f] to [1-9-f-11]; or Formula (A)-VI or Formula (AA)-VI which is described in Aspect [1-9-g] to [1-9-g-2], in Formula (B)-1, the isothiazole group is preferably bonded to a p-position relative to a bonding position with the linker moiety containing X.

[1-18-b] When the ring A is Formula (A)-III described in Aspect [1-9-d] and the ring A'-V- is bonded to a p-position relative to a bonding position with a linker moiety containing X, specifically, the ring A' is Formula (A3)-III-2 described in Aspect [1-9-d-10], in Formula (B)-1, the isothiazole group is preferably bonded to an m-position relative to a bonding position with the linker moiety containing X.

[1-18-c] In Formula (B), Formula (B)-1, Formula (BB1)-1, Formula (BB2)-1, Formula (BB1)-1a, Formula (BB1)-1b, Formula (BB2)-1a or Formula (BB2)-1b, $R^1$ is preferably a halogen atom, a $C_{1-4}$ alkyl group optionally substituted with 1 to 5 halogen atom(s), a $C_{1-4}$ alkoxy group optionally substituted with 1 to 5 halogen atom(s), or a cyano group and more specifically, $R^1$ is preferably a fluorine atom, a chlorine atom, a bromine atom, methyl, ethyl, propyl, isopropyl, butyl, isobutyl, sec-butyl, tert-butyl, trifluoromethyl, methoxy, trifluoromethoxy, or cyano. p is preferably 0 or 1.

In Formula (B), Formula (B)-1, Formula (BB1)-1, Formula (BB2)-1, Formula (BB1)-1a, Formula (BB1)-1b, Formula (BB2)-1a or Formula (BB2)-1b, $R^2$ is preferably a hydrogen atom or a halogen atom, more specifically, a hydrogen atom, a fluorine atom, a chlorine atom, or a bromine atom, and more preferably, a hydrogen atom.

[1-19] The preferable compounds of the compound of Formula (I) in the above-mentioned aspect [1] are compounds of Formula (I)-B1 or Formula (I)-B2:

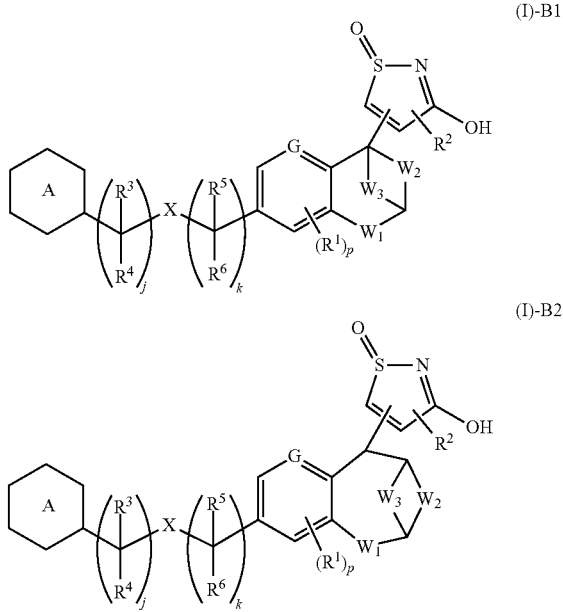

(where the definition of p, j, k, $R^1$, $R^2$, $R^3$, $R^4$, $R^5$ and $R^6$ is the same of the definition in Formula (1) described in the above-mentioned aspect [1]; G, $W_1$, $W_2$ and $W_3$ are the same of the definition in Formula (BB1) or Formula (BB2) described in the above-mentioned aspect [1-17]).

More specifically, the preferred aspect of p, j, k, ring A, X, $R^1$, $R^2$, $R^3$, $R^4$, $R^5$ and $R^6$ is the same as the preferred aspect described any one of Aspect [1-1] to [1-10], and the preferred aspect of G, $W_1$, $W_2$ and $W_3$ is the same as the preferred aspect described in Aspect [1-17].

[1-19-a] The preferable compounds of Formula (I)-B1 or Formula (I)-B2 are compounds in which a ring A is a $C_{6-14}$ aryl group which is optionally substituted with 1 to 5 substituent(s) L, or a 3- to 14-membered heterocyclic group which is optionally substituted with 1 to 5 substituent(s) L, and a linker moiety containing X is Formula (c1) or Formula (c2) described in Aspect [1-10].

The more preferable compounds are compounds in which a ring A is a phenyl group which is optionally substituted with 1 to 5 substitutent(s) L, a phthaladinyl group which is optionally substituted with 1 to 5 substituent(s) L, or Formula (A)-VIII described in Aspect [1-9-j], and a linker moiety containing X is Formula (c1).

The further preferable compounds are compounds in which a ring A is a phenyl group (the phenyl group is optionally substituted with 1 to 3 substituent(s) arbitrarily selected from halogen atom, cyano group, $C_{1-6}$ alkyl group, halogenated $C_{1-6}$ alkyl group, $C_{1-6}$ alkoxy group or —$SF_5$), a phthaladinyl group (the phthaladinyl group is optionally substituted with 1 to 3 substituent(s) arbitrarily selected from halogen atom, cyano group, $C_{1-6}$ alkyl group, halogenated $C_{1-6}$ alkyl group, $C_{1-6}$ alkoxy group or —$SF_5$) or Formula (A)-VIII, and a linker moiety containing X is Formula (c1).

[1-20] Based on the above descriptions, by accordingly combining Aspects [1-1] to [1-19] of the present invention and the preferable aspects thereof and further, the definitions of the substituents, various preferable aspects of the compound of Formula (I) of Aspect [1] can optionally be formed.

[1-21] Preferable examples of the compound of Formula (I) in Aspect [1] include the compounds below.

5-(4-(5-bromo-2,3-dihydro-1H-inden-1-yloxy)phenyl) isothiazole-3-ole 1-oxide (A) (Example 1);

5-(4-(((2',6'-dimethyl-4'-(3-(methylsulfonyl)propoxy-[1,1'-biphenyl]-3-yl)methyl)aminophenyl)-3-hydroxyisothiazole 1-oxide (A) (Example 2);

5-(4-(((1R)-4-bromo-2,3-dihydro-1H-inden-1-yloxy)phenyl) isothiazole-3-ole 1-oxide (A) (Example 3);

5-(4-(((1R)-4-(2-ethoxy-5-fluorophenyl)-2,3-dihydro-1H-inden-1-yl)oxy)phenyl)-3-hydroxyisothiazole 1-oxide (A) (Example 4);

3-hydroxy-5-(4-(((R)-4-(p-tolyl)-2,3-dihydro-1H-inden-1-yl)oxy)phenyl)isothiazole 1-oxide (A) (Example 5);

5-(4-(((R)-4-(4-chlorophenyl)-2,3-dihydro-1H-inden-1-yl)oxy)phenyl)-3-hydroxyisothiazole 1-oxide (A) (Example 6);

5-(4-(((R)-4-(4-ethoxyphenyl)-2,3-dihydro-1H-inden-1-yl)oxy)phenyl)-3-hydroxyisothiazole 1-oxide (A) (Example 7);

5-(4-(((R)-4-(3-chlorophenyl)-2,3-dihydro-1H-inden-1-yl)oxy)phenyl)-3-hydroxyisothiazole 1-oxide (A) (Example 8);

5-(4-(((R)-4-(2-ethylphenyl)-2,3-dihydro-1H-inden-1-yl)oxy)phenyl)-3-hydroxyisothiazole 1-oxide (A) (Example 9);

5-(4-(((R)-4-(2-chlorophenyl)-2,3-dihydro-1H-inden-1-yl)oxy)phenyl)-3-hydroxyisothiazole 1-oxide (A) (Example 10);

5-(4-(((R)-4-(2-fluorophenyl)-2,3-dihydro-1H-inden-1-yl)oxy)phenyl)-3-hydroxyisothiazole 1-oxide (A) (Example 11);

5-(4-(((R)-4-(3,5-difluorophenyl)-2,3-dihydro-1H-inden-1-yl)oxy)phenyl)-3-hydroxyisothiazole 1-oxide (A) (Example 12);

5-(4-(((R)-4-(3-fluoro-4-methylphenyl)-2,3-dihydro-1H-inden-1-yl)oxy)phenyl)-3-hydroxyisothiazole 1-oxide (A) (Example 13);

5-(4-(((R)-4-(3-chloro-5-methoxyphenyl)-2,3-dihydro-1H-inden-1-yl)oxy)phenyl)-3-hydroxyisothiazole 1-oxide (A) (Example 14);

5-(4-(((R)-4-(2-chloro-5-methylphenyl)-2,3-dihydro-1H-inden-1-yl)oxy)phenyl)-3-hydroxyisothiazole 1-oxide (A) (Example 15);

5-(4-(((R)-4-(4-chloro-2-fluorophenyl)-2,3-dihydro-1H-inden-1-yl)oxy)phenyl)-3-hydroxyisothiazole 1-oxide (A) (Example 16);

5-(4-(((R)-4-(2,3-difluorophenyl)-2,3-dihydro-1H-inden-1-yl)oxy)phenyl)-3-hydroxyisothiazole 1-oxide (A) (Example 17);

5-(4-(((R)-4-(4-chloro-2-ethoxyphenyl)-2,3-dihydro-1H-inden-1-yl)oxy)phenyl)-3-hydroxyisothiazole 1-oxide (A) (Example 18);

5-(4-(((R)-4-(2-ethoxypyridin-3-yl)-2,3-dihydro-1H-inden-1-yl)oxy)phenyl)-3-hydroxyisothiazole 1-oxide (A) (Example 19);

5-(4-(((R)-4-(4-ethylphenyl)-2,3-dihydro-1H-inden-1-yl)oxy)phenyl)-3-hydroxyisothiazole 1-oxide (A) (Example 20);

5-(4-(((R)-4-(4-fluorophenyl)-2,3-dihydro-1H-inden-1-yl)oxy)phenyl)-3-hydroxyisothiazole 1-oxide (A) (Example 21);

5-(4-(((R)-4-(4-n-propylphenyl)-2,3-dihydro-1H-inden-1-yl)oxy)phenyl)-3-hydroxyisothiazole 1-oxide (A) (Example 22);

5-(4-(((R)-4-(4-methoxyphenyl)-2,3-dihydro-1H-inden-1-yl)oxy)phenyl)-3-hydroxyisothiazole 1-oxide (A) (Example 23);

5-(4-(((R)-4-(3-methylphenyl)-2,3-dihydro-1H-inden-1-yl)oxy)phenyl)-3-hydroxyisothiazole 1-oxide (A) (Example 24);

5-(4-(((R)-4-(4-vinylphenyl)-2,3-dihydro-1H-inden-1-yl)oxy)phenyl)-3-hydroxyisothiazole 1-oxide (A) (Example 25);

5-(4-(((R)-4-(4-isopropylphenyl)-2,3-dihydro-1H-inden-1-yl)oxy)phenyl)-3-hydroxyisothiazole 1-oxide (A) (Example 26);

5-(4-(((R)-4-(2-methylphenyl)-2,3-dihydro-1H-inden-1-yl)oxy)phenyl)-3-hydroxyisothiazole 1-oxide (A) (Example 27);

5-(4-(((R)-4-(4-isobutylphenyl)-2,3-dihydro-1H-inden-1-yl)oxy)phenyl)-3-hydroxyisothiazole 1-oxide (A) (Example 28);

5-(4-(((R)-4-(3-fluorophenyl)-2,3-dihydro-1H-inden-1-yl)oxy)phenyl)-3-hydroxyisothiazole 1-oxide (A) (Example 29);

5-(4-(((R)-4-(3-methoxyphenyl)-2,3-dihydro-1H-inden-1-yl)oxy)phenyl)-3-hydroxyisothiazole 1-oxide (A) (Example 30);

5-(4-(((R)-4-(4-isopropoxyphenyl)-2,3-dihydro-1H-inden-1-yl)oxy)phenyl)-3-hydroxyisothiazole 1-oxide (A) (Example 31);

5-(4-(((R)-4-(3-ethoxyphenyl)-2,3-dihydro-1H-inden-1-yl)oxy)phenyl)-3-hydroxyisothiazole 1-oxide (A) (Example 32);

5-(4-(((R)-4-(4-tert-butylphenyl)-2,3-dihydro-1H-inden-1-yl)oxy)phenyl)-3-hydroxyisothiazole 1-oxide (A) (Example 33);

5-(4-(((R)-4-(2-isopropylphenyl)-2,3-dihydro-1H-inden-1-yl)oxy)phenyl)-3-hydroxyisothiazole 1-oxide (A) (Example 34);

5-(4-(((R)-4-(naphthalene-1-yl)-2,3-dihydro-1H-inden-1-yl)oxy)phenyl)-3-hydroxyisothiazole 1-oxide (A) (Example 35);

5-(4-(((R)-4-(2,4-dimethylphenyl)-2,3-dihydro-1H-inden-1-yl)oxy)phenyl)-3-hydroxyisothiazole 1-oxide (A) (Example 36);

5-(4-(((R)-4-(2,5-dimethylphenyl)-2,3-dihydro-1H-inden-1-yl)oxy)phenyl)-3-hydroxyisothiazole 1-oxide (A) (Example 37);

5-(4-(((R)-4-(4-fluoro-3-methylphenyl)-2,3-dihydro-1H-inden-1-yl)oxy)phenyl)-3-hydroxyisothiazole 1-oxide (A) (Example 38);

5-(4-(((R)-4-(4-fluoro-2-methylphenyl)-2,3-dihydro-1H-inden-1-yl)oxy)phenyl)-3-hydroxyisothiazole 1-oxide (A) (Example 39);

5-(4-(((R)-4-(4-methoxy-2-methylphenyl)-2,3-dihydro-1H-inden-1-yl)oxy)phenyl)-3-hydroxyisothiazole 1-oxide (A) (Example 40);

5-(4-(((R)-4-(5-fluoro-2-methylphenyl)-2,3-dihydro-1H-inden-1-yl)oxy)phenyl)-3-hydroxyisothiazole 1-oxide (A) (Example 41);

5-(4-(((R)-4-(2-benzyloxyphenyl)-2,3-dihydro-1H-inden-1-yl)oxy)phenyl)-3-hydroxyisothiazole 1-oxide (A) (Example 42);

5-(4-(((R)-4-(2-chloro-4-methylphenyl)-2,3-dihydro-1H-inden-1-yl)oxy)phenyl)-3-hydroxyisothiazole 1-oxide (A) (Example 43);

5-(4-(((R)-4-(4-ethoxy-3-fluorophenyl)-2,3-dihydro-1H-inden-1-yl)oxy)phenyl)-3-hydroxyisothiazole 1-oxide (A) (Example 44);

5-(4-(((R)-4-(2-methoxy-5-methylphenyl)-2,3-dihydro-1H-inden-1-yl)oxy)phenyl)-3-hydroxyisothiazole 1-oxide (A) (Example 45);

5-(4-(((R)-4-(2,5-difluorophenyl)-2,3-dihydro-1H-inden-1-yl)oxy)phenyl)-3-hydroxyisothiazole 1-oxide (A) (Example 46);

5-(4-(((R)-4-(4-benzyloxy-2-methylphenyl)-2,3-dihydro-1H-inden-1-yl)oxy)phenyl)-3-hydroxyisothiazole 1-oxide (A) (Example 47);

5-(4-(((R)-4-(2-chloro-4-methoxyphenyl)-2,3-dihydro-1H-inden-1-yl)oxy)phenyl)-3-hydroxyisothiazole 1-oxide (A) (Example 48);

5-(4-(((R)-4-(2,4-dimethoxyphenyl)-2,3-dihydro-1H-inden-1-yl)oxy)phenyl)-3-hydroxyisothiazole 1-oxide (A) (Example 49);

5-(4-(((R)-4-(4-methylnaphthalen-1-yl)-2,3-dihydro-1H-inden-1-yl)oxy)phenyl)-3-hydroxyisothiazole 1-oxide (A) (Example 50);

5-(4-(((R)-4-(4-fluoro-2-methoxyphenyl)-2,3-dihydro-1H-inden-1-yl)oxy)phenyl)-3-hydroxyisothiazole 1-oxide (A) (Example 51);

5-(4-(((R)-4-(2-chloro-5-methoxyphenyl)-2,3-dihydro-1H-inden-1-yl)oxy)phenyl)-3-hydroxyisothiazole 1-oxide (A) (Example 52);

5-(4-(((R)-4-(2-fluoro-5-methoxyphenyl)-2,3-dihydro-1H-inden-1-yl)oxy)phenyl)-3-hydroxyisothiazole 1-oxide (A) (Example 53);

5-(4-(((R)-4-(2,5-dimethoxyphenyl)-2,3-dihydro-1H-inden-1-yl)oxy)phenyl)-3-hydroxyisothiazole 1-oxide (A) (Example 54);

5-(4-(((R)-4-(5-chloro-2-methoxyphenyl)-2,3-dihydro-1H-inden-1-yl)oxy)phenyl)-3-hydroxyisothiazole 1-oxide (A) (Example 55);

5-(4-(((R)-4-(5-fluoro-2-methoxyphenyl)-2,3-dihydro-1H-inden-1-yl)oxy)phenyl)-3-hydroxyisothiazole 1-oxide (A) (Example 56);

5-(4-(((R)-4-(4-benzyloxy-3-fluorophenyl)-2,3-dihydro-1H-inden-1-yl)oxy)phenyl)-3-hydroxyisothiazole 1-oxide (A) (Example 57);

5-(4-(((R)-4-(5-chloro-2-ethoxyphenyl)-2,3-dihydro-1H-inden-1-yl)oxy)phenyl)-3-hydroxyisothiazole 1-oxide (A) (Example 58);

5-(4-(((R)-4-(2-fluoro-3-methoxyphenyl)-2,3-dihydro-1H-inden-1-yl)oxy)phenyl)-3-hydroxyisothiazole 1-oxide (A) (Example 59);

5-(4-(((R)-4-(3-chloro-4-ethoxyphenyl)-2,3-dihydro-1H-inden-1-yl)oxy)phenyl)-3-hydroxyisothiazole 1-oxide (A) (Example 60);

5-(4-(((R)-4-(2-benzyloxy-4-fluorophenyl)-2,3-dihydro-1H-inden-1-yl)oxy)phenyl)-3-hydroxyisothiazole 1-oxide (A) (Example 61);

5-(4-(((R)-4-(2-benzyloxy-5-fluorophenyl)-2,3-dihydro-1H-inden-1-yl)oxy)phenyl)-3-hydroxyisothiazole 1-oxide (A) (Example 62);

5-(4-(((R)-4-(3-trifluoromethylphenyl)-2,3-dihydro-1H-inden-1-yl)oxy)phenyl)-3-hydroxyisothiazole 1-oxide (A) (Example 63);

5-(4-(((R)-4-(2-trifluoromethylphenyl)-2,3-dihydro-1H-inden-1-yl)oxy)phenyl)-3-hydroxyisothiazole 1-oxide (A) (Example 64);

5-(4-(((R)-4-(2-trifluoromethoxyphenyl)-2,3-dihydro-1H-inden-1-yl)oxy)phenyl)-3-hydroxyisothiazole 1-oxide (A) (Example 65);

5-(4-(((R)-4-(5-fluoro-2-trifluoromethylphenyl)-2,3-dihydro-1H-inden-1-yl)oxy)phenyl)-3-hydroxyisothiazole 1-oxide (A) (Example 66);

5-(4-(((R)-4-(2-fluoro-5-trifluoromethylphenyl)-2,3-dihydro-1H-inden-1-yl)oxy)phenyl)-3-hydroxyisothiazole 1-oxide (A) (Example 67);

5-(4-(((R)-4-(2-chloro-5-trifluoromethylphenyl)-2,3-dihydro-1H-inden-1-yl)oxy)phenyl)-3-hydroxyisothiazole 1-oxide (A) (Example 68);

5-(4-(((R)-4-(4-chloro-2-trifluoromethylphenyl)-2,3-dihydro-1H-inden-1-yl)oxy)phenyl)-3-hydroxyisothiazole 1-oxide (A) (Example 69);

5-(4-(((R)-4-(2-(methylsulfonyl)phenyl)-2,3-dihydro-1H-inden-1-yl)oxy)phenyl)-3-hydroxyisothiazole 1-oxide (A) (Example 70);

5-(4-(((R)-4-(6-methylpyridin-3-yl)-2,3-dihydro-1H-inden-1-yl)oxy)phenyl)-3-hydroxyisothiazole 1-oxide (A) (Example 71);

5-(4-(((R)-4-(5-methylpyridin-3-yl)-2,3-dihydro-1H-inden-1-yl)oxy)phenyl)-3-hydroxyisothiazole 1-oxide (A) (Example 72);

5-(4-(((R)-4-(5-chloropyridin-3-yl)-2,3-dihydro-1H-inden-1-yl)oxy)phenyl)-3-hydroxyisothiazole 1-oxide (A) (Example 73);

5-(4-(((R)-4-(6-chloropyridin-3-yl)phenyl)-2,3-dihydro-1H-inden-1-yl)oxy)phenyl)-3-hydroxyisothiazole 1-oxide (A) (Example 74);

5-(4-(((R)-4-(2-chloropyridin-3-yl)-2,3-dihydro-1H-inden-1-yl)oxy)phenyl)-3-hydroxyisothiazole 1-oxide (A) (Example 75);

5-(4-(((R)-4-(6-isopropyl-2-chloropyridin-3-yl)-2,3-dihydro-1H-inden-1-yl)oxy)phenyl)-3-hydroxyisothiazole 1-oxide (A) (Example 76);

5-((1R)-1-(4-(3-hydroxy-1-oxidoisothiazol-5-yl)phenoxy)-2,3-dihydro-1H-inden-4-yl) picoline amide (A) (Example 77);

5-(4-(((R)-4-(6-(cyclopropylmethoxy)pyridin-3-yl)-2,3-dihydro-1H-inden-1-yl)oxy)phenyl)-3-hydroxyisothiazole 1-oxide (A) (Example 78);

1-(5-(((1R)-1-(4-(3-hydroxy-1-oxidoisothiazol-5-yl)phenoxy)-2,3-dihydro-1H-inden-4-yl)thiophene-2-yl)ethanone (A) (Example 79);

5-(4-(((R)-4-(dibenzo[b,d]furan-4-yl)-2,3-dihydro-1H-inden-1-yl)oxy)phenyl)-3-hydroxyisothiazole 1-oxide (A) (Example 80);

5-(4-(((R)-4-(5-chlorothiophen-2-yl)-2,3-dihydro-1H-inden-1-yl)oxy)phenyl)-3-hydroxyisothiazole 1-oxide (A) (Example 81);

3-hydroxy-5-(4-(((R)-4-(thiophen-3-yl)-2,3-dihydro-1H-inden-1-yl)oxy)phenyl)isothiazole 1-oxide (A) (Example 82);

4-(((1R)-1-(4-(3-hydroxy-1-oxidoisothiazol-5-yl)phenoxy)-2,3-dihydro-1H-inden-4-yl)oxy)benzonitrile (A) (Example 83);

3-hydroxy-5-(4-(((R)-4-(3-(trifluoromethyl)phenoxy)-2,3-dihydro-1H-inden-1-yl)oxy) phenyl)isothiazole 1-oxide (A) (Example 84);

3-hydroxy-5-(4-(((R)-4-(pyridin-3-yloxy)-2,3-dihydro-1H-inden-1-yl)oxy)phenyl)isothiazole 1-oxide (A) (Example 85);

3-(((1R)-1-(4-(3-hydroxy-1-oxidoisothiazol-5-yl)phenoxy)-2,3-dihydro-1H-inden-4-yl)oxy)benzonitrile (A) (Example 86);

3-hydroxy-5-(4-(((R)-4-(4-(trifluoromethyl)phenoxy)-2,3-dihydro-1H-inden-1-yl)oxy) phenyl)isothiazole 1-oxide (A) (Example 87);

3-hydroxy-5-(4-(((R)-4-(4-(2-hydroxyethyl)phenoxy)-2,3-dihydro-1H-inden-1-yl)oxy) phenyl)isothiazole 1-oxide (A) (Example 88);

3-hydroxy-5-(4-(((R)-4-(3-(2-hydroxyethyl)phenoxy)-2,3-dihydro-1H-inden-1-yl)oxy) phenyl)isothiazole 1-oxide (A) (Example 89);

3-hydroxy-5-(4-(((R)-4-phenoxy-2,3-dihydro-1H-inden-1-yl)oxy)phenyl)isothiazole 1-oxide (A) (Example 90);

3-hydroxy-5-(4-(((R)-4-(3-methoxyphenoxy)-2,3-dihydro-1H-inden-1-yl)oxy)phenyl)isothiazole 1-oxide (A) (Example 91);

3-hydroxy-5-(4-(((R)-4-(4-methoxyphenoxy)-2,3-dihydro-1H-inden-1-yl)oxy)phenyl)isothiazole 1-oxide (A) (Example 92);

3-hydroxy-5-(4-(((R)-4-(p-tolyloxy)-2,3-dihydro-1H-inden-1-yl)oxy)phenyl)isothiazole 1-oxide (A) (Example 93);

3-hydroxy-5-(4-(((R)-4-(m-tolyloxy)-2,3-dihydro-1H-inden-1-yl)oxy)phenyl)isothiazole 1-oxide (A) (Example 94);

3-hydroxy-5-(4-(((R)-4-(o-tolyloxy)-2,3-dihydro-1H-inden-1-yl)oxy)phenyl)isothiazole 1-oxide (A) (Example 95);

5-(4-(((R)-4-(2,6-dimethylphenoxy)-2,3-dihydro-1H-inden-1-yl)oxy)phenyl)-3-hydroxyisothiazole 1-oxide (A) (Example 96);

3-hydroxy-5-(4-(((R)-4-((6-(3-hydroxy-3-methylbutoxy)pyridin-3-yl)oxy)-2,3-dihydro-1H-inden-1-yl)oxy)phenyl)isothiazole 1-oxide (A) (Example 97);

5-(4-(((R)-4-((6-(2-ethoxyethoxy)pyridin-3-yl)oxy)-2,3-dihydro-1H-inden-1-yl)oxy)phenyl)-3-hydroxyisothiazole 1-oxide (A) (Example 98);

3-hydroxy-5-(4-(((R)-4-(3-(trifluoromethoxy)phenoxy-2,3-dihydro-1H-inden-1-yl)oxy) phenyl)isothiazole 1-oxide (A) (Example 99);

3-hydroxy-5-(4-(((R)-4-((6-methoxypyridin-3-yl)oxy-2,3-dihydro-1H-inden-1-yl)oxy) phenyl)isothiazole 1-oxide (A) (Example 100);

3-hydroxy-5-(4-(((R)-4-((6-(3-hydroxy-3-methylbutoxy)-2-methylpyridin-3-yl)oxy)-2,3-dihydro-1H-inden-1-yl)oxy) phenyl)isothiazole 1-oxide (A) (Example 101);

5-(4-(((R)-4-((6-(2-ethoxyethoxy)-2-methylpyridin-3-yl)oxy-2,3-dihydro-1H-inden-1-yl)oxy)phenyl)-3-hydroxyisothiazole 1-oxide (A) (Example 102);

3-hydroxy-5-(4-(((R)-4-(4-(trifluoromethoxy)phenoxy-2,3-dihydro-1H-inden-1-yl)oxy) phenyl)isothiazole 1-oxide (A) (Example 103);

3-hydroxy-5-(4-(((R)-4-(quinolin-3-yloxy)-2,3-dihydro-1H-inden-1-yl)oxy)phenyl)isothiazole 1-oxide (A) (Example 104);

3-hydroxy-5-(4-(((R)-4-((6-methoxy-4-methylpyridin-3-yl)oxy-2,3-dihydro-1H-inden-1-yl)oxy)phenyl)isothiazole 1-oxide (A) (Example 105);

3-hydroxy-5-(4-(((R)-4-((6-methoxy-2-methylpyridin-3-yl)oxy-2,3-dihydro-1H-inden-1-yl)oxy)phenyl)isothiazole 1-oxide (A) (Example 106);

3-hydroxy-5-(4-(((R)-4-(4-(methylsulfonyl)phenoxy)-2,3-dihydro-1H-inden-1-yl)oxy) phenyl)isothiazole 1-oxide (A) (Example 107);

5-(4-(((R)-4-(4-(2-ethoxyethoxy)-2,6-dimethylphenoxy)-2,3-dihydro-1H-inden-1-yl)oxy)phenyl)-3-hydroxyisothiazole 1-oxide (A) (Example 108);

3-hydroxy-5-(4-(((R)-4-((6-morpholinopyridin-3-yl)oxy)-2,3-dihydro-1H-inden-1-yl)oxy)phenyl)isothiazole 1-oxide (A) (Example 109);

3-hydroxy-5-(4-(((R)-4-((2-methoxypyrimidin-5-yl)oxy)-2,3-dihydro-1H-inden-1-yl)oxy)phenyl)isothiazole 1-oxide (A) (Example 110);

3-hydroxy-5-(4-(((R)-4-(thiophen-3-yloxy)-2,3-dihydro-1H-inden-1-yl)oxy)phenyl)isothiazole 1-oxide (A) (Example 111);

3-hydroxy-5-(4-(((R)-4-(3-(3-hydroxy-3-methylbutoxy)phenoxy)-2,3-dihydro-1H-inden-1-yl)oxy)phenyl)isothiazole 1-oxide (A) (Example 112);

3-hydroxy-5-(4-(((R)-4-(4-(3-hydroxy-3-methylbutoxy)phenoxy)-2,3-dihydro-1H-inden-1-yl)oxy)phenyl)isothiazole 1-oxide (A) (Example 113);

3-hydroxy-5-(4-(((R)-4-((2-methoxypyridin-4-yl)oxy)-2,3-dihydro-1H-inden-1-yl)oxy) phenyl)isothiazole 1-oxide (A) (Example 114);

3-hydroxy-5-(4-(((R)-4-(4-(3-(methylsulfonyl)propoxy)phenoxy)-2,3-dihydro-1H-inden-1-yl)oxy)phenyl)isothiazole 1-oxide (A) (Example 115);

3-hydroxy-5-(4-(((R)-4-((6-(3-(methylsulfonyl)propoxy)pyridin-3-yl)oxy)-2,3-dihydro-1H-inden-1-yl)oxy)phenyl)isothiazole 1-oxide (A) (Example 116);

3-hydroxy-5-(4-(((R)-4-((2-methyl-6-(3-(methylsulfonyl)propoxy)pyridin-3-yl)oxy)-2,3-dihydro-1H-inden-1-yl)oxy)phenyl)isothiazole 1-oxide (A) (Example 117);

6-(((1R)-1-(4-(3-hydroxy-1-oxidoisothiazol-5-yl)phenoxy)-2,3-dihydro-1H-inden-4-yl)oxy)nicotinonitrile (A) (Example 118);

5-(((1R)-1-(4-(3-hydroxy-1-oxidoisothiazol-5-yl)phenoxy)-2,3-dihydro-1H-inden-4-yl)oxy)picolinonitrile (A) (Example 119);

3-hydroxy-5-(4-(spiro[5.5]undec-1-ene-2-ylmethoxy)phenyl)isothiazole 1-oxide (A) (Example 120);

5-(4-((1-(2,6-dimethylphenyl)pyrrolidin-3-yl)methoxy)phenyl)-3-hydroxyisothiazole 1-oxide (A) (Example 121);

3-hydroxy-5-(4-(spiro[4.5]dec-6-ene-7-ylmethoxy)phenyl)isothiazole 1-oxide (A) (Example 122);

3-hydroxy-5-(4-((4-(spiro[inden-1,4'-piperidin]-1'-ylmethyl)benzyl)oxy)phenyl)isothiazole 1-oxide (A) (Example 123);

3-hydroxy-5-(4-((4-((1-methylspiro[indoline-3,4'-piperidin]-1'-yl)methyl)benzyl)oxy) phenyl)isothiazole 1-oxide (A) (Example 124);

4-(3-((4-(3-hydroxy-1-oxidoisothiazole-5-yl)phenoxy)methyl)phenoxy)benzonitrile (A) (Example 125);

3-hydroxy-5-(4-(((R)-4-((2-methylpyridin-3-yl)oxy-2,3-dihydro-1H-inden-1-yl)oxy) phenyl)isothiazole 1-oxide (A) (Example 126);

3-hydroxy-5-(4-(((R)-4-((3-methoxypyridin-5-yl)oxy-2,3-dihydro-1H-inden-1-yl)oxy) phenyl)isothiazole 1-oxide (A) (Example 127);

3-(((1R)-1-(4-(3-hydroxy-1-oxidoisothiazol-5-yl)phenoxy)-2,3-dihydro-1H-inden-4-yl)oxy)benzamide (A) (Example 128);

4-(((1R)-1-(4-(3-hydroxy-1-oxidoisothiazol-5-yl)phenoxy)-2,3-dihydro-1H-inden-4-yl)oxy)benzamide (A) (Example 129);

3-hydroxy-5-(4-(((R)-4-((6-methylpyridin-2-yl)oxy-2,3-dihydro-1H-inden-1-yl)oxy) phenyl)isothiazole 1-oxide (A) (Example 130);

4-(((1R)-1-(4-(3-hydroxy-1-oxidoisothiazol-5-yl)phenoxy)-2,3-dihydro-1H-inden-4-yl)oxy)-2-(2-oxooxazolidine-3-yl)benzonitrile (A) (Example 131);

3-hydroxy-5-(4-(((R)-4-((3-methoxypyridin-2-yl)oxy)-2,3-dihydro-1H-inden-1-yl)oxy) phenyl)isothiazole 1-oxide (A) (Example 132);

3-hydroxy-5-(4-(((R)-4-((4-methylpyridin-2-yl)oxy)-2,3-dihydro-1H-inden-1-yl)oxy) phenyl)isothiazole 1-oxide (A) (Example 133);

3-hydroxy-5-(4-(((R)-4-((5-methylpyridin-2-yl)oxy)-2,3-dihydro-1H-inden-1-yl)oxy) phenyl)isothiazole 1-oxide (A) (Example 134);

3-hydroxy-5-(4-(((R)-4-((2-methylpyridin-4-yl)oxy)-2,3-dihydro-1H-inden-1-yl)oxy) phenyl)isothiazole 1-oxide (A) (Example 135);

4-(((1R)-1-(4-(3-hydroxy-1-oxidoisothiazol-5-yl)phenoxy)-2,3-dihydro-1H-inden-4-yl)oxy)-N-methylbenzamide (A) (Example 136);

4-(((1R)-1-(4-(3-hydroxy-1-oxidoisothiazol-5-yl)phenoxy)-2,3-dihydro-1H-inden-4-yl)oxy)-N,N-dimethylbenzamide (A) (Example 137);

4-((3-(4-(3-hydroxy-1-oxidoisothiazol-5-yl)phenoxy)-2,3-dihydrobenzofuran-7-yl)oxy) benzonitrile (A) (Example 138);

3-hydroxy-5-(4-((7-phenoxy-2,3-dihydrobenzofuran-3-yl)oxy)phenyl)isothiazole 1-oxide (A) (Example 139);

3-hydroxy-5-(4-((7-((6-methoxypyridin-3-yl)oxy)-2,3-dihydrobenzofuran-3-yl)oxy)phenyl)isothiazole 1-oxide (A) (Example 140);

3-hydroxy-5-(4-((7-((6-(3-hydroxy-3-methylbutoxy)-2-methylpyridin-3-yl)oxy)-2,3-dihydrobenzofuran-3-yl)oxy)phenyl)isothiazole 1-oxide (A) (Example 141);

3-hydroxy-5-(4-((7-((6-(3-hydroxy-3-methylbutoxy)-2-methylpyridin-3-yl)-2,3-dihydrobenzofuran-3-yl)oxy)phenyl)isothiazole 1-oxide (A) (Example 142);

3-hydroxy-5-(4-((7-(4-(3-hydroxy-3-methylbutoxy)-2,6-dimethylphenyl)-2,3-dihydrobenzofuran-3-yl)oxy)phenyl)isothiazole 1-oxide (A) (Example 143);

4-(((1R)-1-(4-(3-hydroxy-1-oxidoisothiazol-5-yl)phenoxy)-2,3-dihydro-1H-inden-4-yl)oxy)-N-(2-methoxyethyl)-N-methylbenzamide (A) (Example 146);

4-(((1R)-1-(4-(3-hydroxy-1-oxidoisothiazol-5-yl)phenoxy)-2,3-dihydro-1H-inden-4-yl)oxy)phenyl)(pyrrolidin-1-yl)methanone (A) (Example 147);

3-hydroxy-5-(4-(((R)-4-((6-methoxypyridin-2-yl)oxy)-2,3-dihydro-1H-inden-1-yl)oxy) phenyl)isothiazole 1-oxide (A) (Example 149);

5-(4-((7-bromo-2,3-dihydrobenzofuran-3-yl)oxy)phenyl)-3-hydroxyisothiazole 1-oxide (A) (Example 150);

5-(4-((7-(2,6-dimethyl-4-(3-(methylsulfonyl)propoxy)phenyl)-2,3-dihydrobenzofuran-3-yl)oxy)phenyl)-3-hydroxyisothiazole 1-oxide (A) (Example 151);

3-hydroxy-5-(4-((7-(m-tolyloxy)-2,3-dihydrobenzofuran-3-yl)oxy)phenyl)isothiazole 1-oxide (A) (Example 155);

4-((1R)-1-(4-(3-hydroxy-1-oxidoisothiazol-5-yl)phenoxy)-2,3-dihydro-1H-inden-4-yl) benzonitrile (A) (Example 156);

5-((1R)-1-(4-(3-hydroxy-1-oxidoisothiazol-5-yl)phenoxy)-2,3-dihydro-1H-inden-4-yl) picolinonitrile (A) (Example 157);

5-(4-(((R)-4-(3,4-dihydroquinoline-1(2H)-yl)-2,3-dihydro-1H-inden-1-yl)oxy)phenyl)-3-hydroxyisothiazole 1-oxide (A) (Example 158);

3-hydroxy-5-(4-((4-phenoxybenzyl)oxy)phenyl)isothiazole 1-oxide (A) (Example 159);

3-hydroxy-5-(4-((4-phenoxybenzyl)oxy)phenyl)isothiazole 1-oxide (B) (Example 160);

3-hydroxy-5-(4-(2-phenoxyphenethoxy)phenyl)isothiazole 1-oxide (A) (Example 161);

3-hydroxy-5-(4-(4-phenoxyphenethoxy)phenyl)isothiazole 1-oxide (A) (Example 162);

3-hydroxy-5-(3-(3-phenoxyphenethoxy)phenyl)isothiazole 1-oxide (A) (Example 163);

3-hydroxy-5-(4-{[4-(spiro[inden-1,4'-piperidin]-1'-ylmethyl)benzyl]amino}phenyl)isothiazole 1-oxide (A) (Example 1P);

3-hydroxy-5-(4-{[4-((1-methylspiro[indolin-3,4'-piperidin]-1'-yl)methyl)benzyl]amino}phenyl)isothiazole 1-oxide (A) (Example 2P);

or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the isomer, or a pharmaceutically acceptable solvate of the salt or a pharmaceutically acceptable solvate of the isomer.

In addition, the compounds of Structural Formulae 12 to 19 below in (Example 3P) to (Example 113P), or salts thereof, or solvates thereof, or optical isomers thereof are also mentioned.

[1-21-a] More preferable examples of the compound of Formula (I) in Aspect [1] include the compounds below.

1) 4-(((1R)-1-(4-(3-hydroxy-1-oxidoisothiazol-5-yl)phenoxy)-2,3-dihydro-1H-inden-4-yl)oxy)benzonitrile (A);
2) 3-hydroxy-5-(4-(((R)-4-((6-methoxypyridin-3-yl)oxy-2,3-dihydro-1H-inden-1-yl)oxy)phenyl)isothiazole 1-oxide (A);
3) 3-hydroxy-5-(4-(((R)-4-((6-(3-hydroxy-3-methylbutoxy)-2-methylpyridin-3-yl)oxy)-2,3-dihydro-1H-inden-1-yl)oxy)phenyl)isothiazole 1-oxide (A);
4) 5-(4-(((R)-4-(4-(2-ethoxyethoxy)-2,6-dimethylphenoxy)-2,3-dihydro-1H-inden-1-yl)oxy)phenyl)-3-hydroxyisothiazole 1-oxide (A);
5) 3-hydroxy-5-(4-(((R)-4-((2-methyl-6-(3-(methylsulfonyl)propoxy)pyridin-3-yl)oxy)-2,3-dihydro-1H-inden-1-yl)oxy)phenyl)isothiazole 1-oxide (A);
6) 3-hydroxy-5-(4-((7-phenoxy-2,3-dihydrobenzofuran-3-yl)oxy)phenyl)isothiazole 1-oxide (A);
7) 3-hydroxy-5-(4-((7-((6-methoxypyridin-3-yl)oxy)-2,3-dihydrobenzofuran-3-yl)oxy)phenyl)isothiazole 1-oxide (A));
8) 3-hydroxy-5-(4-((7-((6-(3-hydroxy-3-methylbutoxy)-2-methylpyridin-3-yl)oxy)-2,3-dihydrobenzofuran-3-yl)oxy)phenyl)isothiazole 1-oxide (A);
9) 3-hydroxy-5-(4-((7-((6-(3-hydroxy-3-methylbutoxy)-2-methylpyridin-3-yl)-2,3-dihydrobenzofuran-3-yl)oxy)phenyl)isothiazole 1-oxide (A);
10) 3-hydroxy-5-(4-((7-(4-(3-hydroxy-3-methylbutoxy)-2,6-dimethylphenyl)-2,3-dihydrobenzofuran-3-yl)oxy)phenyl)isothiazole 1-oxide (A);

or a pharmaceutically acceptable salt of the compound, or a pharmaceutically acceptable solvate of the salt or a pharmaceutically acceptable solvate of the compound, and optical isomers of the compounds, or a pharmaceutically acceptable salt of the isomer, or a pharmaceutically acceptable solvate of the salt or a pharmaceutically acceptable solvate of the isomer.

[2] A second aspect of the present invention is a pharmaceutical composition comprising a compound of described in Formula (I), or a pharmaceutically acceptable salt of the compound, or a pharmaceutically acceptable solvate of the compound or a pharmaceutically acceptable solvate of the salt,

[3] A third aspect of the present invention is a prophylactic agent and/or a therapeutic agent for a GPR40-involving disease, characterized by containing as an active ingredient, at least one of the compound described in Formula (I), or a pharmaceutically acceptable salt of the compound, or a pharmaceutically acceptable solvate of the compound or a pharmaceutically acceptable solvate of the salt,

[3-1] Specifically, a prophylactic agent and/or a therapeutic agent for each disease of diabetes [more specifically, any one of or all of Type 1 diabetes (insulin-dependent diabetes), Type 2 diabetes (non-insulin-dependent diabetes), and borderline type diabetes (impaired glucose tolerance (IGT) and/or impaired fasting glycemia (IFG))], obesity, and adiposity, characterized by containing as an active ingredient, at least one of the compound described in Formula (I), a pharmaceutically acceptable salt of the compound, and a pharmaceutically acceptable solvate of the compound or the salt. An inhibitor of Type 2 diabetes in the impaired glucose tolerance is also included in examples of the above prophylactic agent and therapeutic agent. A therapeutic agent for sulfonylurea secondary failure diabetes is also included in the examples thereof, and by the therapeutic agent, also in (administration-ineffective) diabetic patients who cannot obtain a satisfactory hypoglycemic effect even by being administrated with a sulfonylurea agent (such as glibenclamide and glimepiride) or a rapid-acting insulin secretagogues (such as mitiglinide), insulin secretion effect or hypoglycemic effect can be obtained.

Here, in relationship between the blood glucose level and the disease, the diabetes is characterized by exhibiting a fasting blood glucose level of 126 mg/dL or more, or a casual blood glucose level or a 2 hours value of the 75 g oral glucose tolerance test (OGTT) of 200 mg/dL or more. The borderline type diabetes (called also as glucose tolerance disorders) refers to an impaired fasting glycemia (IFG) in which the fasting blood glucose level is 110 mg/dL or more and less than 126 mg/dL and/or an impaired glucose tolerance (IGT) in which a 2 hours value of the 75 g OGTT is 140 mg/dL or more and less than 200 mg/dL.

The insulin resistance refers to a pathological condition in which insulin becomes unable to lower the blood glucose level in the organism and is evaluated by a quantitative glucose clamp technique or HOMA-IR in clinical practice. It is known that the insulin resistance causes a hyperinsulinemia and becomes a risk of a hypertension and a coronary artery disease.

The "adiposity" is defined by the Japan Society for the Study of Obesity as "a pathological condition requiring medically a weight reduction in the case where an obesity-derived or -related health impairment is combined or such a combination is expected". The "obesity" defined here is evaluated by measuring BMI (body mass index, kg/m$^2$). Generally, a body having a BMI of 25 or more is diagnosed as obesity. Examples of the result of the therapy include the reduction of BMI.

[4] A fourth aspect of the present invention is an insulin secretagogues, characterized by containing as an active ingredient, at least one of the compound described in Formula (I), or a pharmaceutically acceptable salt of the compound, or a pharmaceutically acceptable solvate of the compound or a pharmaceutically acceptable solvate of the salt.

[5] A fifth aspect of the present invention is a GPR40 activating agent containing one or more of the compound described in Formula (I), or a pharmaceutically acceptable salt of the compound, or a pharmaceutically acceptable solvate of the compound or a pharmaceutically acceptable solvate of the salt, In the second to fifth aspects and preferred aspects thereof, more preferred substituents and a combination thereof described in Formula (I) are according to descriptions described in the first aspect.

In each aspect as described in [1] to [5] of the present invention, it is preferred to use a compound having a $EC_{50}$ value of preferably, 3 µM or less, more preferably, 1 µM or less, further preferably, 300 nM or less, and most preferably, 100 nM or less, when the GPR40 agonist action is measured by a method accordingly selected (for example, the below described pharmacological test example 1 (an agonist action on relative to GPR40 of human origin)).

In the above aspects of the present invention, the "therapeutic agent" is not only for treating diseases or symptoms, but also for improving diseases or symptoms.

In all of the above aspects, when the term "compound" is used, the compound refers also to a "pharmaceutically acceptable salt of the compound". In addition, there is the case where the compound of the present invention has an asymmetric carbon, and thus, the compound of the present invention includes a mixture of various stereoisomers such as a geometric isomer, a tautomer, and an optical isomer, and an isolated stereoisomer. The compound described in Formula (I) may have an axial asymmetry due to a steric hindrance and an isomer caused by the axial asymmetry (axial chirality) is also included in the compound of Formula (I). The isolation and the purification of such stereoisomers can be performed by a person skilled in the art by an ordinary technique through an optical resolution or an asymmetric synthesis using a preferential crystallization or a column chromatography.

The compound of Formula (I) of the present invention may form an acid addition salt or a salt with a base depending on the type of the substituent. Such salt is not particularly limited so long as the salt is a pharmaceutically acceptable salt. Specific examples thereof include acid addition salts with: mineral acids such as hydrochloric acid, hydrobromic acid, hydriodic acid, sulfuric acid, nitric acid, and phosphoric acid; organic carboxylic acids, for example, an aliphatic monocarboxylic acid such as formic acid, acetic acid, propionic acid, butyric acid, valeric acid, enanthic acid, capric acid, myristic acid, palmitic acid, stearic acid, lactic acid, sorbic acid, and mandelic acid, an aromatic monocarboxylic acid such as benzoic acid and salicylic acid, an aliphatic dicarboxylic acid such as oxalic acid, malonic acid, succinic acid, fumaric acid, maleic acid, malic acid, and tartaric acid, an aliphatic tricarboxylic acid such as citric acid, cinnamic acid, glycolic acid, pyruvic acid, oxylic acid, salicylic acid, and N-acetylcysteine; organic sulfonic acids, for example, an aliphatic sulfonic acid such as methanesulfonic acid, ethanesulfonic acid, and 2-hydroxyethanesulfonic acid, and an aromatic sulfonic acid such as benzenesulfonic acid and p-toluenesulfonic acid; and acidic amino acids such as aspartic acid and glutamic acid, salts (including besides mono salts, disodium salts and dipotassium salts) with a metal, for example, alkali metals such as lithium, sodium, potassium, and cesium, and alkaline earth metals such as magnesium, calcium, and barium, salts with a metal such as aluminum, iron, copper, nickel, cobalt, and zinc, salts with an organic base such as methylamine, ethylamine, tert-butylamine, tert-octylamine, diethylamine, triethylamine, cyclohexylamine, dibenzylamine, ethanolamine, diethanolamine, triethanolamine, piperidine, morpholine, pyridine, lysine, arginine, ornithine, ethylenediamine, N-methylglucamine, glucosamine, a phenylglycine alkyl ester, and guanidine, and salts with glycine, histidine, choline, and ammonium.

These salts can be obtained by an ordinary method including, for example, mixing an equivalent of the compound of the present invention with a solution containing a desired acid, base, or the like, and collecting a desired salt by filtration or distillation-off of a solvent. The compound of the present invention or a salt of the compound can form a solvate with a solvent such as water, ethanol, and glycerol.

The salt of the compound of the present invention includes a mono-salt and a di-salt. The compound of the present invention can form both of an acid addition salt and a salt with a base simultaneously depending on the type of the substituent in the side chains. Furthermore, the present invention encompasses also hydrates, various pharmaceutically acceptable solvates, and crystal polymorphs of the compound of Formula (I) of the present invention. Here, needless to say, the present invention is not limited to the compounds described in Examples below and encompasses all of the compounds of Formula (I) of the present invention and pharmaceutically acceptable salts of the compounds.

The compound of the present invention may be labeled with an isotope (such as $^{3}H$, $^{14}C$, and $^{35}S$).

[Method for Producing the Compound of the Present Invention]

Methods for producing the compound of Formula (I) of the present invention will be described below.

The compound of Formula (I) of the present invention, a salt of the compound, and a solvate of the compound or the salt can be produced by a combination of commonly known chemical production methods. Typical production methods will be described below.

In each Formula in the production methods below, each definition of ring A, ring A', $R^1$, $R^2$, $R^3$, $R^4$, $R^5$, $R^6$, $R^7$, $R^8$, $R^9$, $R^{10}$, $R^{11}$, $R^{12}$, X, V, p, q, q1, r, r1, s, j, k, n1, n2, and n3 is the same as each definition in Formula (I), Formula (II), Formula (III), Formula (IV), Formula (V), Formula (A), Formula (A)-III, Formula (A)-IV, and Formula (A)-V described in the first aspect above unless otherwise specified.

In the production methods, the definition of R' is a $C_{1-6}$ alkyl group such as a methyl group and an ethyl group unless otherwise specified.

In the production methods, the definition of R" is a hydrogen atom, a hydroxy group, or a $C_{1-6}$ alkoxy group such as a methoxy group and an ethoxy group unless otherwise specified.

In the production methods, the definition of Y is a halogen atom unless otherwise specified.

In the production methods, the definition of Z is a leaving group including a hydroxy group, a halogen atom, and a sulfonyloxy group such as a methanesulfonyloxy group, a p-toluenesulfonyloxy group, and a trifluoromethanesulfonyloxy group unless otherwise specified.

In the production methods, the definition of W is boronic acid, a boronic ester, or a trifluoroborate salt unless otherwise specified.

In the production methods, for the definitions of $W^1$ and $W^2$, $W^2$ is boronic acid, a boronic ester, or a trifluoroborate salt when $W^1$ is a hydroxy group, a halogen atom, or a trifluoromethanesulfonyloxy group, and $W^2$ is a hydroxy group, a halogen atom, or a trifluoromethanesulfonyloxy group when $W^1$ is a boronic acid, a boronic ester, or a trifluoroborate salt unless otherwise specified.

In the production methods, the definition of $P^1$ is a protective group for a hydroxy group (—OH), a thiol group (—SH), or an imino group (—NH—) unless otherwise specified. Examples of the protective group for a hydroxy group include an alkoxyalkyl group such as a methoxymethyl group, a methoxyethoxymethyl group, and a tetrahydropyranyl group; an arylmethyl group such as a benzyl group and a triphenylmethyl group; a silyl group such as a triethylsilyl group and a t-butyldimethylsilyl group; an alkanoyl group such as an acetyl group; an aroyl group such as a benzoyl group; an alkoxycarbonyl group such as a t-butoxycarbonyl group; and an arylmethoxycarbonyl group such as a benzyloxycarbonyl group. Examples of the protective group for a thiol group include an arylmethyl group such as a benzyl group and a triphenylmethyl group; an alkanoyl group such as an acetyl group and a pivaloyl group; and an aroyl group such as a benzoyl group. Examples of the protective group for an imino group include an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; an arylmethyl group such as a benzyl group and a triphenylmethyl group; and an aroyl group such as a benzoyl group.

In the production methods, the definition of $P^2$ is a protective group for a phenolic hydroxy group unless otherwise specified. Examples of the protective group include an alkoxyalkyl group such as a methoxymethyl group, a methoxyethoxymethyl group, and a tetrahydropyranyl group; an arylmethyl group such as a benzyl group; a silyl group such as a trimethylsilyl group and a t-butyldimethylsilyl group; an alkanoyl group such as an acetyl group and a pivaloyl group; an aroyl group such as a benzoyl group; an alkoxycarbonyl group such as a t-butoxycarbonyl group; and an arylmethoxycarbonyl group such as a benzyloxycarbonyl group.

In the production methods, the definition of $P^3$ is a protective group for an imino group (—NH—) unless otherwise specified. Examples of the protective group include an arylmethyl group such as a benzyl group and a triphenylmethyl group; an alkoxyalkyl group such as a methoxymethyl group and a methoxyethoxymethyl group; an alkyl group such as a tert-butyl group; an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; and an aroyl group such as a benzoyl group.

Deprotection methods of such protective groups are different depending on the chemical properties of a protected reactive group (a hydroxy group, a thiol group, or an imino group) and an employed protective group. For example, an acyl-type protective group such as an alkanoyl group, an alkoxycarbonyl group, and an aroyl group can be hydrolyzed using a suitable base such as an alkali metal hydroxide including lithium hydroxide, sodium hydroxide, and potassium hydroxide for the deprotection. An alkoxyalkyl-type protective group such as a methoxymethyl group, a methoxyethoxymethyl group, and a tetrahydropyranyl group, a substituted methoxycarbonyl-type protective group such as a t-butoxycarbonyl group and a para-methoxybenzyloxycarbonyl group, and a silyl-type protective group such as a triethylsilyl group and a t-butyldimethylsilyl group can be removed using a suitable acid such as acetic acid, hydrochloric acid, hydrobromic acid, sulfuric acid, phosphoric acid, trifluoroacetic acid, and trifluoromethanesulfonic acid or a combination of them. The silyl-type protective group can also be removed using a suitable fluorine ion ($F^-$) generating reagent such as tetrabutylammonium fluoride and hydrogen fluoride. An arylmethoxycarbonyl group such as a benzyloxycarbonyl group, a para-methoxybenzyloxycarbonyl group, and a para-nitrobenzyloxycarbonyl group and an arylmethyl group such as a benzyl group can be removed by hydrogenolysis using a palladium carbon catalyst. A benzyl group can be removed by Birch reduction using metallic sodium in liquid ammonia. A triphenylmethyl group can be removed using a suitable acid such as acetic acid, hydrochloric acid, hydrobromic acid, sulfuric acid, phosphoric acid, trifluoroacetic acid, and trifluoromethanesulfonic acid or a combination of them. It can also be removed by Birch reduction using metallic sodium in liquid ammonia and removed by hydrogenolysis using a palladium carbon catalyst.

During the production of the compound of Formula (I) of the present invention, when it has a reactive group such as a hydroxy group, an amino group, and a carboxy group, such a group may be properly protected in any reaction step, and the protective group may be removed in a suitable step. Above-mentioned methods for introducing and removing such protective groups are properly employed depending on the type of a group to be protected or a protective group. For example, such introduction and removal can be performed by methods described in [Protective Groups in Organic Synthesis, edited by Greene et al, the fourth edition (2007), John Wiley & Sons].

Required starting materials are commercially available or can be easily obtained from commercial products by usual production methods in organic chemistry.

Reaction conditions in the production methods are as follows unless otherwise specified. The reaction temperature is in a range from −78° C. to the reflux temperature of a solvent, and the reaction time is a time sufficient for a reaction. Examples of the reaction inert solvent include, but are not limited to, an aromatic hydrocarbon solvent such as toluene, benzene and xylen; alcholic solvent such as methanol, ethanol, 2-propanol; a polar solvent such as water, acetonitrile, N,N-dimethylformamide, dimethyl sulfoxide, and 1,3-dimethyl-2-imidazolidinone; a basic solvent such as triethylamine and pyridine; a halogenated solvent such as chloroform, methylene chloride, and 1,2-dichloroethane; an ether solvent such as 1,2-dimethoxyethane, cycropenthylmethylether, diethyl ether, tetrahydrofuran, and dioxane; and a mixed solvent of them. Such solvents can be properly selected depending on reaction conditions. Examples of the base include, but are not limited to, an inorganic base such as sodium carbonate, potassium carbonate, cesium carbonate, sodium hydroxide, potassium hydroxide, and sodium hydride; and an organic base such as triethylamine, N,N-diisopropylethylamine, pyridine, N,N-dialkylaniline, lithium diisopropylamide, and lithiumbistrimethylsilylamide. Examples of the acid include, but are not limited to, a mineral acid such as hydrochloric acid, sulfuric acid and nitric acid, and an organic acid such as methanesulfonic acid and p-toluenesulfonic acid.

Hereinafter, production methods will be described, but the present invention is not limited to these methods.

The compound of Formula (I) of the present invention can be obtained from a compound of Formula (C-I).

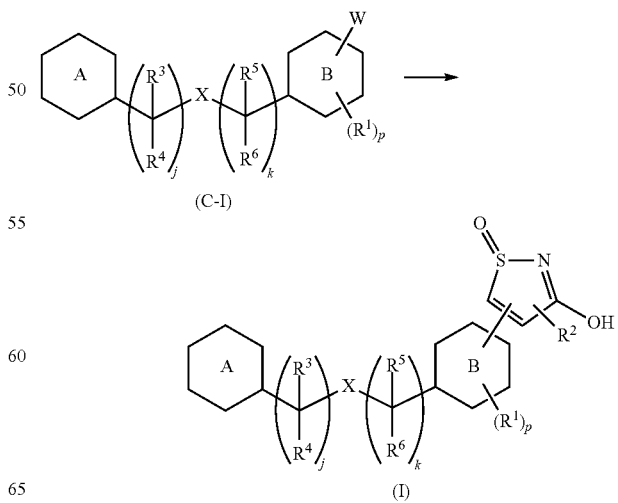

And, the compound of Formula (I)-A of the present invention can be obtained from a compound of Formula (IX).

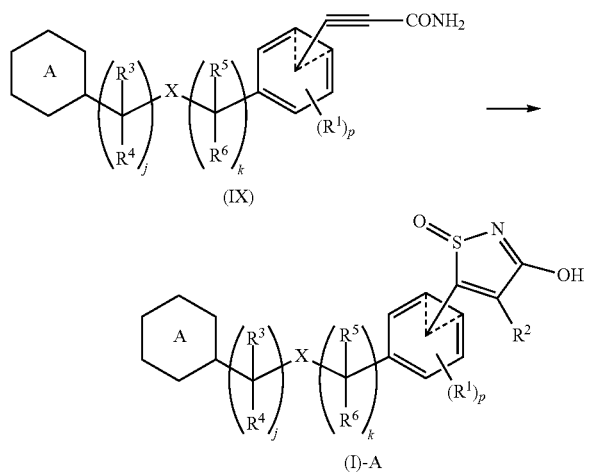

(1) Methods for producing the compound of Formula (I) or Formula (I)-A of the present invention will be described below.

<Production Method A>
<When $R^2$=H in Formula (I)-A>

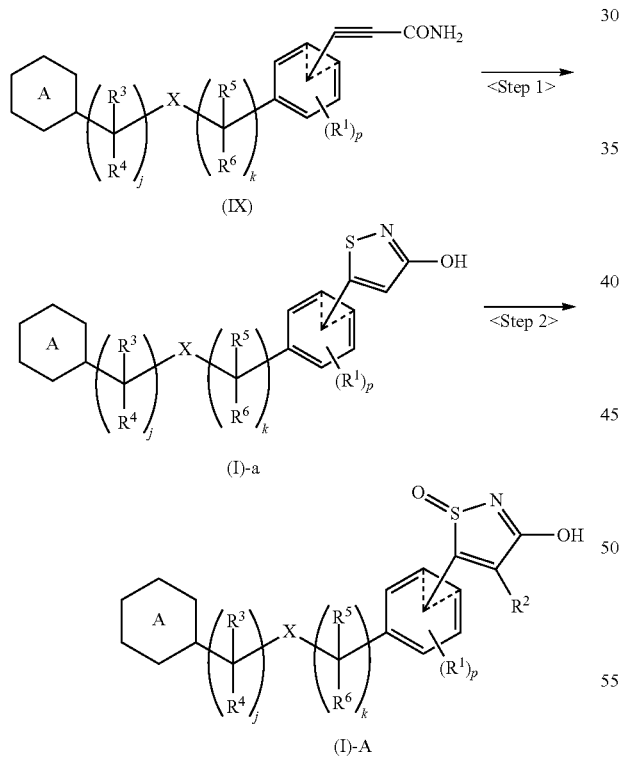

<Step 1>
The compound of Formula (IX) obtained in <Production Method E> or <Production Method F> below is subjected to isothiazole ring formation reaction. In accordance with a method known in the literature, for example, the method described in [Heterocyclic Compounds, New Edition, Applications, pp. 41-57 (2004), Kodansha Ltd.], [Chemische Berichte, vol. 94, p. 2950 (1961)], or [Chemische Berichte, vol. 96, p. 944 (1963)], a compound of Formula (I)-a can be produced by reacting the compound of Formula (IX) with a thiol (SH) source such as sodium hydrosulfide and hydrogen sulfide gas in a reaction inert solvent such as methanol, ethanol, and water or in a mixed solvent of them at a temperature from 0° C. to a reflux temperature of the solvent, and then by reacting the obtained thiol adduct in the presence of a halogen such as iodine and bromine and in the presence or absence of a base such as pyridine and potassium carbonate in a reaction inert solvent such as methanol, ethanol, ethyl acetate, and water or a mixed solvent of them at a temperature from 0° C. to a reflux temperature of the solvent.

<Step 2>
The sulfur atom in the compound of Formula (I)-a is oxidized. In accordance with a method known in the literature, for example, the method described in [Jikken Kagaku Koza (Experimental Chemistry Course), the fourth edition, vol. 20, Organic Synthesis V, Oxidation Reaction, pp. 276-280 (1992), Maruzen Co., Ltd.], a compound of Formula (I)-A can be produced by reacting the compound of Formula (I)-a in the presence of a peracid or a peroxide such as hydrogen peroxide water, m-chloroperbenzoic acid (MCPBA), peracetic acid, trifluoroperacetic acid, Oxone (registered trademark) (DuPont), and tert-butylhydroperoxide (TBHP) in a reaction inert solvent including a halogenated solvent such as dichloromethane and chloroform, an aromatic hydrocarbon solvent such as toluene and benzene, and a polar solvent such as acetonitrile, methanol, acetone, and water or in a mixed solvent of them at a temperature from 0° C. to a reflux temperature of the solvent. In the oxidation reaction, selection of an oxidizing agent and suitable selection of a reagent amount, a reaction temperature, a reaction time, a solvent, and the like can produce a sulfoxide and a sulfone separately. The sulfoxide and the sulfone can be separated through a common technique such as column chromatography.

<Production Method B>
<When $R^2$=H in Formula (I)-A>

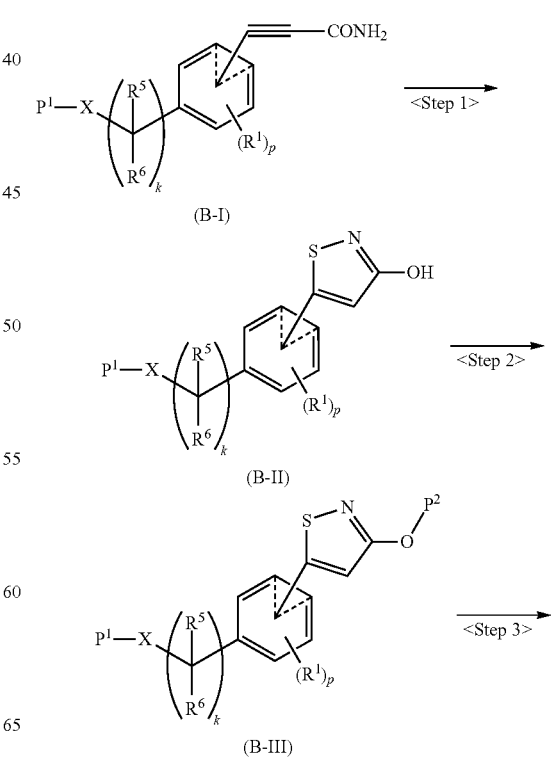

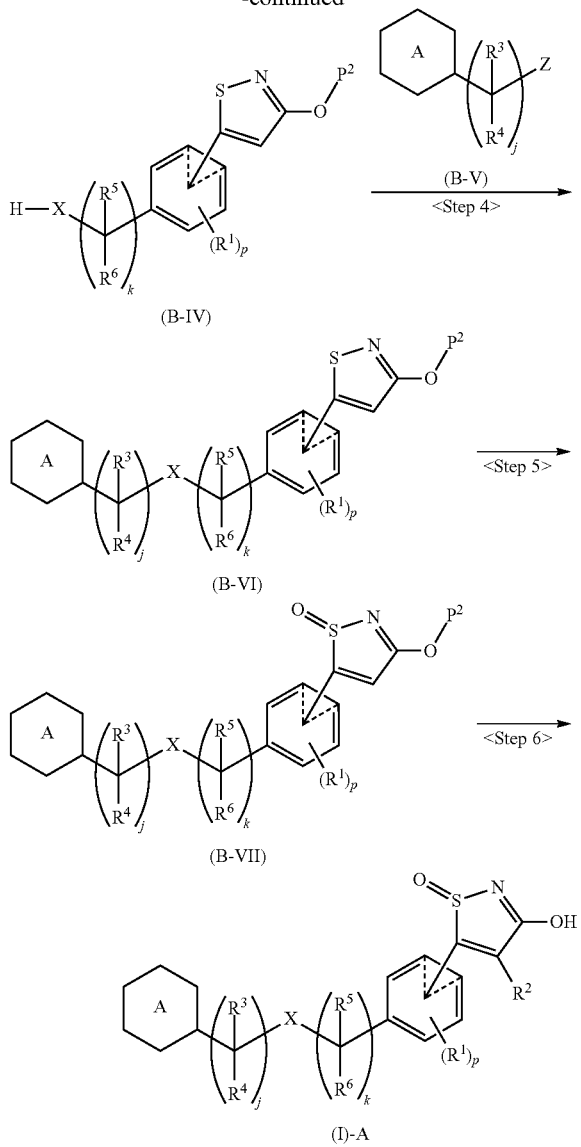

<Step 1>
A compound of Formula (B-I) is subjected to isothiazole ring formation reaction. A compound of Formula (B-II) can be produced by reacting the compound of Formula (B-I) (it is known in the art or can be easily produced from a known compound as described later in (Production Method E), and is a compound that is obtained by proper protection) in a similar manner to that in <Step 1> in (Production Method A).

<Step 2>
The compound of Formula (B-II) is protected with a protective group $P^2$. A compound of Formula (B-III) can be produced by reacting the compound of Formula (B-II) with the protective group $P^2$ by a method suitable for the protective group.

<Step 3>
The protective group P' in the compound of Formula (B-III) is deprotected. A compound of Formula (B-IV) can be produced by deprotecting the protective group P' in the compound of Formula (B-III) by a method suitable for the protective group.

<Step 4>
The compound of Formula (B-IV) is subjected to substitution reaction with a compound of Formula (B-V).

<When Z≠Hydroxy Group>
In accordance with a method known in the literature, for example, the methods described in [Jikken Kagaku Koza (Experimental Chemistry Course), the fourth edition, vol. 20, Organic Synthesis II, Alcohol and Amine, pp. 187-200 and 284-292 (1992), Maruzen Co., Ltd.] and [Jikken Kagaku Koza (Experimental Chemistry Course), the fourth edition, vol. 20, Organic Synthesis VI, Hetero Element- or Main Group Metal Element-Containing Compound, pp. 319-350 (1992), Maruzen Co., Ltd.], a compound of Formula (B-VI) can be produced by the substitution reaction of the compound of Formula (B-IV) in the presence of the compound of Formula (B-V) in the presence or absence of a base such as triethylamine, pyridine, sodium hydride, sodium hydroxide, and potassium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<When Z=Hydroxy Group, X=Oxygen Atom, and k=0>
In accordance with a method known in the literature, for example, the method described in [Journal of Medicinal Chemistry, vol. 51 (23), pp. 7640-7644 (2008)], a compound of Formula (B-VI) can be produced by Mitsunobu reaction of the compound of Formula (B-IV) in the presence of the compound of Formula (B-V) in the presence of an organophosphorus compound such as triphenylphosphine and an azo compound such as azodicarboxylic acid ester and azodicarboxylic amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<When Z=Hydroxy Group, X=Nitrogen Atom, and k=0>
In accordance with a method known in the literature, for example, the methods described in [WO 2010/143733 pamphlet, p. 71 [0179]: Step 2 in Reaction scheme 1], [Tetrahedron Letters, vol. 36, pp. 6373-6374 (1995)], and [Tetrahedron Letters, vol. 38, pp. 5831-5834 (1997)], a compound of Formula (B-VI) can be produced by Mitsunobu reaction of the compound of Formula (B-IV) in the presence of the compound of Formula (B-V) in the presence of an organophosphorus compound such as triphenylphosphine and an azo compound such as azodicarboxylic acid ester and azodicarboxylic amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

The compound of Formula (B-V) used in this step is known in the art or can be produced from a corresponding known compound in accordance with a method known in the literature as described in (Production Method M), (Production Method N), (Production Method O), and (Production Method P) below. For example, it can be produced from a corresponding compound in accordance with the methods described in [WO 2005/063729 pamphlet, Reference Examples 2 and 3, for example], [WO 2005/086661 pamphlet, Example 18, for example], [WO 2008/001931 pamphlet, Reaction Scheme 2, Reference Examples 15-19, for example], [WO 2009/039943 pamphlet, pp. 51-52], [WO 2009/054423 pamphlet, Production Examples 12, 24, 37, for example], [WO 2010/085525 pamphlet, Examples 2-5, 3-3, and 4-4, for example], and [WO 2010/091176 pamphlet, Example 1-3, for example]. Examples of the compound of Formula (B-V) include compounds that are obtained by properly protecting the produced compounds.

In Formula (I) in WO 2009/039943 pamphlet, a compound that is represented by a formula similar to Formula (A)-IX in the present application is represented, as Formula (B-V), by Formula III in WO 2009/039943 pamphlet, p. 52. By reacting the compound under the condition described in <When Z≠hydroxy group> described above, a compound of Formula (B-VI) (X=nitrogen atom) can be produced.

<Step 5>

The sulfur atom in the compound of Formula (B-VI) is oxidized. A compound of Formula (B-VII) can be produced by reacting the compound of Formula (B-VI) in a similar manner to that in <Step 2> in (Production Method A).

<Step 6>

The protective group $P^2$ in the compound of Formula (B-VII) is deprotected. The compound of Formula (I)-A can be produced by deprotecting the protective group $P^2$ in the compound of Formula (B-VII) by a method suitable for the protective group.

<Production Method C>

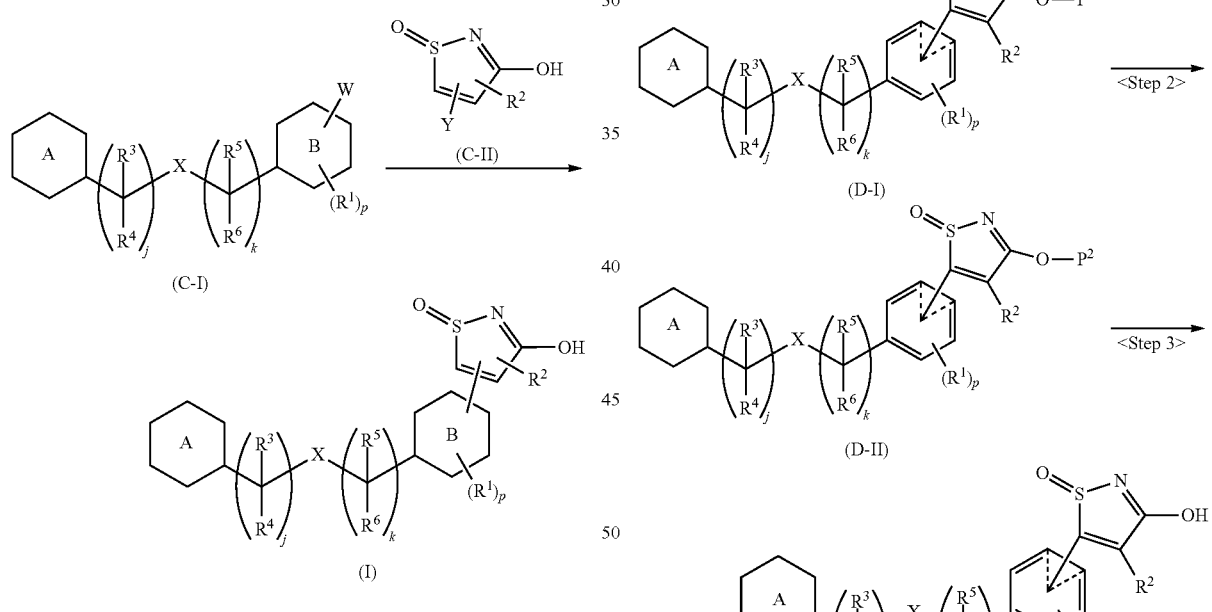

(C-I)

(C-II)

(I)

A compound of Formula (C-I) obtained in (Production Method H) below is subjected to substitution reaction with a compound of Formula (C-II) obtained in (Production Method I) below. In accordance with a method known in the literature, for example, the methods described in [Jikken Kagaku Koza (Experimental Chemistry Course), the fifth edition, vol. 18, Synthesis of Organic Compound VI, Organic Synthesis Using Metal, pp. 327-352 (2004), Maruzen Co., Ltd.] and [Journal of Medicinal Chemistry, vol. 48 (20), pp. 6326-6339 (2005)], the compound of Formula (I) can be produced by reacting the compound of Formula (C-I) in the presence of the compound of Formula (C-II) in the presence of a palladium catalyst such as palladium (II) acetate, tetrakis triphenylphosphine palladium, tris(dibenzylideneacetone)dipalladium, bis (dibenzylideneacetone)palladium, and [1,1'-bis(diphenylphosphino)ferrocene]dichloropalladium (II), a phosphine reagent such as triphenylphosphine, tris(tert-butyl)phosphine, tris(o-tolyl)phosphine, 2-dicyclohexylphosphino-2', 6'-dimethoxybiphenyl, and 2-dicyclohexylphosphino-2',4', 6'-triisopropylbiphenyl, and an organic or inorganic base such as triethylamine, N,N-diisopropylethylamine, and potassium phosphate using a reaction inert solvent such as toluene, xylene, N,N-dimethylformamide, and N,N-dimethylacetamide or a mixed solvent of them at a temperature from 0° C. to a reflux temperature of the solvent. Alternatively, it can be produced using tetramethylammonium chloride, tetrabutylammonium chloride, or the like in place of the phosphine reagent in a similar method.

<Production Method D>

<When $R^2$≠Hydrogen Atom in Formula (I)-A>

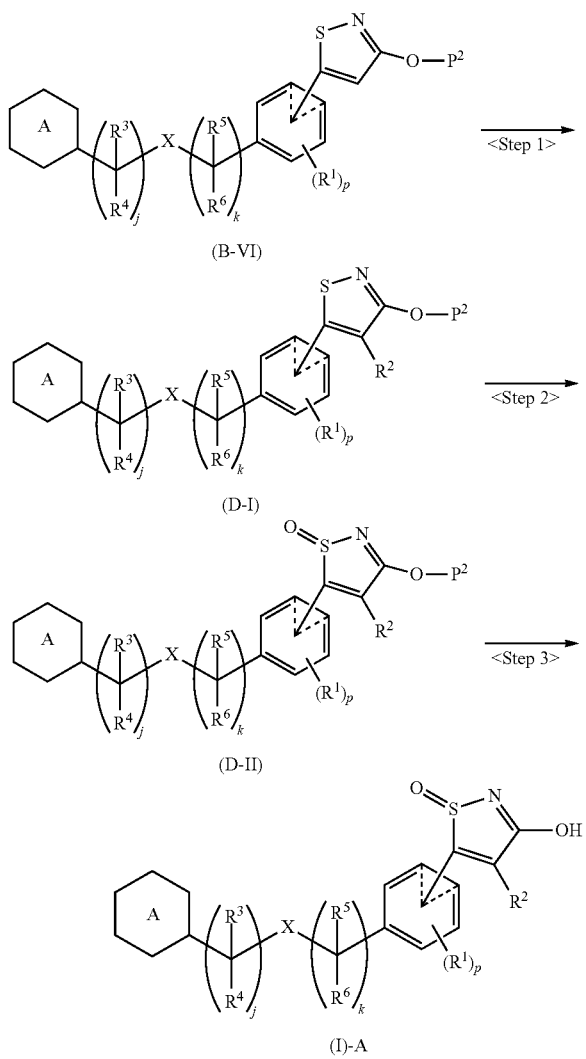

(B-VI)

(D-I)

(D-II)

(I)-A

<Step 1>

The compound of Formula (B-VI) obtained in <Step 4> in (Production Method B) above is subjected to substitution reaction on the isothiazole ring.

<When $R^2$=Halogen Atom>

In accordance with a method known in the literature, for example, the method described in [WO 1997/031906 pamphlet, Example 68 (b)], a compound of Formula (D-I) can be produced by halogenating the compound of Formula (B-VI) in the presence of a corresponding halogenating agent such as N-fluorodibenzenesulfonimide, N-chlorosuccinimide, N-bromosuccinimide, and N-iodosuccinimide in the presence of a base such as n-butyllithium, lithium diisopropylamide, lithium bis(trimethylsilyl)amide, sodium bis(trimethylsilyl)amide, and potassium bis(trimethylsilyl)amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from −78° C. to a reflux temperature of the solvent.

<When $R^2$=Cyano Group>

In accordance with a method known in the literature, for example, the method described in [Tetrahedron Letters, vol. 40 (47), pp. 8193-8195 (1999)], a compound of Formula (D-I) can be produced by reacting the compound of Formula (D-I) ($R^2$=I, Br) obtained in <When $R^2$=halogen atom> in <Step 1> in (Production Method D) in the presence of a corresponding cyanating agent such as zinc cyanide and potassium ferrocyanide in the presence of a palladium catalyst such as palladium (II) acetate, tetrakis triphenylphosphine palladium, tris(dibenzylideneacetone)dipalladium, and [1,1′-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, and potassium phosphate using a reaction inert solvent such as toluene, xylene, N,N-dimethylformamide, and N,N-dimethylacetamide or a mixed solvent of them at a temperature from 0° C. to a reflux temperature of the solvent. Alternatively, it can be produced using tetramethylammonium chloride, tetrabutylammonium chloride, or the like in place of the phosphine reagent in a similar method.

<Step 2>

The sulfur atom in the compound of Formula (D-I) is oxidized. A compound of Formula (D-II) can be produced by reacting the compound of Formula (D-I) in a similar manner to that in <Step 2> in (Production Method A).

<Step 3>

The protective group $P^2$ in the compound of Formula (D-II) is deprotected. The compound of Formula (I)-A can be produced by reacting the compound of Formula (D-II) in a similar manner to that in <Step 6> in (Production Method B).

(2) Next, methods for producing compounds of Formula (IX), Formula (B-I), and Formula (B-II) will be described.

The compounds of Formula (IX) and Formula (B-I) can be produced by the methods below.

<Production Method E>

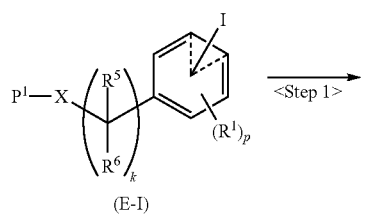

(E-I)

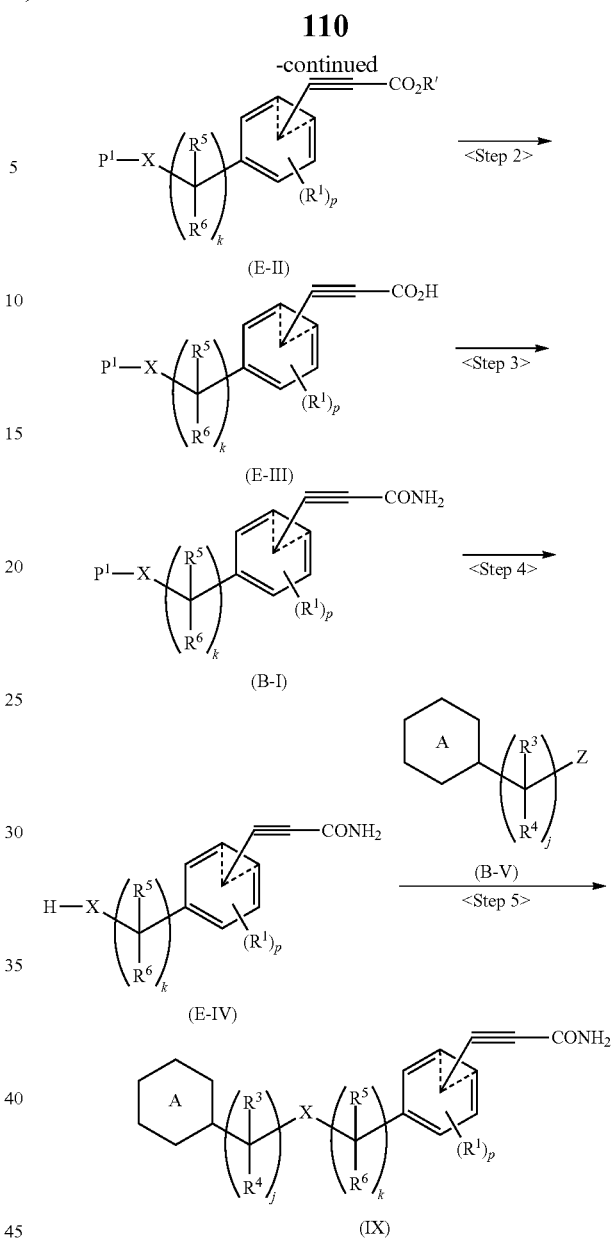

<Step 1>

A compound of Formula (E-I) is subjected to alkynylation. In accordance with a method known in the literature, for example, the methods described in [Jikken Kagaku Koza (Experimental Chemistry Course), the fourth edition, vol. 19, Organic Synthesis I, Hydrocarbon and Halogenated Compounds, pp. 318-335 (1992), Maruzen Co., Ltd.] and [WO 2008/066131 pamphlet, Reference Example 1], a compound of Formula (E-II) can be produced by reacting the compound of Formula (E-I) that is known in the art or can be easily produced from a known compound, in the presence of a corresponding propiolic acid ester such as methyl propiolate and ethyl propiolate and copper oxide (II) using a reaction inert solvent such as toluene, xylene, N,N-dimethylformamide, and N,N-dimethylacetamide or a mixed solvent of them at a temperature from 0° C. to a reflux temperature of the solvent.

Alternatively, the compound of Formula (E-II) can be produced by reaction in the presence of an ortho ester of a corresponding propiolic acid such as 3,3,3-triethoxypropyne or a corresponding propiolic acid ester such as methyl propiolate and ethyl propiolate in the presence of copper iodide (I) or zinc bromide in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, potassium phosphate, and potassium carbonate using a reaction inert solvent such as toluene, xylene, N,N-dimethylformamide, and N,N-dimethylacetamide or a mixed solvent of them at a temperature from 0° C. to a reflux temperature of the solvent.

<Step 2>

The compound of Formula (E-II) is hydrolyzed. In accordance with a method known in the literature, for example, the method described in [Jikken Kagaku Koza (Experimental Chemistry Course), the fourth edition, vol. 22, Organic Synthesis IV, Acid, Amino Acid, and Peptide, pp. 1-43 (1992), Maruzen Co., Ltd.], a compound of Formula (E-III) can be produced by reacting the compound of Formula (E-II) in the presence of a base such as lithium hydroxide, sodium hydroxide, potassium hydroxide, lithium carbonate, sodium carbonate, and potassium carbonate using a reaction inert solvent such as water, methanol, ethanol, 2-propanol, N,N-dimethylformamide, 1,4-dioxane, and tetrahydrofuran or a mixed solvent of them at a temperature from 0° C. to a reflux temperature of the solvent.

<Step 3>

The compound of Formula (E-III) is subjected to amidation reaction. In accordance with a method known in the literature, for example, the method described in [Jikken Kagaku Koza (Experimental Chemistry Course), the fourth edition, vol. 22, Organic Synthesis IV, Acid, Amino Acid, and Peptide, pp. 191-309 (1992), Maruzen Co., Ltd.], a compound of Formula (B-I) can be produced by reacting the compound of Formula (E-III) with aqueous ammonia or ammonia gas in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxytris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), and 4-(4,6-dimethoxy-1,3,5-triazin-2-yl)-4-methylmorpholinium chloride (DMTMM) in a reaction inert solvent including a halogenated solvent such as dichloromethane and chloroform, an ether solvent such as diethyl ether and tetrahydrofuran, an aromatic hydrocarbon solvent such as toluene and benzene, a polar solvent such as N,N-dimethylformamide, and an alcoholic solvent such as methanol, ethanol, and 2-propanol or in a mixed solvent of them in the presence or absence of a base such as triethylamine and pyridine at a temperature from 0° C. to a reflux temperature of the solvent. When the compound of Formula (E-III) is converted into an acid chloride, in accordance with the method described in [Jikken Kagaku Koza (Experimental Chemistry Course), the fourth edition, vol. 22, Organic Synthesis IV, Acid, Amino Acid, and Peptide, pp. 144-146 (1992), Maruzen Co., Ltd.] and the like, the compound of Formula (B-I) can be produced by reacting the acid chloride in the presence of a base such as triethylamine and pyridine in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<Step 4>

The protective group P' in the compound of Formula (B-I) is deprotected. A compound of Formula (E-IV) can be produced by reacting the compound of Formula (B-I) in a similar manner to that in <Step 3> in (Production Method B).

<Step 5>

The compound of Formula (E-IV) is subjected to substitution reaction with a compound of Formula (B-V). A compound of Formula (IX) can be produced by reacting the compound of Formula (E-IV) with the compound of Formula (B-V) in a similar manner to that in <Step 4> in (Production Method B).

The compound of Formula (IX) can also be produced by the following method.

<Production Method F>

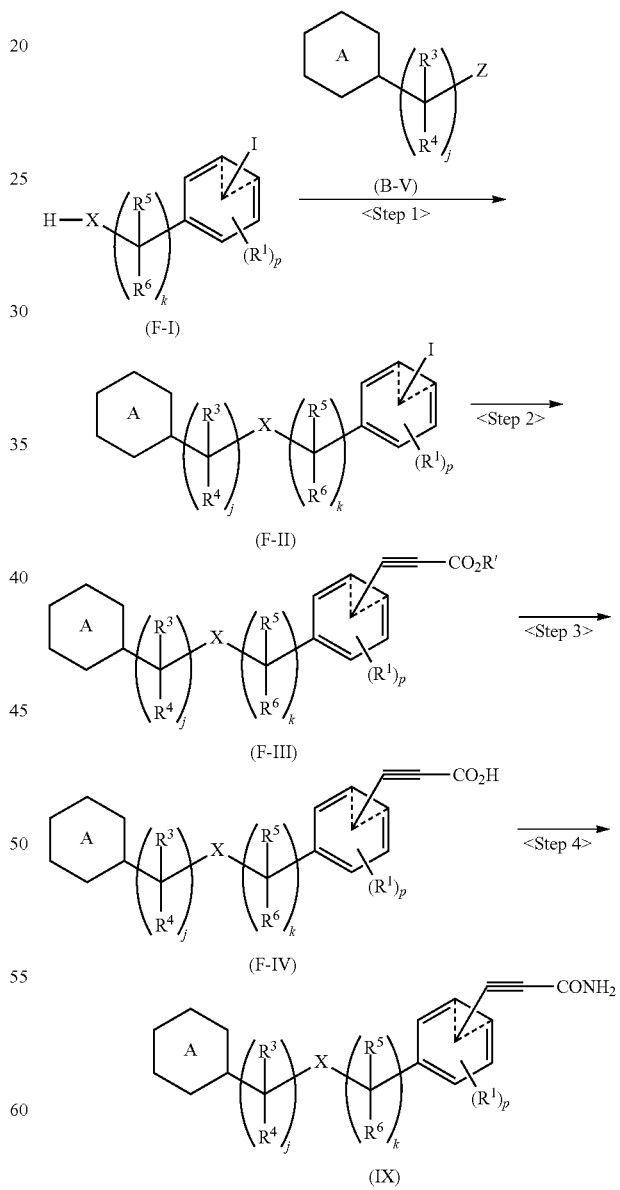

<Step 1>

A compound of Formula (F-I) is subjected to substitution reaction with a compound of Formula (B-V). A compound of Formula (F-II) can be produced by reacting the compound of Formula (F-I) that is known in the art or can be easily produced from a known compound with the compound of Formula (B-V) in a similar manner to that in <Step 4> in (Production Method B).

<Step 2>

The compound of Formula (F-II) is subjected to alkynylation. A compound of Formula (F-III) can be produced by reacting the compound of Formula (F-II) in a similar manner to that in <Step 1> in (Production Method E).

<Step 3>

The compound of Formula (F-III) is hydrolyzed. A compound of Formula (F-IV) can be produced by reacting the compound of Formula (F-III) in a similar manner to that in <Step 2> in (Production Method E).

<Step 4>

The compound of Formula (F-IV) is subjected to amidation reaction. A compound of Formula (IX) can be produced by reacting the compound of Formula (F-IV) in a similar manner to that in <Step 3> in (Production Method E).

The compound of Formula (B-II) can also be produced by the following method.

<Production Method G>

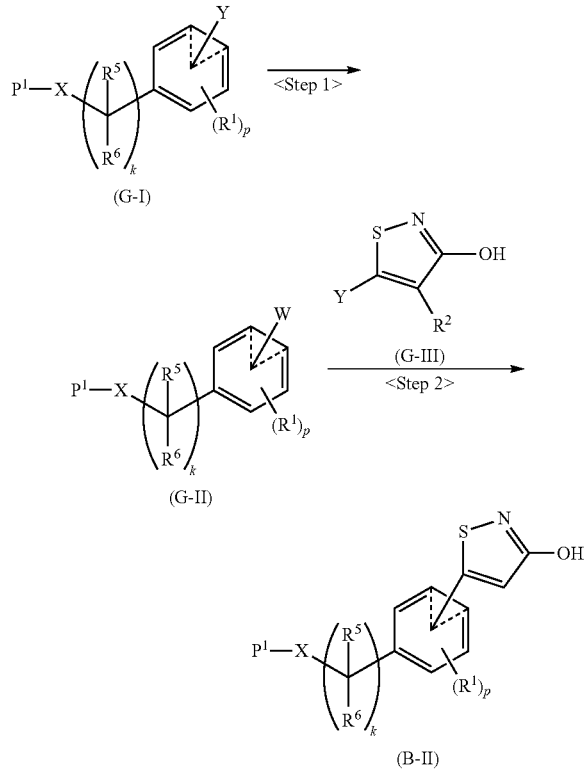

<Step 1>

A compound of Formula (G-I) is subjected to boration reaction.

<When W=Boronic Ester>

In accordance with a method known in the literature, for example, the method described in [The Journal of Organic Chemistry, vol. 60, pp. 7508-2665 (1995)], a boronic ester of Formula (G-II) can be produced by reacting the compound of Formula (G-I) that is known in the art or can be easily produced from a known compound in the presence of a diboronic ester such as bis(pinacolato)diboron and bis(neopentylglycolato)diboron in the presence of a palladium catalyst such as palladium (II) acetate, tetrakis triphenylphosphine palladium, tris(dibenzylideneacetone)dipalladium, and [1,1'-bis(diphenylphosphino)ferrocene]dichloropalladium (II) in the presence or absence of a phosphine reagent such as triphenylphosphine, tris(tert-butyl)phosphine, tris(o-tolyl)phosphine, and 2-dicyclohexylphosphino-2',6'-dimethoxybiphenyl and an organic or inorganic base such as triethylamine, N,N-diisopropylethylamine, and potassium acetate using a reaction inert solvent such as toluene, N,N-dimethylformamide, dimethyl sulfoxide, and 1,4-dioxane or a mixed solvent of them at a temperature from 0° C. to a reflux temperature of the solvent. Alternatively, it can be produced using tetramethylammonium chloride, tetrabutylammonium chloride, or the like in place of the phosphine reagent in a similar method.

<When W=Boronic Acid>

In accordance with a method known in the literature, for example, the method described in [Chemische Berichte, vol. 42, p. 3090 (1909)], a boronic acid of Formula (G-II) can be produced by reacting the compound of Formula (G-I) using a reaction inert solvent such as toluene, tetrahydrofuran, and 1,4-dioxane or a mixed solvent of them in the presence of an alkyllithium such as n-butyllithium and sec-butyllithium, a Grignard reagent such as isopropyl magnesium chloride, or metal magnesium, with a trialkyl borate such as trimethyl borate and triisopropyl borate at a temperature from −78° C. to room temperature, followed by reaction with an acid such as hydrochloric acid and sulfuric acid at a temperature from 0° C. to a reflux temperature of the solvent.

<When W=Trifluoroborate Salt>

In accordance with a method known in the literature, for example, the method described in [Chemical Reviews, vol. 108, pp. 288-325 (2008)], a trifluoroborate salt of Formula (G-II) can be produced by reacting the compound of Formula (G-II) (W=boronic ester or boronic acid) obtained in <When W=boronic ester or boronic acid> in <Step 1> in (Production Method G) in the presence of potassium hydrogen difluoride (KHF$_2$) using a reaction inert solvent such as methanol, ethanol, and water or a mixed solvent of them at a temperature from 0° C. to a reflux temperature of the solvent.

<When W=Boronic Acid N-methylimino Diacetic Acid (MIDA) Ester>

In accordance with a method known in the literature, for example, the method described in [Journal of Organometallic Chemistry, vol. 307 (1), pp. 1-6 (1986)], a boronic acid N-methylimino diacetic acid (MIDA) ester of Formula (G-II) can be produced by reacting the compound of Formula (G-II) (W=boronic acid) obtained in <When W=boronic acid> in <Step 1> in (Production Method G) in the presence of N-methyliminodiacetic acid (MIDA) using a reaction inert solvent such as benzene, toluene, xylene, and dimethyl sulfoxide or a mixed solvent of them at a temperature from 0° C. to a reflux temperature of the solvent.

<Step 2>

The compound of Formula (G-II) is subjected to substitution reaction with a compound of Formula (G-III). A compound of Formula (B-II) can be produced by reacting the compound of Formula (G-II) with the compound of Formula (G-III) that is known in the art or can be easily produced from a known compound in a similar manner to that in (Production Method C).

(3) Next, a method for producing the compound of Formula (C-I) will be described.

<Production Method H>

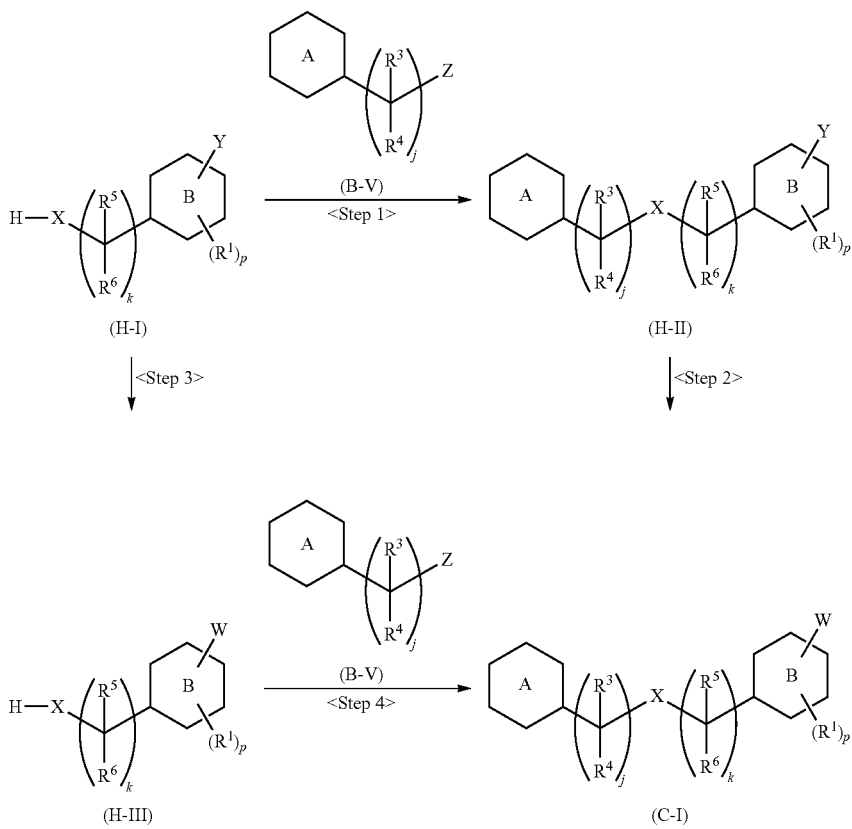

<Step 1>

A compound of Formula (H-I) is subjected to substitution reaction with a compound of Formula (B-V). A compound of Formula (H-II) can be produced by reacting the compound of Formula (H-I) that is known in the art or can be easily produced from a known compound with the compound of Formula (B-V) in a similar manner to that in <Step 4> in (Production Method B).

<Step 2>

The compound of Formula (H-II) is subjected to boration reaction. The compound of Formula (C-I) can be produced by reacting the compound of Formula (H-II) in a similar manner to that in <Step 1> in (Production Method G).

<Step 3>

The compound of Formula (H-I) is subjected to boration reaction. A compound of Formula (H-III) can be produced by reacting the compound of Formula (H-I) in a similar manner to that in <Step 1> in (Production Method G).

<Step 4>

The compound of Formula (H-III) is subjected to substitution reaction with the compound of Formula (B-V). The compound of Formula (C-I) can be produced by reacting the compound of Formula (H-III) with the compound of Formula (B-V) in a similar manner to that in <Step 4> in (Production Method B).

(4) Next, a method for producing the compound of Formula (C-II) will be described.

<Production Method I>

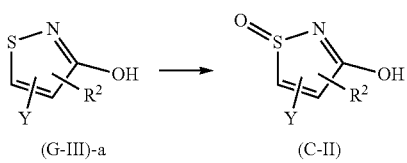

The sulfur atom in a compound of Formula (G-III)-a is oxidized. A compound of Formula (C-II) can be produced by reacting the that is known in the art or can be easily produced from a known compound with a compound of Formula (G-III)-a in a similar manner to that in <Step 2> in (Production Method A).

The compound of Formula (C-II) includes optical isomers. The optical isomers can be separated through optical resolution using column chromatography or asymmetric synthesis by a person skilled in the art based on conventional techniques. For example, each enantiomer can be obtained using preparative chromatography as described in Step 1 in Reference Example 1 described later.

(5) The compound of Formula (I) or Formula (I)-A can also be produced by the following method.

<Production Method J>
<When X=Oxygen Atom in Formula (I)-A Above>

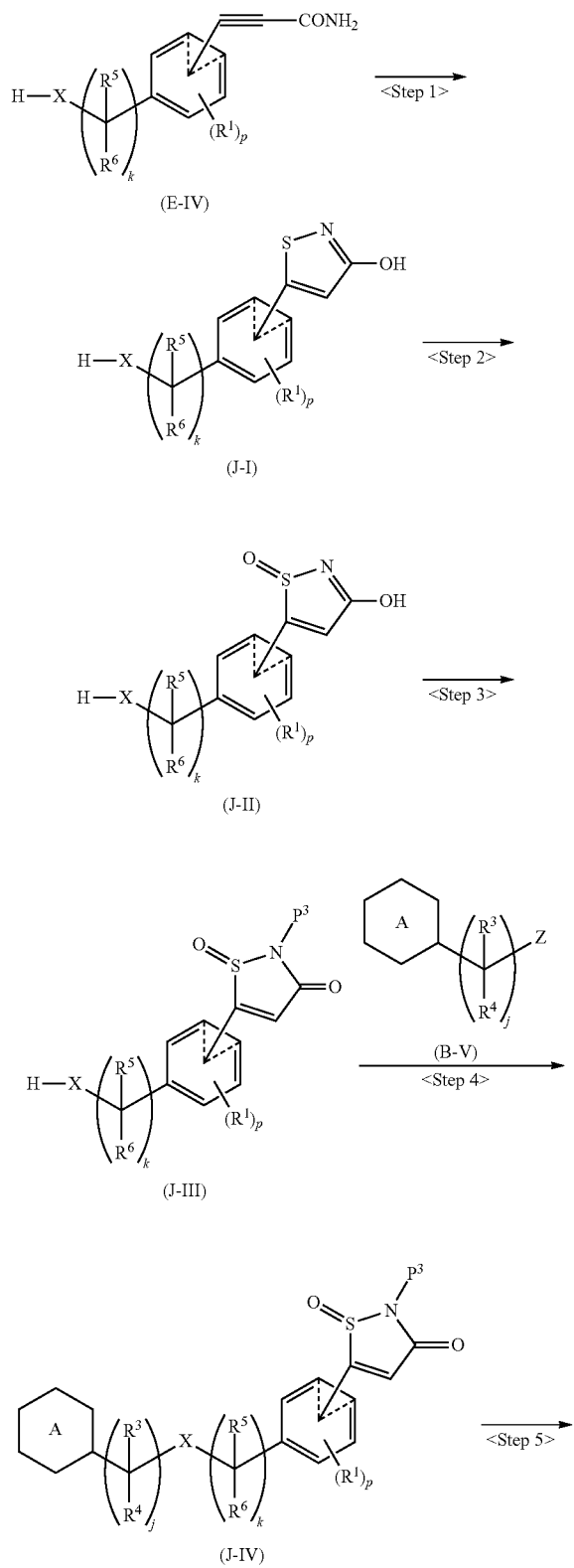

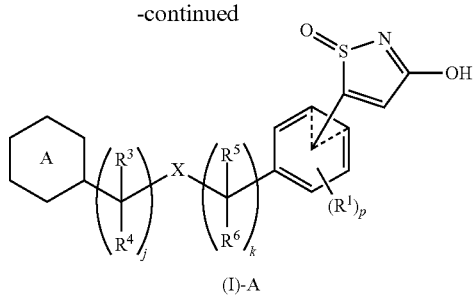

<Step 1>
A compound of Formula (E-IV) is subjected to isothiazole ring formation reaction. A compound of Formula (J-I) can be produced by reacting the compound of Formula (E-IV) in a similar manner to that in <Step 1> in (Production Method A).

<Step 2>
The sulfur atom in the compound of Formula (J-I) is oxidized. A compound of Formula (J-II) can be produced by reacting the compound of Formula (J-I) in a similar manner to that in <Step 2> in (Production Method A).

<Step 3>
The compound of Formula (J-II) is protected with a protective group $P^3$. A compound of Formula (J-III) can be produced by reacting the compound of Formula (J-II) with the protective group $P^3$ by a method suitable for the protective group.

<Step 4>
The compound of Formula (J-III) is subjected to substitution reaction with a compound of Formula (B-V). A compound of Formula (J-IV) can be produced by reacting the compound of (J-III) with the compound of Formula (B-V) in a similar manner to that in <Step 4> in (Production Method B).

<Step 5>
The protective group $P^3$ in the compound of Formula (J-IV) is deprotected. The compound of Formula (I)-A can be produced by deprotecting the protective group $P^3$ in the compound of Formula (J-IV) by a method suitable for the protective group.

<Production Method J-1>
<When X=Oxygen Atom in Formula (I) Above>

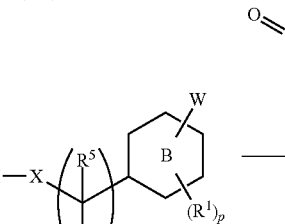

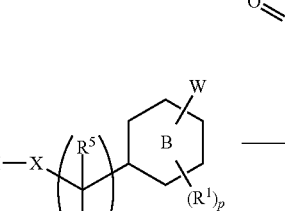

119

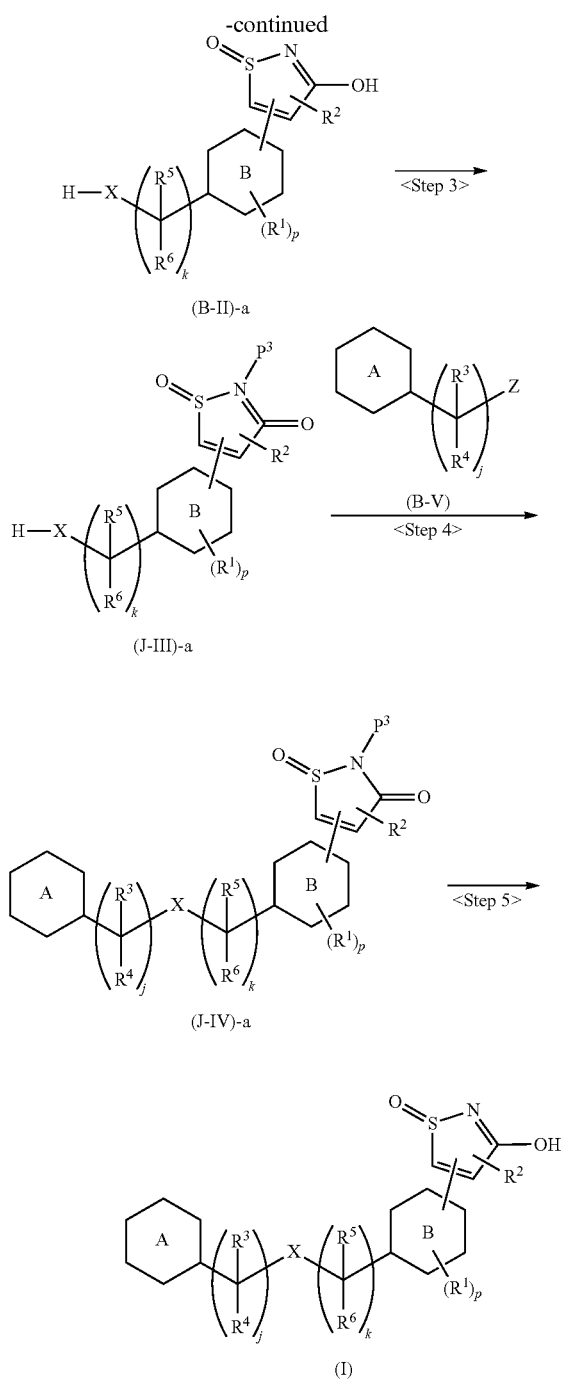

(B-II)-a (J-III)-a (J-IV)-a (I)

<Step 1>
A compound of Formula (G-II)-a can be produced in a similar manner to that in <Step 1> in (Production Method G).
<Step 2>
A compound of Formula (B-II)-a can be produced in a similar manner to that in <Step 2> in (Production Method G).
<Step 3>
A compound of Formula (J-III)-a can be produced in a similar manner to that in <Step 3> in (Production Method J).
<Step 4>
A compound of Formula (J-IV)-a can be produced in a similar manner to that in <Step 4> in (Production Method J).

120

<Step 5>
A compound of Formula (I) can be produced in a similar manner to that in <Step 5> in (Production Method J).

<Production Method K>
<When, in Formula (I)-A above, the ring A is Partial Structural Formula (A1),

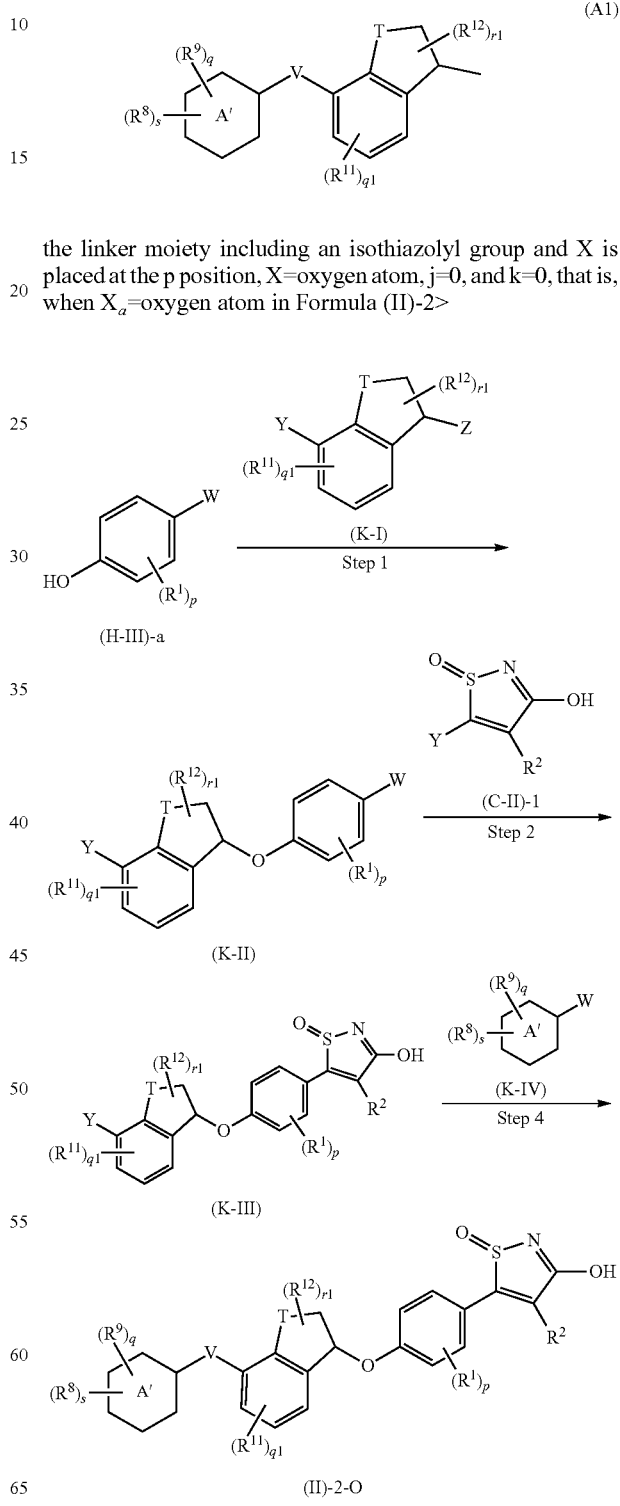

the linker moiety including an isothiazolyl group and X is placed at the p position, X=oxygen atom, j=0, and k=0, that is, when $X_a$=oxygen atom in Formula (II)-2>

<Step 1>
A compound of Formula (H-III)-a is subjected to substitution reaction with a compound of Formula (K-I). A compound of Formula (K-II) can be produced by reacting the compound of Formula (H-III)-a that is known in the art or can be easily produced from a known compound with the compound of Formula (K-I) in a similar manner to that in <Step 4> in (Production Method B).
<Step 2>
The compound of Formula (K-II) is subjected to substitution reaction with a compound of Formula (C-II)-1. A compound of Formula (K-111) can be produced by reacting the compound of Formula (K-II) with the compound of Formula (C-II)-1 in a similar manner to that in (Production Method C).
<Step 3>
The compound of Formula (K-III) is subjected to substitution reaction with a compound of Formula (K-IV).
<When V=Single Bond>
A compound of Formula (II)-2-O can be produced by reacting the compound of Formula (K-III) with the compound of Formula (K-IV) in a similar manner to that in (Production Method C).
<When V=Oxygen Atom>
In accordance with a method known in the literature, for example, the method described in [Tetrahedron Letters, vol. 49, pp. 1851-1855 (2008)], a compound of Formula (II)-2-O can be produced by reacting the compound of Formula (K-III) in the presence of the compound of Formula (K-IV) in the presence of a copper catalyst such as copper iodide (I), copper bromide (I), copper chloride (I), and copper oxide (I), a base such as potassium phosphate, potassium carbonate, and sodium tert-butoxide, and an additive such as 1-butylimidazole, 1-methylimidazole, and 2,2'-bipyridine using a reaction inert solvent such as toluene, xylene, 1,4-dioxane, and N-methylpyrrolidone or a mixed solvent of them at a temperature from 0° C. to a reflux temperature of the solvent.

In accordance with another method known in the literature, for example, the method described in [Journal of the American Chemical Society, vol. 121, pp. 4369-4378 (1999)], the compound of Formula (II)-2-O can also be produced by reaction in the presence of the compounds of Formula (K-III) and Formula (K-IV) in the presence of a palladium catalyst such as palladium (II) acetate, tetrakis triphenylphosphine palladium, tris(dibenzylideneacetone)dipalladium, bis(dibenzylideneacetone)palladium, and [1,1'-bis(diphenylphosphino)ferrocene]dichloropalladium (II), a phosphine reagent such as (2-biphenyl)di-(tert-butyl)phosphine, 2-di-(tert-butyl)-2'-(N,N-dimethylamino)biphenyl, and 2-dicyclohexyl-2'-(N,N-dimethylamino)biphenyl, and a base such as potassium phosphate, sodium hydride, and sodium tert-butoxide using a reaction inert solvent such as dichloromethane, 1,4-dioxane, tetrahydrofuran, toluene, and N,N-dimethylformamide or a mixed solvent of them at a temperature from 0° C. to a reflux temperature of the solvent.

The compound of Formula (K-IV) used in this step is known in the art or can be easily produced from a known compound. Specifically, in accordance with a method known in the literature, for example, the methods described in [WO 2005/063729 pamphlet, Reference Example 1, for example], [WO 2008/001931 pamphlet, <Step 4A> in Reaction Scheme 2, Reference Examples 1 and 54, for example], and [WO 2009/054423 pamphlet, Production Example 37, for example], a corresponding halogenated derivative can be produced from a corresponding compound. Furthermore, the compound of Formula (K-IV) can be produced by boration reaction of the halogenated derivative in a similar manner to that in <Step 1> in (Production Method G).

The compound of Formula (K-I) includes optical isomers because the carbon atom to which Z is bonded is an asymmetric carbon. The isomers are known in the art or can be easily produced from a known compound, and each enantiomer can be obtained through optical resolution using column chromatography or asymmetric synthesis by a person skilled in the art based on conventional techniques. For example, the isomers are separated with an optical resolution column, and each absolute configuration can be determined in accordance with the method described in [Agric. Biol. Chem., vol. 46 (10), pp. 2579-2585 (1982)]. Furthermore, the enantiomers can be obtained in accordance with the method described in [WO 2009/157418 pamphlet, Example 51 and Example 52].

Each enantiomer of Formula (K-II), Formula (K-III), and Formula (II)-2-O can be produced using such an enantiomer.

(6) The compound of Formula (E-IV) can also be produced by the following method.
<Production Method L>
<When X=Oxygen Atom in Formula (E-IV) Above>

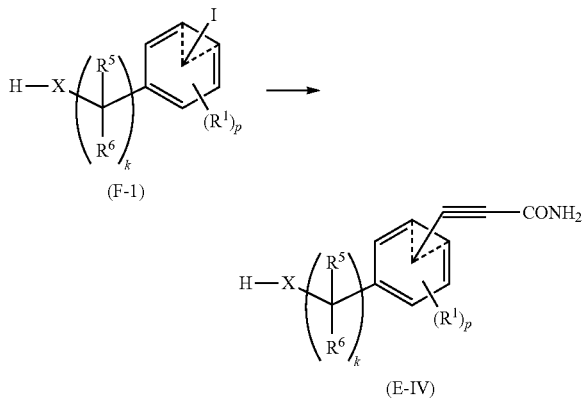

A compound of Formula (F-I) is subjected to alkynylation. The compound of Formula (E-IV) can be produced by reacting the compound of Formula (F-I) that is known in the art or can be easily produced from a known compound with propiolic amide in a similar manner to that in <Step 1> in (Production Method E).

(7) Hereinafter, the method for producing the compound of Formula (B-V) of the present invention will be described in further detail.

(7-1) As typical examples, methods for producing a compound of Formula (B-V)-II having Partial Structural Formula (A1) above described in (Production Method K) above will be described.
<Production Method M>

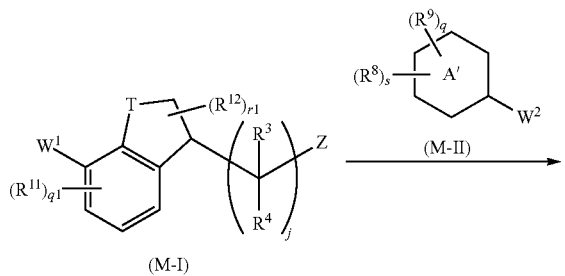

-continued

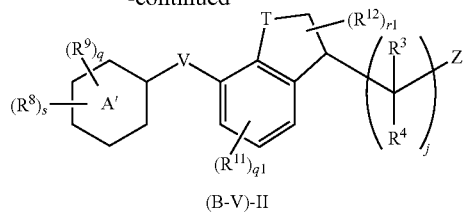

(B-V)-II

A compound of Formula (M-I) is subjected to substitution reaction on a ring.

<When V=Single Bond>

A compound of Formula (B-V)-II can be produced by reacting the compound of Formula (M-I) that is known in the art or can be easily produced from a known compound with a compound of Formula (M-II) (where at least one of $W^1$ and $W^2$ is a halogen atom or a trifluoromethanesulfonyloxy group) in a similar manner to that in (Production Method C).

<When V=Oxygen Atom>

In accordance with a method known in the literature, for example, the method described in [Tetrahedron Letters, vol. 44, pp. 3863-3865 (2003)], a compound of Formula (B-V)-II can be produced by reacting the compound of Formula (M-I) in the presence of a compound of Formula (M-II) (where at least one of $W^1$ and $W^2$ is a hydroxy group) in the presence of a copper catalyst such as copper (II) acetate and copper (II) trifluoroacetate and a base such as triethylamine, N,N-diisopropylethylamine, and pyridine using a reaction inert solvent such as dichloromethane, 1,4-dioxane, tetrahydrofuran, and N,N-dimethylformamide or a mixed solvent of them at a temperature from 0° C. to a reflux temperature of the solvent.

When $R^8$ or $R^9$ is an electron-withdrawing group or the ring A' is heteroaryl, the compound of Formula (B-V)-II can also be produced by reacting the compound of Formula (M-I) ($W^1$=hydroxy group) with the compound of Formula (M-II) ($W^2$=halogen atom) in a similar manner to that in <Step 4> in (Production Method B).

The compound of Formula (M-II) used in this step is known in the art or can be easily produced from a known compound. Specifically, in accordance with a method known in the literature, for example, the methods described in [WO 2005/063729 pamphlet, Reference Example 1, for example], [WO 2008/001931 pamphlet, <Step 4A> in Reaction Scheme 2, Reference Examples 1 and 54, for example], and [WO 2009/054423 pamphlet, Production Example 37, for example], a corresponding halogenated derivative can be produced from a corresponding compound. Furthermore, a boronic acid derivative can be produced by boration reaction of the halogenated derivative in a similar manner to that in <Step 1> in (Production Method G).

The compound of Formula (M-I) includes optical isomers because the carbon atom in the ring, to which the linker moiety including Z is bonded, is an asymmetric carbon. As with Formula (K-I) above, the isomers are known in the art or can be easily produced from a known compound, and each enantiomer can be obtained through optical resolution using column chromatography or asymmetric synthesis by a person skilled in the art based on conventional techniques. Each enantiomer of Formula (B-V)-II can be produced using such an enantiomer.

<Production Method N>
<When j=0 and Z=OH in Formula (B-V)-II>

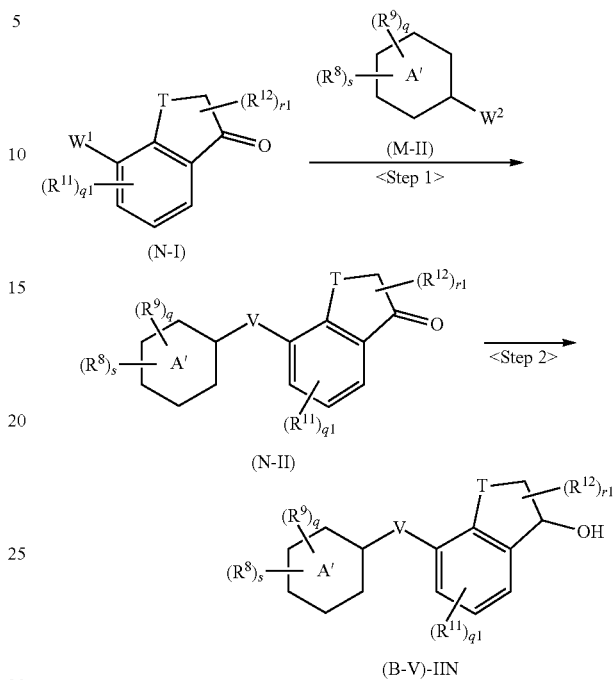

<Step 1>

A compound of Formula (N-I) is subjected to substitution reaction on a ring.

<When V=Single Bond>

A compound of Formula (N-II) can be produced by reacting the compound of Formula (N-I) that is known in the art or can be easily produced from a known compound with a compound of Formula (M-II) in a similar manner to that in <When V=single bond> in (Production Method M).

<When V=Oxygen Atom>

A compound of Formula (N-II) can be produced by reacting the compound of Formula (N-I) with a compound of Formula (M-II) in a similar manner to that in <When V=oxygen atom> in (Production Method M).

<Step 2>

The compound of Formula (N-II) is subjected to reduction. In accordance with a method known in the literature, for example, the methods described in [Jikken Kagaku Koza (Experimental Chemistry Course), the fourth edition, vol. 26, Organic Synthesis VIII, Asymmetric Synthesis, Reduction, Sugar, and Labelled Compound, pp. 234-245 (1992), Maruzen Co., Ltd.] and the like, a compound of Formula (B-V)-IIN can be produced by reacting the compound of Formula (N-II) in the presence of sodium borohydride, diisobutylaluminum hydride (DIBAH), lithium aluminum hydride (LAH), lithium triethoxyaluminum hydride, borane-tetrahydrofuran ($BH_3$.THF), borane-dimethyl sulfide ($BH_3$-$Me_2S$), and the like using a reaction inert solvent including an ether solvent such as diethyl ether, tetrahydrofuran, 1,2-dimethoxyethane, and 1,4-dioxane, a halogenated solvent such as dichloromethane, chloroform, and 1,2-dichloroethane, and an alcoholic solvent such as methanol and ethanol or a mixed solvent of them at a temperature from 0° C. to a reflux temperature of the solvent.

In accordance with a method known in the literature, for example, the methods described in [WO 2005/063729 pamphlet, Reference Examples 2 and 3, for example], [WO 2008/001931 pamphlet, Reaction Scheme 2, Reference Examples 15-19, for example], and [WO 2009/054423 pamphlet, Production Examples 12, 24, and 37, for example], the compound of Formula (B-V)-IIN can also be produced from a corresponding compound.

(7-2) As other typical examples, methods for producing a compound of Formula (B-V)-III having Partial Structural Formula (A)-III:

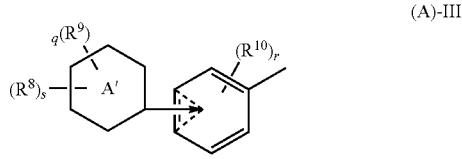

(A)-III will be described.

<Production Method O>

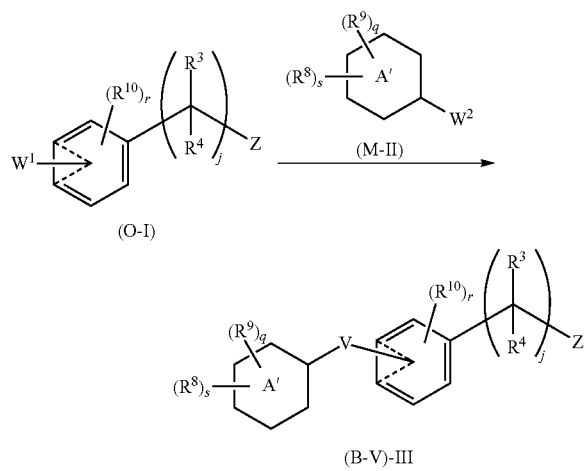

A compound of Formula (O-I) is subjected to substitution reaction on the benzene ring.

<When V=Single Bond>

A compound of Formula (B-V)-III can be produced by reacting the compound of Formula (O-I) that is known in the art or can be easily produced from a known compound with a compound of Formula (M-II) in a similar manner to that in <When V=single bond> in (Production Method M).

<When V=Oxygen Atom>

A compound of Formula (B-V)-III can be produced by using the compound of Formula (O-I) and the compound of Formula (M-II) in a similar manner to that in <When V=oxygen atom> in (Production Method M).

<Production Method P>

<When j=1, $R^3$, $R^4$=H, and Z=OH in Formula (B-V)-III Above>

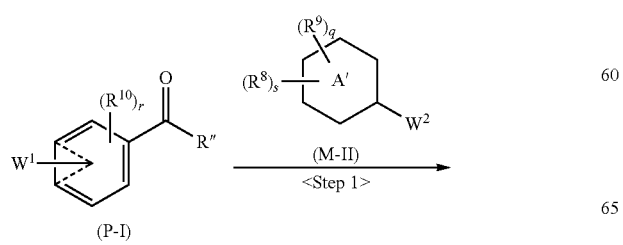

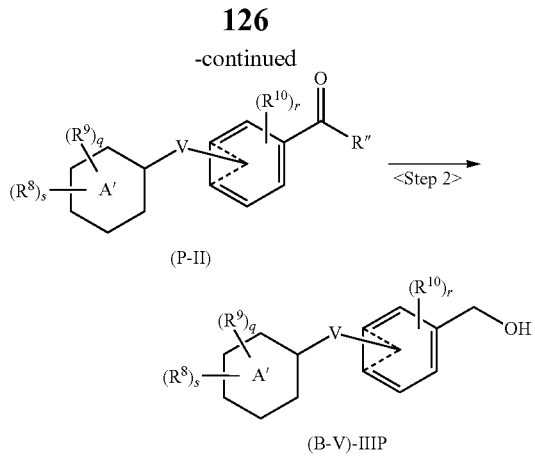

<Step 1>

A compound of Formula (P-I) is subjected to substitution reaction on the benzene ring.

<When V=Single Bond>

A compound of Formula (P-II) can be produced by reacting the compound of Formula (P-I) that is known in the art or can be easily produced from a known compound with a compound of Formula (M-II) in a similar manner to that in <When V=single bond> in (Production Method M).

<When V=Oxygen Atom>

A compound of Formula (P-II) can be produced by using the compound of Formula (P-I) and the compound of Formula (M-II) in a similar manner to that in <When V=oxygen atom> in (Production Method M).

<Step 2>

The compound of Formula (P-II) is subjected to reduction. A compound of Formula (B-V)-IIIP can be produced by reacting the compound of Formula (P-II) in a similar manner to that in <Step 2> in (Production Method N).

The compound of Formula (B-V)-IIIP can also be produced from a corresponding compound in accordance with a method known in the literature, for example, the methods described in [WO 2005/063729 pamphlet, Reference Examples 2 and 3, for example], [WO 2008/001931 pamphlet, Reaction Scheme 2, Reference Examples 15-19, for example], [WO 2008/130514 pamphlet, Method A, Method C, for example], [WO 2009/048527 pamphlet, Reaction Formulae 5 and 6, Example 66.6, for example], and [WO 2009/054423 pamphlet, Production Examples 12, 24, and 37, for example].

(7-3) As another typical example, a method for producing a compound of Formula (B-V)-IV having Partial Structural Formula (A)-IV:

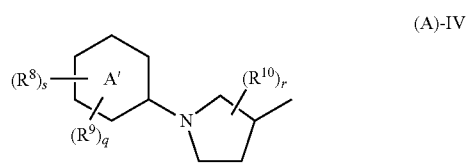

(A)-IV will be described.

<Production Method Q>

<When the Ring A is Partial Structural Formula (A)-IV Above, j=1, $R^3$, $R^4$=H, and Z=OH in Formula (B-V) Above>

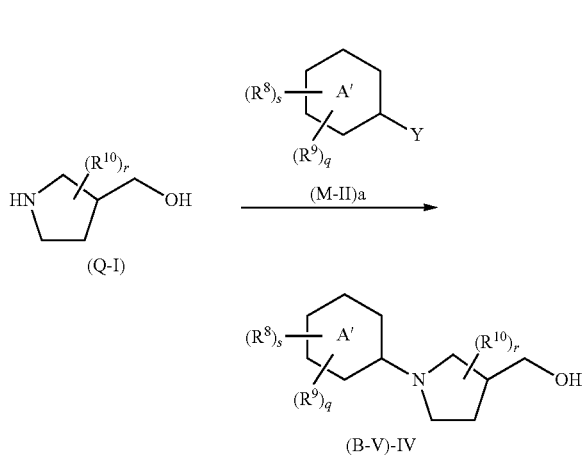

A compound of Formula (Q-I) is subjected to substitution reaction. A compound of Formula (B-V)-IV can be produced by reacting the compound of Formula (Q-I) that is known in the art or can be easily produced from a known compound with a compound of Formula (M-II)a under conditions for conventional substitution reaction (for example, a method similar to that in Step 1 in Example 121 below).

(7-3) As other typical examples, methods for producing a compound of Formula (B-V)-V having Partial Structural Formula (AA1)-V-1:

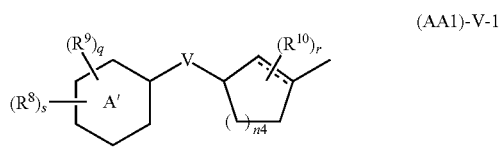

will be described.

<Production Method Q-1>

<When the Ring A is Partial Structural Formula (AA1)-V-1 Above (with Proviso that V=Oxygen Atom), j=1, $R^3$, $R^4$=H, and Z=OH in Formula (B-V) Above>

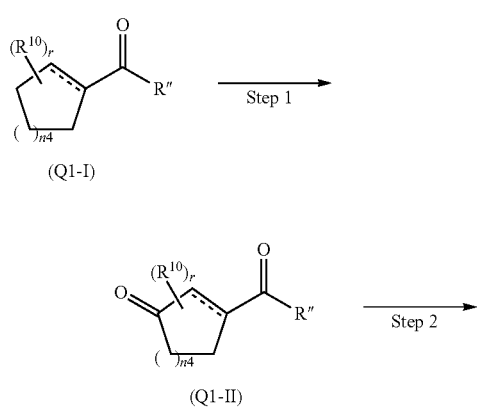

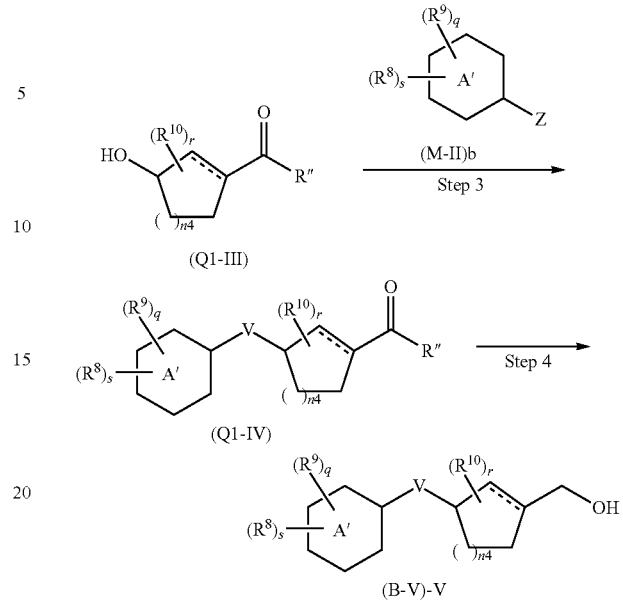

<Step 1>

A compound of Formula (O1-I) is subjected to oxidation reaction. In accordance with a method known in the literature, for example, the method described in [The Journal of Organic Chemistry, vol. 43, pp. 2057 (1978)], a compound of Formula (Q1-II) can be produced by reacting the compound of Formula (O1-I) that is known in the art or can be easily produced from a known compound with chromium trioxide ($CrO_3$) in the presence of 3,5-dimethylpyrazole using a reaction inert solvent such as methylene chloride, 1,2-dichloroethane, acetonitrile, benzene and the like, or a mixed solvent of them at a temperature from 0° C. to a reflux temperature of the solvent.

<Step 2>

A compound of Formula (Q1-II) is subjected to reduction reaction. A compound of Formula (Q1-III) can be produced by reacting the compound of Formula (Q1-II) with sodium boron hydride and cerium chloride in a similar manner to that in <Step 2> in (Production Method N).

<Step 3>

A compound of Formula (Q1-III) is subjected to substitution reaction with a compound of Formula (M-II)b. A compound of Formula (Q1-IV) can be produced by by reacting the compound of Formula (M-II)b that is known in the art or can be easily produced from a known compound with a compound of Formula (Q1-III) in a similar manner to that in <Step 4> in (Production Method B).

<Step 4>

A compound of Formula (Q1-IV) is subjected to reduction reaction. A compound of Formula (B-V)-V can be produced by reacting the compound of Formula (Q1-IV) with diisobutylaluminum hydride in a similar manner to that in <Step 2> in (Production Method N).

(7-4) As other typical examples, methods for producing a compound of Formula (B-V)-VI having Partial Structural Formula (AA)-VI:

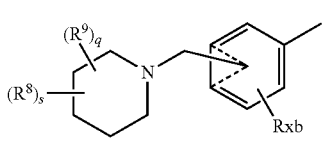
(AA)-VI will be described.
<Production Method Q-2>
<When the Ring A is Partial Structural Formula (AA)-VI Above, j=1, $R^3$, $R^4$=H, and Z=OH in Formula (B-V) Above>

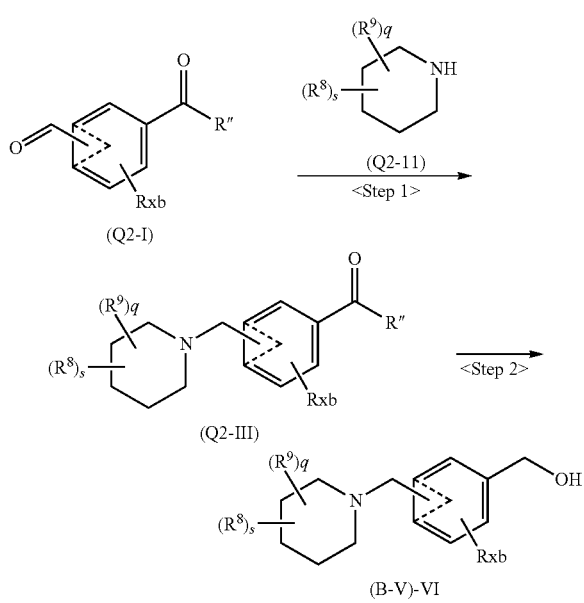

<Step 1>
A compound of Formula (Q2-I) is subjected to reductive amination. In accordance with a method known in the literature, for example, the method described in [The Journal of Organic Chemistry, vol. 61, pp. 3849-3862 (1996)], a compound of Formula (Q1-III) can be produced by reacting the compound of Formula (Q2-I) and the compound of Formula (Q2-II) that are known in the art or can be easily produced from a known compound in the presence of a reducing agent such as sodium triacetoxyborohydride and sodium cyanoborohydride in the presence or absence of a catalytic amount of acetic acid using a reaction inert solvent such as dichloromethane, 1,2-dichloroethane, tetrahydrofuran, acetonitrile, toluene and the like, or a mixed solvent of them at a temperature from 0° C. to a reflux temperature of the solvent.
<Step 2>
A compound of Formula (Q2-III) is subjected to reduction reaction. A compound of Formula (B-V)-VI can be produced with the compound of Formula (Q2-III) in a similar manner to that in <Step 2> in (Production Method N).
(8) The compound of Formula (C-I) can also be produced by the following method.
<Production Method R>
<When the Ring A is Partial Structural Formula (A)-III Described in (Production Method O) Above, the Ring B is Benzen Ring, the Linker Moiety Including an Isothiazolyl Group Bonding Moiety and X is Placed at the p Position, j=1, k=0, $R^3$, $R^4$=H, and X=$NR^7$ in Formula (C-I) Above>

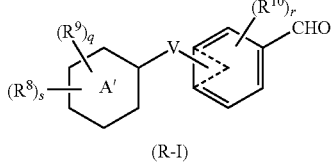
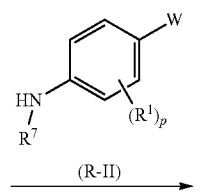
(R-I)       (R-II)

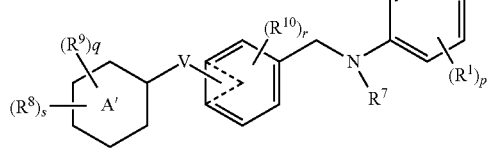
(C-I)-III

A compound of Formula (R-I) is subjected to reductive amination. A compound of Formula (C-I)-III can be produced by reacting the compound of Formula (R-I) (the compound of Formula (R-I) is included in the compound of Formula (P-II), and can be easily produced from a known compound as described in <Step 1> in (Production Method P)) with a compound of Formula (R-II) (it is known in the art or can be easily produced from a known compound) in a similar manner to that in <Step 1> in (Production Method Q-2).
<Production Method R-1>
<When the Ring A is Partial Structural Formula (A):

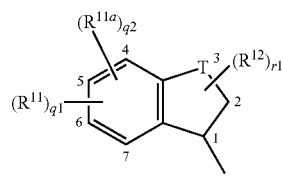
(A)

the Ring B is a Benzene Ring, the Linker Moiety Including an Isothiazolyl Group Bonding Moiety and X is Placed at the p Position, j, k=0, and X=NH in Formula (C-I) Above>

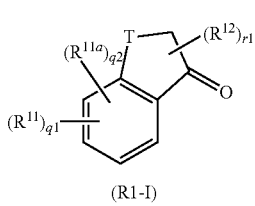
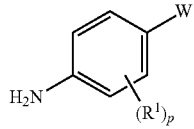
(R1-I)       (R1-II)
            Step 1

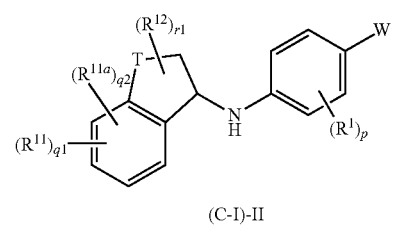
(C-I)-II

A compound of Formula (R1-I) is subjected to reductive amination. A compound of Formula (C-I)-II can be produced by reacting the compound of Formula (R1-I) (it is known in the art or can be easily produced from a known compound as described above in <Step 1> in (Production Method N) above and the like) with a compound of Formula (R1-II) (it is known in the art or can be easily produced from a known compound) in a similar manner to that in (Production Method R) (<Step 1>).

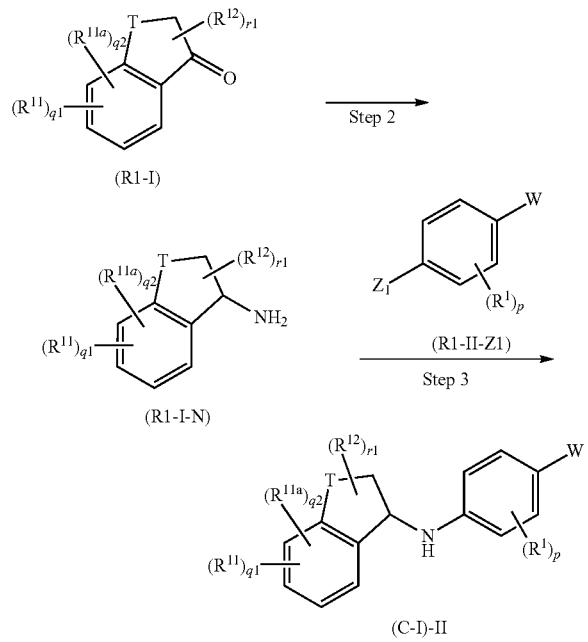

The compound of Formula (C-I)-II can also be produced by reacting the compound of Formula (R1-I) with hydroxylamine hydrochloride to obtain an oxim, then subjecting the oxim to hydrogenation with hydrogen and Pd—C to to produce a compound of Formula (R1-I-N) (<Step 2>), followed by reaction of the obtained compound of (R1-I-N) with a compound of Formula (R1-II-Z1) (<Step 3>). In Formula (R1-II-Z1) above, $Z_1$ is a group other than a hydroxy group in Z above.

<Step 2> above can be carried out with reference to known conditions for reductive amination, for example, in [WO 2006/083454 pamphlet, p 62, Steps A and B in Preparative Example] and [WO 2010/143733 pamphlet, Reference Example 68]. <Step 3> above can be carried out in accordance with known conditions for substitution reaction, for example, in [WO 2010/143733 pamphlet, [0184], Step 7].

<Production Method S>
<When the Ring a is Partial Structural Formula (A)-V:

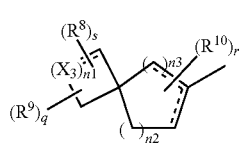

the Ring B is a Benzene Ring, the Linker Moiety Including an Isothiazolyl Group Bonding Moiety and X is Placed at the p Position, j=1, k=0, $R^3$, $R^4$=H, and X=Oxygen Atom in Formula (C-I) Above>

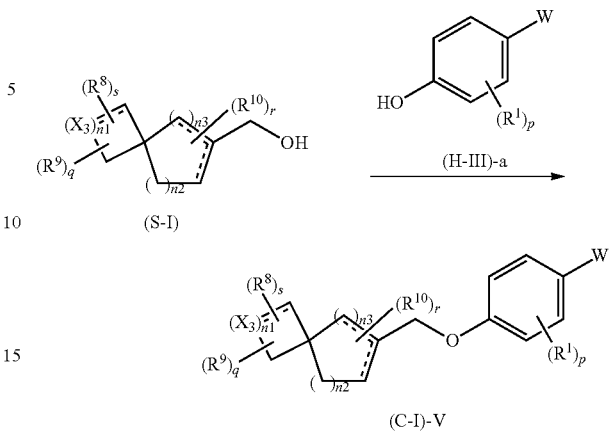

A compound of Formula (S-I) is subjected to substitution reaction with a compound of Formula (H-III)-a. A compound of Formula (S-I)-V can be produced using the compound of Formula (H-III)-a that is known in the art or can be easily produced from a known compound and the compound of Formula (S-I) in a similar method to that in <Step 4> in (Production Method B) or in accordance with the method described in [WO 2009/054479 pamphlet, Step 1 or Step 1' in Production Method A1 (for example, Step 6 in Example 41)]. For example, condensation is carried out in a solvent at room temperature or under heating. Examples of the reagent include 1,1'-(diazocarbonyl)dipiperidine and triphenylphosphine. Examples of the solvent include ether solvents such as tetrahydrofuran.

The compound of Formula (S-I) above is known in the art or can be easily produced from a known compound with reference to, for example, [WO 2009/054479 pamphlet, Production Methods B, C, D and the like (paragraphs [0185] to [0264])].

(8-1) Hereinafter, the method for producing the compound of Formula (S-I) of the present invention will be described in further detail.

<Production Method S-1>
<When n3=1, the Broken Line Adjacent to the Carbon Atom in the n3 Moiety is a Double Bond, and Other Broken Lines are Single Bonds in Formula (S-I) Above>

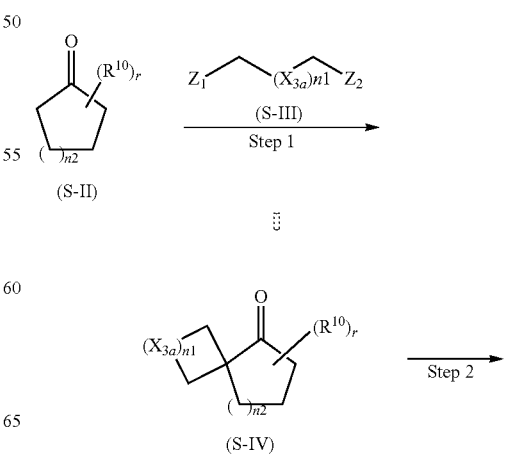

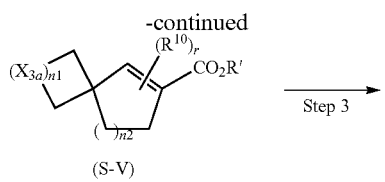

(S-V)

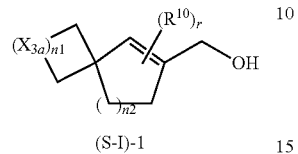

(S-I)-1

<Step 1>

A compound of Formula (S-II) is subjected to substitution reaction with a compound of Formula (S-III) (where each of $X_{3a}$s is independently —$CR_{V1a}R_{V2a}$— or —$NR_{V3a}$—; each of $R_{V1a}$, $R_{V2a}$, and $R_{V3a}$ is independently a hydrogen atom, —OH, or —$NH_2$; $Z_1$ and $Z_2$ are the same as defined for Z above; and $Z_1$ and $Z_2$ are preferably a halogen atom, in Formula (S-III)). A compound of Formula (S-IV) can be produced using the compound of Formula (S-II) that is known in the art or can be easily produced from a known compound and the compound of Formula (S-III) in accordance with the method described in [WO 2009/054479 pamphlet, Production Method D1-1 (for example, Step 1 in Example 41 and Step 4 in Example 104)]. For example, condensation is carried out in a solvent at room temperature or under heating in the presence of a base. Examples of the base include potassium tert-butoxide and sodium hydride. Examples of the solvent include aromatic hydrocarbon solvents such as toluene.

<Step 2>

A compound of Formula (S-V) can be produced from the compound of Formula (S-IV) in accordance with the method described in [WO 2009/054479 pamphlet, Steps 1 to 4 in Production Method C1-1 (for example, Steps 2 to 4 in Example 41)].

<Step 3>

A compound of Formula (S-I)-1 can be produced from the compound of Formula (S-V) in accordance with the method described in [WO 2009/054479 pamphlet, Step 5 in Production Method C1-1 (for example, Step 5 in Example 41)].

<Production Method T>

<When the Ring A is Partial Structural Formula (A)-VI:

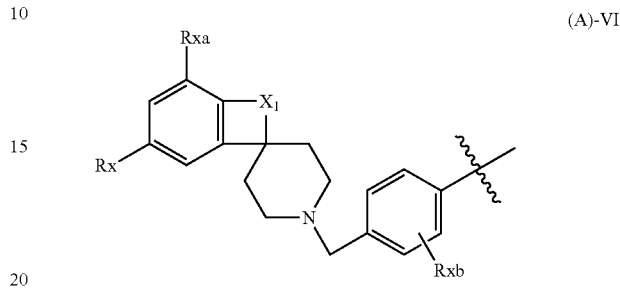

(A)-VI the Ring B is a Benzene Ring, the Linker Moiety Including an Isothiazolyl Group and X is Placed at the p Position, j=1, k=0, and $R^3$, $R^4$=H in Formula (C-I) Above>

As shown in the scheme below, in accordance with Scheme I in WO 2011/046851 pamphlet, pp. 8-9, a substituted benzyl bromide of Formula (1) is reacted with a suitable substituted spiropiperidine of Formula (SP) or its hydrochloric acid salt or trifluoroacetic acid salt in the presence of a suitable base such as diisopropylethylamine and cesium carbonate to give a compound of Formula (4) in step 1a. The ester is properly reduced in step 2 with diisobutylaluminum hydride, lithium aluminum hydride, sodium borohydride, or the like to give a substituted benzyl alcohol of Formula (B-V). The compound of Formula (B-V) can be properly used in (Production Method B), (Production Method E), (Production Method F), (Production Method H), and (Production Method J) above. Alternatively, the compound of Formula (B-V) can also be obtained by reduction in step 1b instead of step 1a to give a compound of Formula (2), followed by reaction with the compound of Formula (SP) in step 1c in the same manner as in the above.

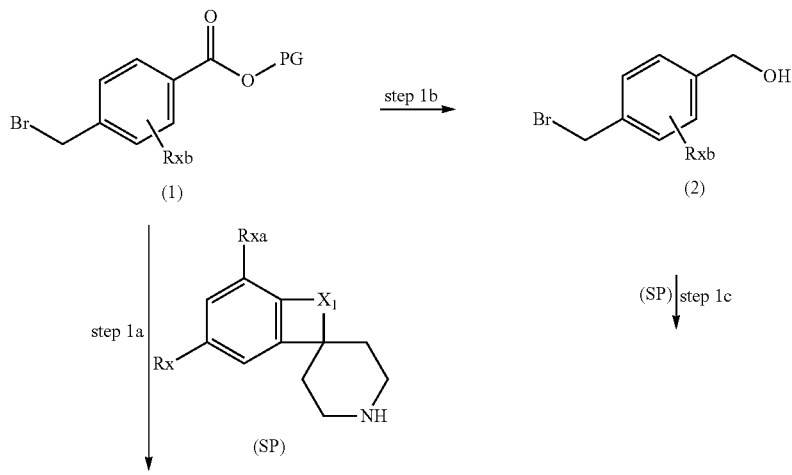

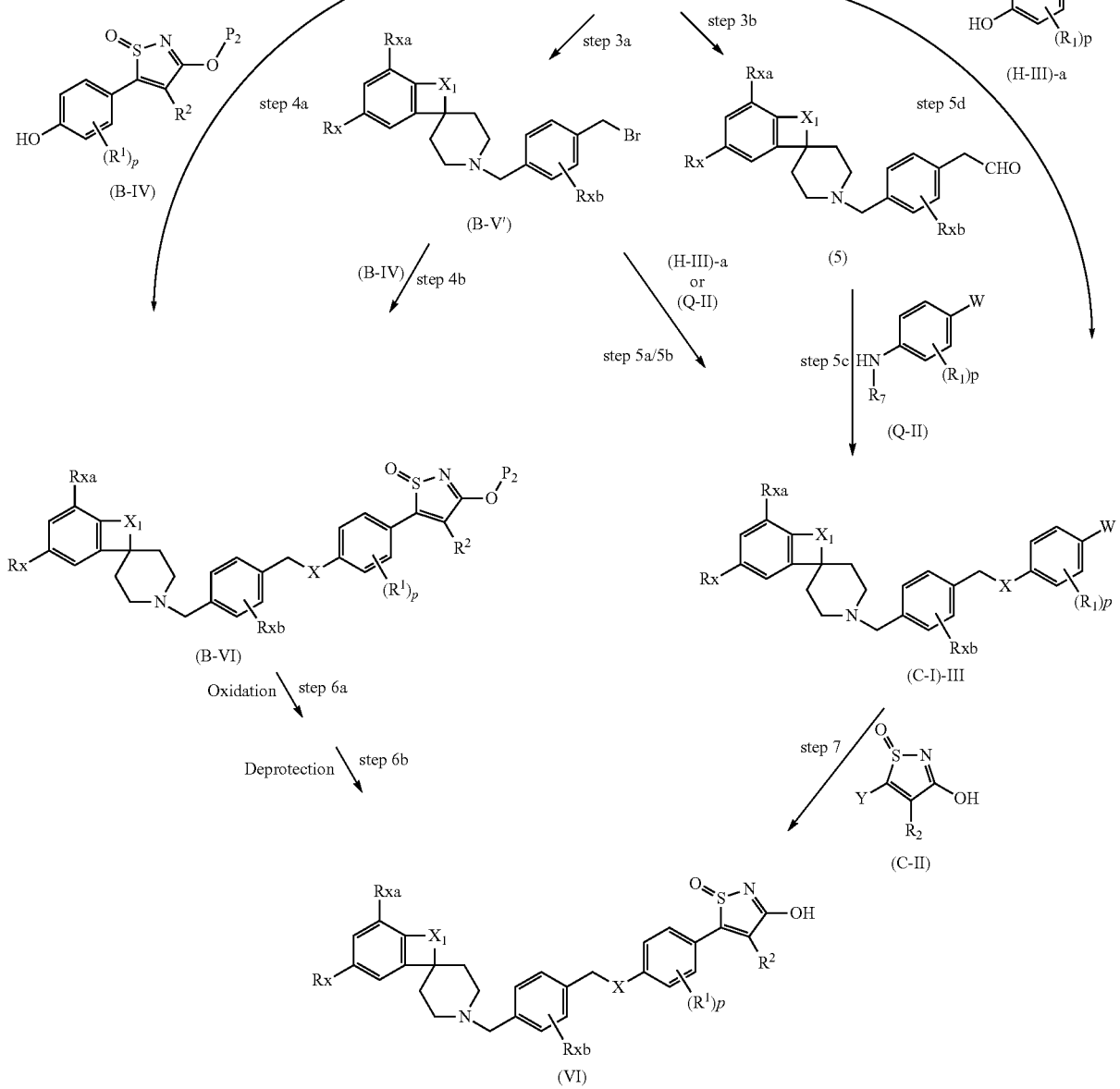

Here, the compound of Formula (B-V) is further reacted with a phenol derivative of Formula (B-IV) by Mitsunobu reaction in step 4a in the presence of a suitable phosphine such as triphenylphosphine and triethylphosphine and an azodicarbonyl such as ADDP or an azodicarboxylate such as DEAD, and then the product is properly oxidized and deprotected in steps 6a and 6b to give a final compound of Formula (VI) (X=oxygen atom).

Another pathway may be employed. That is, the compound of Formula (B-V) is derived to a benzyl bromide of Formula (B-V') in step 3a with a suitable brominating agent such as phosphorus tribromide, and then the benzyl bromide is reacted with the phenol derivative of Formula (B-IV) above in step 4b to give the compound of Formula (B-VI).

The compound of Formula (B-V') is also reacted with a compound of Formula (H-III)-a or a compound of Formula (Q-II) in step 5a/b to give a corresponding compound of Formula (C-I)-III (X=oxygen atom or —$NR^7$—). Alternatively, the compound of Formula (C-I)-III can be derived from the compound of Formula (B-V) by oxidation with a suitable oxidizing agent such as Dess-Martin reagent to give an aldehyde of Formula (5) in step 3b, followed by oxidative amination with a compound of Formula (Q-II) in step 5c. Alternatively, the compound of Formula (C-I)-III (X=oxygen atom or —NR$_7$—) can also be derived from the compound of Formula (B-V) by direct Mitsunobu reaction with a compound of Formula (H-III)-a in step 5d.

The compound of Formula (C-I)-III is reacted with a compound of Formula (C-II) in step 7 to give a final compound of Formula (VI) (X=oxygen atom or —NR$_7$—).

Alternatively, through the synthetic route shown below, the compound of Formula (B-VI) can also be obtained by reaction using a known or suitable benzyl bromide derivative to give an intermediate, followed by reaction with a substituted spiropiperidine of Formula (SP). Each definition of substituents and reference signs is the same as in the above.

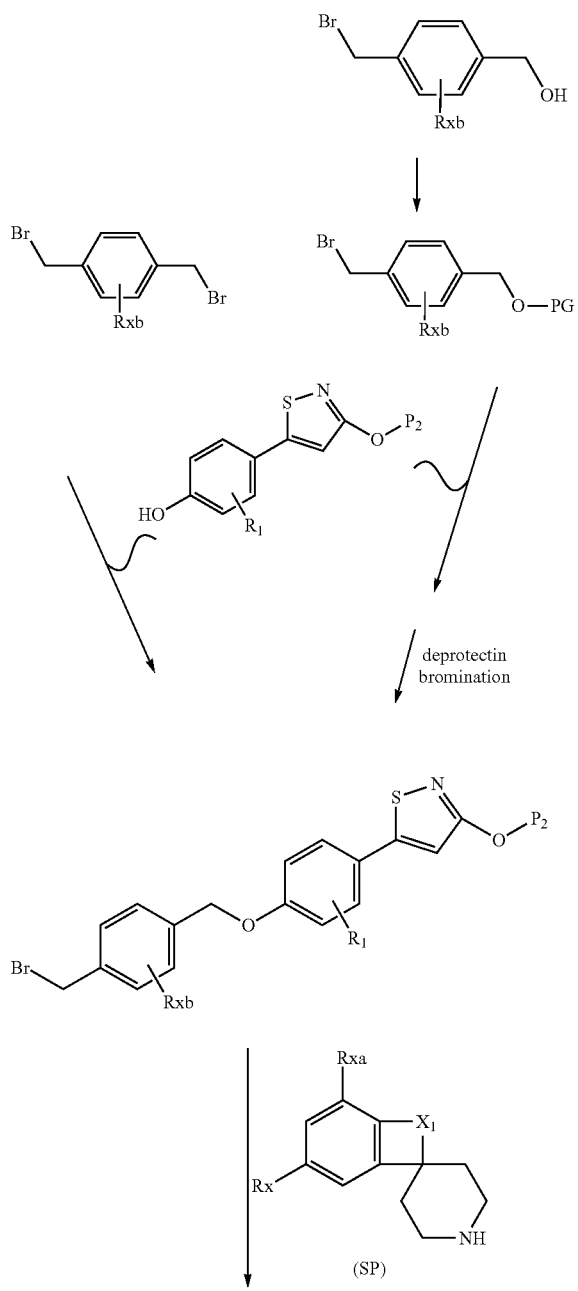

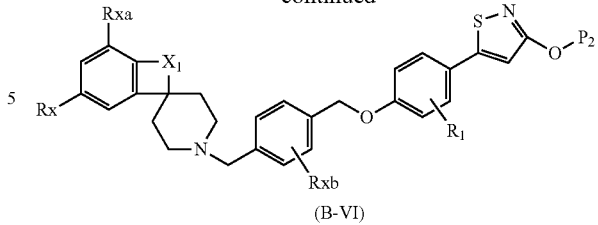

(B-VI)

In particular, a method for producing a compound of Formula (B-V) where X$_1$ is —N(Rz)CH$_2$— can be with reference to WO 2011/064851 pamphlet, pp. 10-11. In accordance with Scheme II in the literature, a protected piperidine-4-carboaldehyde is reacted with a phenylhydrazine that is optionally substituted at the 2-position and/or 4-position to give a substituted spiro[indoline-3,4'-piperidine]. The product is, as necessary, further alkylated, and then is deprotected to give the compound of Formula (SP) suited for the present invention.

Fortunately, WO 2011/046851 pamphlet discloses in pp. 29-31, as specific known compounds of Formula (B-V) suitably used for Production Method U of the present invention, (4-(spiro[inden-1,4'-piperidin]-1'-ylmethyl)phenyl)methanol as well as [3-chloro-4-(spiro[inden-1,4'-piperidin]-1'-ylmethyl)phenyl]methanol, [2-methoxy-4-(spiro[inden-1,4'-piperidin]-1'-ylmethyl)phenyl]methanol, [3-fluoro-4-(spiro[inden-1,4'-piperidin]-1'-ylmethyl)phenyl]methanol, [4-(spiro[inden-1,4'-piperidin]-1'-ylmethyl)-3-(trifluoromethyl)phenyl]methanol, [3-chloro-4-[(1-methylspiro[indoline-3,4'-piperidin]-1'-yl)methyl]phenyl]methanol, [4-(spiro[indane-1,4'-piperidin]-1'-ylmethyl)-3-(trifluoromethyl)phenyl]methanol, and [4-(spiro[indane-1,4'-piperidin]-1'-ylmethyl)phenyl]methanol.

As other usable compounds of Formula (B-V'), WO 2011/046851 pamphlet also discloses, in pp. 31-32, corresponding bromomethyl derivatives as Prep No. 56-61.

Suitable selection of each route in (Production Method T) can produce, for example, the compounds in Example 123, Example 124, Example 1P, and Example 2P in the literature.

Hereinbefore, the method for producing a compound substituted with an isothiazole ring at the p position with respect to the hetero atom X has been described. Furthermore, a m-isomer that can be properly obtained or synthesized is used in place of the starting material of Formula (1) or Formula (2) to produce a corresponding compound substituted with the isothiazole ring at the m position with respect to the hetero atom X in a similar manner.

<Production Method Ta>

It can be understood that another substituted spiropiperidine of Formula (SP') is used in place of the substituted spiropiperidine of Formula (SP) in each production route in (Production Method T) to give each compound of Formula (B-Va), Formula (B-Va'), Formula (C-1)-IIIa, Formula (B-VIa), and Formula (VIa) having the moiety of Formula (SP') that replaces the moiety of Formula (SP) in each compound of Formula (B-V), Formula (B-V'), Formula (C-1)-III, Formula (B-VI), and Formula (VI).

Furthermore, each compound of Formula (B-V), Formula (B-V'), Formula (B-Va), and Formula (B-Va') described in (Production Method T) and (Production Method Ta) can be used as the compound of Formula (B-V) in (Production Method B) to (Production Method J) above in each step (for example, in <Step 4> in (Production Method B)).

<Production Method Tb>

In place of the starting material of Formula (1) or Formula (2) used in steps 1a, 1b, and 1c in (Production Method T) or (Production Method Ta), in accordance with the description of scheme I or scheme III in pp. 5 to 10 in WO 2011/066183 pamphlet, a corresponding bromomethyl-heteroarylcarboxylic acid derivative of Formula (1) or a methyl alcohol of bromomethyl-heteroaryl of Formula (2):

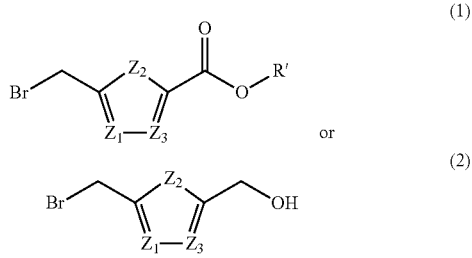

(where each definition of $Z_1$, $Z_2$, and $Z_3$ is the same as that in Formula (A2) IV described in Aspect [1-9-e-3]) is used to produce the compound in Aspect [1-9-e-9] or [1-9-e-9a] having a 5-membered heteroaryl in the molecule.

[Concomitant Drug Containing Compound of the Present Invention]

The compound and pharmaceutical composition of the present invention can be used in combination with other drugs or medicines by a general method performed in medical practice. Particularly, such combination is used for the prevention, progress delay, and therapies of the mediating state of the GPR40 agonist, and is further particularly used against at least one disease selected from a group consisting of diabetes (Type 1 diabetes, Type 2 diabetes, and borderline type diabetes (impaired glucose tolerance (IGT) and/or impaired fasting glycemia (IFG))), insulin resistance, hyperinsulinemia, obesity, adiposity, and various diseases derived from or related to such diseases.

Examples of an insulin sensitizer and an anti-diabetic drug include 1) PPAR gamma agonists (specifically, pioglitazone, rosiglitazone, troglitazone, ciglitazone, darglitazone, englitazone, netoglitazone, etc.), 2) biguanide agents (specifically, metformin, buformin, phenformin, etc.), 3) sulfonylureas (specifically, tolbutamide, acetohexamide, chlorpropamide, glibenclamide, gliclazide, glipizide, glimepiride, glipentide, gliquidone, glisolamide, tolazamide, etc.), 4) rapid-acting insulin secretagogues (specifically, nateglinide, mitiglinide, repaglinide, etc.), 5) alpha-glucosidase inhibitors (specifically, acarbose, voglibose, miglitol, camiglibose, adiposin, emiglitate, pradimicin Q, salbostatin, etc.), 6) insulin or insulin derivatives (specifically, insulin zinc suspensions, insulin lispro, insulin aspart, regular insulin, NPH insulin, insulin glargine, insulin detemir, mixed insulin, etc.), 7) GLP-1 and GLP-1 agonists (specifically, exenatide, liraglutide, lixisenatide, taspoglutide, etc.), 8) DPP-IV inhibitors (specifically, sitagliptin, vildagliptin, alogliptin, saxagliptin, linagliptin, teneligliptin, NVP-DPP-728, etc.), 9) alpha-2 antagonists (specifically, midaglizole, isaglidole, deriglidole, idazoxan, efaroxan, etc.), and 10) SGLT2 inhibitors. Examples of the insulin sensitizer and the anti-diabetic drug also include a combination drug containing two or more of the components described above (specifically, pioglitazone/metformin, pioglitazone/glimepiride, etc.).

Examples of the insulin sensitizer and the anti-diabetic drug also include a hypolipidemic agent and a dyslipidemia therapeutic agent. Examples of the hypolipidemic agent and the dyslipidemia therapeutic agent include 1) omega-3 fatty acids (specifically, ethyl icosapentate (EPA-E preparation), docosahexaenoic acid (DHA), etc.), 2) HMG-CoA reductase inhibitors (specifically, atorvastatin, simvastatin, pitavastatin, itavastatin, fluvastatin, lovastatin, pravastatin, rivastatin, rosuvastatin, etc.), 3) HMG-CoA synthase inhibitors, 4) cholesterol absorption inhibitors (specifically, ezetimibe), 5) acyl-CoA-cholesterol acyltransferase (ACAT) inhibitors, 6) CETP inhibitors, 7) squalene synthase inhibitors, 8) antioxidants (specifically, probucol, etc.), 9) PPAR alpha agonists (specifically, clofibrate, etofibrate, fenofibrate, bezafibrate, ciprofibrate, gemfibrozil, KRP-101, etc.), 10) PPAR delta agonists, 11) LXR agonists, 12) FXR agonists (specifically, INT-747, etc.), 13) MTTP inhibitors, 14) squalene epoxidase inhibitors, and 15) bile acid absorption inhibitors (specifically, cholestyramine, colestipol, etc).

In addition, examples of the insulin sensitizer and the anti-diabetic drug also include an anti-obesity agent. Specific examples of the anti-obesity agent include 1) CB-1 receptor antagonists (specifically, rimonabant, SR-147778, BAY-65-2520, etc.), 2) monoamine reuptake inhibitors (specifically, sibutramine, mazindol, etc.), 3) serotonin reuptake inhibitors (specifically, fluoxetine, paroxetine, etc.), 4) lipase inhibitors (specifically, orlistat, cetilistat, etc.), 5) neuropeptide Y (NPY) receptor antagonists (specifically, S-2367, etc.), 6) peptide YY (PYY) receptor antagonists, and 7) adrenergic beta-3 receptor agonists (specifically, KRP-204, TRK-380/TAC-301, etc).

The therapies can be performed in combination with not only other drugs, but also other therapies. Examples of the therapies include the improvement of lifestyle through weight control, exercise therapy, and diet therapy, and radiotherapy.

Against GPR40-involving diseases except for diabetes and obesity, the therapies can be performed in combination with drugs used in respective fields.

Examples of the concomitant drug include, preferably, PPAR gamma agonists (more preferably, pioglitazone and rosiglitazone), biguanide agents (more preferably, metformin and buformin), sulfonylureas (more preferably, glibenclamide, gliclazide, and glimepiride), rapid-acting insulin secretagogues (more preferably, nateglinide and mitiglinide), alpha-glucosidase inhibitors (more preferably, acarbose, voglibose, and miglitol), insulin or insulin derivatives, and DPP-IV inhibitors (more preferably, sitagliptin, vildagliptin, and alogliptin).

The combined use of the concomitant drug and conventional drugs against the diseases described above enables the dosage of the conventional drugs to be reduced, which can reduce the side effects of the conventional drugs. It is needless to say the combining method using the drugs is not limited to the diseases, and the drugs to be used in combination are not limited to the compounds exemplified above.

To use the compound of the present invention in combination with the drug to be used in combination, they may be individual preparations or be a drug combination. In the form of individual preparations, the compound and the drug can be taken at the same time or can be administered at different time.

[Producing Preparations of Prophylactic or Therapeutic Agents of the Present Invention]

The medicines of the present invention are administered in the form of pharmaceutical compositions.

The pharmaceutical compositions of the present invention may include at least the compound of Formula (I) or Formula (II) of the present invention and are produced in combination with pharmaceutically acceptable additives. More in detail, various dosage forms can be prepared by appropriately combining the compound of the present invention and, for example, excipients (for example, lactose, white soft sugar, mannitol, microcrystalline cellulose, silicic acid, corn starch, and potato starch), bonding agents (for example, celluloses (hydroxypropyl cellulose (HPC), hydroxypropylmethylcellulose (HPMC), microcrystalline cellulose, saccharide (lactose, mannitol, white soft sugar, sorbitol, erythritol, and xylitol), starches (corn starch and potato starch), gelatinized starch, dextrin, polyvinylpyrrolidone (PVP), macrogol, polyvinyl alcohol (PVA)), lubricants (for example, magnesium stearate, calcium stearate, talc, and carboxymethylcellulose), disintegrants (for example, starches (corn starch and potato starch), sodium carboxymethyl starch, carmellose, carmellose calcium, croscarmellose sodium, and, crospovidone), coating agents (for example, celluloses (hydroxypropyl cellulose (HPC), hydroxypropylmethylcellulose (HPMC), aminoalkylmethacrylate copolymers E, and methacrylic copolymers LD), plasticizers (for example, triethyl citrate and macrogol), masking agents (for example, titanium oxide), colorants, flavoring agents, antiseptics (for example, benzalkonium chloride and p-hydroxybenzoate esters), tonicity agents (for example, glycerin, sodium chloride, calcium chloride, mannitol, and dextrose), pH regulators (for example, sodium hydroxide, potassium hydroxide, sodium carbonate, hydrochloric acid, sulfuric acid, and buffer solutions such as phosphate buffer solutions), stabilizing agents (for example, sugar, sugar alcohol, and xanthan gum), dispersants, antioxidants (for example, ascorbic acid, butylated hydroxyanisole (BHA), propyl gallate, and dl-alpha-tocopherol), buffer agents, preservatives (for example, paraben, benzyl alcohol, and benzalkonium chloride), perfumes (for example, vanillin, l-menthol, and rose oil), solubilizing agents (for example, polyoxyethylene hydrogenated castor oil, polysorbate 80, polyethylene glycol, phospholipid cholesterol, and triethanolamine), absorbefacients (for example, sodium glycolate, sodium edetate, sodium caprate, acylcarnitines, and limonene), gelators, suspending agents, emulsifiers, and, generally used suitable additives and solvents.

Examples of the various dosage forms include tablets, capsules, granules, powderes, pills, aerosols, inhalants, ointments, adhesive patches, suppositories, injections, troches, liquids, spirits, suspensions, extracts, and elixirs. The dosage forms can be administered to patients through oral administration, subcutaneous injection, intramuscular injection, intranasal administration, transdermal administration, intravenous injection, intraarterial injection, perineural administration, epidural administration, administration in subdural cavity, intraventricular administration, rectal administration, inhalation, or the like.

The dosage of the compound of the present invention is generally, 0.005 mg to 3.0 g, preferably, 0.05 mg to 2.5 g, and more preferably, 0.1 mg to 1.5 g per day for adults, but can be reduced or increased as needed depending on symptoms or administration routes.

The compound can be administered as a whole at once or be separately administered by being divided into two to six doses through oral administration or parenteral administration, or can be administered through repeated administration such as intravenous infusion.

The present specification incorporates, as references, the whole publications cited in the present specification, for example, related-art documents, publications of unexamined applications, patent publications, and other patent documents.

PHARMACOLOGICAL TEST EXAMPLES

The present invention is specifically described below with reference to test examples but is not limited to them.

The following pharmacological test examples 1 to 7 provide methods for investigating the efficacy of the compound of the present invention.

Pharmacological Test Example 1

Agonist Action on GPR40 of Human Origin

A CHO cell strain stably expressing GPR40 of human origin was used to determine the agonist action of a subject compound. This cell strain was seeded in a clear bottom 96 well plate at $4 \times 10^4$ cells/100 pt/well. The cell strain was cultured in a $CO_2$ incubator overnight using a Ham's F-12 medium containing a 10% fetal bovine serum, 100 U/mL penicillin, 0.1 mg/mL streptomycin, and 400 μg/mL Geneticin. Calcium 4 Assay Kit (Molecular Devices) was used as a fluorescent calcium indicator. One mL of 77 mg/mL probenecid (Invitrogen) was added to 100 mL of a calcium indicator solution to prepare a solution (loading solution) mixed with a 20 mM HEPES-containing Hanks' balanced salt solution (HBSS) in equal proportions. To the cells from which the culture solution is removed, 200 μl of the loading solution was added, and the cells were cultured in a CO2 incubator for 1 hour. The subject compound was diluted with a 20 mM HEPES-containing HBSS and was added to the cells by 50 μL, and the change in the $Ca^{2+}$ concentration was measured with an intracellular ion analyzer. The $EC_{50}$ value of the subject compound was calculated using the dose-response curve of fluorescence intensity variation. Table 1 indicates the compound of the present invention having an $EC_{50}$ value of less than 0.3 μM as A and the compound of the present invention having an $EC_{50}$ value of 0.3 μM or more and less than 3 μM as B.

TABLE 1

| Compound of Examples | $EC_{50}$ values |
|---|---|
| 1 | A |
| 2 | A |
| 3 | A |
| 4 | A |
| 5 | A |
| 6 | B |
| 7 | B |
| 8 | A |
| 9 | A |
| 10 | A |
| 11 | A |
| 12 | A |
| 13 | A |
| 14 | A |
| 15 | A |
| 16 | B |
| 17 | A |
| 18 | B |
| 19 | A |
| 20 | B |
| 21 | A |
| 22 | A |
| 23 | A |
| 24 | A |
| 25 | B |
| 26 | B |
| 27 | A |
| 28 | A |
| 29 | A |
| 30 | A |

TABLE 1-continued

| Compound of Examples | EC$_{50}$ values |
|---|---|
| 31 | B |
| 32 | B |
| 33 | B |
| 34 | B |
| 35 | A |
| 36 | A |
| 37 | A |
| 38 | A |
| 39 | A |
| 40 | A |
| 41 | A |
| 42 | A |
| 43 | A |
| 44 | B |
| 45 | A |
| 46 | A |
| 47 | A |
| 48 | A |
| 49 | A |
| 50 | B |
| 51 | A |
| 52 | A |
| 53 | A |
| 54 | A |
| 55 | B |
| 56 | A |
| 57 | B |
| 58 | A |
| 59 | A |
| 60 | A |
| 61 | B |
| 62 | B |
| 63 | B |
| 64 | A |
| 65 | A |
| 66 | A |
| 67 | A |
| 68 | B |
| 69 | B |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | B |
| 121 | B |
| 122 | A |
| 123 | B |
| 124 | B |
| 125 | A |
| 126 | A |
| 127 | A |
| 128 | A |
| 129 | A |
| 130 | A |
| 131 | A |
| 132 | B |
| 133 | A |
| 134 | A |
| 135 | A |
| 136 | A |
| 137 | A |
| 138 | A |
| 140 | A |
| 141 | A |
| 144-a | A |
| 144-b | B |
| 145-a | A |
| 145-b | B |
| 146 | A |
| 147 | A |
| 148-a | A |
| 148-b | B |
| 149 | A |
| 150 | A |
| 151 | A |
| 152-a | A |
| 153-a | A |
| 154-a | A |
| 155 | A |
| 156 | A |
| 157 | B |
| 158 | A |
| 159 | A |
| 160 | A |
| 161 | A |
| 162 | A |
| 163 | B |

Pharmacological Test Example 2

Oral Glucose Tolerance Test

A reduction of blood glucose excursion of a subject compound after glucose load is examined using male C57BL/6J mice or SD rats fasted overnight. The subject compound is suspended with a solvent (for example, 0.5% carboxymethylcellulose) and is orally administered before glucose load. The solvent is singly administered to the control group. Blood specimen collection is performed before compound administration (pre-administration blood collection), after compound administration and immediately before glucose load, during glucose load, after 15, 30, 60, and 120 minutes, and the blood glucose level of the collected blood is measured. The reduction of blood glucose excursion is obtained by orally administering a dosage of 0.3 to 10 mg/kg of the preferable compound of the compound of the present invention.

Pharmacological Test Example 3

Solubility Test (1) DMSO Precipitation Solubility (Kinetic Solubility)

A 10 mM DMSO solution of the compound of the present invention is added to a 50 mM phosphate buffer solution (pH 7.4) to the final concentration of 100 μM. The resultant solution is incubated with stirring at 600 rpm for 1.5 hours at room temperature, and then is filtered through a filter plate (4 μm, MultiScreen Solubility Filter Plate, (Millipore)). The absorbance of the obtained filtrate is measured at the maximum absorption wavelength using a plate reader (Powerscan HT, (Dainippon Pharmaceutical)). In this process, DMSO solutions of known concentration of the test compound (1, 3, 10, 30, and 100 μM) are prepared as standard solutions for a calibration curve. The absorbance of each of the standard solutions is measured to generate a calibration curve. The solubility (μM) of the compound is calculated using the absorbance values of the filtrate and the standard solutions.

(2) Crystal Solubility (Thermodynamic Solubility)

The compound of the present invention is added to water so as to be 1 mg/mL. The resultant solution is incubated at 37° C. for 24 hours, and then is centrifuged. The obtained supernatant is analyzed by HPLC to detect the peak at the maximum absorption wavelength, and thus, the peak area is calculated. Similarly, DMSO solutions of known concentration of the test compound (0.03, 0.1, 0.3, 1, 3, and 10 μg/mL) are prepared as standard solutions for a calibration curve. The peak area of each of the standard solutions is measured. The solubility (μg/mL) of the compound is calculated using the peak areas of the obtained calibration curve.

Pharmacological Test Example 4

Metabolic Stability Test

The 10 mM DMSO solution of the compound of the present invention is added to a solution containing liver microsome (human, mouse, or rat; XenoTech) and a NADPH generating systems (water containing beta-NADP, Glucose-6-Phosphate, G-6-PDH(Y), and $MgCl_2$) to the final concentration of 1 μM. The resultant solution is incubated at 37° C. for 20 minutes, and then the reaction is terminated by adding acetonitrile. Similarly, samples are collected at predetermined times during the incubation, and then the reaction is terminated. Each reaction solution is filtrated by centrifugation using a filter plate (MultiScreen HTS-HV plate, (Millipore)). The test compound in the filtrate is measured by high performance liquid chromatogram/mass spectrometry. Similarly, a sample with a reaction time of 0 minutes is measured as a control. The compound concentration of the control is regarded as 100%, and the residual ratio of the compound in each reaction solution is calculated. These residual ratios are plotted with respect to the time, and the metabolic clearance CL (μL/mg/min) is calculated from the slope of the obtained regression line.

Pharmacological Test Example 5 hERG Inhibition Test by Patch-Clamp Technique

An effect against a human ether-a-go-go related gene (hERG) channel is measured using a fully automatic patch-clamp system (Patchliner (Nanion)). To confirm the hERG $I_{Kr}$ current of a cell (hERG-HEK (Upstate)), the membrane potential is kept at −80 mV, and a depolarizing pulse is applied to the cell on a regular basis. After the generated current became stable, a test compound is added. The effect of the test compound against the hERG channel is confirmed from the change in tail current induced by a repolarizing pulse at −40 mV for 0.5 seconds subsequent to a depolarizing pulse at 40 mV for 0.5 seconds. The stimulation is performed at a frequency of once every 10 seconds. The measurement is performed at room temperature. The hERG channel inhibition rate is calculated as the reduction rate (suppression rate) of a tail current two minutes after the application of the test compound relative to the maximum tail current before the application.

The calculated suppression rate shows the possibility that drug-induced QT prolongation followed by fatal side effects (such as ventricular tachycardia and sudden death).

Pharmacological Test Example 6

Pharmacokinetics Study (Cassette Dosing PK)

The compound of the present invention is orally administrated in a single dose to 7- or 8-week-old male C57BL/6J Jcl mice or SD rats at 1 mg/kg (the vehicle is DMSO:Tween 80:ultrapure water=1:1:8 and 10 mL/kg). After the administration, the blood of the mouse is collected from the abdominal aorta after 0.25, 0.5, 1, and 2 hours, and the blood of the rat is collected from the jugular vein after 0.5, 1, 2, and 4 hours. The blood is centrifuged (3000 rpm, 15 minutes, and 4° C.) to obtain plasma, and the test compound in the plasma is measured by high performance liquid chromatogram/mass spectrometry. Similarly, standard solutions of known concentration of the test compound (0.01, 0.02, 0.05, 0.1, 0.2, 0.5, and 1 μg/mL) are measured to generate a calibration curve. The concentration (μg/mL) of the compound in the plasma is calculated using the calibration curve, and the maximum concentration in the plasma is indicated by Cmax (μg/mL).

Pharmacological Test Example 7

Safety Assessment Study

The compound of the present invention is orally administrated in a single dose to mice or rats. No death is confirmed and no noticeable behavior disorder is observed, and therefore the safety of the compound of the present invention is shown.

Pharmacological Test Example 8

Brain Penetration Study

Rats (male, SD, 7-9 weeks) are given single oral dose of invention compounds at 1 mg/10 mL/kg (solvent: 0.5% CMC) after overnight fasting. Blood samples are collected from jugular vein at 1 h after the administration and centrifuged (3,000 rpm, 15 min, 4° C.) to give plasma.

Cerebral cortexes are obtained at the same time points as for blood samples.

Plasma concentrations (μg/mL) of invention compounds are measured by LC-MS/MS and quantitated using standard solution (0.01, 0.02, 0.05, 0.1, 0.2, 0.5, 1 ug/mL) treated as well as invention compounds samples.

Cerebral cortexes are homogenized with water, and after addition of methanol they are mixed and centrifuged (14,000 rpm, 10 min, 4° C.) to give supernatants for measuring by LC-MS/MS.

Cerebral cortex concentrations (μg/mL) of invention compounds are measured by LC-MS/MS and quantitated using standard solution (0.01, 0.02, 0.05, 0.1, 0.2, 0.5, 1 ug/mL) treated as well as invention compounds samples.

Brain-to-plasma ratio (B/P ratio) of invention compound is calculated from plasma and cerebral cortex concentrations. B/P ratio is a good and common parameter for assessing extent of brain penetration, therefore it is possible to compare the extent of brain penetration among the invention compounds.

As a result, the compound of the present invention showed an excellent GPR40 agonist action and reduced blood glucose excursion in the single oral dose glucose tolerance test using normal mice or rats. In the safety assessment study, no abnormality, indicating low toxicity of the compound of the present invention.

By performing the tests described above, the compound of the present invention is confirmed to have favorable properties in one regard, such as solubility, metabolic stability, pharmacokinetics, the avoidance of an hERG channel inhibition, and brain penetration.

Substituting the 2,3-dihydro-1H-indene A ring with a nitrile substituted phenoxy group provided the unexpected benefit of an action of strong lowering a blood glucose level and a lower brain penetration relative to substitution of the 2,3-dihydro-1H-indene A ring with an unsubstituted phenoxy group.

Substituting the 2,3-dihydro-1H-indene A ring with a substituted pyridine-oxy-group provided the unexpected benefit of an action of strong lowering a blood glucose level relative to substituting the 2,3-dihydro-1H-indene A ring with a substituted pyridine group.

Replacing the 2,3-dihydro-1H-indene A ring with a 2,3-dihydrobenzofuran A ring provided the unexpected benefit of decreased inhibition of cytP-450 (CYP2C9) relative to the 2,3-dihydro-1H-indene A ring.

Accordingly, the compound of the present invention is expected to be used as a GPR40 agonist for insulin secretagogues and prophylactic and/or therapeutic agents against diabetes (particularly, Type 2 diabetes or borderline type diabetes), obesity, and adiposity.

PREPARATION EXAMPLE

Hereinafter, Examples of the pharmaceutical composition of the present invention are described.

Preparation Example 1

Tablet

| | |
|---|---|
| Compound of Example 2 | 100 g |
| Lactose | 137 g |
| Crystalline cellulose | 30 g |
| Hydroxypropyl cellulose | 15 g |
| Sodium carboxymethyl starch | 15 g |
| Magnesium stearate | 3 g |

The above components are weighed and then are uniformly mixed. The mixture is formed into tablets to have a weight of 150 mg.

Preparation Example 2

Film Coating

| | |
|---|---|
| Hydroxypropylmethylcellulose | 9 g |
| Macrogol 6000 | 1 g |
| Titanium oxide | 2 g |

The above components are weighed. Subsequently, hydroxypropylmethylcellulose and macrogol 6000 are dissolved into water to disperse titanium oxide. The resultant liquid is film coated on 300 g of the tablets of Preparation Example 1 to obtain film-coated tablets.

Preparation Example 3

Capsules

| | |
|---|---|
| Compound of Example 6 | 50 g |
| Lactose | 435 g |
| Magnesium stearate | 15 g |

The above components are weighed and then are uniformly mixed. The mixture is filled into adequate hard capsules by a weight of 300 mg with a capsule inserter to produce capsules.

Preparation Example 4

Capsules

| | |
|---|---|
| Compound of Example 8 | 100 g |
| Lactose | 63 g |
| Corn starch | 25 g |
| Hydroxypropyl cellulose | 10 g |
| Talc | 2 g |

The above components are weighed, and then the compound of Example 8, lactose, and corn starch are uniformly mixed. A hydroxypropyl cellulose aqueous solution is added to the resultant mixture to produce granules by wet granulation. Talc is uniformly mixed with the granules, and the mixture is filled into adequate hard capsules by a weight of 200 mg to produce capsules.

Preparation Example 5

Powders

| | |
|---|---|
| Compound of Example 11 | 200 g |
| Lactose | 790 g |
| Magnesium stearate | 10 g |

The above components are weighed and then are uniformly mixed to produce 20% powdered drugs.

Preparation Example 6

Granules and Fine Granules

| | |
|---|---|
| Compound of Example 13 | 100 g |
| Lactose | 200 g |
| Crystalline cellulose | 100 g |
| Partially pregelatinized starch | 50 g |
| Hydroxypropyl cellulose | 50 g |

The above components are weighed, and the compound of Example 13, lactose, crystalline cellulose, and partially pregelatinized starch are uniformly mixed. A hydroxypropyl cellulose (HPC) aqueous solution is added to the resultant mixture to produce granules or fine granules by wet granulation. The granules or fine granules are dried to be formulation of granules or fine granules.

EXAMPLES

Next, in order to describe the present invention further in detail, there are described Examples which should not be construed as limiting the scope of the present invention.

For the measurement of the nuclear magnetic resonance spectrum (NMR), JEOL JNM-ECX400 FT-NMR (manufactured by JEOL Ltd.) or JEOL JNM-ECX300 FT-NMR (manufactured by JEOL Ltd.) were used. LC/MS was measured by one of the methods below. Waters FractionLynx MS system (manufactured by Waters Corporation) was used, as the column, SunFire column (4.6 mm×5 cm, 5 µm) (manufactured by Waters Corporation) was used, and as a mobile phase, [Method A] methanol:0.05% acetic acid aqueous solution=1:9 (0 min)→10:0 (5 min)→10:0 (7 min) (gradient condition) or [Method B] methanol:0.05% trifluoroacetic acid aqueous solution=1:9 (0 min)→10:0 (5 min)→10:0 (7 min) (gradient condition) was used. Alternatively, SHIMADZU LCMS system (manufactured by SHIMADZU CORPORATION) was used, as the column, Xtimate C18 column (2.1 mm×3 cm, 3 µm) (manufactured by Welch Materials) was used, and as a mobile phase, [Method C] 0.019% trifluoroacetic acid acetonitrile solution: 0.038% trifluoroacetic acid aqueous solution=3:7 (0.90 min)→9:1 (1.50 min)→9:1 (1.51 min)→3:7 (2.00 min) (gradient condition), [Method D] 0.019% trifluoroacetic acid acetonitrile solution:0.038% trifluoroacetic acid aqueous solution=1:9 (0.90 min)→8:2 (1.50 min)→8:2 (1.51 min)→1:9 (2.00 min) (gradient condition), or [Method E] 0.019% trifluoroacetic acid acetonitrile solution:0.038% trifluoroacetic acid aqueous solution=0:10 (0.90 min)→3:7 (1.50 min)→3:7 (1.51 min)→0:10 (2.00 min) (gradient condition) was used. For the preparative isolation system, gradient conditions accordingly changed according to the type of the compound were used.

Reference Example 1

Optical Resolution of (Rac)-5-chloroisothiazol-3-ol 1-oxide

<Step 1> Synthesis of 5-chloroisothiazol-3-ol 1-oxide

To a suspension of 5-chloroisothiazol-3-ol (31.8 g) in dichloromethane (640 mL), m-chloroperbenzoic acid (content: 65%) (60.7 g) was added under ice-cooling and the resultant reaction mixture was stirred at room temperature for 15 hours. The reaction mixture was filtered and the filtrate was concentrated under reduced pressure. To the resultant residue, dichloromethane was added and precipitates were filtered off. The filtrate was concentrated under reduced pressure and the resultant residue was purified by silica gel chromatography (eluate; n-hexane:ethyl acetate=67:33 to 60:40) to obtain the subject compound (26.0 g) as a white solid.

<Step 2> Optical Resolution of (Rac)-5-chloroisothiazol-3-ol 1-oxide

The compound (30.5 g) obtained in (Reference Example 1) <Step 1> was subjected to an optical resolution using a preparative chromatography (column: CHIRALPAK AS-H (5 cm×25 cm) (manufactured by Daicel Chemical Industries, Ltd.), eluate: carbon dioxide:methanol=86:14 (v/v), flow rate: 200 g/sec, detection: UV 238 nm) to obtain each enantiomer of the subject compound.

Primary fraction (14.7 g, white solid, >99% ee, retention time 4.8 min (enantiomer A: Reference Example 1 (A)))

Secondary fraction (14.1 g, white solid, >98% ee, retention time 5.3 min (enantiomer B: Reference Example 1 (B)))

The optical purity and the retention time were determined under the following conditions.

Column: CHIRALPAK AD-H (0.46 cm×25 cm) (manufactured by Daicel Chemical Industries, Ltd.),
Eluate: methanol:acetic acid=100:0.1 (v/v),
Flow rate: 1.0 mL/min,
Detection: UV 282 nm,
Column temperature: 40° C.

Hereinafter, the compound synthesized using the enantiomer A (Reference Example 1(A)) obtained in (Reference Example 1) <Step 2> is expressed as "name of the compound+(A)" and the compound synthesized using the enantiomer B (Reference Example 1(B)) obtained in (Reference Example 1) <Step 2> is expressed as "name of the compound+(B)".

Reference Example 2

Synthesis of 4-hydroxyphenyl boronic acid N-methylimino diacetic acid ester

A suspension of 4-hydroxyphenyl boronic acid (10.3 g) and N-methylimino diacetic acid (11.0 g) in dimethylsulfoxide (37 mL)-toluene (333 mL) was heated and refluxed for 1.5 hours. From the resultant reaction mixture, toluene was distilled off under reduced pressure and the reaction mixture was poured into water (400 mL), followed by stirring the resultant reaction mixture for 1.5 hours. From the reaction mixture, precipitates were filtered and the precipitates were washed with water, followed by drying the precipitates under reduced pressure to obtain the subject compound (16.4 g) as a gray white solid.

Reference Example 3

Synthesis of ((1S)-1-((tetrahydro-2H-pyran-2-yl)oxy)-2,3-dihydro-1H-inden-4-yl)boronic acid <Step 1> Synthesis of 2-(((S)-4-bromo-2,3-dihydro-1H-inden-1-yl)oxy)tetrahydro-2H-pyran 3,4-dihydro-2H-pyran (10.6 mL) was dissolved in methylene chloride (16.2 mL), and to the resultant solution, a 4M hydrogen chloride solution in 1,4-dioxane (31.1 µL) was added, and to the resultant reaction mixture, (1S)-4-bromo- 2,3-dihydro-1H-inden-1-ol (10.0 g) that is commercially available or can be obtained by a publicly known method was added, followed by stirring the resultant reaction mixture at room temperature for 3 hours. To the reaction mixture, a saturated sodium hydrogen carbonate aqueous solution (60 mL) was added, followed by extracting the resultant reaction mixture with methylene chloride (60 mL), and the organic phase was washed with a saturated saline (60 mL), followed by drying the organic phase over anhydrous sodium sulfate. From the organic phase, the solvent was distilled off under reduced pressure, followed by purifying the resultant residue by silica gel column chromatography (eluate; n-hexane:ethyl acetate=95:5), and from the resultant, the solvent was distilled off under reduced pressure to obtain the subject compound (15 g). The compound is a mixture of diastereomers.

<Step 2> Synthesis of 5,5-dimethyl-2-((1S)-1-((tetrahydro-2H-pyran-2-yl)oxy)-2,3-dihydro-1H-inden-4-yl)-1,3,2-dioxaborinane To a solution of the compound (14.0 g) obtained in (Reference Example 3) <Step 1> in 1,4-dioxane (213 mL), 5,5,5',5'-tetramethyl-2,2'-di(1,3,2-dioxaborinane) (17.3 g), potassium acetate (18.8 g), and a 1,1'-bis(diphenylphosphino) ferrocene-dichloro palladium (II)-dichloromethane complex (2.61 g) were sequentially added, followed by heating and refluxing the resultant reaction mixture for 3 hours. To the reaction mixture, water (300 mL) was added, and the resultant reaction mixture was filtered by cerite filtration, followed by washing the filtered insoluble materials with ethyl acetate (250 mL). To the filtrate, a saturated saline (200 mL) was added and the resultant reaction mixture was subjected to a phase separation, followed by extracting the resultant with ethyl acetate (200 mL), and the organic phase was dried over anhydrous sodium sulfate. From the organic phase, the solvent was distilled off under reduced pressure, followed by purifying the resultant residue by silica gel column chromatography (eluate; n-hexane:ethyl acetate=70:30), and from the resultant, the solvent was distilled off under reduced pressure to obtain the subject compound (15.3 g) as an orange oily substance. The compound is a mixture of diastereomers.

<Step 3> Synthesis of ((1S)-1-((tetrahydro-2H-pyran-2-yl)oxy)-2,3-dihydro-1H-inden-4-yl) boronic acid To a solution of the compound (8.20 g) obtained in (Reference Example 3) <Step 2> in ethyl acetate (370 mL), water (1.10 L) was added, followed by stirring the resultant reaction mixture at room temperature for 16 hours. The reaction mixture was extracted with ethyl acetate and the organic phase was washed with a saturated saline (200 mL), followed by drying the resultant organic phase over anhydrous sodium sulfate. From the organic phase, the solvent was distilled off under reduced pressure, followed by purifying the resultant residue by silica gel column chromatography (eluate; n-hexane:ethyl acetate=90:10 to 50:50), and from the resultant, the solvent was distilled off under reduced pressure to obtain the subject compound (3.00 g) as a yellowish-white solid. The compound is a mixture of diastereomers.

Example 1

Synthesis of 5-(4-((5-bromo-2,3-dihydro-1H-inden-1-yl)oxy)phenyl)-3-hydroxyisothiazole 1-oxide (A)

<Step 1> Synthesis of 5-bromo-2,3-dihydro-1H-inden-1-ol 5-bromo-2,3-dihydro-1H-inden-1-one (2.0 g) was dissolved in methanol (20 mL), and to the resultant solution, sodium borohydride (0.54 g) was added at room temperature, followed by stirring the resultant reaction mixture at room temperature for 14 hours. To the reaction mixture, 1M hydrochloric acid (50 mL) was added, followed by extracting the resultant reaction mixture with ethyl acetate (50 mL) three times, and the organic phase was washed sequentially with water (50 mL) and a saturated saline (50 mL) and was dried over anhydrous sodium sulfate. From the organic phase, the solvent was distilled off under reduced pressure to obtain the subject compound (2.0 g) as a pale yellow solid.

<Step 2> Synthesis of 4-((5-bromo-2,3-dihydro-1H-inden-1-yl)oxy)phenyl boronic acid N-methylimino diacetic acid ester To a solution of the compound (1.0 g) obtained in Example 1 <Step 1>, the compound (1.4 g) obtained in (Reference Example 2), and tri-n-butylphosphine (2.9 mL) in tetrahydrofuran (20 mL), 1,1'-azobis(N,N-dimethylformamide) (2.0 g) was added under ice-cooling and the resultant reaction mixture was stirred at room temperature for 2 hours. From the reaction mixture, the solvent was distilled off under reduced pressure, followed by purifying the resultant residue by silica gel column chromatography (eluate; n-hexane:ethyl acetate=50:50 to 0:100), and from the resultant, the solvent was distilled off under reduced pressure to obtain a crude product (0.25 g) of the subject compound.

<Step 3> Synthesis of 5-(4-((5-bromo-2,3-dihydro-1H-inden-1-yl)oxy)phenyl)-3-hydroxyisothiazole 1-oxide (A)

To a solution of the compound (0.10 g) obtained in (Example 1) <Step 2> in 1,4-dioxane (3.5 mL), a 1M sodium hydroxide aqueous solution (1.4 mL), the enantiomer A (Reference Example 1(A)) (41 mg) obtained in (Reference Example 1) <Step 2>, 2-dicyclohexylphosphino-2',6'-dimethoxybiphenyl (SPhos; 20 mg), and bis(dibenzylideneacetone) palladium (14 mg) were sequentially added, and the resultant reaction mixture was heated with stirring at 100° C. for 3 hours. To the reaction mixture, a saturated ammonium chloride aqueous solution (10 mL) and ethyl acetate (15 mL) were added, followed by extracting the reaction mixture with ethyl acetate (15 mL) three times, and the organic phase was washed sequentially with water (20 mL) and a saturated saline (20 mL) and was dried over anhydrous sodium sulfate. From the organic phase, the solvent was distilled off, and the resultant residue was subjected to a preparative purification by LC/MS to obtain the subject compound (26 mg).

Example 2

Synthesis of 5-(4-(((2',6'-dimethyl-4'-(3-(methylsulfonyl)propoxy)-[1,1'-biphenyl]-3-yl)methyl)amino)phenyl)-3-hydroxyisothiazole 1-oxide (A)

<Step 1> Synthesis of N-((2',6'-dimethyl-4'-(3-(methylsulfonyl)propoxy)-[1,1'-biphenyl]-3-yl)methyl)-4-(4,4,5,5-tetramethyl-1,3,2-dioxaborolan-2-yl) aniline 2',6'-dimethyl-4'-(3-(methylsulfonyl)propoxy)-[1,1'-biphenyl]-3-carbaldehyde (1.0 g) synthesized according to a method described in [WO 2008/001931 pamphlet, (Reference Example 18)] and 4-(4,4,5,5-tetramethyl-1,3,2-dioxaborolan-2-yl)aniline (0.63 g) were dissolved in methylene chloride (10 mL), and to the resultant solution, sodium triacetoxyborohydride (1.84 g) was added, followed by stirring the resultant reaction mixture at room temperature for 14 hours. To the reaction mixture, water (20 mL) was added, followed by extracting the reaction mixture with methylene chloride (20 mL) twice, and the resultant organic phase was washed sequentially with water (50 mL) and a saturated saline (50 mL) and was dried over anhydrous sodium sulfate. From the organic phase, the solvent was distilled off under reduced pressure to obtain the subject compound (1.4 g) as a colorless amorphous solid.

<Step 2> Synthesis of 5-(4-(((2',6'-dimethyl-4'-(3-(methylsulfonyl)propoxy)-[1,1'-biphenyl]-3-yl)methyl)amino)phenyl)-3-hydroxyisothiazole 1-oxide (A)

According to the method of (Example 1) <Step 3>, from the compound (0.10 g) obtained in (Example 2) <Step 1>, the subject compound (47 mg) was obtained.

Example 3

Synthesis of 5-((4-(((1R)-4-bromo-2,3-dihydro-1H-inden-1-yl)oxy)phenyl)-3-hydroxyisothiazole 1-oxide (A)

<Step 1> Synthesis of 4-(((1R)-4-bromo-2,3-dihydro-1H-inden-1-yl)oxy)phenyl boronic acid N-methylimino diacetic acid ester According to the method of (Example 1) <Step 2>, from (1S)-4-bromo-2,3-dihydro-1H-inden-1-ol (153 mg) that is commercially available or can be obtained by a publicly known method, the subject compound (178 mg) was obtained as an amorphous solid.

<Step 2> Synthesis of 5-(4-(((1R)-4-bromo-2,3-dihydro-1H-inden-1-yl)oxy)phenyl)-3-hydroxyisothiazole 1-oxide (A)

According to the method of (Example 1) <Step 3>, from the compound (178 mg) obtained in (Example 3) <Step 1>, the subject compound (25 mg) was obtained as an amorphous solid.

Example 4

Synthesis of 5-(4-(((1R)-4-(2-ethoxy-5-fluorophenyl)-2,3-dihydro-1H-inden-1-yl)oxy)phenyl)-3-hydroxyisothiazole 1-oxide (A)

To a solution of the compound (0.30 g) obtained in (Example 3) <Step 2> in 1,4-dioxane (6.0 mL), potassium carbonate (0.21 g), water (3.0 mL), (2-ethoxy-5-fluorophenyl) boronic acid (0.12 g), 2-dicyclohexylphosphino-2',4',6'-triisopropylbiphenyl (XPhos; 71 mg), and bis(dibenzylideneacetone) palladium (43 mg) were sequentially added, and the resultant reaction mixture was heated with stirring at 100° C. for 4 hours. To the reaction mixture, 1M hydrochloric acid (10 mL) was added, followed by extracting the reaction mixture with ethyl acetate (10 mL) three times, and the organic phase was washed with a saturated saline (10 mL) and was dried over anhydrous sodium sulfate. From the organic phase, the solvent was distilled off under reduced pressure, followed by purifying the resultant residue by silica gel column chromatography (eluate; n-hexane:ethyl acetate=70:30 to 50:50), and from the resultant, the solvent was distilled off under reduced pressure, followed by triturating the resultant solid with methanol to obtain the subject compound (96 mg) as a colorless solid.

The compounds of (Example 5) to (Example 82) below were synthesized by the same method as or a method equivalent to the method of (Example 4) from each corresponding boronic acid or boronic acid ester.

Example 5

3-hydroxy-5-(4-(((1R)-4-(p-tolyl)-2,3-dihydro-1H-inden-1-yl)oxy)phenyl)isothiazole 1-oxide (A)

Example 6

5-(4-(((R)-4-(4-chlorophenyl)-2,3-dihydro-1H-inden-1-yl)oxy)phenyl)-3-hydroxyisothiazole 1-oxide (A)

Example 7

5-(4-(((R)-4-(4-ethoxyphenyl)-2,3-dihydro-1H-inden-1-yl)oxy)phenyl)-3-hydroxyisothiazole 1-oxide (A)

Example 8

5-(4-(((R)-4-(3-chlorophenyl)-2,3-dihydro-1H-inden-1-yl)oxy)phenyl)-3-hydroxyisothiazole 1-oxide (A)

Example 9

5-(4-(((R)-4-(2-ethylphenyl)-2,3-dihydro-1H-inden-1-yl)oxy)phenyl)-3-hydroxyisothiazole 1-oxide (A)

Example 10

5-(4-(((R)-4-(2-chlorophenyl)-2,3-dihydro-1H-inden-1-yl)oxy)phenyl)-3-hydroxyisothiazole 1-oxide (A)

Example 11

5-(4-(((R)-4-(2-fluorophenyl)-2,3-dihydro-1H-inden-1-yl)oxy)phenyl)-3-hydroxyisothiazole 1-oxide (A)

Example 12

5-(4-(((R)-4-(3,5-difluorophenyl)-2,3-dihydro-1H-inden-1-yl)oxy)phenyl)-3-hydroxyisothiazole 1-oxide (A)

Example 13

5-(4-(((R)-4-(3-fluoro-4-methylphenyl)-2,3-dihydro-1H-inden-1-yl)oxy)phenyl)-3-hydroxyisothiazole 1-oxide (A)

Example 14

5-(4-(((R)-4-(3-chloro-5-methoxyphenyl)-2,3-dihydro-1H-inden-1-yl)oxy)phenyl)-3-hydroxyisothiazole 1-oxide (A)

Example 15

5-(4-(((R)-4-(2-chloro-5-methylphenyl)-2,3-dihydro-1H-inden-1-yl)oxy)phenyl)-3-hydroxyisothiazole 1-oxide (A)

Example 16)

5-(4-(((R)-4-(4-chloro-2-fluorophenyl)-2,3-dihydro-1H-inden-1-yl)oxy)phenyl)-3-hydroxyisothiazole 1-oxide (A)

Example 17

5-(4-(((R)-4-(2,3-difluorophenyl)-2,3-dihydro-1H-inden-1-yl)oxy)phenyl)-3-hydroxyisothiazole 1-oxide (A)

Example 18

5-(4-(((R)-4-(4-chloro-2-ethoxyphenyl)-2,3-dihydro-1H-inden-1-yl)oxy)phenyl)-3-hydroxyisothiazole 1-oxide (A)

Example 19

5-(4-(((R)-4-(2-ethoxypyridin-3-yl)-2,3-dihydro-1H-inden-1-yl)oxy)phenyl)-3-hydroxyisothiazole 1-oxide (A)

Example 20

5-(4-(((R)-4-(4-ethylphenyl)-2,3-dihydro-1H-inden-1-yl)oxy)phenyl)-3-hydroxyisothiazole 1-oxide (A)

Example 21

5-(4-(((R)-4-(4-fluorophenyl)-2,3-dihydro-1H-inden-1-yl)oxy)phenyl)-3-hydroxyisothiazole 1-oxide (A)

Example 22

5-(4-(((R)-4-(4-n-propylphenyl)-2,3-dihydro-1H-inden-1-yl)oxy)phenyl)-3-hydroxyisothiazole 1-oxide (A)

Example 23

5-(4-(((R)-4-(4-methoxyphenyl)-2,3-dihydro-1H-inden-1-yl)oxy)phenyl)-3-hydroxyisothiazole 1-oxide (A)

Example 24

5-(4-(((R)-4-(3-methylphenyl)-2,3-dihydro-1H-inden-1-yl)oxy)phenyl)-3-hydroxyisothiazole 1-oxide (A)

Example 25

5-(4-(((R)-4-(4-vinylphenyl)-2,3-dihydro-1H-inden-1-yl)oxy)phenyl)-3-hydroxyisothiazole 1-oxide (A)

Example 26

5-(4-(((R)-4-(4-isopropylphenyl)-2,3-dihydro-1H-inden-1-yl)oxy)phenyl)-3-hydroxyisothiazole 1-oxide (A)

Example 27

5-(4-(((R)-4-(2-methylphenyl)-2,3-dihydro-1H-inden-1-yl)oxy)phenyl)-3-hydroxyisothiazole 1-oxide (A)

Example 28

5-(4-(((R)-4-(4-isobutylphenyl)-2,3-dihydro-1H-inden-1-yl)oxy)phenyl)-3-hydroxyisothiazole 1-oxide (A)

Example 29

5-(4-(((R)-4-(3-fluorophenyl)-2,3-dihydro-1H-inden-1-yl)oxy)phenyl)-3-hydroxyisothiazole 1-oxide (A)

Example 30

5-(4-(((R)-4-(3-methoxyphenyl)-2,3-dihydro-1H-inden-1-yl)oxy)phenyl)-3-hydroxyisothiazole 1-oxide (A)

Example 31

5-(4-(((R)-4-(4-isopropoxyphenyl)-2,3-dihydro-1H-inden-1-yl)oxy)phenyl)-3-hydroxyisothiazole 1-oxide (A)

Example 32

5-(4-(((R)-4-(3-ethoxyphenyl)-2,3-dihydro-1H-inden-1-yl)oxy)phenyl)-3-hydroxyisothiazole 1-oxide (A)

Example 33

5-(4-(((R)-4-(4-tert-butylphenyl)-2,3-dihydro-1H-inden-1-yl)oxy)phenyl)-3-hydroxyisothiazole 1-oxide (A)

Example 34

5-(4-(((R)-4-(2-isopropylphenyl)-2,3-dihydro-1H-inden-1-yl)oxy)phenyl)-3-hydroxyisothiazole 1-oxide (A)

Example 35

5-(4-(((R)-4-(naphthalen-1-yl)-2,3-dihydro-1H-inden-1-yl)oxy)phenyl)-3-hydroxyisothiazole 1-oxide (A)

Example 36

5-(4-(((R)-4-(2,4-dimethylphenyl)-2,3-dihydro-1H-inden-1-yl)oxy)phenyl)-3-hydroxyisothiazole 1-oxide (A)

Example 37

5-(4-(((R)-4-(2,5-dimethylphenyl)-2,3-dihydro-1H-inden-1-yl)oxy)phenyl)-3-hydroxyisothiazole 1-oxide (A)

Example 38

5-(4-(((R)-4-(4-fluoro-3-methylphenyl)-2,3-dihydro-1H-inden-1-yl)oxy)phenyl)-3-hydroxyisothiazole 1-oxide (A)

Example 39

5-(4-(((R)-4-(4-fluoro-2-methylphenyl)-2,3-dihydro-1H-inden-1-yl)oxy)phenyl)-3-hydroxyisothiazole 1-oxide (A)

Example 40

5-(4-(((R)-4-(4-methoxy-2-methylphenyl)-2,3-dihydro-1H-inden-1-yl)oxy)phenyl)-3-hydroxyisothiazole 1-oxide (A)

Example 41

5-(4-(((R)-4-(5-fluoro-2-methylphenyl)-2,3-dihydro-1H-inden-1-yl)oxy)phenyl)-3-hydroxyisothiazole 1-oxide (A)

Example 42

5-(4-(((R)-4-(2-benzyloxyphenyl)-2,3-dihydro-1H-inden-1-yl)oxy)phenyl)-3-hydroxyisothiazole 1-oxide (A)

Example 43

5-(4-(((R)-4-(2-chloro-4-methylphenyl)-2,3-dihydro-1H-inden-1-yl)oxy)phenyl)-3-hydroxyisothiazole 1-oxide (A)

Example 44

5-(4-(((R)-4-(4-ethoxy-3-fluorophenyl)-2,3-dihydro-1H-inden-1-yl)oxy)phenyl)-3-hydroxyisothiazole 1-oxide (A)

Example 45

5-(4-(((R)-4-(2-methoxy-5-methylphenyl)-2,3-dihydro-1H-inden-1-yl)oxy)phenyl)-3-hydroxyisothiazole 1-oxide (A)

Example 46

5-(4-(((R)-4-(2,5-difluorophenyl)-2,3-dihydro-1H-inden-1-yl)oxy)phenyl)-3-hydroxyisothiazole 1-oxide (A)

Example 47

5-(4-(((R)-4-(4-benzyloxy-2-methylphenyl)-2,3-dihydro-1H-inden-1-yl)oxy)phenyl)-3-hydroxyisothiazole 1-oxide (A)

Example 48

5-(4-(((R)-4-(2-chloro-4-methoxyphenyl)-2,3-dihydro-1H-inden-1-yl)oxy)phenyl)-3-hydroxyisothiazole 1-oxide (A)

Example 49

5-(4-(((R)-4-(2,4-dimethoxyphenyl)-2,3-dihydro-1H-inden-1-yl)oxy)phenyl)-3-hydroxyisothiazole 1-oxide (A)

Example 50

5-(4-(((R)-4-(4-methylnaphthalen-1-yl)-2,3-dihydro-1H-inden-1-yl)oxy)phenyl)-3-hydroxyisothiazole 1-oxide (A)

Example 51

5-(4-(((R)-4-(4-fluoro-2-methoxyphenyl)-2,3-dihydro-1H-inden-1-yl)oxy)phenyl)-3-hydroxyisothiazole 1-oxide (A)

Example 52

5-(4-(((R)-4-(2-chloro-5-methoxyphenyl)-2,3-dihydro-1H-inden-1-yl)oxy)phenyl)-3-hydroxyisothiazole 1-oxide (A)

Example 53

5-(4-(((R)-4-(2-fluoro-5-methoxyphenyl)-2,3-dihydro-1H-inden-1-yl)oxy)phenyl)-3-hydroxyisothiazole 1-oxide (A)

Example 54

5-(4-(((R)-4-(2,5-dimethoxyphenyl)-2,3-dihydro-1H-inden-1-yl)oxy)phenyl)-3-hydroxyisothiazole 1-oxide (A)

Example 55

5-(4-(((R)-4-(5-chloro-2-methoxyphenyl)-2,3-dihydro-1H-inden-1-yl)oxy)phenyl)-3-hydroxyisothiazole 1-oxide (A)

Example 56

5-(4-(((R)-4-(5-fluoro-2-methoxyphenyl)-2,3-dihydro-1H-inden-1-yl)oxy)phenyl)-3-hydroxyisothiazole 1-oxide (A)

Example 57

5-(4-(((R)-4-(4-benzyloxy-3-fluorophenyl)-2,3-dihydro-1H-inden-1-yl)oxy)phenyl)-3-hydroxyisothiazole 1-oxide (A)

Example 58

5-(4-(((R)-4-(5-chloro-2-ethoxyphenyl)-2,3-dihydro-1H-inden-1-yl)oxy)phenyl)-3-hydroxyisothiazole 1-oxide (A)

Example 59

5-(4-(((R)-4-(2-fluoro-3-methoxyphenyl)-2,3-dihydro-1H-inden-1-yl)oxy)phenyl)-3-hydroxyisothiazole 1-oxide (A)

Example 60

5-(4-(((R)-4-(3-chloro-4-ethoxyphenyl)-2,3-dihydro-1H-inden-1-yl)oxy)phenyl)-3-hydroxyisothiazole 1-oxide (A)

Example 61

5-(4-(((R)-4-(2-benzyloxy-4-fluorophenyl)-2,3-dihydro-1H-inden-1-yl)oxy)phenyl)-3-hydroxyisothiazole 1-oxide (A)

Example 62

5-(4-(((R)-4-(2-benzyloxy-5-fluorophenyl)-2,3-dihydro-1H-inden-1-yl)oxy)phenyl)-3-hydroxyisothiazole 1-oxide (A)

Example 63

5-(4-(((R)-4-(3-trifluoromethylphenyl)-2,3-dihydro-1H-inden-1-yl)oxy)phenyl)-3-hydroxyisothiazole 1-oxide (A)

Example 64

5-(4-(((R)-4-(2-trifluoromethylphenyl)-2,3-dihydro-1H-inden-1-yl)oxy)phenyl)-3-hydroxyisothiazole 1-oxide (A)

Example 65

5-(4-(((R)-4-(2-trifluoromethoxyphenyl)-2,3-dihydro-1H-inden-1-yl)oxy)phenyl)-3-hydroxyisothiazole 1-oxide (A)

Example 66

5-(4-(((R)-4-(5-fluoro-2-trifluoromethylphenyl)-2,3-dihydro-1H-inden-1-yl)oxy)phenyl)-3-hydroxyisothiazole 1-oxide (A)

Example 67

5-(4-(((R)-4-(2-fluoro-5-trifluoromethylphenyl)-2,3-dihydro-1H-inden-1-yl)oxy)phenyl)-3-hydroxyisothiazole 1-oxide (A)

Example 68

5-(4-(((R)-4-(2-chloro-5-trifluoromethylphenyl)-2,3-dihydro-1H-inden-1-yl)oxy)phenyl)-3-hydroxyisothiazole 1-oxide (A)

Example 69

5-(4-(((R)-4-(4-chloro-2-trifluoromethylphenyl)-2,3-dihydro-1H-inden-1-yl)oxy)phenyl)-3-hydroxyisothiazole 1-oxide (A) (Example 70)

5-(4-(((R)-4-(2-(methylsulfonyl)phenyl)-2,3-dihydro-1H-inden-1-yl)oxy)phenyl)-3-hydroxyisothiazole 1-oxide (A)

Example 71

5-(4-(((R)-4-(6-methylpyridin-3-yl)-2,3-dihydro-1H-inden-1-yl)oxy)phenyl)-3-hydroxyisothiazole 1-oxide (A)

Example 72

5-(4-(((R)-4-(5-methylpyridin-3-yl)-2,3-dihydro-1H-inden-1-yl)oxy)phenyl)-3-hydroxyisothiazole 1-oxide (A)

Example 73

5-(4-(((R)-4-(5-chloropyridin-3-yl)-2,3-dihydro-1H-inden-1-yl)oxy)phenyl)-3-hydroxyisothiazole 1-oxide (A)

Example 74

5-(4-(((R)-4-(6-chloropyridin-3-yl)-2,3-dihydro-1H-inden-1-yl)oxy)phenyl)-3-hydroxyisothiazole 1-oxide (A)

Example 75

5-(4-(((R)-4-(2-chloropyridin-3-yl)-2,3-dihydro-1H-inden-1-yl)oxy)phenyl)-3-hydroxyisothiazole 1-oxide (A)

Example 76

5-(4-(((R)-4-(6-isopropyl-2-chloropyridin-3-yl)-2,3-dihydro-1H-inden-1-yl)oxy)phenyl)-3-hydroxyisothiazole 1-oxide (A)

Example 77

5-((1R)-1-(4-(3-hydroxy-1-oxidoisothiazole-5-yl)phenoxy)-2,3-dihydro-1H-inden-4-yl)picolinamide (A)

Example 78

5-(4-(((R)-4-(6-(cyclopropylmethoxy)pyridin-3-yl)-2,3-dihydro-1H-inden-1-yl)oxy)phen yl)-3-hydroxyisothiazole 1-oxide (A)

Example 79

1-(5-((1R)-1-(4-(3-hydroxy-1-oxidoisothiazol-5-yl)phenoxy)-2,3-dihydro-1H-inden-4-yl)thiophen-2-yl)ethanone (A)

Example 80

5-(4-(((R)-4-(dibenzo[b.d]furan-4-yl)-2,3-dihydro-1H-inden-1-yl)oxy)phenyl)-3-hydroxy isothiazole 1-oxide (A)

Example 81

5-(4-(((R)-4-(5-chlorothiophen-2-yl)-2,3-dihydro-1H-inden-1-yl)oxy)phenyl)-3-hydroxyisothiazole 1-oxide (A)

Example 82

3-hydroxy-5-(4-(((R)-4-(thiophen-3-yl)-2,3-dihydro-1H-inden-1-yl)oxy)phenyl)isothiazole 1-oxide (A)

Example 83

Synthesis of 4-((((1R)-1-(4-(3-hydroxy-1-oxidoisothiazole-5-yl)phenoxy)-2,3-dihydro-1H-inden-4-yl)oxy)benzonitrile (A)

<Step 1> Synthesis of 4-(((1S)-1-((tetrahydro-2H-pyran-2-yl)oxy)-2,3-dihydro-1H-inden-4-yl)oxy)benzonitrile To a solution of the compound (0.50 g) obtained in (Reference Example 3) <Step 3> in methylene chloride (16 mL), 4-hydroxybenzonitrile (0.19 g), copper acetate (II) (0.32 g), and triethylamine (0.22 mL) were added, followed by stirring the resultant reaction mixture at room temperature in an oxygen atmosphere for 3 days. The resultant reaction mixture was filtered by cerite filtration, and from the filtrate, the solvent was distilled off under reduced pressure, followed by purifying the resultant residue by silica gel column chromatography, and from the resultant, the solvent was distilled off under reduced pressure to obtain the subject compound (0.42 g) as a colorless oily substance. The compound is a mixture of diastereomers.

<Step 2> Synthesis of (S)-4-((1-hydroxy-2,3-dihydro-1H-inden-4-yl)oxy)benzonitrile The compound (0.40 g) obtained in (Example 83) <Step 1> was dissolved in a mixed solvent (8.0 mL) of methanol and tetrahydrofuran at 1:1, and to the resultant solution, 1M hydrochloric acid (4.0 mL) was added, followed by stirring the resultant reaction mixture at room temperature for 18 hours. To the reaction mixture, a 1M sodium hydroxide aqueous solution was added to adjust the reaction mixture to be basic, and the resultant reaction mixture was extracted with ethyl acetate, was washed with a saturated saline, and was dried over anhydrous sodium sulfate. From the organic phase, the solvent was distilled off under reduced pressure to obtain the subject compound (0.29 g).

<Step 3> Synthesis of (R)-4-((4-(4-cyanophenoxy)-2,3-dihydro-1H-inden-1-yl)oxy)phenyl boronic acid N-methylimino diacetic acid ester According to the method of (Example 1) <Step 2>, from the compound (0.3 g) obtained in (Example 83) <Step 2>, a mixture (330 mg) containing the subject compound was obtained.

<Step 4> Synthesis of 4-(((1R)-1-(4-(3-hydroxy-1-oxidoisothiazol-5-yl)phenoxy)-2,3-dihydro-1H-inden-4-yl)oxy)benzonitrile (A)

According to the method of (Example 1) <Step 3>, from the compound (0.2 g) obtained in (Example 83) <Step 3>, the subject compound (92 mg) was obtained as a pale yellow solid.

The compounds of (Example 84) to (Example 89) below were synthesized by the same method as or a method equivalent to the method of (Example 83) using each corresponding substituted phenol derivative.

Example 84

3-hydroxy-5-(4-(((R)-4-(3-(trifluoromethyl)phenoxy)-2,3-dihydro-1H-inden-1-yl)oxy)phenyl)isothiazole 1-oxide (A)

Example 85

3-hydroxy-5-(4-(((R)-4-(pyridin-3-yloxy)-2,3-dihydro-1H-inden-1-yl)oxy)phenyl)isothiazole 1-oxide (A)

Example 86

3-(((1R)-1-(4-(3-hydroxy-1-oxidoisothiazol-5-yl)phenoxy)-2,3-dihydro-1H-inden-4-yl)oxy)benzonitrile (A)

Example 87

3-hydroxy-5-(4-(((R)-4-(4-(trifluoromethyl)phenoxy)-2,3-dihydro-1H-inden-1-yl)oxy)phenyl)isothiazole 1-oxide (A)

Example 88

3-hydroxy-5-(4-(((R)-4-(4-(2-hydroxyethyl)phenoxy)-2,3-dihydro-1H-inden-1-yl)oxy)phenyl)isothiazole 1-oxide (A)

Example 89

3-hydroxy-5-(4-(((R)-4-(3-(2-hydroxyethyl)phenoxy)-2,3-dihydro-1H-inden-1-yl)oxy)phenyl)isothiazole 1-oxide (A)

Example 90

Synthesis of 3-hydroxy-5-(4-(((R)-4-phenoxy-2,3-dihydro-1H-inden-1-yl)oxy)phenyl)isothiazole 1-oxide (A)

<Step 1> Synthesis of (S)-4-phenoxy-2,3-dihydro-1H-inden-1-ol

A mixed solution of (1S)-4-bromo-2,3-dihydro-1H-inden-1-ol (1.0 g) that is commercially available or can be obtained by a publicly known method, 1-butylimidazole (0.308 mL), copper iodide (I) (89.4 mg), potassium carbonate (1.30 g), phenol (0.495 mL), and toluene (4.7 mL) was heated with stirring in a sealed tube at 120 to 130° C. for 15 hours. The reaction solution was left to reach room temperature, and to the reaction mixture, a saturated ammonium chloride aqueous solution (40 mL) was added, followed by filtering the resultant reaction mixture by cerite filtration with washing the mixture with ethyl acetate. The filtrate was subjected to a phase separation, and the organic phase was washed sequentially with a saturated ammonium chloride aqueous solution (40 mL), a 1M sodium hydroxide aqueous solution (40 mL) twice, and a saturated saline (50 mL), followed by drying the organic phase over anhydrous sodium sulfate. From the organic phase, the solvent was distilled off under reduced pressure, followed by purifying the resultant residue by silica gel column chromatography (eluate; n-hexane:ethyl acetate=85:15 to 60:40), and from the resultant, the solvent was distilled off under reduced pressure to obtain the subject compound (0.65 g) as a brown oily substance.

\<Step 2\> Synthesis of (R)-4-((4-phenoxy-2,3-dihydro-1H-inden-1-yl)oxy)phenyl boronic acid N-methylimino diacetic acid ester According to the method of (Example 1) \<Step 2\>, from the compound (0.63 g) obtained in (Example 90) \<Step 1\>, the subject compound (0.97 g) was obtained as a whitish-orange solid.

\<Step 3\> Synthesis of 3-hydroxy-5-(4-(((R)-4-phenoxy-2,3-dihydro-1H-inden-1-yl)oxy)phenyl)isothiazole 1-oxide (A)

According to the method of (Example 1) \<Step 3\>, from the compound (0.38 g) obtained in (Example 90) \<Step 2\>, the subject compound (172 mg) was obtained as a pale yellow solid.

The compounds of (Example 91) to (Example 95) below were synthesized by the same method as or a method equivalent to the method of (Example 90) using each corresponding substituted phenol derivative.

Example 91

3-hydroxy-5-(4-(((R)-4-(3-methoxyphenoxy)-2,3-dihydro-1H-inden-1-yl)oxy)phenyl)isothiazole 1-oxide (A)

Example 92

3-hydroxy-5-(4-(((R)-4-(4-methoxyphenoxy)-2,3-dihydro-1H-inden-1-yl)oxy)phenyl)isothiazole 1-oxide (A)

Example 93

3-hydroxy-5-(4-(((R)-4-(p-tolyloxy)-2,3-dihydro-1H-inden-1-yl)oxy)phenyl)isothiazole 1-oxide (A)

Example 94

3-hydroxy-5-(4-(((R)-4-(m-tolyloxy)-2,3-dihydro-1H-inden-1-yl)oxy)phenyl)isothiazole 1-oxide (A)

Example 95

3-hydroxy-5-(4-(((R)-4-(o-tolyloxy)-2,3-dihydro-1H-inden-1-yl)oxy)phenyl)isothiazole 1-oxide (A)

Example 96

Synthesis of 5-(4-(((R)-4-(2,6-dimethylphenoxy)-2,3-dihydro-1H-inden-1-yl)oxy)phenyl)-3-hydroxyisothiazole 1-oxide (A)

\<Step 1\> Synthesis of (S)-4-(2,6-dimethylphenoxy)-2,3-dihydro-1H-inden-1-ol

A mixed solution of (1S)-4-hydroxy-2,3-dihydro-1H-inden-1-ol (1.0 g) that is commercially available or can be obtained by a publicly known method, 1-butylimidazole (0.875 mL), copper iodide (I) (0.254 g), potassium carbonate (1.84 g), 2,6-dimethyl-bromobenzene (1.38 mL), and toluene (20 mL) was heated with stirring at 120 to 132° C. for 18 hours. To the reaction solution under ice-cooling, water (125 mL) and a 28% ammonia aqueous solution (5 mL) were added, followed by filtration, and the filtered insoluble materials were washed with ethyl acetate. The aqueous phase was extracted with ethyl acetate (20 mL), and the organic phase was washed sequentially with a 1M sodium hydroxide aqueous solution (125 mL) and a saturated saline (150 mL) and was dried over anhydrous sodium sulfate. From the organic phase, the solvent was distilled off under reduced pressure, followed by purifying the resultant residue by silica gel column chromatography (eluate; n-hexane:ethyl acetate=92:8 to 60:40), and from the resultant, the solvent was distilled off under reduced pressure to obtain the subject compound (0.38 g) as a white solid.

\<Step 2\> Synthesis of (R)-4-((4-(2,6-dimethylphenoxy)-2,3-dihydro-1H-inden-1-yl)oxy)phenyl boronic acid N-methylimino diacetic acid ester According to the method of (Example 1) \<Step 2\>, from the compound (0.38 g) obtained in (Example 96) \<Step 1\>, a mixture (598 mg) containing the subject compound was obtained as an orange amorphous solid.

\<Step 3\> Synthesis of 5-(4-(((R)-4-(2,6-dimethylphenoxy)-2,3-dihydro-1H-inden-1-yl)oxy)phenyl)-3-hydroxyisothiazole 1-oxide (A)

According to the method of (Example 1) \<Step 3\>, from the compound (0.16 g) obtained in (Example 96) \<Step 2\>, the subject compound (31 mg) was obtained as a pale red solid.

The compounds of (Example 97) and (Example 98) below were synthesized by the same method as or a method equivalent to the method of (Example 96) from each corresponding aryl halide.

Example 97

3-hydroxy-5-(4-(((R)-4-((6-(3-hydroxy-3-methylbutoxy)pyridin-3-yl)oxy)-2,3-dihydro-1H-inden-1-yl)oxy)phenyl)isothiazole 1-oxide (A)

Example 98

5-(4-(((R)-4-((6-(2-ethoxyethoxy)pyridin-3-yl)oxy)-2,3-dihydro-1H-inden-1-yl)oxy)phenyl)-3-hydroxyisothiazole 1-oxide (A)

Example 99

Synthesis of 3-hydroxy-5-(4-(((R)-4-(3-(trifluoromethoxy)phenoxy)-2,3-dihydro-1H-inden-1-yl)oxy)phenyl)isothiazole 1-oxide (A)

\<Step 1\> Synthesis of (S)-4-(3-(trifluoromethoxy)phenoxy)-2,3-dihydro-1H-inden-1-ol (1S)-4-hydroxy-2,3-dihydro-1H-inden-1-ol (0.4 g) that is commercially available or can be obtained by a publicly known method and 3-trifluoromethoxyphenyl boronic acid (0.66 g) were dissolved in methylene chloride (30.0 mL), and to the resultant solution, molecular sieves 4A (powder; 0.5 g), copper acetate (II) (0.53 g), and triethylamine (1.86 mL) were added, followed by stirring the resultant reaction mixture at room temperature in an oxygen atmosphere for 16 hours. To the reaction mixture, a silica gel (10 g) was added, and the resultant reaction mixture was filtered by cerite filtration and was washed with a mixed solvent (100 mL) of n-hexane and ethyl acetate at 1:1, followed by distilling off the solvent under reduced pressure. The resultant residue was purified by silica gel column chromatography (eluate; n-hexane:ethyl acetate=80:20 to 50:50), and from the resultant, the solvent was distilled off under reduced pressure to obtain the subject compound (0.54 g) as a colorless amorphous.

<Step 2> Synthesis of (4-(((R)-4-(3-(trifluoromethoxy)phenoxy)-2,3-dihydro-1H-inden-1-yl)oxy)phenyl) boronic acid From the compound (0.47 g) obtained in (Example 99) <Step 1>, by carrying out a reaction according to the method of (Example 1) <Step 2> and subjecting the resultant residue to a preparative purification by LC/MS, the subject compound (0.20 g) was obtained as a colorless amorphous.

<Step 3> Synthesis of 3-hydroxy-5-(4-(((R)-4-(3-(trifluoromethoxy)phenoxy)-2,3-dihydro-1H-inden-1-yl)oxy)phenyl)isothiazole 1-oxide (A)

According to the method of (Example 1) <Step 3>, from the compound (0.20 g) obtained in (Example 99) <Step 2>, the subject compound (101 mg) was obtained as a white solid.

The compounds of (Example 100) to (Example 105) below were synthesized by the same method as or a method equivalent to the method of (Example 99) from each corresponding boronic acid.

Example 100

3-hydroxy-5-(4-(((R)-4-((6-methoxypyridin-3-yl)oxy)-2,3-dihydro-1H-inden-1-yl)oxy)phenyl)isothiazole 1-oxide (A)

Example 101

3-hydroxy-5-(4-(((R)-4-((6-(3-hydroxy-3-methylbutoxy)-2-methylpyridin-3-yl)oxy)-2,3-dihydro-1H-inden-1-yl)oxy)phenyl)isothiazole 1-oxide (A)

Example 102

5-(4-(((R)-4-((6-(2-ethoxyethoxy)-2-methylpyridin-3-yl)oxy)-2,3-dihydro-1H-inden-1-yl)oxy)phenyl)-3-hydroxyisothiazole 1-oxide (A)

Example 103

3-hydroxy-5-(4-(((R)-4-(4-(trifluoromethoxy)phenoxy)-2,3-dihydro-1H-inden-1-yl)oxy)phenyl)isothiazole 1-oxide (A)

Example 104

3-hydroxy-5-(4-(((R)-4-(quinolin-3-yloxy)-2,3-dihydro-1H-inden-1-yl)oxy)phenyl)isothiazole 1-oxide (A)

Example 105

3-hydroxy-5-(4-(((R)-4-((6-methoxy-4-methylpyridin-3-yl)oxy)-2,3-dihydro-1H-inden-1-yl)oxy)phenyl)isothiazole 1-oxide (A)

Example 106

Synthesis of 3-hydroxy-5-(4-(((R)-4-((6-methoxy-2-methylpyridin-3-yl)oxy)-2,3-dihydro-1H-inden-1-yl)oxy)phenyl)isothiazole 1-oxide (A)

<Step 1> Synthesis of (S)-4-((6-methoxy-2-methylpyridin-3-yl)oxy)-2,3-dihydro-1H-inden-1-ol According to the method of (Example 99) <Step 1>, from (1S)-4-hydroxy-2,3-dihydro-1H-inden-1-ol (0.50 g) that is commercially available or can be obtained by a publicly known method and (6-methoxy-2-methylpyridin-3-yl) boronic acid (0.667 g), the subject compound (230 mg) was obtained as a yellowish-white solid.

<Step 2> Synthesis of (R)-(4-((−4-((6-methoxy-2-methylpyridin-3-yl)oxy)-2,3-dihydro-1H-inden-1-yl)oxy)phen yl) boronic acid N-methylimino diacetic acid ester According to the method of (Example 1) <Step 2>, from the compound (0.22 g) obtained in (Example 106) <Step 1>, the subject compound (319 mg) was obtained as a whitish-green solid.

<Step 3> Synthesis of 3-hydroxy-5-(4-(((R)-4-((6-methoxy-2-methylpyridin-3-yl)oxy)-2,3-dihydro-1H-inden-1-yl)oxy)phenyl)isothiazole 1-oxide (A)

According to the method of (Example 1) <Step 3>, from the compound (0.31 g) obtained in (Example 106) <Step 2>, the subject compound (154 mg) was obtained as a yellowish-white solid.

The compounds of (Example 107) to (Example 114) below were synthesized by the same method as or a method equivalent to the method of (Example 106) from each corresponding boronic acid.

Example 107

3-hydroxy-5-(4-(((R)-4-(4-(methylsulfonyl)phenoxy)-2,3-dihydro-1H-inden-1-yl)oxy)phenyl)isothiazole 1-oxide (A)

Example 108

5-(4-(((R)-4-(4-(2-ethoxyethoxy)-2,6-dimethylphenoxy)-2,3-dihydro-1H-inden-1-yl)oxy)phenyl)-3-hydroxyisothiazole 1-oxide (A)

Example 109

3-hydroxy-5-(4-(((R)-4-((6-morpholinopyridin-3-yl)oxy)-2,3-dihydro-1H-inden-1-yl)oxy) phenyl)isothiazole 1-oxide (A)

Example 110

3-hydroxy-5-(4-(((R)-4-((2-methoxypyrimidin-5-yl)oxy)-2,3-dihydro-1H-inden-1-yl)oxy) phenyl)isothiazole 1-oxide (A)

Example 111

3-hydroxy-5-(4-(((R)-4-(thiophen-3-yloxy)-2,3-dihydro-1H-inden-1-yl)oxy)phenyl)isothiazole 1-oxide (A)

Example 112

3-hydroxy-5-(4-(((R)-4-(3-(3-hydroxy-3-methylbutoxy)phenoxy)-2,3-dihydro-1H-inden-1-yl)oxy)phenyl)isothiazole 1-oxide (A)

Example 113

3-hydroxy-5-(4-(((R)-4-(4-(3-hydroxy-3-methylbutoxy)phenoxy)-2,3-dihydro-1H-inden-1-yl)oxy)phenyl)isothiazole 1-oxide (A)

Example 114

3-hydroxy-5-(4-(((R)-4-((2-methoxypyridin-4-yl)oxy)-2,3-dihydro-1H-inden-1-yl)oxy)phenyl)isothiazole 1-oxide (A)

Example 115

Synthesis of 3-hydroxy-5-(4-(((R)-4-(4-(3-(methylsulfonyl)propoxy)phenoxy)-2,3-dihydro-1H-inden-1-yl)oxy)phenyl)isothiazole 1-oxide (A)

<Step 1> Synthesis of 1-bromo-4-(3-(methylsulfonyl)propoxy)benzene

A mixed solution of 3-(methylsulfonyl)propyl 4-methylbenzenesulfonate (1.86 g) that can be obtained by a publicly known method, 4-bromophenol (1.0 g), potassium carbonate (1.20 g), and N,N-dimethylformamide (15 mL) was heated with stirring at 80° C. for 13 hours. The reaction mixture was left to reach room temperature, and to the reaction mixture, water was added, followed by filtering the deposited solid to obtain the subject compound (1.50 g) as a white solid.

<Step 2> Synthesis of (S)-4-(4-(3-(methylsulfonyl)propoxy)phenoxy)-2,3-dihydro-1H-inden-1-ol A mixed solution of (1S)-4-hydroxy-2,3-dihydro-1H-inden-1-ol (0.3 g) that is commercially available or can be obtained by a publicly known method, 2,2,6,6-tetramethyl-3,5-heptanedione (0.29 g), copper iodide (I) (95.1 mg), cesium carbonate (1.63 g), the compound (0.64 g) obtained in (Example 115) <Step 1>, and N-methylpyrrolidone (4.0 mL) was heated with stirring at 120° C. for 12 hours. The reaction solution was left to reach room temperature, followed by filtration, and the resulting insoluble materials were washed with ethyl acetate. From the resultant reaction mixture, the solvent was distilled off under reduced pressure, followed by purifying the resultant residue by NH silica gel column chromatography (eluate; n-hexane:ethyl acetate=50:50 to 0:100), and from the resultant, the solvent was distilled off under reduced pressure to obtain the subject compound (418 mg) as a colorless solid.

<Step 3> Synthesis of (R)-(4-((4-(4-(3-(methylsulfonyl)propoxy)phenoxy)-2,3-dihydro-1H-inden-1-yl)oxy)phenyl) boronic acid N-methylimino diacetic acid ester According to the method of (Example 1) <Step 2>, from the compound (408 mg) obtained in (Example 115) <Step 2>, the subject compound (425 mg) was obtained.

<Step 4> Synthesis of 3-hydroxy-5-(4-(((R)-4-(4-(3-(methylsulfonyl)propoxy)phenoxy)-2,3-dihydro-1H-inden-1-yl)oxy)phenyl)isothiazole 1-oxide (A)

According to the method of (Example 1) <Step 3>, from the compound (0.30 g) obtained in (Example 115) <Step 3>, the subject compound (92 mg) was obtained.

The compounds of (Example 116) and (Example 117) below were synthesized by the same method as or a method equivalent to the method of (Example 115) from each corresponding aryl halide.

Example 116

3-hydroxy-5-(4-(((R)-4-((6-(3-(methylsulfonyl)propoxy)pyridin-3-yl)oxy)-2,3-dihydro-1H-inden-1-yl)oxy)phenyl)isothiazole 1-oxide (A)

Example 117

3-hydroxy-5-(4-(((R)-4-((2-methyl-6-(3-(methylsulfonyl)propoxy)pyridin-3-yl)oxy)-2,3-dihydro-1H-inden-1-yl)oxy)phenyl)isothiazole 1-oxide (A)

Example 118

Synthesis of 6-(((1R)-1-(4-(3-hydroxy-1-oxidoisothiazol-5-yl)phenoxy)-2,3-dihydro-1H-inden-4-yl)oxy)nicotinonitrile (A)

<Step 1> Synthesis of (S)-6-((1-hydroxy-2,3-dihydro-1H-inden-4-yl)oxy)nicotinonitrile A mixed solution of (1S)-4-hydroxy-2,3-dihydro-1H-inden-1-ol (1 g) that is commercially available or can be obtained by a publicly known method, 6-chloronicotinonitrile (0.92 g), potassium carbonate (1.84 g), and N,N-dimethylformamide (10 mL) was heated and refluxed for 24 hours. The resultant reaction mixture was filtered by cerite filtration, and the filtrate was diluted with water, was extracted with ethyl acetate, was washed with a saturated saline, and was dried over anhydrous sodium sulfate. From the organic phase, the solvent was distilled off under reduced pressure, followed by purifying the resultant residue by silica gel column chromatography (eluate; n-hexane:ethyl acetate=100:0 to 60:40), and from the resultant, the solvent was distilled off under reduced pressure to obtain the subject compound (1.42 g) as an oily substance.

<Step 2> Synthesis of (R)-(4-((4-((5-cyanopyridin-2-yl)oxy)-2,3-dihydro-1H-inden-1-yl)oxy)phenyl) boronic acid N-methylimino diacetic acid ester According to the method of (Example 1) <Step 2>, from the compound (1.33 g) obtained in (Example 118) <Step 1>, the subject compound (1.58 g) was obtained as a gray amorphous.

<Step 3> Synthesis of 6-(((1R)-1-(4-(3-hydroxy-1-oxidoisothiazol-5-yl)phenoxy)-2,3-dihydro-1H-inden-4-yl)oxy)nicotinonitrile (A)

According to the method of (Example 1) <Step 3>, from the compound (0.30 g) obtained in (Example 118) <Step 2>, the subject compound (58 mg) was obtained as a pale yellow solid.

The compound of (Example 119) below was synthesized by the same method as or a method equivalent to the method of (Example 118) from each corresponding aryl halide.

Example 119

5-(((1R)-1-(4-(3-hydroxy-1-oxidoisothiazol-5-yl) phenoxy)-2,3-dihydro-1H-inden-4-yl)oxy)picolinonitrile (A)

Example 120

Synthesis of 3-hydroxy-5-(4-(spiro[5.5]undec-1-en-2-ylmethoxy)phenyl)isothiazole 1-oxide (A)<

<Step 1> Synthesis of (4-(spiro[5.5]undec-1-en-2-ylmethoxy)phenyl) boronic acid N-methylimino diacetic acid ester According to the method of (Example 1) <Step 2>, from spiro[5.5]undeca-1-ene-2-methanol (435 mg) synthesized according to a method described in [WO 2009/054479 pamphlet, (Example 41)], the subject compound (500 mg) was obtained.

<Step 2> Synthesis of 3-hydroxy-5-(4-(spiro[5.5] undec-1-en-2-ylmethoxy)phenyl)isothiazole 1-oxide (A)

According to the method of (Example 1) <Step 3>, from the compound (500 mg) obtained in (Example 120) <Step 1>, the subject compound (108 mg) was obtained as a pale yellow solid.

Example 121

Synthesis of 5-(4-((1-(2,6-dimethylphenyl)pyrrolidin-3-yl)methoxy)phenyl)-3-hydroxyisothiazole 1-oxide (A)

<Step 1> Synthesis of (1-(2,6-dimethylphenyl)pyrrolidin-3-yl)methanol

To a solution of 2-bromo-1,3-dimethylbenzene (500 mg), pyrrolidine-3-yl methanol hydrochloride (409 mg), bis (dibenzylideneacetone) palladium (155 mg), and 2-dicyclohexylphosphino-2',6'-dimethoxybiphenyl (SPhos; 222 mg) in tetrahydrofuran (5 mL), molecular sieves 4A (powder; 410 mg) were added. To the mixed solution, a solution (8.9 mL) of 1.0 M lithium hexamethyldisilazide in tetrahydrofuran was added, and the resultant reaction mixture was heated and refluxed for 2.5 hours. To the reaction solution, saturated sodium bicarbonate water and ethyl acetate were added, and the resultant reaction mixture was extracted with ethyl acetate. The organic phase was washed with a saturated saline and was dried over anhydrous sodium sulfate. From the organic phase, the solvent was distilled off under reduced pressure, followed by purifying the resultant residue by silica gel column chromatography (eluate; n-hexane:ethyl acetate=100:0 to 75:25), and from the resultant, the solvent was distilled off under reduced pressure to obtain the subject compound (154 mg) as a yellow oily substance.

<Step 2> Synthesis of 2-(4-((1-(2,6-dimethylphenyl) pyrrolidin-3-yl)methoxy)phenyl)-6-methyl-1,3,6,2-dioxazaborocane-4,8-dione According to the method of (Example 1) <Step 2>, from the compound (150 mg) obtained in (Example 121) <Step 1>, the subject compound (103 mg) was obtained as a pale yellow solid.

<Step 3> Synthesis of 5-(4-((1-(2,6-dimethylphenyl) pyrrolidin-3-yl)methoxy)phenyl)-3-hydroxyisothiazole 1-oxide (A)

According to the method of (Example 1) <Step 3>, from the compound (100 mg) obtained in (Example 121) <Step 2>, the subject compound (64 mg) was obtained as a yellow solid.

Example 122

Synthesis of 3-hydroxy-5-(4-(spiro[4.5]dec-6-en-7-ylmethoxy)phenyl)isothiazole 1-oxide (A)

<Step 1> Synthesis of (4-(spiro[4.5]dec-1-en-2-ylmethoxy)phenyl) boronic acid N-methylimino diacetic acid ester According to the method of (Example 1) <Step 2>, from spiro[4.5]deca-6-ene-7-methanol (0.40 g) synthesized according to a method described in [WO 2009/054479 pamphlet, (Example 7)], the subject compound (567 mg) was obtained as a white solid.

<Step 2> Synthesis of 3-hydroxy-5-(4-(spiro[4.5] dec-6-en-7-ylmethoxy)phenyl)isothiazole 1-oxide (A)

According to the method of (Example 1) <Step 3>, from the compound (0.30 g) obtained in (Example 122) <Step 1>, the subject compound (175 mg) was obtained as a white solid.

Example 123

Synthesis of 3-hydroxy-5-(4-((4-(spiro[inden-1,4'-piperidin]-1'-ylmethyl)benzyl)oxy)phenyl)isothiazole 1-oxide (A)

<Step 1> Synthesis of (4-((4-(spiro[inden-1,4'-piperidin]-1'-ylmethyl)benzyl)oxy)phenyl) boronic acid N-methylimino diacetic acid ester According to the method of (Example 1) <Step 2>, from (4-(spiro[inden-1,4'-piperidin]-1'-ylmethyl)phenyl)methanol (0.70 g) synthesized according to a method described in [WO 2011/046851 pamphlet, (preparation 48)], the subject compound (798 mg) was obtained as a white amorphous solid.

<Step 2> Synthesis of 3-hydroxy-5-(4-((4-(spiro [inden-1,4'-piperidin]-1'-ylmethyl)benzyl)oxy)phenyl)isothiazole 1-oxide (A)

According to the method of (Example 1) <Step 3>, from the compound (0.40 g) obtained in (Example 123) <Step 1>, the subject compound (198 mg) was obtained as a pale yellow amorphous solid.

Example 124

Synthesis of 3-hydroxy-5-(4-((4-((1-methylspiro [indolin-3,4'-piperidin]-1'-yl)methyl)benzyl)oxy) phenyl)isothiazole 1-oxide (A)

<Step 1> Synthesis of 4-((1-methylspiro[indolin-3, 4'-piperidin]-1'-yl)methyl) benzoic acid A mixed solution of 1-methylspiro[indolin-3,4'-piperidine] (1.0 g) synthesized according to a method described in

[WO 2011/046851 pamphlet, (preparation 15)], 4-(bromomethyl) benzoic acid (1.08 g), and N,N-diisopropylethylamine (2.61 mL) in ethanol (20 mL) was heated and refluxed for 2 hours. To the resultant reaction mixture, N,N-diisopropylethylamine (1.04 mL) was further added, and the resultant reaction mixture was heated and refluxed for 2 hours. The reaction solution was left to reach room temperature, and from the reaction solution, the solvent was distilled off under reduced pressure to obtain a mixture (2.37 g) containing the subject compound. The resultant mixture was used in the next reaction without further purification.

<Step 2> Synthesis of (4-((1-methylspiro[indolin-3,4'-piperidin]-1'-yl)methyl)phenyl)methanol The compound obtained in (Example 124) <Step 1> was dissolved in tetrahydrofuran (60 mL), and to the resultant solution, lithium aluminum hydride (0.87 g) was added under ice-cooling, followed by stirring the resultant reaction mixture for 1 hour under ice-cooling. To the resultant reaction mixture, lithium aluminum hydride (0.87 g) was further added under ice-cooling, followed by stirring the resultant reaction mixture for 1 hour under ice-cooling. To the reaction solution, a 1M sodium hydroxide aqueous solution (1.76 mL), water (1.76 mL), and a 1M sodium hydroxide aqueous solution (5.28 mL) were added, and the resultant solution was filtered by cerite filtration. From the filtrate, the solvent was distilled off under reduced pressure, and the resultant residue was purified by silica gel column chromatography, followed by distilling off the solvent under reduced pressure to obtain the subject compound (1.11 g) as a colorless oily substance.

<Step 3> Synthesis of (4-((4-((1-methylspiro[indolin-3,4'-piperidin]-1'-yl)methyl)benzyl)oxy)phenyl) boronic acid N-methylimino diacetic acid ester According to the method of (Example 1) <Step 2>, from the compound (0.20 g) obtained in (Example 124) <Step 2>, the subject compound (28 mg) was obtained as a white solid.

<Step 4> Synthesis of 3-hydroxy-5-(4-((4-((1-methylspiro[indolin-3,4'-piperidin]-1'-yl)methyl)benzyl)oxy)phenyl)isothiazole 1-oxide (A)

According to the method of (Example 1) <Step 3>, from the compound (28 mg) obtained in (Example 124) <Step 3>, the subject compound (10 mg) was obtained as a yellow amorphous solid.

Example 125

Synthesis of 4-(3-((4-(3-hydroxy-1-oxidoisothiazol-5-yl)phenoxy)methyl)phenoxy)benzonitrile (A)

<Step 1> Synthesis of 4-(3-((4-(6-methyl-4,8-dioxo-1,3,6,2-dioxazaborocan-2-yl)phenoxy)methyl)phenoxy) benzonitrile According to the method of (Example 1) <Step 2>, from 4-(3-(hydroxymethyl)phenoxy)benzonitrile (0.21 g) that is commercially available or is obtained according to a known method, the subject compound (0.32 g) was obtained as colorless solid.

<Step 2> Synthesis of 4-(3-((4-(3-hydroxy-1-oxidoisothiazol-5-yl)phenoxy)methyl)phenoxy)benzonitrile (A)

According to the method of (Example 1) <Step 3>, from the compound (0.15 g) obtained in (Example 125) <Step 1>, the subject compound (0.11 g) was obtained as colorless solid.

The compounds of (Example 126) to (Example 129) below were synthesized by the same method as or a method equivalent to the method of (Example 106) from each corresponding boronic acid ester.

Example 126

3-hydroxy-5-(4-(((R)-4-((2-methylpyridin-3-yl)oxy)-2,3-dihydro-1H-inden-1-yl)oxy) phenyl)isothiazole 1-oxide (A) (Example 127)

3-hydroxy-5-(4-(((R)-4-((3-methoxypyridin-5-yl)oxy)-2,3-dihydro-1H-inden-1-yl)oxy) phenyl) isothiazole 1-oxide (A)

Example 128

3-(((1R)-1-(4-(3-hydroxy-1-oxidoisothiazol-5-yl)phenoxy)-2,3-dihydro-1H-inden-4-yl)oxy)benzamide (A)

Example 129

4-(((1R)-1-(4-(3-hydroxy-1-oxidoisothiazol-5-yl)phenoxy)-2,3-dihydro-1H-inden-4-yl)oxy)benzamide (A)

The compounds of (Example 130) to (Example 134) below were synthesized by the same method as or a method equivalent to the method of (Example 118) from each corresponding boronic acid ester.

Example 130

3-hydroxy-5-(4-(((R)-4-((6-methylpyridin-2-yl)oxy)-2,3-dihydro-1H-inden-1-yl)oxy) phenyl)isothiazole 1-oxide (A)

Example 131

4-(((R)-1-(4-(3-hydroxy-1-oxidoisothiazol-5-yl)phenoxy)-2,3-dihydro-1H-inden-4-yl)oxy)-2-(2-oxooxazolidin-3-yl)benzonitrile (A)

Example 132

3-hydroxy-5-(4-(((R)-4-((3-methoxypyridin-2-yl)oxy)-2,3-dihydro-1H-inden-1-yl)oxy) phenyl) isothiazole 1-oxide (A)

Example 133

3-hydroxy-5-(4-(((R)-4-((4-methylpyridin-2-yl)oxy)-2,3-dihydro-1H-inden-1-yl)oxy) phenyl)isothiazole 1-oxide (A)

Example 134

3-hydroxy-5-(4-(((R)-4-((5-methylpyridin-2-yl)oxy)-2,3-dihydro-1H-inden-1-yl)oxy) phenyl)isothiazole 1-oxide (A)

The compound of (Example 135) below were synthesized by the same method as or a method equivalent to the method of (Example 115) from the corresponding boronic acid ester.

Example 135

3-hydroxy-5-(4-(((R)-4-((2-methylpyridin-4-yl)oxy)-2,3-dihydro-1H-inden-1-yl)oxy) phenyl)isothiazole 1-oxide (A)

Example 136

Synthesis of 4-(((1R)-1-(4-(3-hydroxy-1-oxido-isothiazol-5-yl)phenoxy)-2,3-dihydro-1H-inden-4-yl)oxy)-N-methylbenzamide (A)

<Step 1> Synthesis of methyl (S)-4-((1-hydroxy-2,3-dihydro-1H-inden-4-yl)oxy)benzoate According to the method of (Example 99) <Step 1>, from (1S)-4-hydroxy-2,3-dihydro-1H-inden-1-ol (0.99 g) and (4-(methoxycarbonyl)phenyl)boronic acid (1.31 g) that are commercially available or are obtained according to a known method, the subject compound (0.80 g) was obtained as pale yellow solid.

<Step 2> Synthesis of methyl (R)-4-((1-(4-(6-methyl-4,8-dioxo-1,3,6,2-dioxazaborocane-2-yl)phenoxy)-2,3-dihydro-1H-inden-4-yl)oxy)benzoate According to the method of (Example 1) <Step 2>, from the compound (0.70 g) obtained in (Example 136) <Step 1>, the subject compound (1.0 g) was obtained as pale yellow solid.

<Step 3> Synthesis of methyl 4-(((R)-1-(4-(3-hydroxy-1-oxidoisothiazol-5-yl)phenoxy)-2,3-dihydro-1H-inden-4-yl)oxy) benzoate (A)

According to the method of (Example 1) <Step 3>, from the compound (0.1 g) obtained in (Example 136) <Step 2>, the subject compound (41 mg) was obtained as yellow solid.

<Step 4> Synthesis of 4-(((R)-1-(4-(3-hydroxy-1-oxidoisothiazol-5-yl)phenoxy)-2,3-dihydro-1H-inden-4-yl)oxy)-N-methylbenzamide (A)

To a solution of the compound (38 mg) obtained in (Example 136) <Step 3> in methanol (0.2 ml), 40% methylamine aqueous solution (0.12 g) was added at room temperature, and the resultant mixture was stirred at room temperature for 172 hours. The resultant reaction solution was concentrated under reduced pressure, and saturated ammonium chloride aqueous solution was added to the resultant residue, and methylene chloride and methanol were added thereto, and subjected to phase-separation, and the resultant aqueous phase was extracted with methylene chloride-methanol solution. The resultant organic phases were mixed, and washed with a saturated saline. The resultant organic phase was dried over anhydrous sodium sulfate, filtered, and the solvent was distilled off under reduced pressure to obtain the subject compound (28 mg) as pale brown solid.

Example 137

Synthesis of 4-(((R)-1-(4-(3-hydroxy-1-oxidoisothiazol-5-yl)phenoxy)-2,3-dihydro-1H-inden-4-yl)oxy)-N,N-dimethylbenzamide (A)

<Step 1> Synthesis of (S)-4-((1-hydroxy-2,3-dihydro-1H-inden-4-yl)oxy) benzoic acid To a solution of the compound (0.10 g) obtained in (Example 136) <Step 1> in methanol (0.6 ml), an aqueous solution (0.4 ml) of lithium hydroxide monohydrate (30 mg) was added at room temperature, and the resultant mixture was stirred at room temperature for 17 hours. 1M hydrochloric acid was added to the resultant solution and the resultant solution was extracted with ethyl acetate, and then the resultant organic phase was dried over anhydrous sodium sulfate, filtered, and the solvent was distilled off under reduced pressure to obtain the subject compound (86 mg) as pale yellow amorphous.

<Step 2> Synthesis of (S)-4-((1-hydroxy-2,3-dihydro-1H-inden-4-yl)oxy)-N,N-dimethylbenzamide To a solution of the compound (80 mg) obtained in (Example 137) <Step 1> in methanol (1 ml), 2M dimethylamine in methanol (0.16 ml) and DMT-MM (0.12 g) were added at room temperature, and the resultant mixture was stirred for 64 hours. 0.5M hydrochloric acid was added to the resultant solution and the resultant solution was extracted with ethyl acetate, and then the resultant organic phase was washed with a saturated saline, dried over anhydrous sodium sulfate, filtered, and the solvent was distilled off under reduced pressure to obtain the subject compound (80 mg) as pale yellow solid.

<Step 3> Synthesis of (R)-N,N-dimethyl-4-((1-(4-(6-methyl-4,8-dioxo-1,3,6,2-dioxazaborocane-2-yl) phenoxy)-2,3-dihydro-1H-inden-4-yl)oxy)benzamide According to the method of (Example 1) <Step 2>, from the compound (80 mg) obtained in (Example 137) <Step 2>, a mixture (0.28 g) containing the subject compound was obtained as pale yellow oil.

<Step 4> Synthesis of 4-(((R)-1-(4-(3-hydroxy-1-oxido-isothiazol-5-yl)phenoxy)-2,3-dihydro-1H-inden-4-yl)oxy)-N,N-dimethylbenzamide (A)

According to the method of (Example 1) <Step 3>, from the compound (60 mg) obtained in (Example 137) <Step 3>, the subject compound (18 mg) was obtained as white amorphous.

Example 138

Synthesis of 4-((3-(4-(3-hydroxy-1-oxidoisothiazol-5-yl)phenoxy)-2,3-dihydrobenzofuran-7-yl)oxy) benzonitrile (A)

<Step 1> Synthesis of 2,3-dihydrobenzofuran-3,7-diol

To a solution of trimethylsulfoxonium iodide (16.7 g) in dimethylsufoxide (75 ml), sodium hydride (3.19 g) was added, and the resultant mixture was stirred for 1 hour. A solution of 2,3-dihydroxybenzaldehyde (10 g) in dimethylsufoxide (75 ml) was added thereto and the resultant mixture was stirred for 2 days. To the resultant reaction solution, saturated ammonium chloride aqueous solution was added, and extracted with ethyl acetate. The resultant organic phase was washed with a saturated saline, dried over anhydrous sodium sulfate, and filtered. From the reaction mixture, the solvent was distilled off under reduced pressure, followed by purifying the resultant residue by silica gel column chromatography (eluate; n-hexane:ethyl acetate=100:0 to 80:20), and from the resultant, the solvent was distilled off under reduced pressure to obtain the subject compound (4.2 g) as yellow solid.

<Step 2> Synthesis of 4-((3-hydroxy-2,3-dihydrobenzofuran-7-yl)oxy)benzonitrile

According to the method of (Example 99) <Step 1>, from the compound (3.0 g) obtained in (Example 138) <Step 1>, the subject compound (1.3 g) was obtained as white solid.

<Step 3> Synthesis of 4-((3-(4-(4,4,5,5-tetramethyl-1,3,2-dioxaborolane-2-yl)phenoxy)-2,3-dihydrobenzofuran-7-yl)oxy)benzonitrile According to the method of (Example 1) <Step 2>, from the compound (0.33 g) obtained in (Example 138) <Step 2> and 4-(4,4,5,5-tetramethyl-1,3,2-dioxaborolane-2-yl)phenol (0.28 g), a mixture (0.29 g) containing the subject compound was obtained as white amorphous.

<Step 4> Synthesis of 4-((3-(4-(3-hydroxy-1-oxidoisothiazol-5-yl)phenoxy)-2,3-dihydrobenzofuran-7-yl)oxy)benzonitrile (A)

According to the method of (Example 1) <Step 3>, from the compound (20 mg) obtained in (Example 138) <Step 3>, the subject compound (10 mg) was obtained as pale yellow solid.

The compounds of (Example 139) to (Example 141) below were synthesized by the same method as or a method equivalent to the method of (Example 138) from each corresponding boronic acid ester.

Example 139

3-hydroxy-5-(4-((7-phenoxy-2,3-dihydrobenzofuran-3-yl)oxy)phenyl)isothiazole 1-oxide (A)

Example 140

3-hydroxy-5-(4-((7-((6-methoxypyridin-3-yl)oxy)-2,3-dihydrobenzofuran-3-yl)oxy)phenyl)isothiazole 1-oxide (A)

Example 141

3-hydroxy-5-(4-((7-((6-(3-hydroxy-3-methylbutoxy)-2-methylpyridin-3-yl)oxy)-2,3-dihydrobenzofuran-3-yl)oxy)phenyl)isothiazole 1-oxide (A)

Example 142

Synthesis of 3-hydroxy-5-(4-((7-(6-(3-hydroxy-3-methylbutoxy)-2-methylpyridin-3-yl)-2,3-dihydrobenzofuran-3-yl)oxy)phenyl)isothiazole 1-oxide (A)

<Step 1> Synthesis of 7-bromo-2,3-dihydrobenzofuran-3-ol

According to the method of (Example 138) <Step 1>, from 3-bromo-2-hydroxybenzaldehyde (3.0 g), the subject compound (2.5 g) was obtained as yellow oil.

<Step 2> Synthesis of 2-(4-((7-bromo-2,3-dihydrobenzofuran-3-yl)oxy)phenyl)-4,4,5,5-tetramethyl-1,3,2-dioxa borolane According to the method of (Example 1) <Step 2>, from the compound (1.6 g) obtained in (Example 142) <Step 1> and 4-(4,4,5,5-tetramethyl-1,3,2-dioxaborolane-2-yl)phenol (1.6 g), the subject compound (0.45 g) was obtained as white solid.

<Step 3> Synthesis of 5-(4-((7-bromo-2,3-dihydrobenzofuran-3-yl)oxy)phenyl)-3-hydroxyisothiazole 1-oxide (A)

According to the method of (Example 1) <Step 3>, from the compound (0.40 g) obtained in (Example 142) <Step 2>, the subject compound (0.20 g) was obtained as pale yellow solid.

<Step 4> Synthesis of 3-hydroxy-5-(4-((7-(6-(3-hydroxy-3-methylbutoxy)-2-methylpyridin-3-yl)-2,3-dihydrobenzofuran-3-yl)oxy)phenyl)isothiazole 1-oxide (A)

According to the method of (Example 4), from the compound (30 mg) obtained in (Example 142) <Step 3>, the subject compound (3.0 mg) was obtained as yellow solid.

Example 143

Synthesis of 3-hydroxy-5-(4-((7-(4-(3-hydroxy-3-methylbutoxy)-2,6-dimethylphenyl)-2,3-dihydrobenzofuran-3-yl)oxy)phenyl)isothiazole 1-oxide (A)

According to the method of (Example 4), from the compound (20 mg) obtained in (Example 142) <Step 3>, the subject compound (3.7 mg) was obtained as yellow solid.

Example 144

Synthesis of Optically Active 4-((3-(4-(3-hydroxy-1-oxidoisothiazol-5-yl)phenoxy)-2,3-dihydrobenzofuran-7-yl)oxy)benzonitrile (A)

The compound (75 mg) obtained in (Example 138) was subjected to optical resolution with a preparative chromatography (column: CHIRALPAK AS-H (20 mm×250 mm) manufactured by Daicel Chemical Industries, Ltd., eluate: ethanol (0.1% trifluoroacetic acid was added), flow rate: 3 ml/min.) to obtain each diastereomer of the dihydrobenzofuran moiety of the subject compound.
First fraction (31.8 mg, white solid, >99% ee, retention time: 4.4 min. (diastereomer A: Example 144(A)-a).
Second fraction (31.0 mg, white solid, >99% ee, retention time: 7.4 min. (diastereomer B: Example 144(A)-b).
The optical purity and retention time were determined according to the following condition (column: CHIRALPAK AS-H (0.46 cm×15 cm) manufactured by Daicel Chemical Industries, Ltd., eluate: ethanol (0.1% trifluoroacetic acid was added), flow rate: 1.0 ml/min., column temperature: 40° C.).

Example 145

Synthesis of Optically Active 3-hydroxy-5-(4-((7-phenoxy-2,3-dihydrobenzofuran-3-yl)oxy)phenyl)isothiazole 1-oxide (A)

According to the method of (Example 144), from the compound (75 mg) obtained in (Example 139), each diastereomer of the dihydrobenzofuran moiety of the subject compound was obtained.
First fraction (0.2 mg, white solid, >99% ee, retention time: 3.6 min. (diastereomer A: Example 145(A)-a).

Second fraction (9.4 mg, white solid, >99% ee, retention time: 7.4 min. (diastereomer B: Example 145(A)-b).

The optical purity and retention time were determined according to the following condition (column: CHIRALPAK AY-H (0.46 cm×25 cm) manufactured by Daicel Chemical Industries, Ltd., eluate: ethanol (0.1% trifluoroacetic acid was added), flow rate: 1.0 ml/min., column temperature: 40° C.).

The compounds of (Example 146) to (Example 147) below were synthesized by the same method as or a method equivalent to the method of (Example 137) from each corresponding boronic acid ester.

Example 146

4-(((R)-1-(4-(3-hydroxy-1-oxidoisothiazol-5-yl)phenoxy)-2,3-dihydro-1H-inden-4-yl)oxy)-N-(2-methoxyethyl)-N-methylbenzamide (A)

Example 147

(4-(((R)-1-(4-(3-hydroxy-1-oxidoisothiazol-5-yl)phenoxy)-2,3-dihydro-1H-inden-4-yl)oxy)phenyl)(pyrrolidine-1-yl)methanone (A)

Example 148

Synthesis of Optically Active 3-hydroxy-5-(4-((7-(4-(3-hydroxy-3-methylbutoxy)-2,6-dimethylphenyl)-2,3-dihydrobenzofuran-3-yl)oxy)phenyl)isothiazole 1-oxide (A)

According to the method of (Example 144), from the compound (35 mg) obtained in (Example 143), each diastereomer of the dihydrobenzofuran moiety of the compound was obtained.

First fraction (6.1 mg, pale yellow solid, >99% ee, retention time: 9.0 min. (diastereomer A: Example 148(A)-a).

Second fraction (10.2 mg, pale yellow solid, >99% ee, retention time: 12.0 min. (diastereomer B: Example 148(A)-b).

The optical purity and retention time were determined according to the following condition (column: CHIRALPAK AD-H (0.46 cm×15 cm) manufactured by Daicel Chemical Industries, Ltd., eluate: ethanol (0.1% trifluoroacetic acid was added), flow rate: 1.0 ml/min., column temperature: 40° C.).

Example 149

Synthesis of 3-hydroxy-5-(4-(((R)-4-((6-methoxypyridin-2-yl)oxy)-2,3-dihydro-1H-inden-1-yl)oxy)phenyl)isothiazole 1-oxide (A)

<Step 1> Synthesis of (S)-4-((6-methoxypyridin-2-yl)oxy)-2,3-dihydro-1H-inden-1-ol To a solution in NMP (4 ml) of (1S)-4-hydroxy-2,3-dihydro-1H-inden-1-ol (0.50 g) that is commercially available or can be obtained by a publicly known method, 2-bromo-6-methoxypyridine (0.75 g), copper iodide (I) (0.32 g), 2,2,6,6-tetramethylheptane-3,5-dione (1.1 ml) and cesium carbonate (2.7 g) were added, and the resultant mixture was heated in a microwave oven at 100° C. for 15 minutes. To the mixture, ethyl acetate and water were added, followed by extracting the resultant mixture with ethyl acetate two times, and the organic phase was washed sequentially with water two times and a saturated saline, and then was dried over anhydrous sodium sulfate. From the organic phase, the solvent was distilled off under reduced pressure, followed by purifying the resultant residue by silica gel column chromatography (eluate; n-hexane:ethyl acetate=80:20 to 65:35), and from the resultant, the solvent was distilled off under reduced pressure to obtain the subject compound (0.61 g) as a brown oily substance.

<Step 2> Synthesis of 4-(((R)-4-((6-methoxypyridin-2-yl)oxy)-2,3-dihydro-1H-inden-1-yl)oxy)phenyl boronic acid N-methylimino diacetic acid ester According to the method of (Example 1) <Step 2>, from the compound (0.30 g) obtained in (Example 149) <Step 1>, the subject compound (0.28 g) was obtained as pale yellow amorphous.

<Step 3> Synthesis of 3-hydroxy-5-(4-(((R)-4-((6-methoxypyridin-2-yl)oxy)-2,3-dihydro-1H-inden-1-yl)oxy)phenyl)isothiazole 1-oxide (A)

According to the method of (Example 1) <Step 3>, from the compound (0.28 g) obtained in (Example 149) <Step 2>, the subject compound (0.13 g) was obtained as pale yellow amorphous.

Example 150

Synthesis of Optically Active 5-(4-((7-bromo-2,3-dihydrobenzofuran-3-yl)oxy)phenyl)-3-hydroxy-isothiazole 1-oxide (A)

<Step 1> Optically Active 7-bromo-2,3-dihydrobenzofuran-3-ol

Triethylamine (0.2 ml) was added to formic acid (63 ml), to the resultant mixture, a solution in methylene chloride (2.1 ml) of 7-bromo-2,3-dihydrobenzofuran-3-one (0.10 g) that is commercially available or can be obtained by a publicly known method was added, chloro[(1S,2S)-N-(p-toluenesulfonyl)-1,2-diphenylethylenediamine]-(mesitylene) ruthenium (II) (8.8 mg) was added, and the resultant mixture was stirred at room temperature for 3 hours. To the resultant mixture, ethyl acetate and water were added, followed by extracting the resultant mixture with ethyl acetate, and the organic phase was washed with a saturated saline, and then was dried over anhydrous sodium sulfate. From the organic phase, the solvent was distilled off under reduced pressure, followed by purifying the resultant residue by silica gel column chromatography (eluate; n-hexane:ethyl acetate=5:1 to 3:1), and from the resultant, the solvent was distilled off under reduced pressure to obtain the subject compound (95 mg) as pale orange oil.

<Step 2> Synthesis of optically active 2-(4-((7-bromo-2,3-dihydrobenzofuran-3-yl)oxy)phenyl)-4,4,5,5-tetramethyl-1,3,2-dioxaborolane According to the method of (Example 1) <Step 2>, from the compound (0.35 g) obtained in (Example 150) <Step 1> and 4-(4,4,5,5-tetramethyl-1,3,2-dioxaborolan-2-yl)phenol (0.35 g) that is commercially available or can be obtained by a publicly known method was added, the subject compound (0.14 g) was obtained as yellow oil.

<Step 3> Synthesis of optically active 5-(4-((7-bromo-2,3-dihydrobenzofuran-3-yl)oxy)phenyl)-3-hydroxyisothiazole 1-oxide (A)

According to the method of (Example 1) <Step 3>, from the compound (0.13 g) obtained in (Example 150) <Step 2>, the subject compound (15 mg) was obtained as white solid.

Example 151

Synthesis of Optically Active 5-(4-((7-(2,6-dimethyl-4-(3-(methylsulfonyl)propoxy)phenyl)-2,3-dihydrobenzofuran-3-yl)oxy)phenyl)-3-hydroxyisothiazole 1-oxide (A)

<Step 1> Synthesis of 2-(2,6-dimethyl-4-(3-(methylsulfonyl)propoxy)phenyl)-5,5-dimethyl-1,3,2-dioxaborinane To a solution in 1,4-dioxane (10 ml) of 2-bromo-1,3-dimethyl-5-(3-(methylsulfonyl)propoxy)benzene (1.0 g) and bis(neopentyl glycolato)diboron (1.1 g) that can be obtained by a publicly known method, potassium acetate (0.92 g) and [1,1'-bis(diphenylphosphino)ferrocene] dichloropalladium(II)-dichloromethane adduct (0.25 g) were added, and the resultant mixture was heated and refluxed for 6 hours. To the resultant reaction solution, water was added, followed by extracting the resultant mixture with ethyl acetate, and the organic phase was washed with a saturated saline, and then was dried over anhydrous sodium sulfate. The residue obtained by distilling off the solvent under reduced pressure was purified by NH silica gel column chromatography (eluate; n-hexane:ethyl acetate=100:0 to 80:20) to obtain the subject compound (0.70 g) as pale brown solid.

<Step 2> Synthesis of optically active 5-(4-((7-(2,6-dimethyl-4-(3-(methylsulfonyl) propoxy)phenyl)-2,3-dihydrobenzofuran-3-yl)oxy)phenyl)-3-hydroxyisothiazole 1-oxide (A)

According to the method of (Example 4), from the compound (12 mg) obtained in (Example 150) and the compound (16 mg) obtained in (Example 150) <Step 1>, the subject compound (11 mg) was obtained as pale yellow solid.

Example 152

Synthesis of Optically Active 3-hydroxy-5-(4-((7-((6-methoxypyridin-3-yl)oxy)-2,3-dihydrobenzofuran-3-yl)oxy)phenyl)isothiazole 1-oxide (A)

The compound (85 mg) obtained in (Example 140) was subjected to optical resolution with an optically active HPLC (column: CHIRALPAK AS-H (2 cm×25 cm) manufactured by Daicel Chemical Industries, Ltd., eluate: hexane:ethanol=1:1, flow rate: 1.2 ml/min.) to obtain the isomer of the subject compound.
First fraction (10 mg, white solid, >99% ee, retention time: 10.2 min. (isomer a: Example 152(A)-a).
Second fraction (24 mg, white solid, 92% ee, retention time: 11.7 min. (isomer b: Example 152(A)-b).
The optical purity and retention time were determined according to the following condition (column: CHIRALPAK AS-H (0.46 cm×15 cm) manufactured by Daicel Chemical Industries, Ltd., eluate: ethanol:trifluoroacetic acid=100:0.1 (V/V), flow rate: 1.0 ml/min., column temperature: 40° C.).

The following compounds obtained in (Example 153) and (Example 154) were subjected to optical resolution by the same method as or a method equivalent to the method of (Example 152) to the isomers of the subject compounds.

Example 153

Optically Active 3-hydroxy-5-(4-((7-((6-(3-hydroxy-3-methylbutoxy)-2-methylpyridin-3-yl)oxy)-2,3-dihydrobenzofuran-3-yl)oxy)phenyl)isothiazole 1-oxide (A)-a and -b Example 154

Optically Active 3-hydroxy-5-(4-((7-(6-(3-hydroxy-3-methylbutoxy)-2-methylpyridin-3-yl)-2,3-dihydrobenzofuran-3-yl)oxy)phenyl)isothiazole 1-oxide (A)-a and -b Example 155

Synthesis of Optically Active 3-hydroxy-5-(4-((7-(m-tolyloxy)-2,3-dihydrobenzofuran-3-yl)oxy)phenyl)isothiazole 1-oxide (A)

<Step 1> Synthesis of methyl 2-hydroxy-3-(m-tolyloxy) benzoate

According to the method of (Example 99) <Step 1>, from methyl 2,3-dihydroxybenzoate (1 g) and m-tolyl boronic acid (0.97 g) that are commercially available, the subject compound (0.56 g) was obtained as pale yellow oil.

<Step 2> Synthesis of methyl 2-(2-ethoxy-2-oxoethoxy)-3-(m-tolyloxy) benzoate To a solution in DMF (8.2 ml) of the compound (0.56 g) obtained in (Example 155)<Step 1>, ethyl bromoacetate (0.29 ml) and potassium carbonate (0.59 g) were added, and the resultant mixture was stirred at room temperature for 1 hour. The resultant mixture was filtered to remove insoluble substance, and then saturated ammonium chloride aqueous solution and ethyl acetate were added, followed by extracting the resultant mixture with ethyl acetate, and the combined organic phases were washed with a saturated saline. The resultant organic phase was dried over anhydrous sodium sulfate, and filtered. From the organic phase, the solvent was distilled off under reduced pressure, followed by purifying the resultant residue by silica gel column chromatography (eluate; n-hexane:ethyl acetate=5:1), and from the resultant, the solvent was distilled off under reduced pressure to obtain the subject compound (0.57 g) as a pale yellow oily substance.

<Step 3> Synthesis of 2-(carboxymethoxy)-3-(m-tolyloxy) benzoic acid

To a solution in methanol (8.2 ml) of the compound (0.57 g) obtained in (Example 155) <Step 2>, 1M sodium hydroxide aqueous solution (4.1 ml) was added, and the resultant mixture was heated and refluxed at 70° C. From the resultant reaction solution, the solvent was distilled off under reduced pressure. To the resultant residue, 1M hydrochloric acid was added, followed by extracting the resultant mixture with ethyl acetate, and the organic phase was washed with a saturated saline, dried over anhydrous sodium sulfate, filtered, and then the solvent was distilled off under reduced pressure to obtain the subject compound (0.50 g) as colorless amorphous.

<Step 4> Synthesis of 7-(m-tolyloxy) benzofuran-3-yl acetate

To the compound (0.49 g) obtained in (Example 155) <Step 3>, sodium acetate (0.20 g), acetic anhydride (1.7 ml) and acetic acid (0.26 ml) were added, and the resultant mixture was stirred at 130° C. overnight. To the resultant mixture, water was added, followed by extracting the resultant mixture with ethyl acetate. The resultant organic phase was washed with a saturated saline, dried over anhydrous sodium sulfate, and filtered. From the organic phase, the solvent was distilled off under reduced pressure, followed by purifying the resultant residue by silica gel column chromatography (eluate; n-hexane:ethyl acetate=95:5), and from the resultant, the solvent was distilled off under reduced pressure to obtain the subject compound (0.33 g) as a pale yellow oily substance.

<Step 5> Synthesis of 7-(m-tolyloxy) benzofuran-3 (2H)-one

To a solution in methanol (11.7 ml) of the compound (0.32 g) obtained in (Example 155) <Step 4>, 1M hydrochloric acid (2.9 ml) was added, and the resultant mixture was heated and refluxed at 70° C. for 2.5 hours. From the resultant reaction solution, the solvent was distilled off under reduced pressure, and ethyl acetate was added. The resultant organic phase was dried over anhydrous sodium sulfate, filtered, and then the solvent was distilled off under reduced pressure. The resulting residue was purified by silica gel column chromatography (eluate; n-hexane:ethyl acetate=96:4), followed by distilling off the solvent under reduced pressure to obtain the subject compound (0.21 g) as orange solid.

<Step 6> Synthesis of Optically Active 7-(m-tolyloxy)-2,3-dihydrobenzofuran-3-ol According to the method of (Example 150) <Step 1>, from the compound (0.16 g) obtained in (Example 155) <Step 5>, the subject compound (0.15 g) was obtained as pale brown oil.

<Step 7> Synthesis of Optically Active 4,4,5,5-tetramethyl-2-(4-((7-(m-tolyloxy)-2,3-dihydrobenzofuran-3-yl)oxy)phenyl)-1,3,2-dioxaborolane According to the method of (Example 1) <Step 2>, from the compound (0.14 g) obtained in (Example 155) <Step 6> and 4-(4,4,5,5-tetramethyl-1,3,2-dioxaborolan-2-yl) phenol (0.12 g) that is commercially available or can be obtained by a publicly known method, the subject compound (40 mg) was obtained as pale yellow amorphous.

<Step 8> Synthesis of Optically Active 3-hydroxy-5-(4-((7-(m-tolyloxy)-2,3-dihydrobenzofuran-3-yl)oxy)phenyl)isothiazole 1-oxide (A)

According to the method of (Example 1) <Step 3>, from the compound (38 mg) obtained in (Example 155) <Step 7>, the subject compound (25 mg) was obtained as pale yellow amorphous.

The compound obtained in (Example 3) <Step 2> was subjected to the same method as or a method equivalent to the method of (Example 4) to obtain the following compounds of (Example 156) and (Example 157) being the subject compounds.

Example 156

4-((1R)-1-(4-(3-hydroxy-1-oxidoisothiazol-5-yl)phenoxy)-2,3-dihydro-1H-inden-4-yl) benzonitrile (A)

Example 157

5-((1R)-1-(4-(3-hydroxy-1-oxidoisothiazol-5-yl)phenoxy)-2,3-dihydro-1H-inden-4-yl) picolinonitrile (A)

Example 158

Synthesis of 5-(4-(((R)-4-(3,4-dihydroquinoline-1 (2H)-yl)-2,3-dihydro-1H-inden-1-yl)oxy)phenyl)-3-hydroxyisothiazole 1-oxide (A)

To the compound (0.10 g) obtained in (Example 3) <Step 2>, bis(dibenzylideneacetone) palladium (16 mg), BINAP (34 mg), sodium tert-butoxide (0.14 g), 1,2,3,4-tetrahydroquinoline (40 mg) and toluene (6 ml) were added, and the resultant mixture was heated in a microwave oven at 150° C. for 30 minutes. To the mixture, ethyl acetate and saturated ammonium chloride aqueous solution were added. The solid precipitated by adding ethyl acetate was filtered, and the resultant solid was purified with LC/MS to obtain the subject compound.

Example 159

Synthesis of 3-hydroxy-5-(4-((4-phenoxybenzyl)oxy)phenyl)isothiazole 1-oxide (A)

<Step 1> Synthesis of 4-((4-phenoxybenzyl)oxy)phenyl boronic acid N-methylimino diacetic acid ester According to the method of (Example 1) <Step 2>, from (4-phenoxyphenyl) methanol (0.47 g) that is commercially available or can be obtained by a publicly known method, and the compound (1.4 g) obtained in (Reference Example 2), the subject compound (0.95 g) was obtained as white solid.

<Step 2> Synthesis of 3-hydroxy-5-4-(4-phenoxybenzyl)oxy)phenyl)isothiazole 1-oxide (A)

According to the method of (Example 1) <Step 3>, from the compound (85 mg) obtained in (Example 159) <Step 1>, the subject compound (30 mg) was obtained.

Example 160

Synthesis of 3-hydroxy-5-(4-((4-phenoxybenzyl)oxy)phenyl)isothiazole 1-oxide (B)

According to the method of (Example 1) <Step 3>, from the compound (85 mg) obtained in (Example 159) <Step 1> and enantiomer B (Reference example 1 (B)) obtained in (Reference Example 1) <Step 2>, the subject compound (35 mg) was obtained.

Example 161

Synthesis of 3-hydroxy-5-(4-(2-phenoxyphenethoxy)phenyl)isothiazole 1-oxide (A)

<Step 1> Synthesis of 4-(2-phenoxyphenethoxy)phenyl boronic acid N-methylimino diacetic acid ester According to the method of (Example 1) <Step 2>, from 2-(2-phenoxyphenyl) ethanol (95 mg) that is commercially available or can be obtained by a publicly known method, and the compound (0.13 g) obtained in (Reference Example 2), the subject compound (0.13 g) was obtained as yellow oil.

<Step 2> Synthesis of 3-hydroxy-5-(4-(4-phenoxyphenethoxy)phenyl)isothiazole 1-oxide (A)

According to the method of (Example 1) <Step 3>, from the compound (35 mg) obtained in (Example 161) <Step 1>, the subject compound (23 mg) was obtained.

Example 162

Synthesis of 3-hydroxy-5-(4-(4-phenoxyphenethoxy)phenyl)isothiazole 1-oxide (A)

<Step 1> Synthesis of 4-(4-phenoxyphenethoxy)phenyl boronic acid N-methylimino diacetic acid ester According to the method of (Example 1) <Step 2>, from 2-(4-phenoxyphenyl) ethanol (0.19 g) that is commercially available or can be obtained by a publicly known method, and the compound (0.13 g) obtained in (Reference Example 2), the subject compound (0.38 g) was obtained as yellow oil.

<Step 2> Synthesis of 3-hydroxy-5-(4-(4-phenoxyphenethoxy)phenyl)isothiazole 1-oxide (A)

According to the method of (Example 1) <Step 3>, from the compound (70 mg) obtained in (Example 162) <Step 1>, the subject compound (30 mg) was obtained.

Example 163

Synthesis of 3-hydroxy-5-(3-(3-phenoxyphenethoxy)phenyl)isothiazole 1-oxide (A)

<Step 1> Synthesis of 3-hydroxyphenyl boronic acid N-methylimino diacetic acid ester According to the method of (Example 2), from 3-hydroxyphenyl boronic acid (1.6 g), the subject compound (2.8 g) was obtained as colorless amorphous.

<Step 2> Synthesis of 3-(3-phenoxyphenethoxy)phenyl boronic acid N-methylimino diacetic acid ester According to the method of (Example 1) <Step 2>, from 2-(3-phenoxyphenyl) ethanol (0.10 g) that is commercially available or can be obtained by a publicly known method, and the compound (0.14 g) obtained in (Example 163) <Step 1>, the subject compound (0.11 g) was obtained as yellow oil.

<Step 3> Synthesis of 3-hydroxy-5-(3-(3-phenoxyphenethoxy)phenyl)isothiazole 1-oxide (A)

According to the method of (Example 1) <Step 3>, from the compound (50 mg) obtained in (Example 163) <Step 2>, the subject compound (30 mg) was obtained.

The compounds ((Example 1P) and (Example 2P)) described below and the compounds ((Example 3P) to (Example 113P)) of Structural Formulae 12 to 19, and salts thereof, solvates thereof, and optical isomers thereof can be easily synthesized by either of the production methods above, the methods described in Examples, methods that are obvious to those skilled in the art, and modifications of these.

3-hydroxy-5-(4-{[4-(spiro[inden-1,4'-piperidin]-1'-ylmethyl)benzyl]amino}phenyl) isothiazole 1-oxide (A) (Example 1P);

3-hydroxy-5-(4-{[4-((1-methylspiro[indoline-3,4'-piperidin]-1'-yl)methyl)benzyl]amino}phenyl)isothiazole 1-oxide (A) (Example 2P).

Here, in all of the above Examples, by using the enantiomer B of Reference Example 1 (B) instead of the enantiomer A of Reference Example 1 (A), the enantiomer (B) of a compound corresponding to each Example can be produced.

The structures of the final compounds synthesized in the above (Example 1) to (Example 163) and the compounds of (Example 1P) to (Example 113P) are shown in the figures below (Structural Formulae I to 19). The structural formulae in Structural Formula 10 and 11 in which asterisks (*) is indicated are separated into the diastereomer A and diastereomer B of the structure. LC/MS data and NMR data (no mark: 400 MHz NMR, *: 300 MHz NMR) of these final compounds of Examples are also shown in Tables below (Tables 2, 3, 4, 7 and Table 8). The structures of the intermediate compounds synthesized in Examples respectively and the compounds of Reference Examples are shown in the figures below (Structural Formulae 20 to 24) and LC/MS data of these intermediate compounds and the compounds of Reference Examples and NMR data (no mark: 400 MHz NMR, *: 300 MHz NMR) of these intermediate compounds and the compounds of Reference Examples are also shown in Tables below (Table 5, 6, 7, 9 and Table 10). Here, with respect to the intermediate compound, for example, the compound obtained in (Example 1) <Step 1> is expressed as "(Example 1-1)".

Structural Formula 1
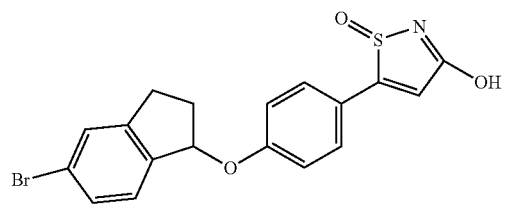
Example 1
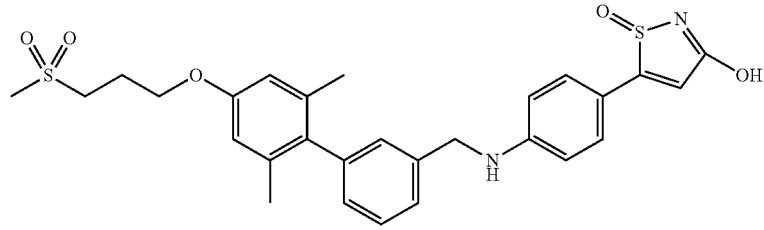
Example 2
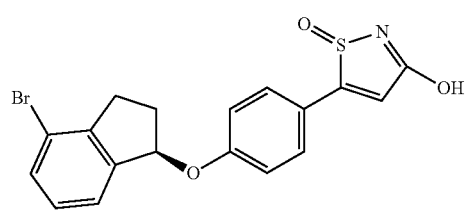
Example 3
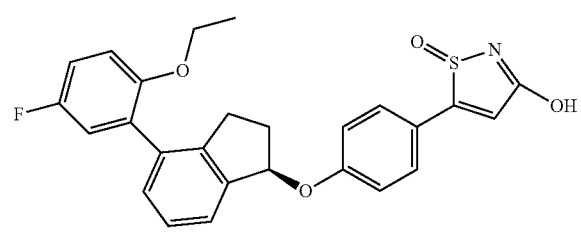
Example 4
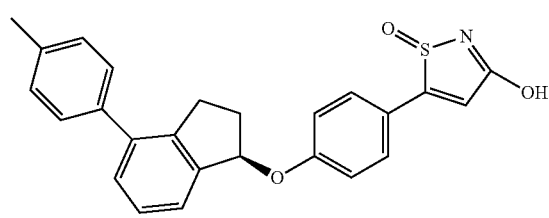
Example 5
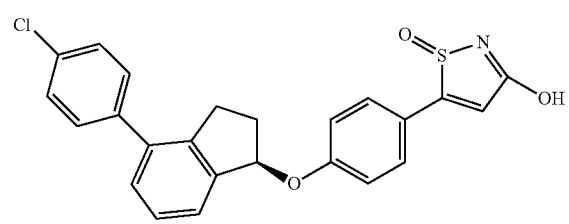
Example 6
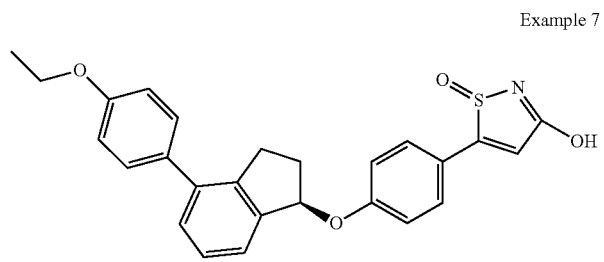
Example 7
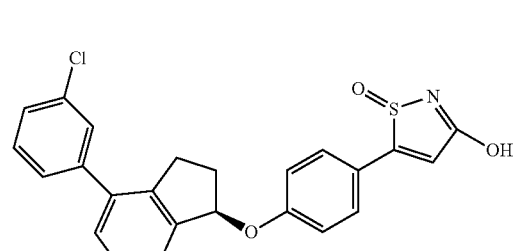
Example 8
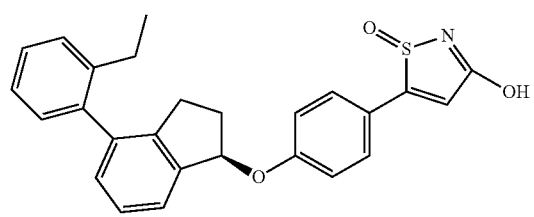
Example 9
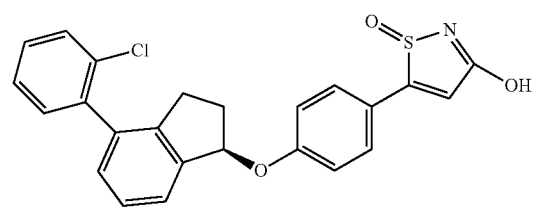
Example 10

-continued
Example 11
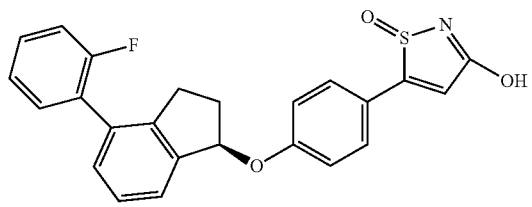
Example 12
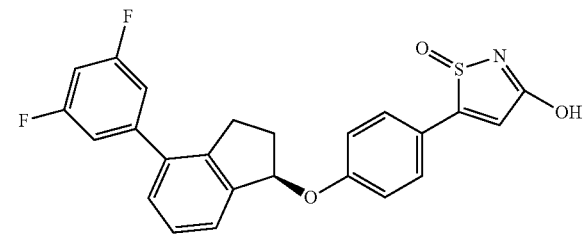
Example 13
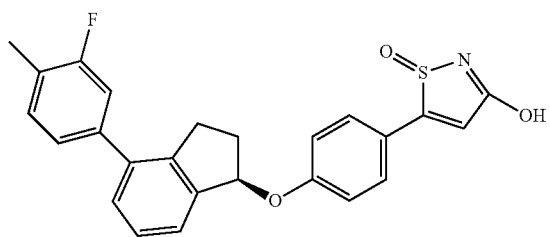
Example 14
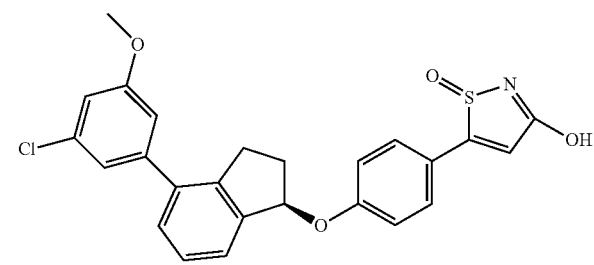
Example 15
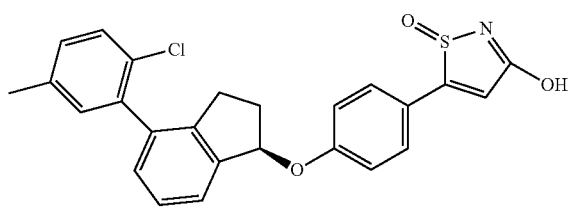
Example 16
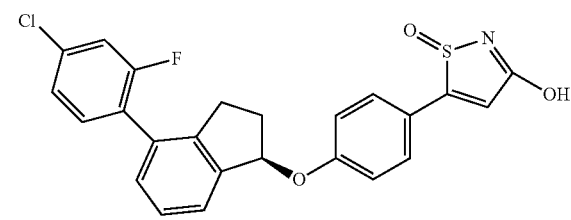
Structural Formula 2
Example 17
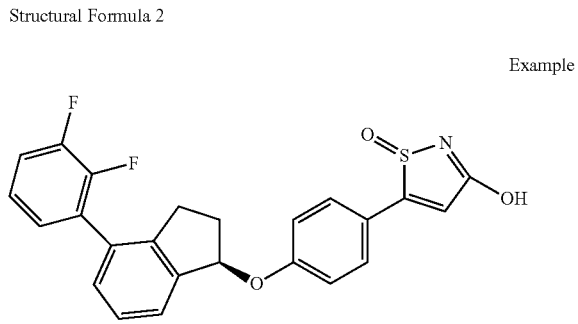
Example 18
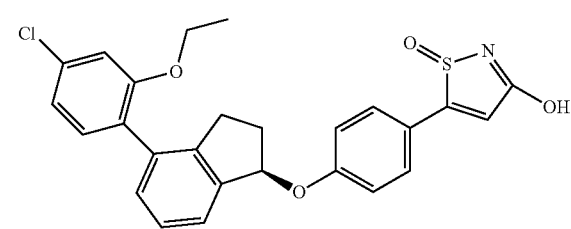
Example 19
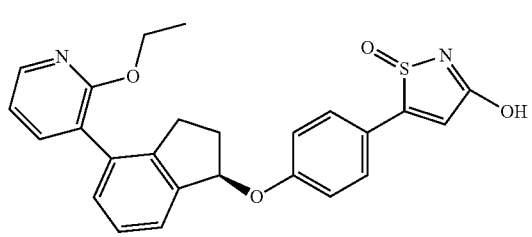
Example 20
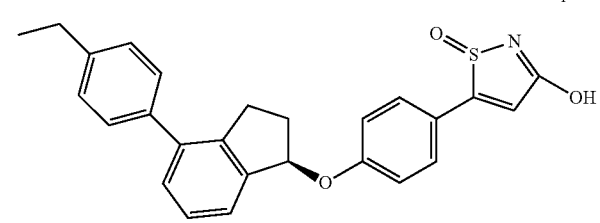
Example 21
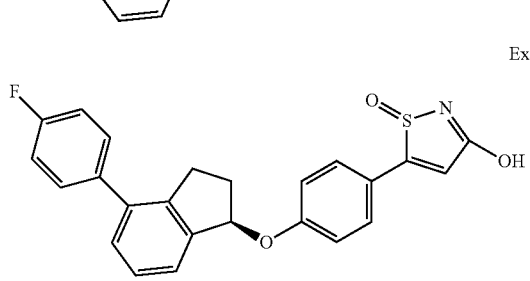
Example 22
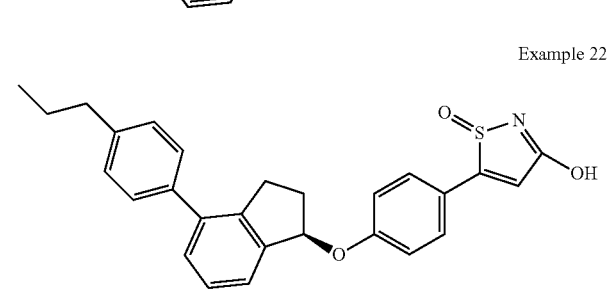

Example 23
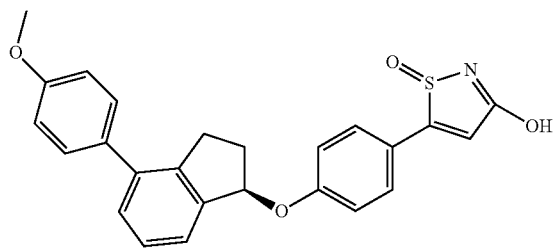
Example 24
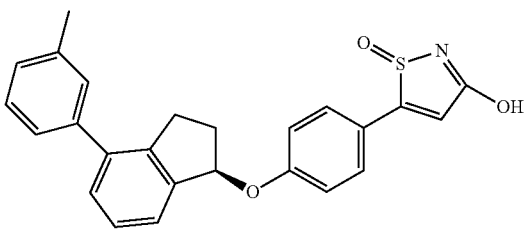
Example 25
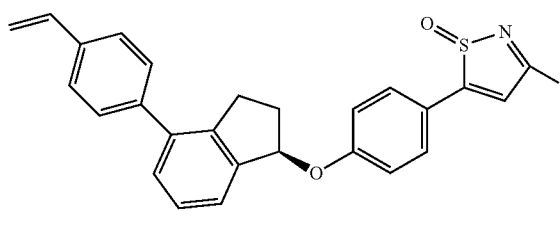
Example 26
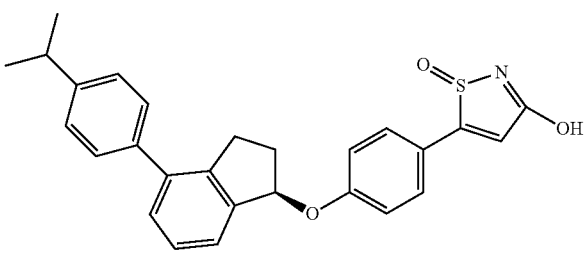
Example 27
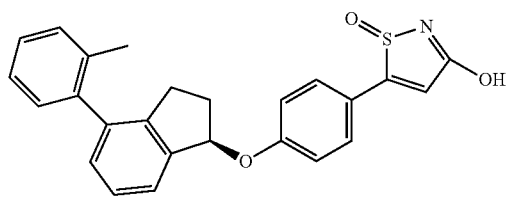
Example 28
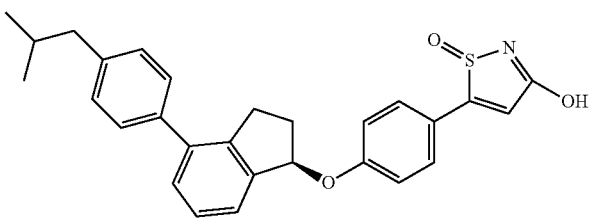
Example 29
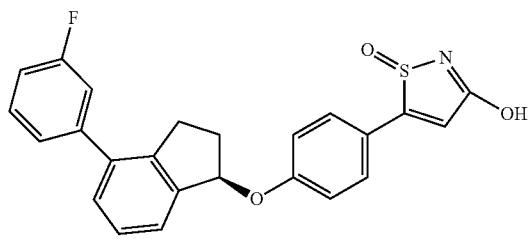
Example 30
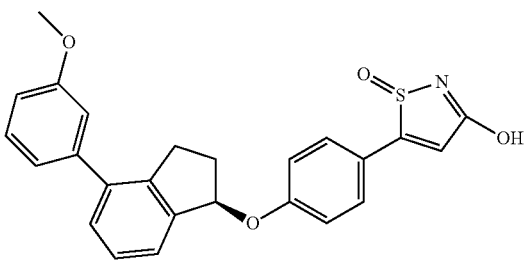
Example 31
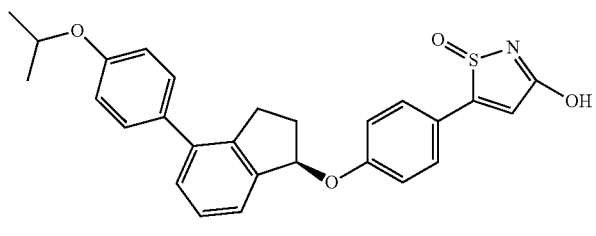
Example 32
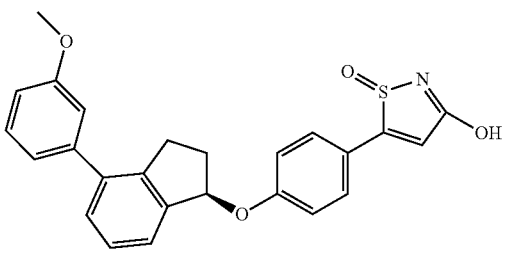

-continued
Structural Formula 3
Example 33
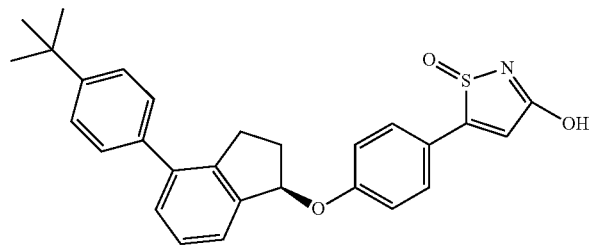
Example 34
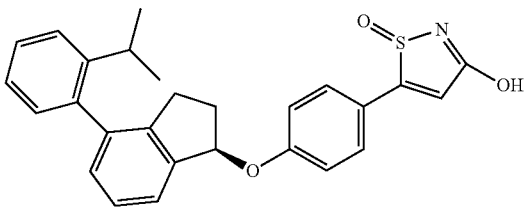
Example 35
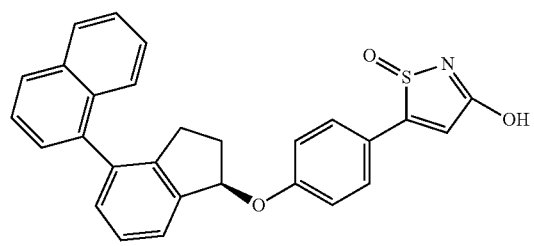
Example 36
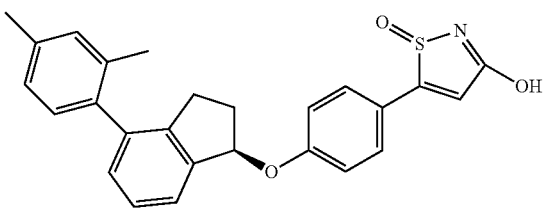
Example 37
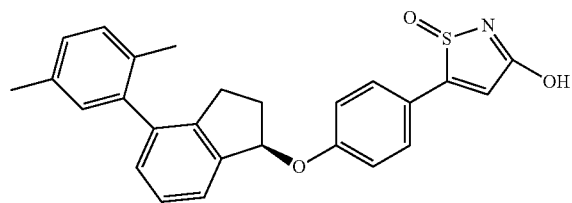
Example 38
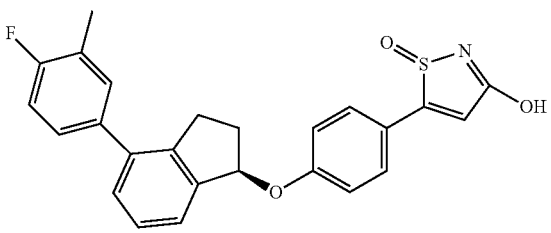
Example 39
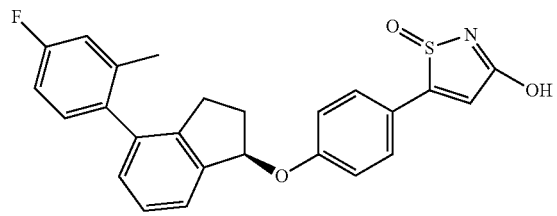
Example 40
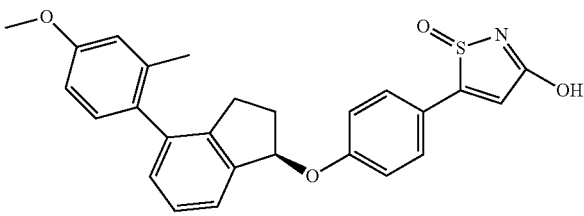
Example 41
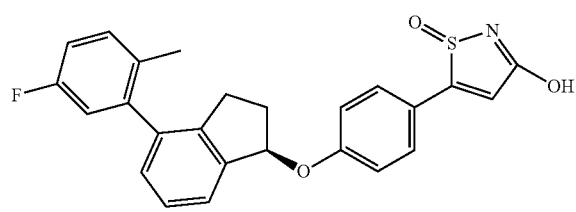
Example 42
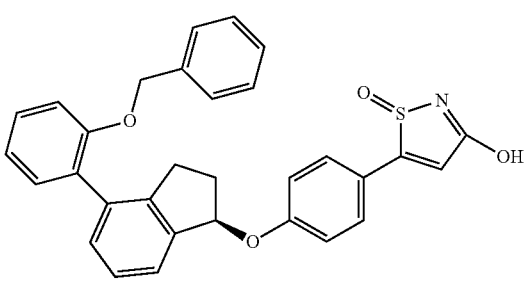
Example 43
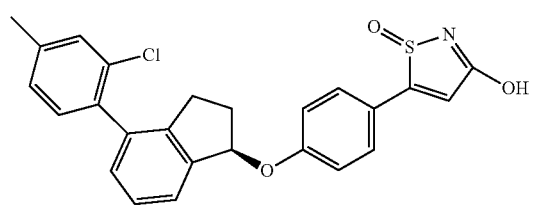
Example 44
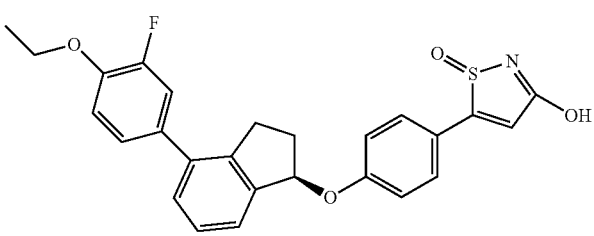

-continued
Example 45
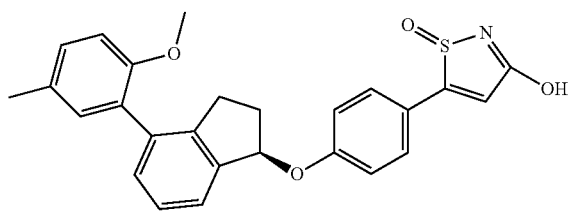
Example 46
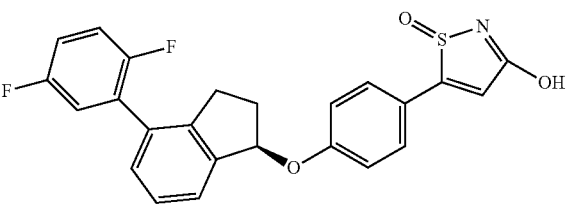
Example 47
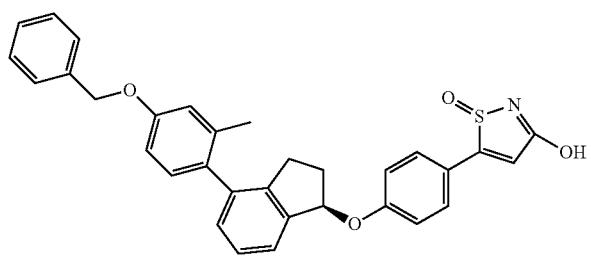
Example 48
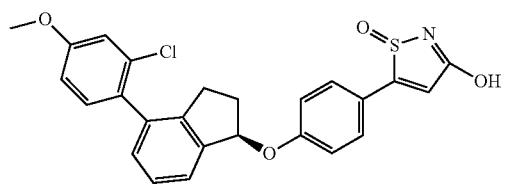
Structural Formula 4
Example 49
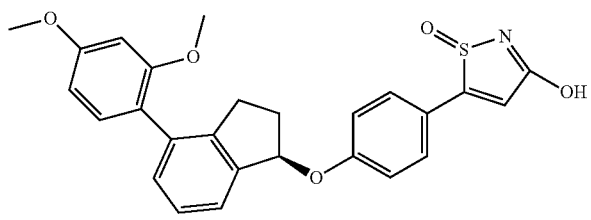
Example 50
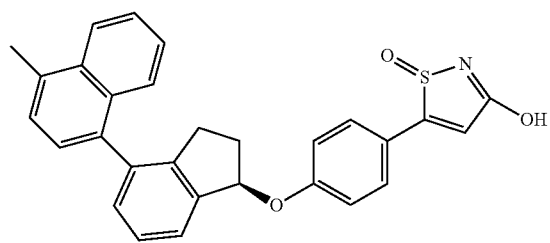
Example 51
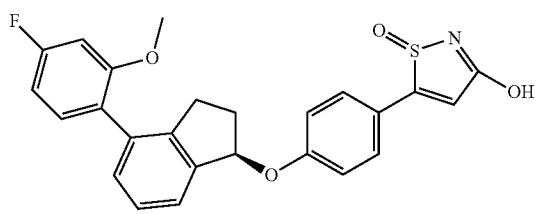
Example 52
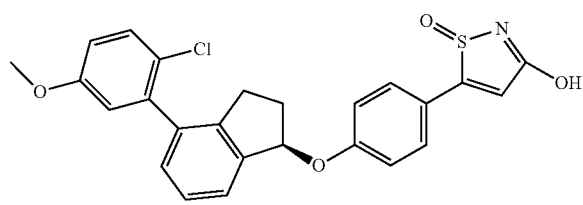
Example 53
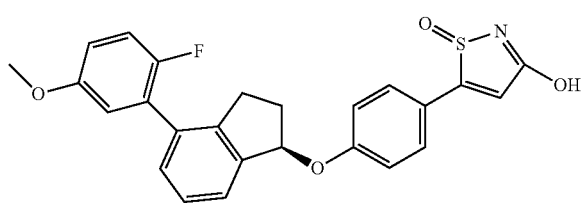
Example 54
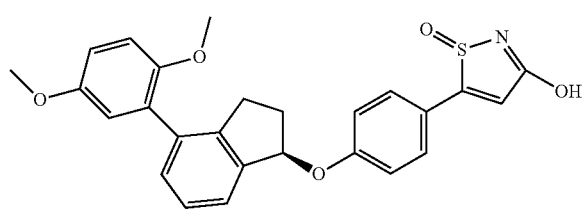
Example 55
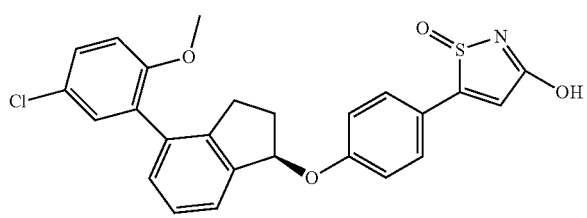
Example 56
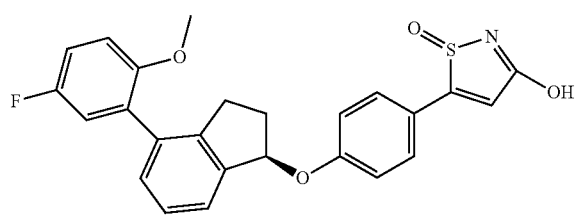

-continued
Example 57
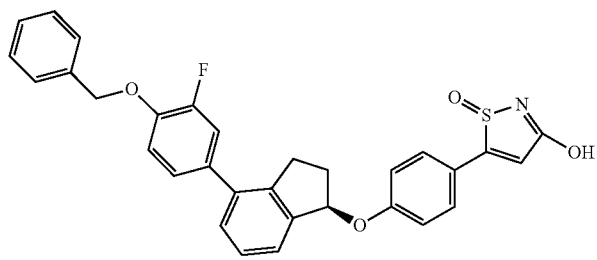
Example 58
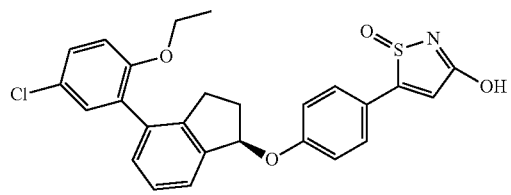
Example 59
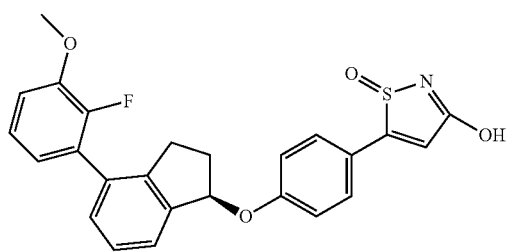
Example 60
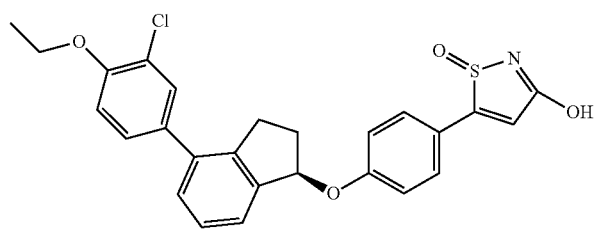
Example 61
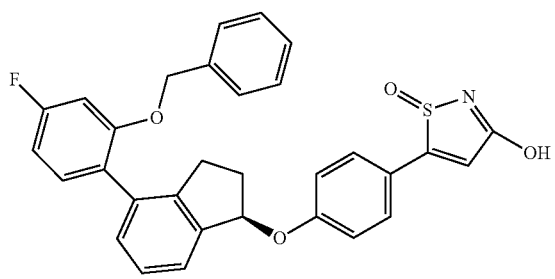
Example 62
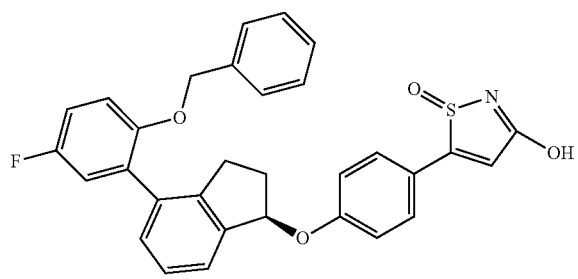
Example 63
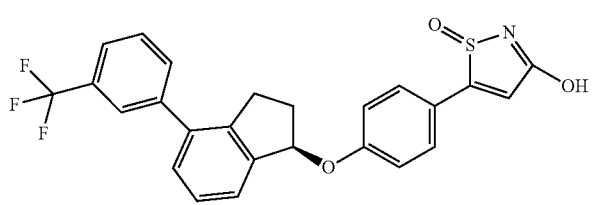
Example 64
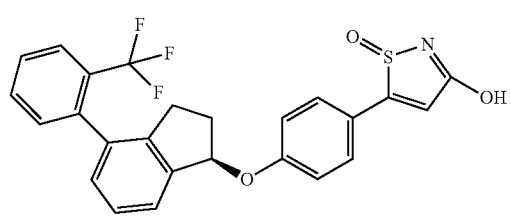
Structural Formula 5
Example 65
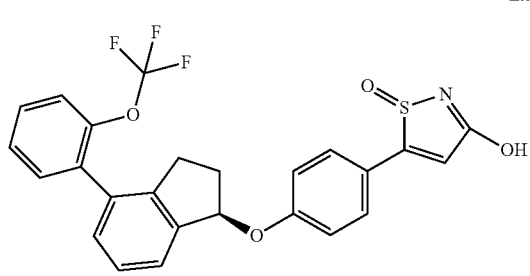
Example 66
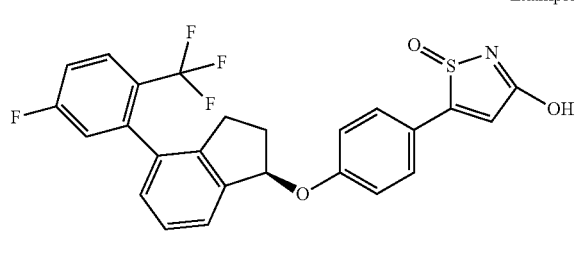
Example 67
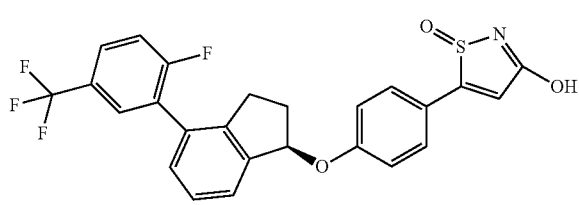
Example 68
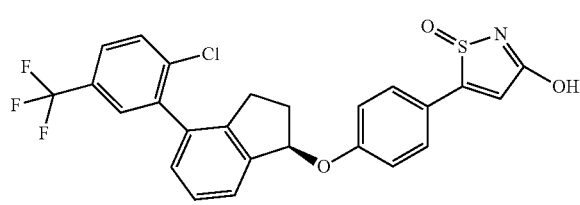

-continued
Example 69
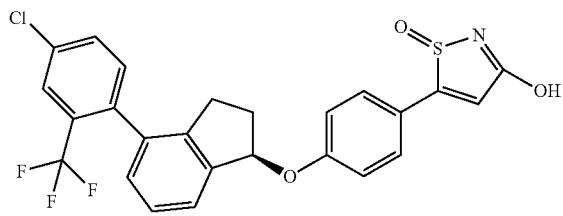
Example 70
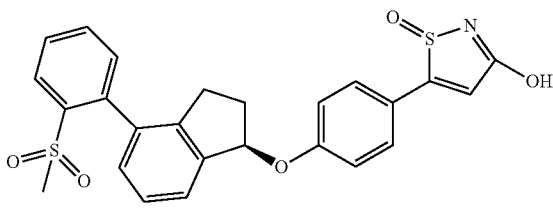
Example 71
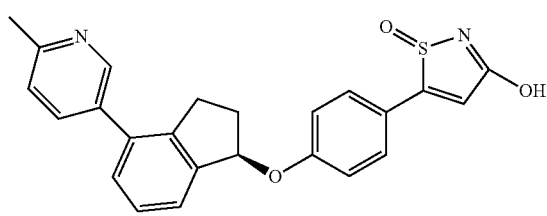
Example 72
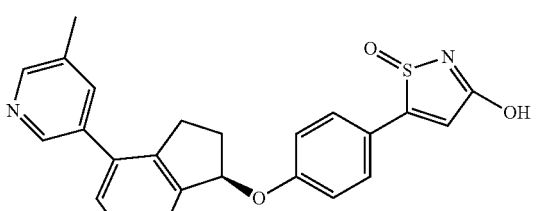
Example 73
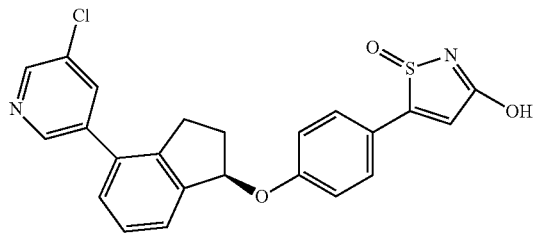
Example 74
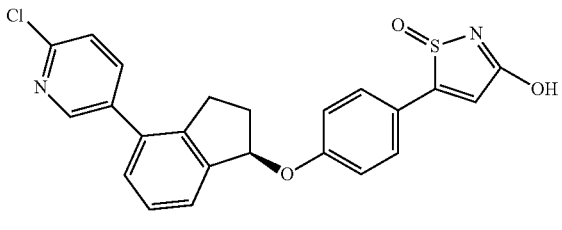
Example 75
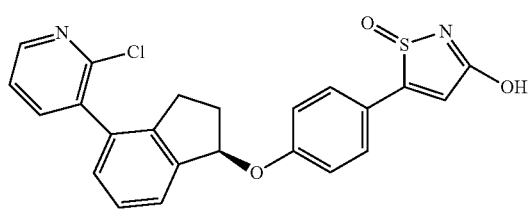
Example 76
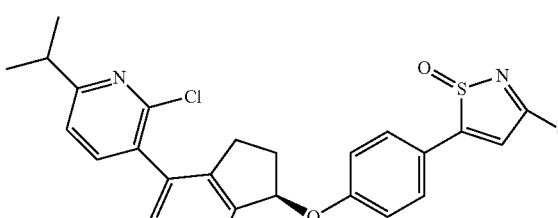
Example 77
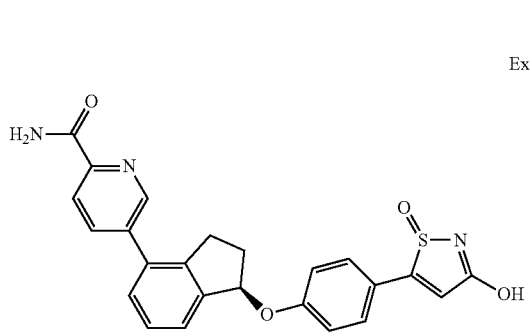
Example 78
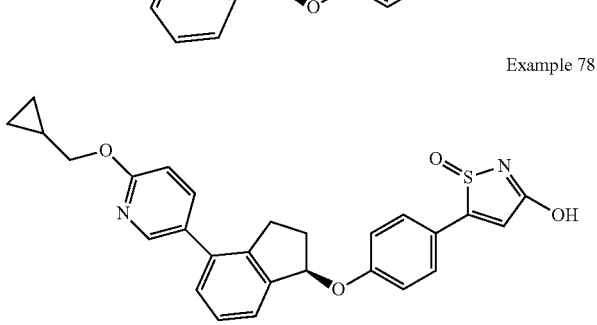
Example 79
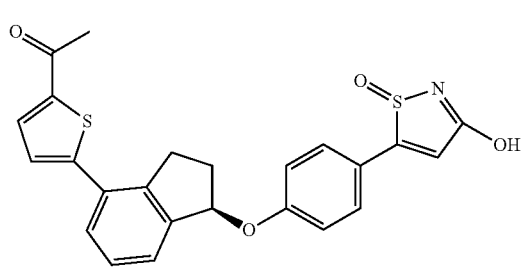
Example 80
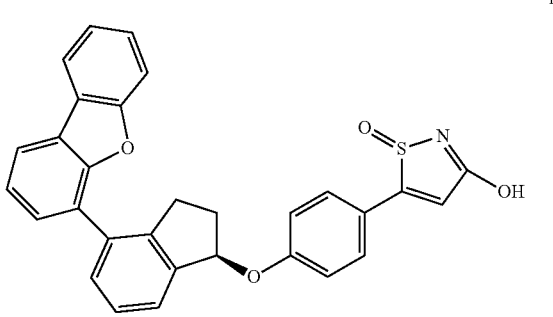

Structural Formula 6
Example 81
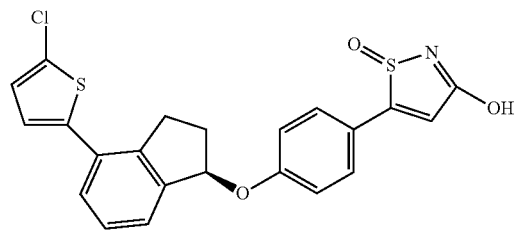
Example 82
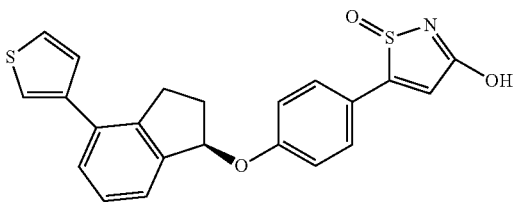
Example 83
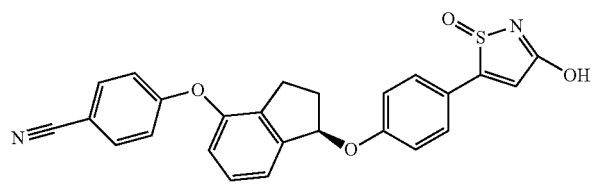
Example 84
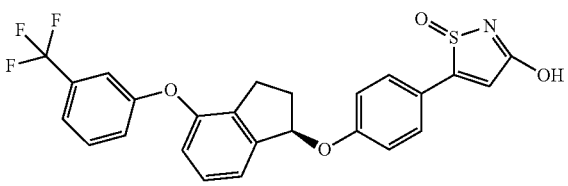
Example 85
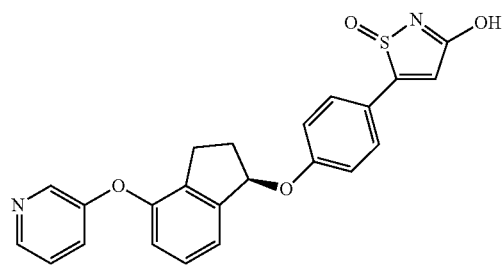
Example 86
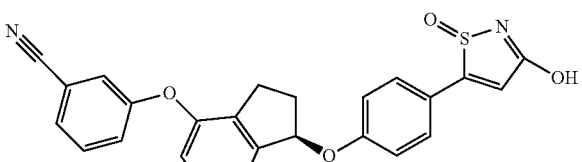
Example 87
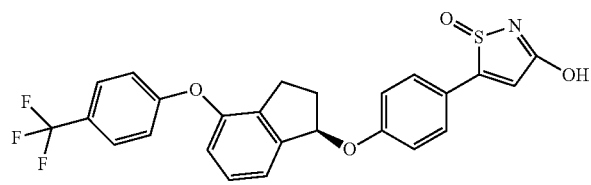
Example 88
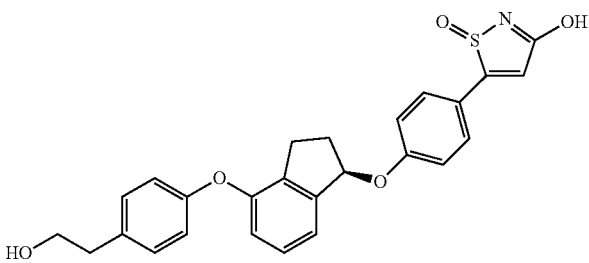
Example 89
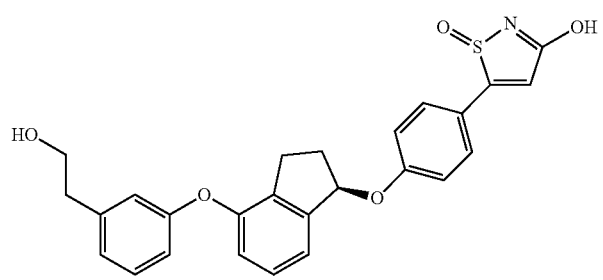
Example 90
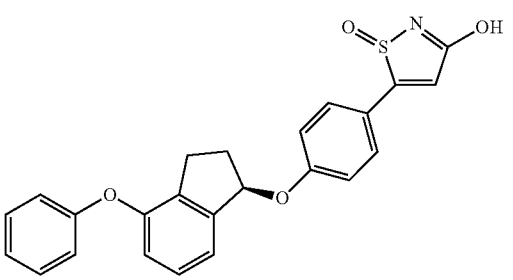

Example 91
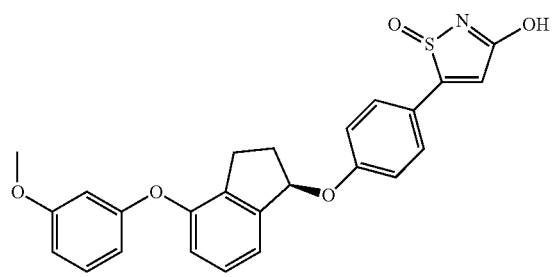
Example 92
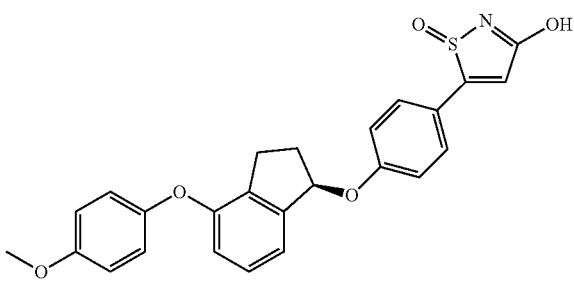
Example 93
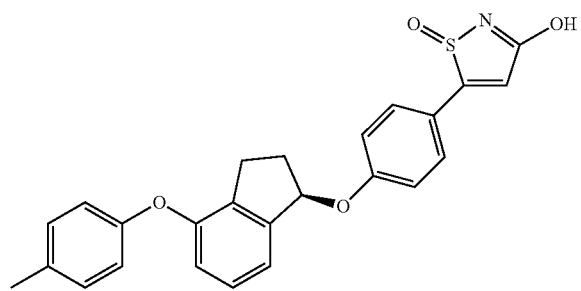
Example 94
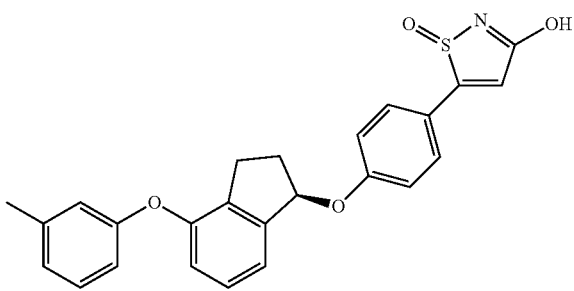
Example 95
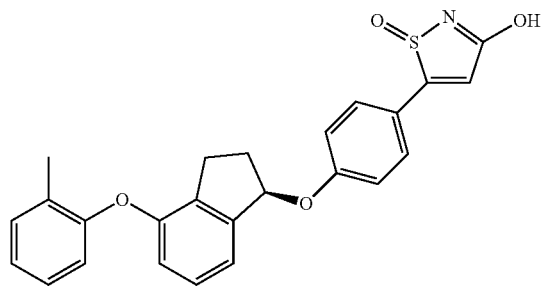
Example 96
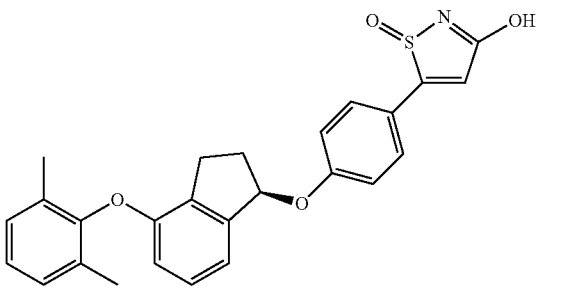
Structural Formula 7
Example 97
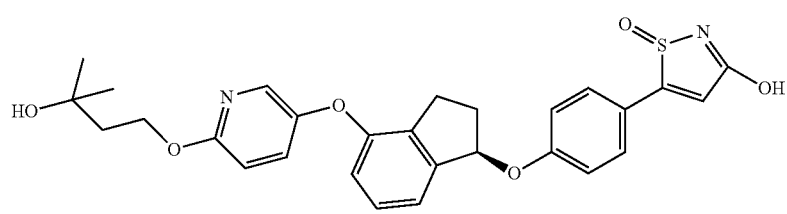
Example 98
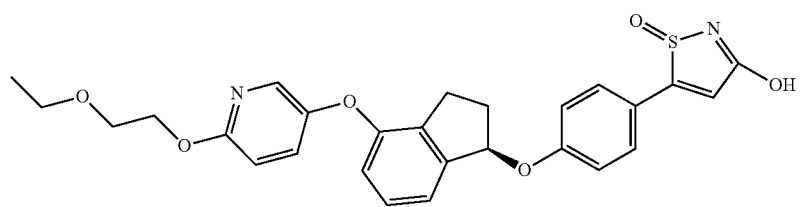

-continued
Example 99
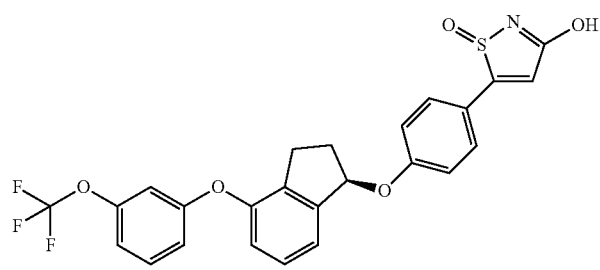
Example 100
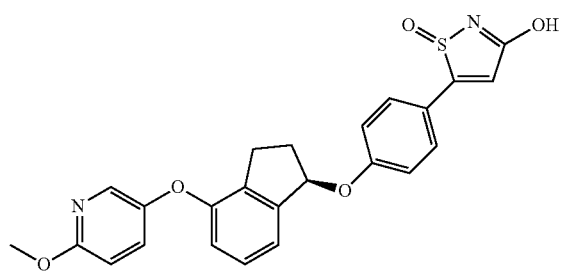
Example 101
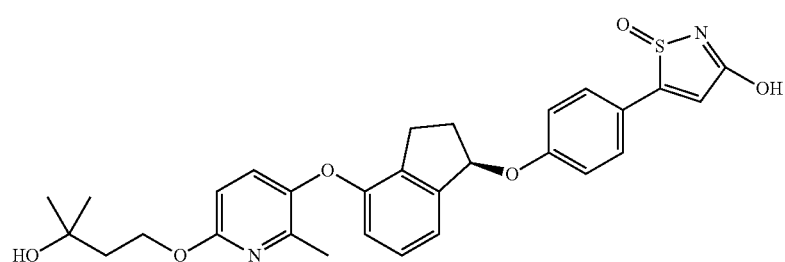
Example 102
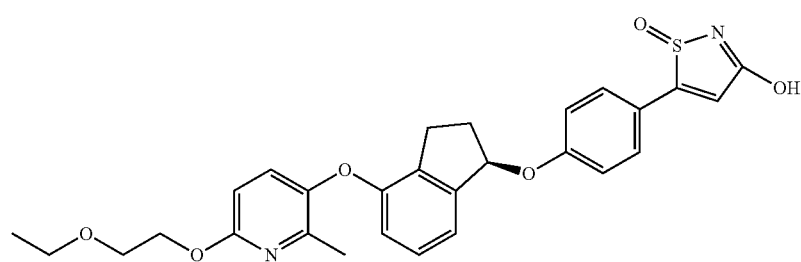
Example 103
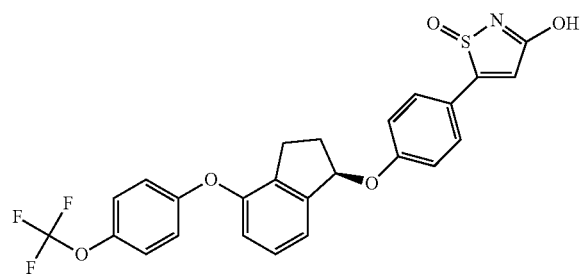
Example 104
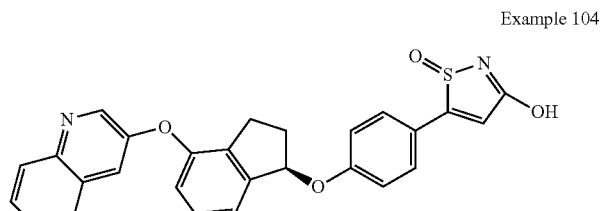
Example 105
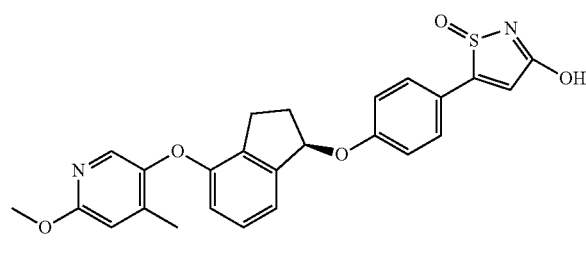
Example 106
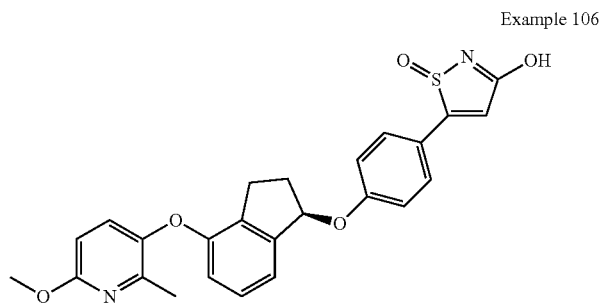

Example 107
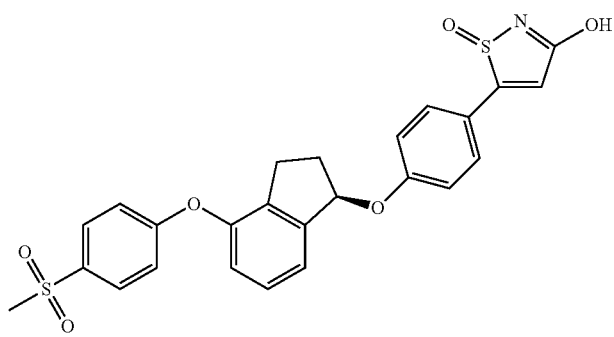
Example 108
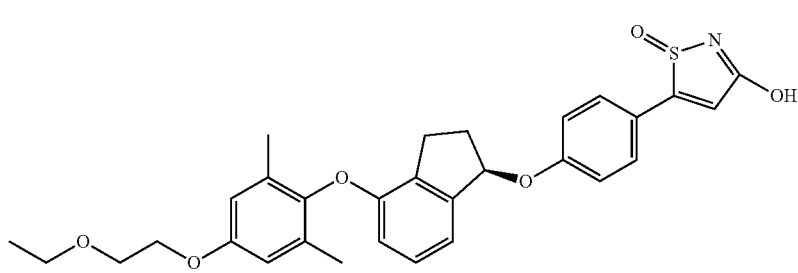
Example 109
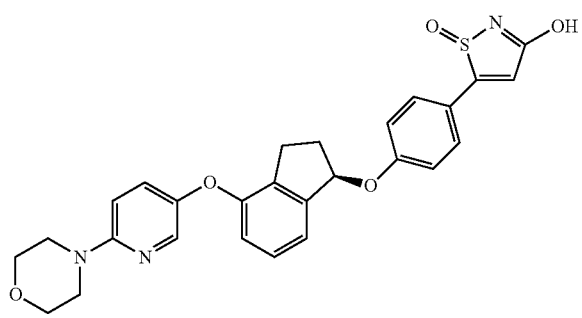
Example 110
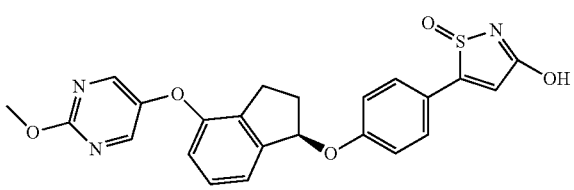
Example 111
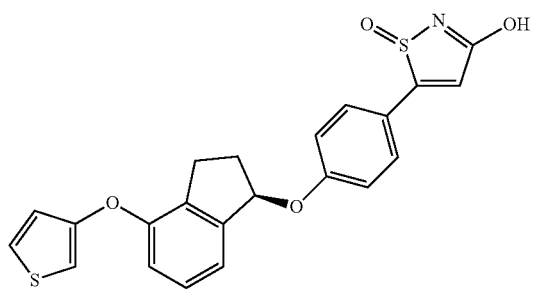
Example 112
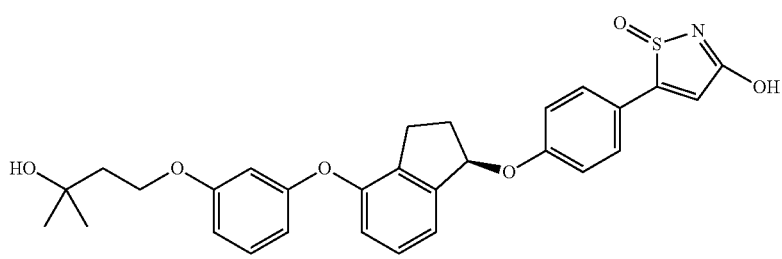

Structural Formula 8
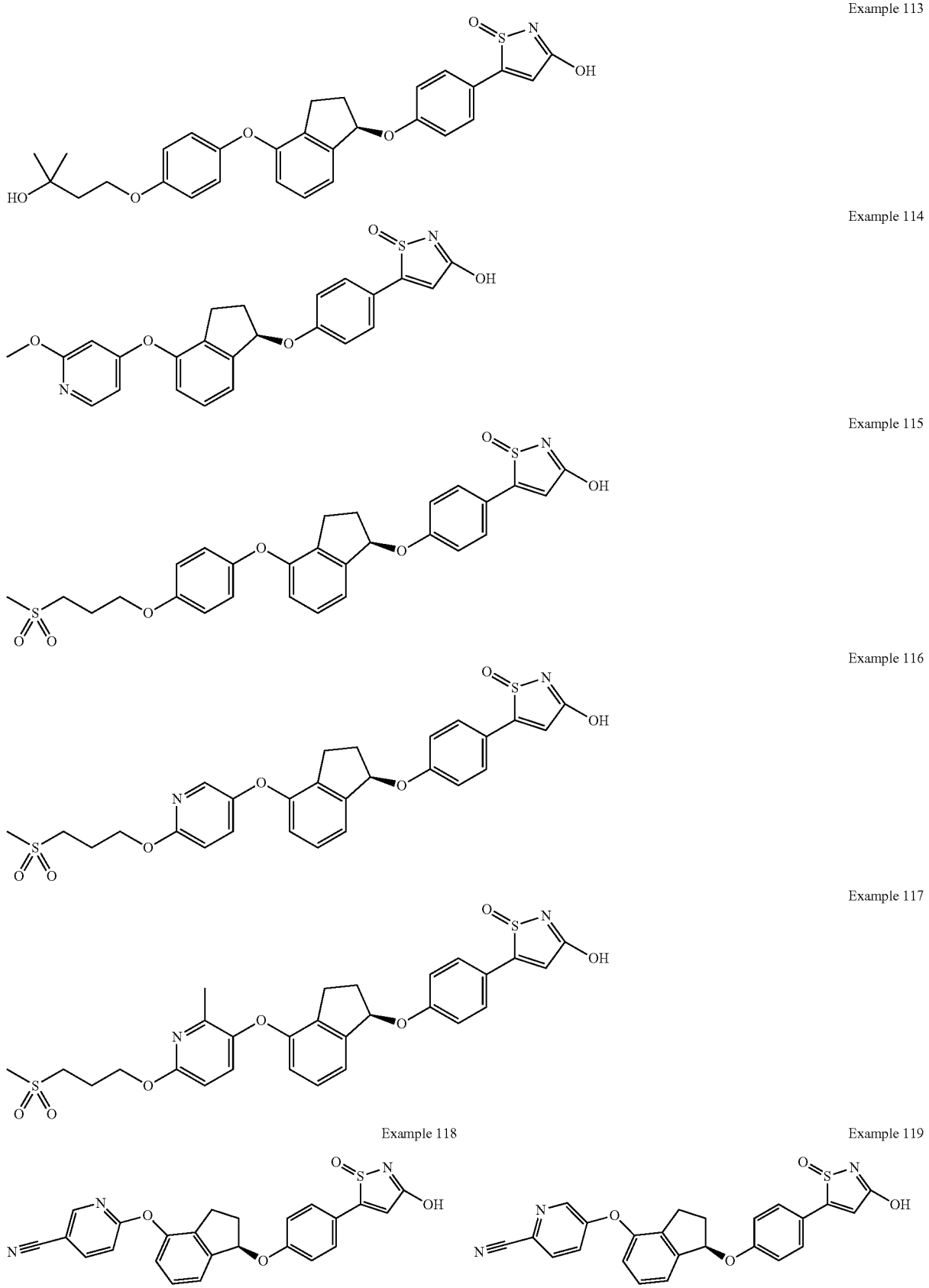
Example 113
Example 114
Example 115
Example 116
Example 117
Example 118
Example 119

Example 120
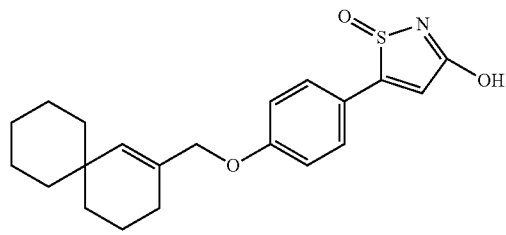
Example 121
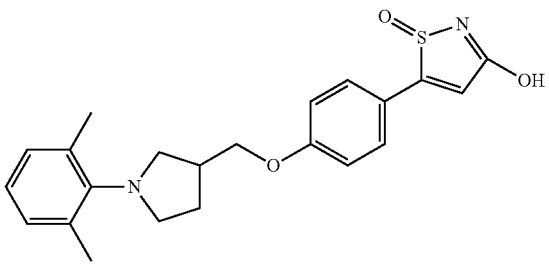
Example 122
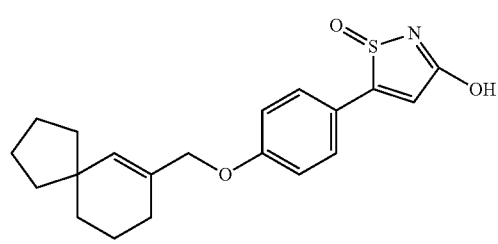
Example 123
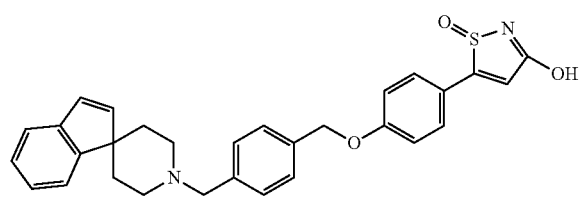
Structural Formula 9
Example 124
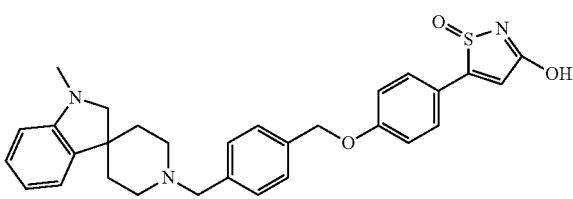
Example 125
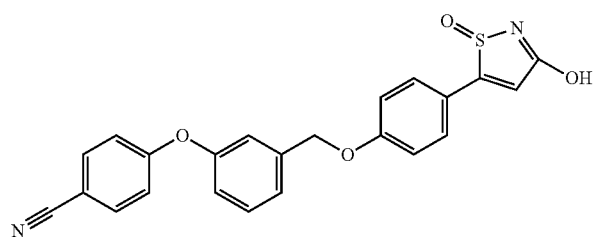
Example 126
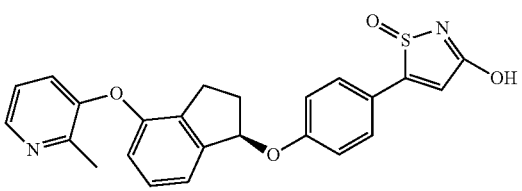
Example 127
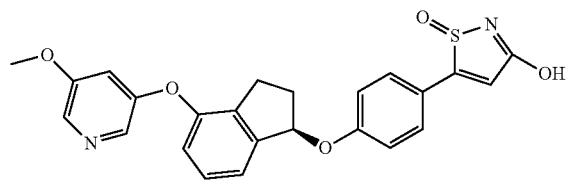
Example 128
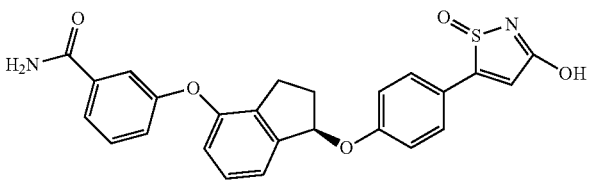
Example 129
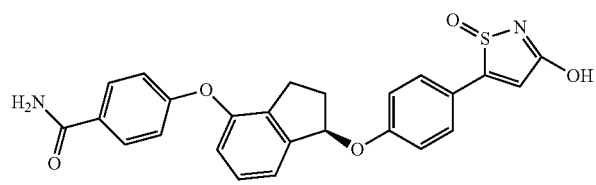
Example 130
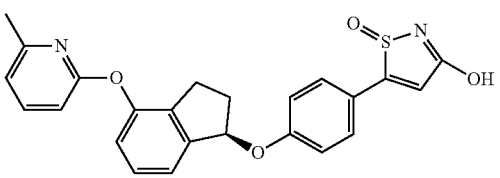

-continued
Example 131
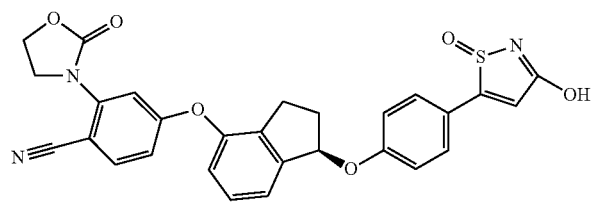
Example 132
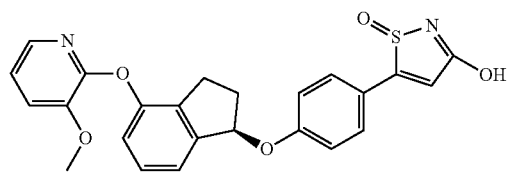
Example 133
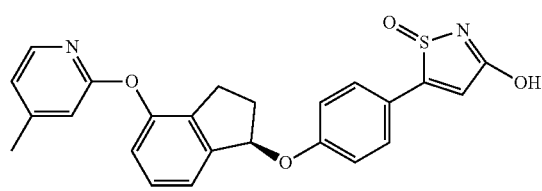
Example 134
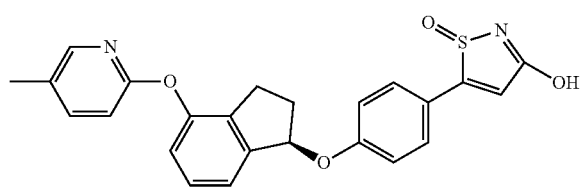
Example 135
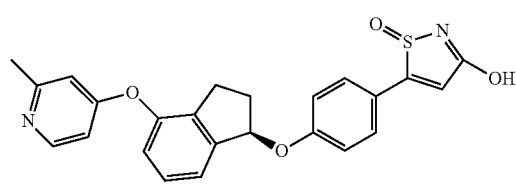
Example 136
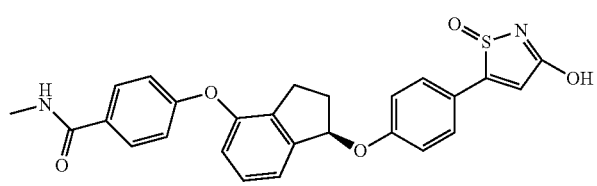
Example 137
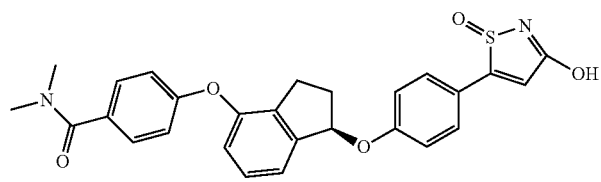
Example 138
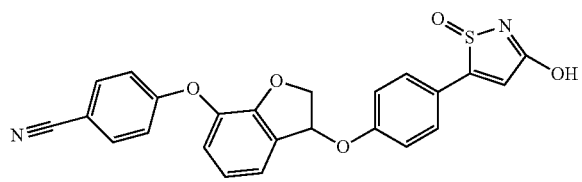
Example 139
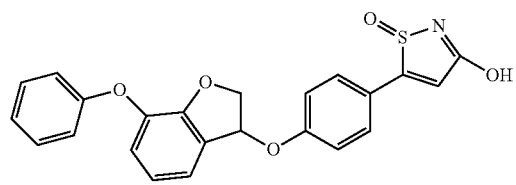
Example 140
Structural Formula 10
Example 141
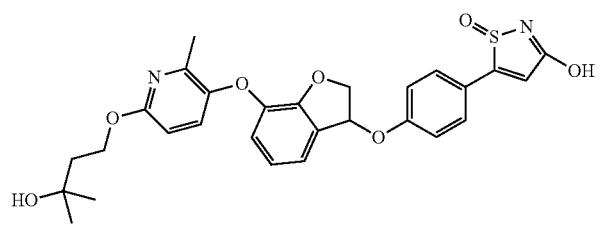
Example 142
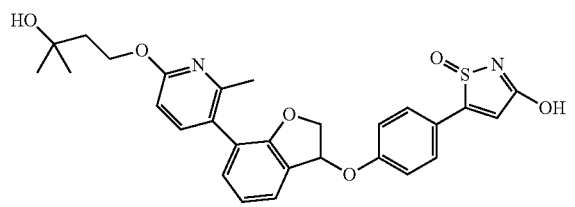
Example 143
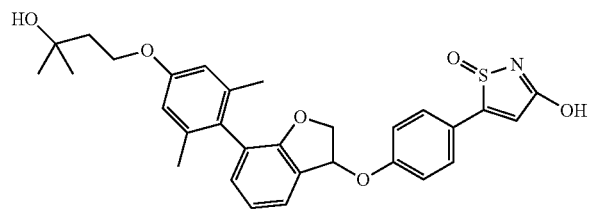
Example 144
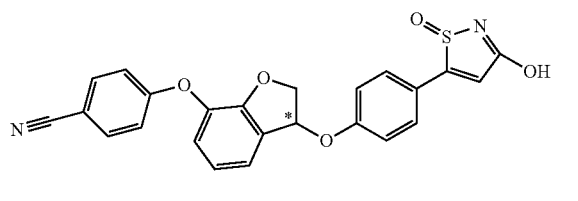

-continued
Example 145
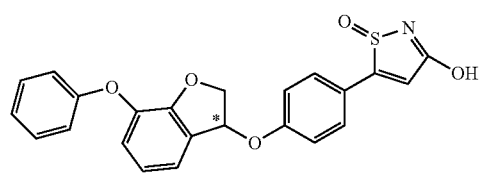
Example 146
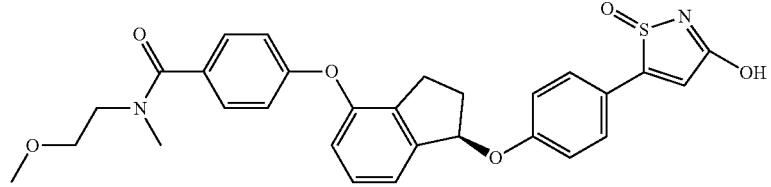
Example 147
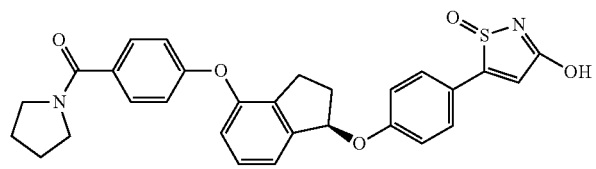
Example 148
Structural Formula 11
Example 149
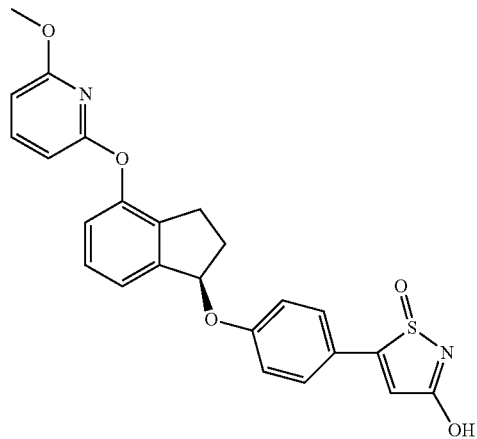
Example 150
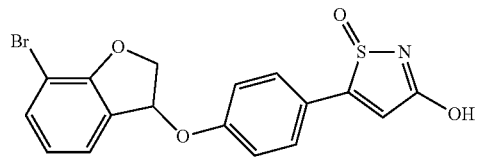
Example 151
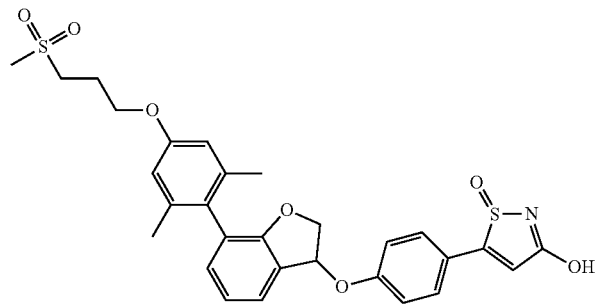
Example 152(A)-a
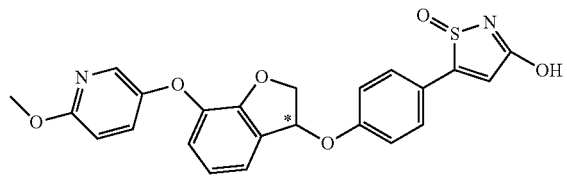

-continued
Example 152(A)-b
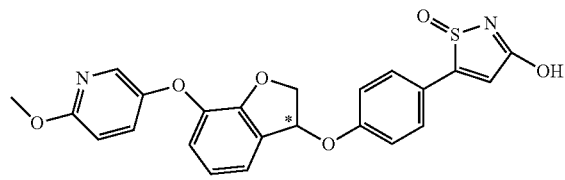
Example 153(A)-a
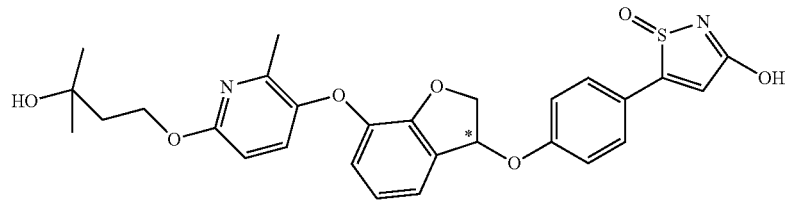
Example 153(A)-b
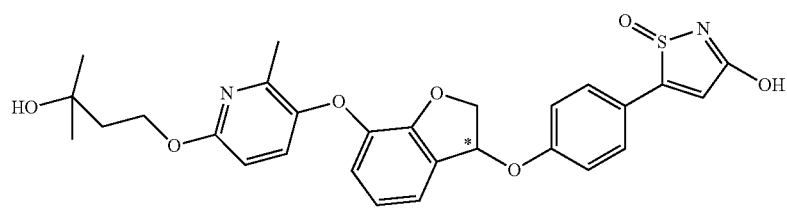
Example 154(A)-a
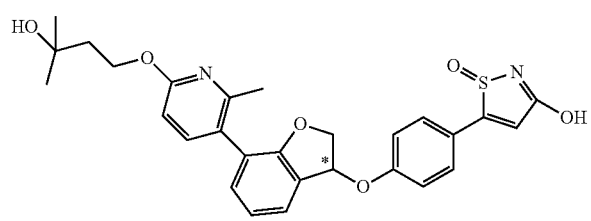
Example 154(A)-b
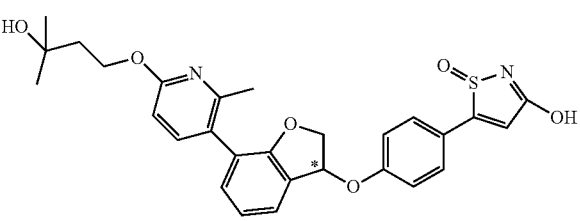
Example 155
Example 156
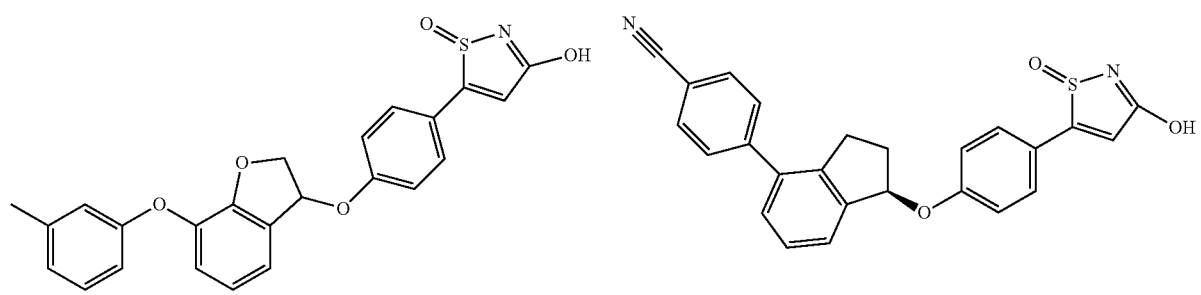
Example 157
Example 158
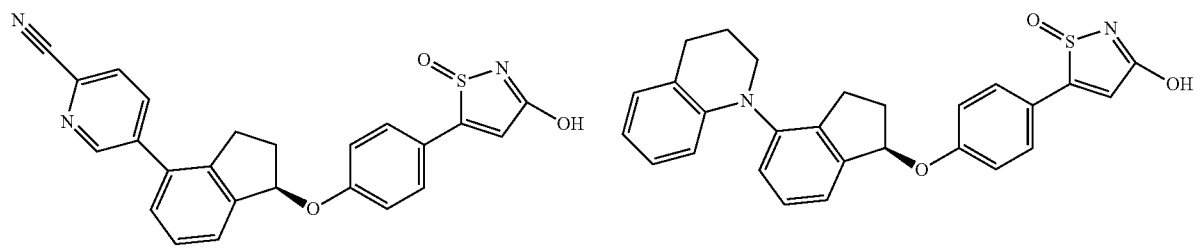

-continued
Example 159
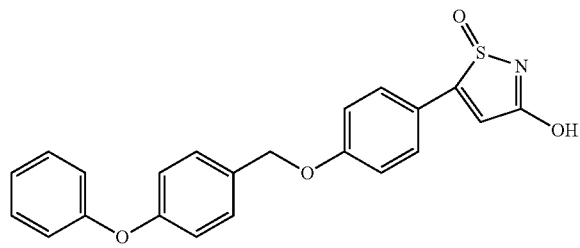
Example 160
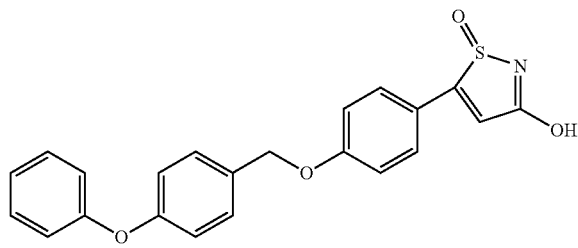
Example 161
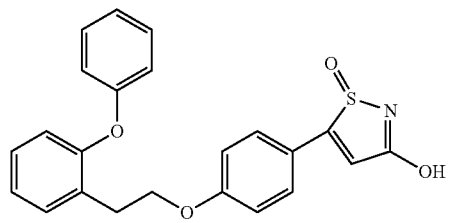
Example 162
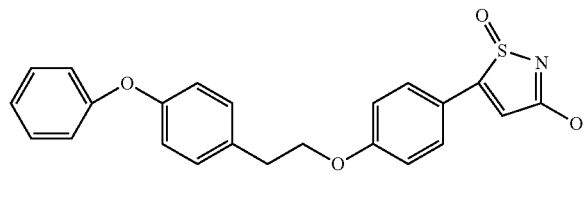
Example 163
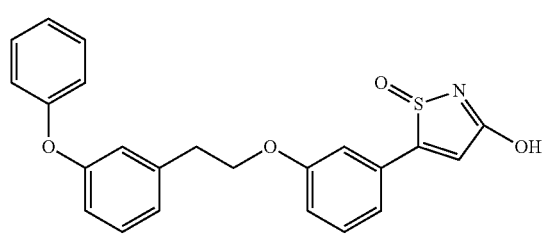
Structural Formula 12
Example 1P
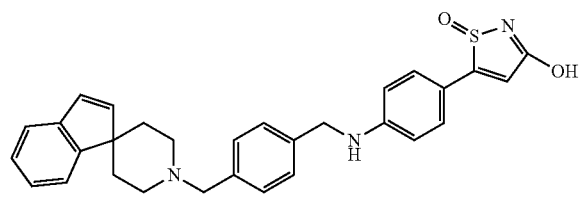
Example 2P
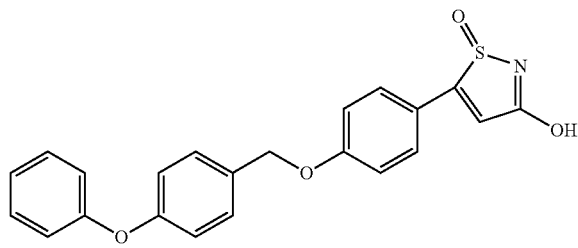
Structural Formula 13
Example 3P
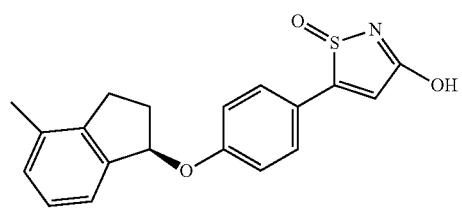
Example 4P
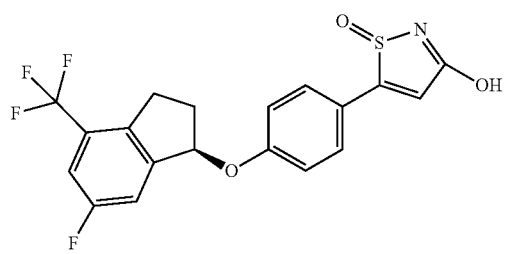
Example 5P
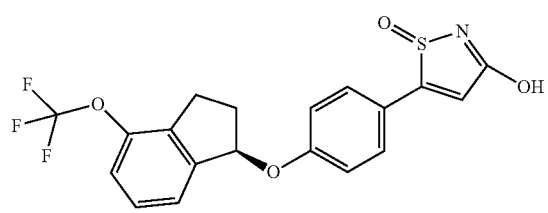
Example 6P
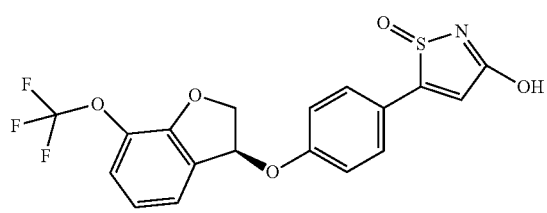

Example 7P
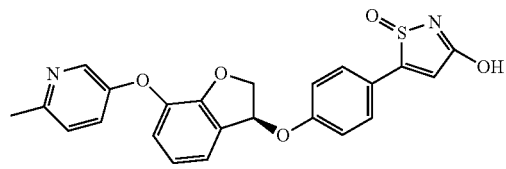
Example 8P
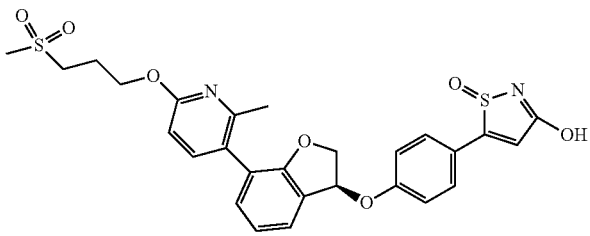
Example 9P
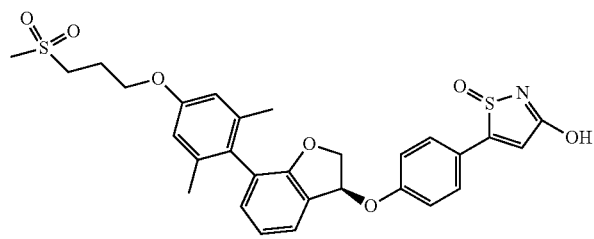
Example 10P
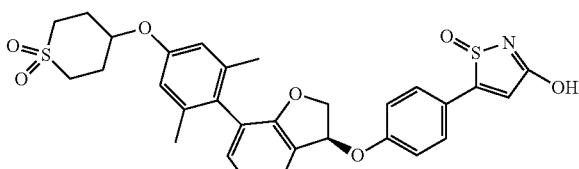
Example 11P
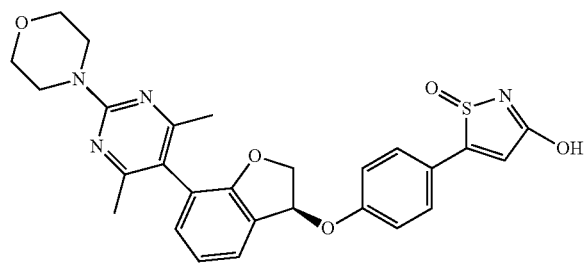
Example 12P
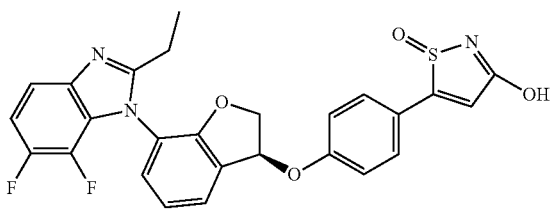
Example 13P
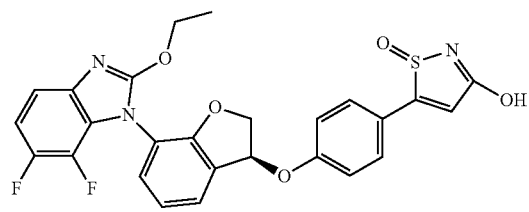
Example 14P
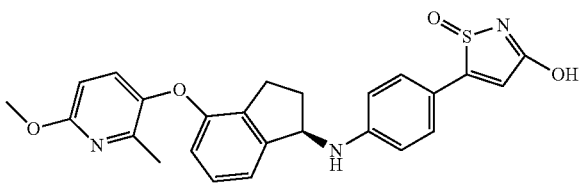
Example 15P
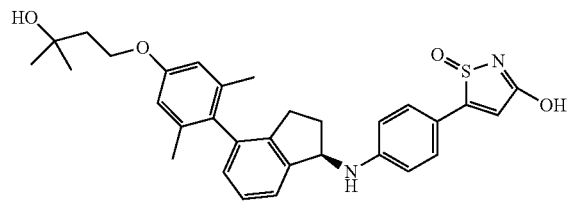
Example 16P
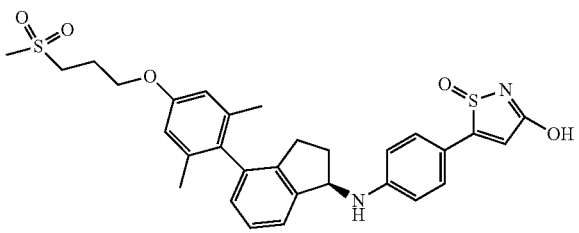
Example 17P
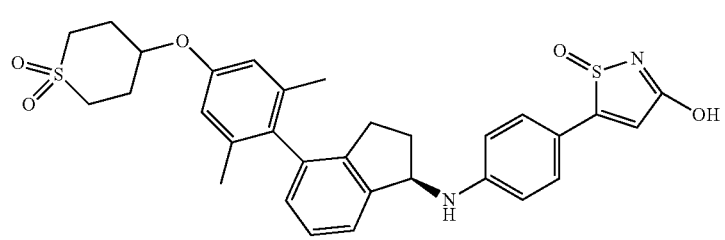

Structural Formula 14
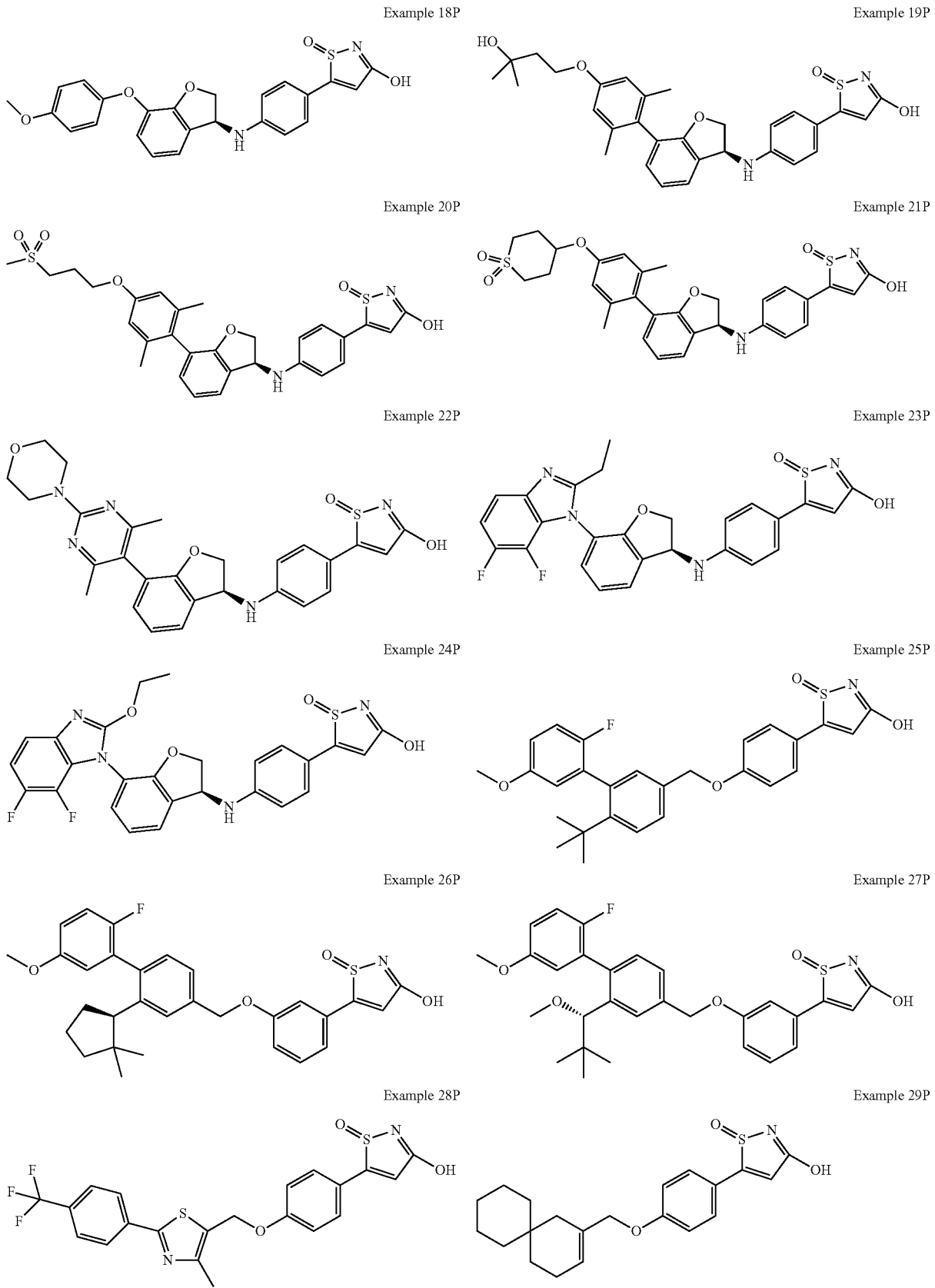

-continued
Example 30P
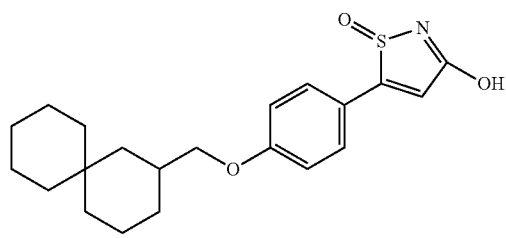
Structural Formula 15
Example 31P
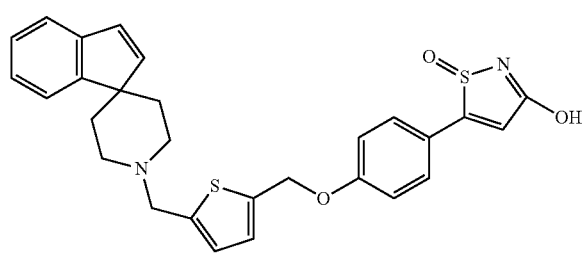
Example 32P
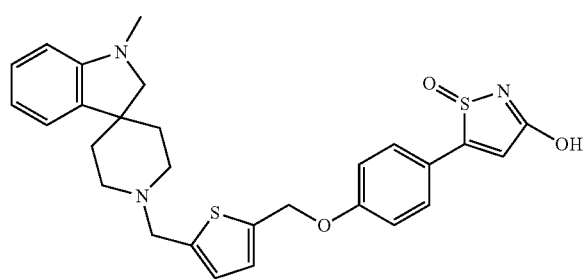
Example 33P
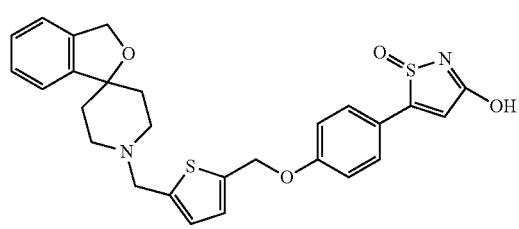
Example 34P
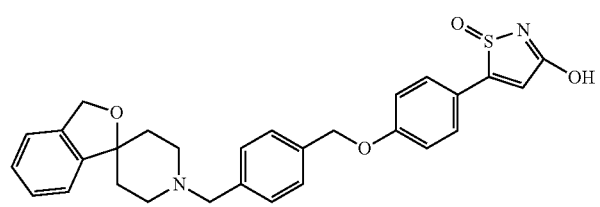
Example 35P
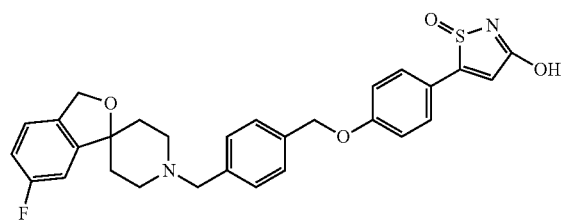
Example 36P
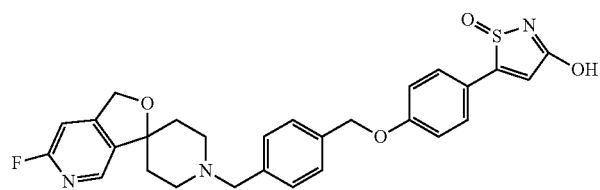
Example 37P
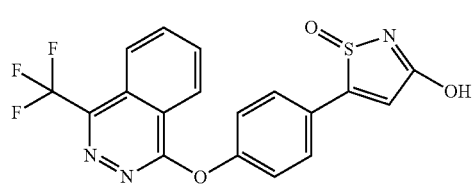
Example 38P
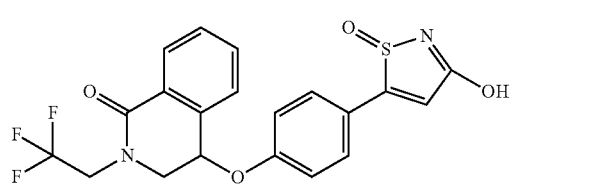
Example 39P
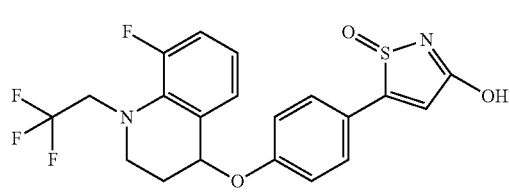
Example 40P
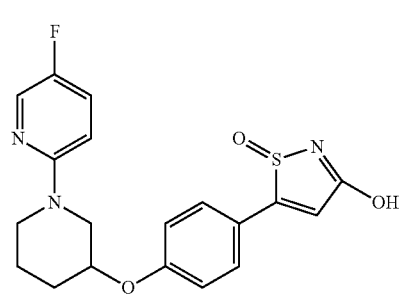

-continued
Example 41P
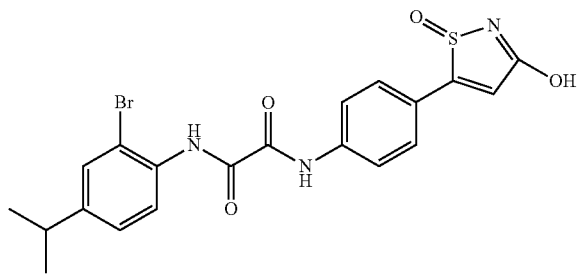
Structural Formula 16
Example 42P
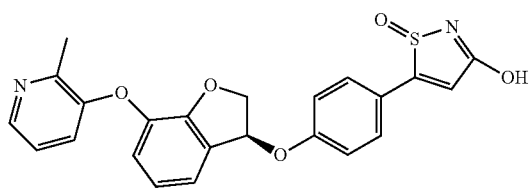
Example 43P
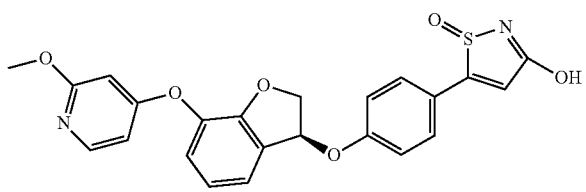
Example 44P
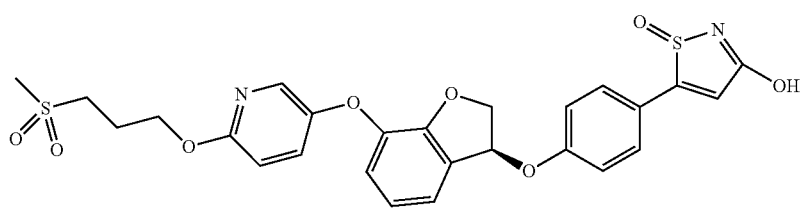
Example 45P
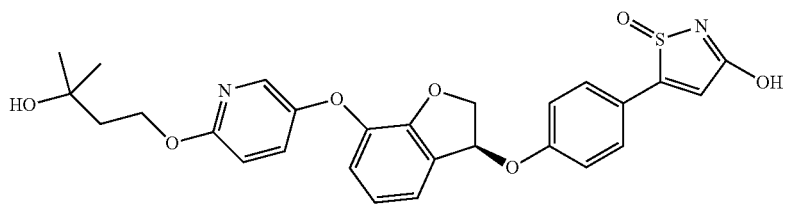
Example 46P
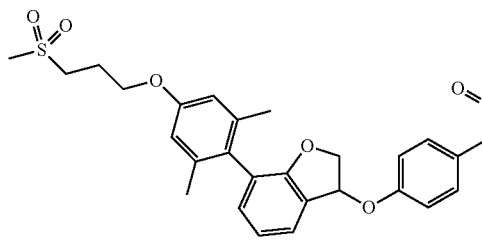
Example 47P
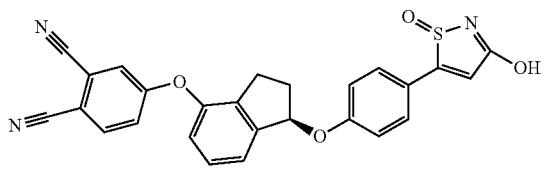
Example 48P
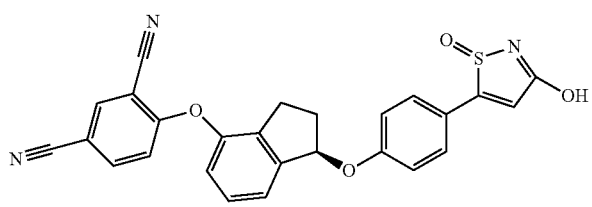
Example 49P
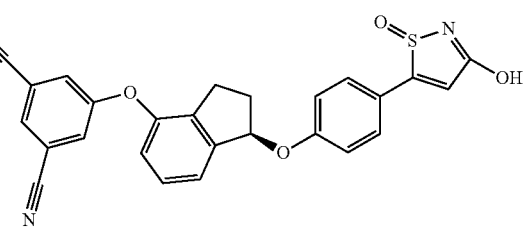

Example 50P
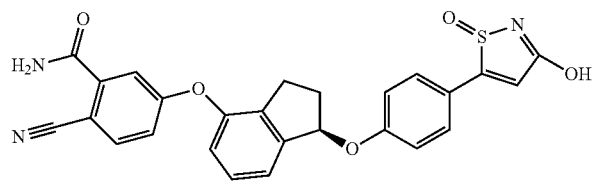
Example 51P
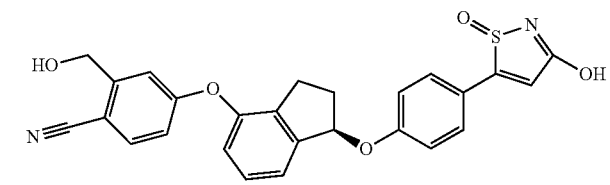
Example 52P
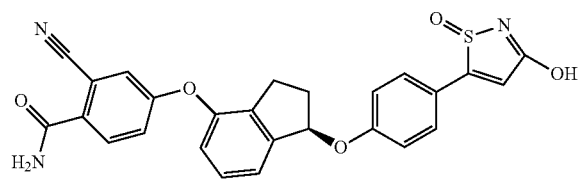
Example 53P
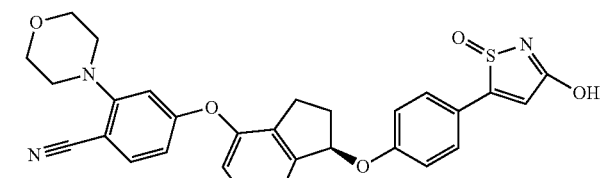
Example 54P
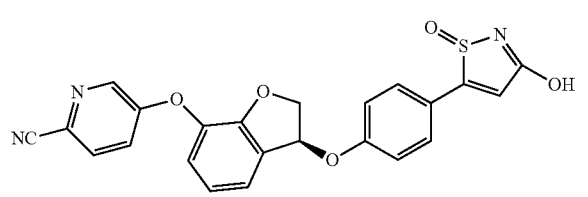
Example 55P
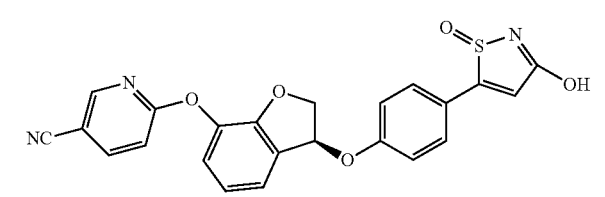
Structural Formula 17
Example 56p
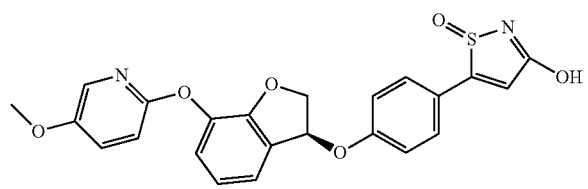
Example 57P
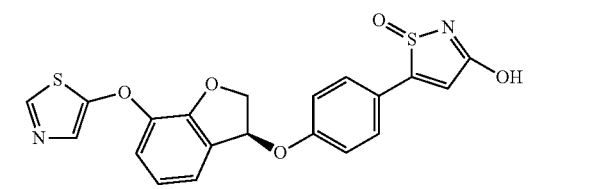
Example 58P
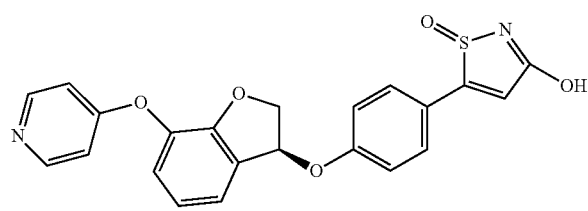
Example 59P
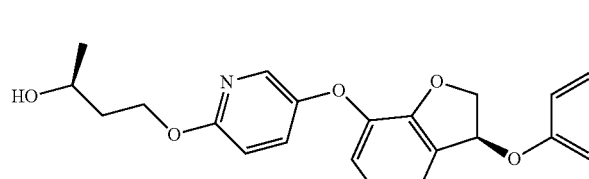
Example 60P
Example 61P
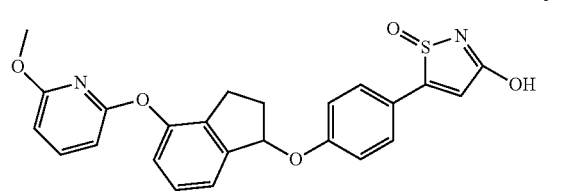
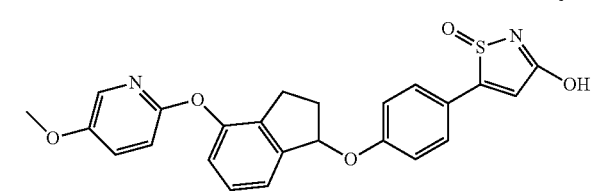

Example 62P
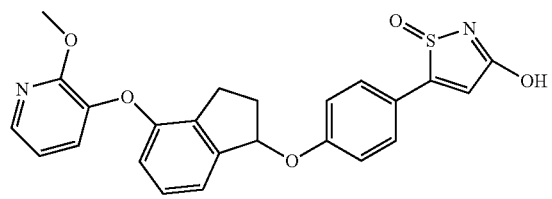
Example 63P
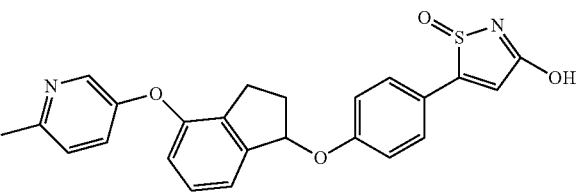
Example 64P
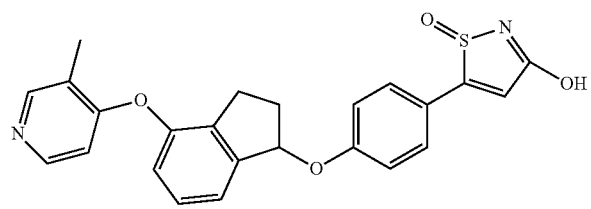
Example 65P
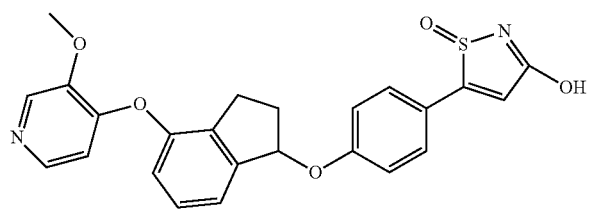
Example 66P
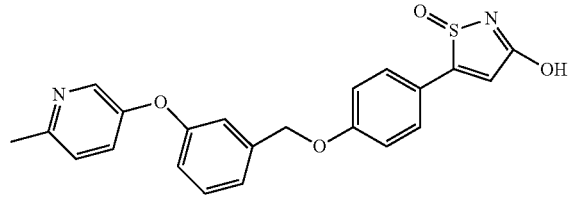
Example 67P
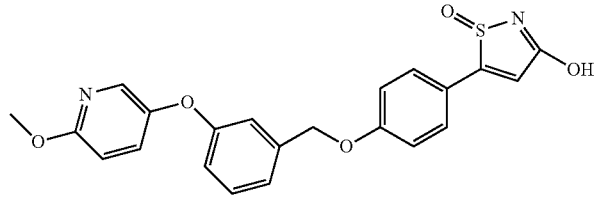
Example 68P
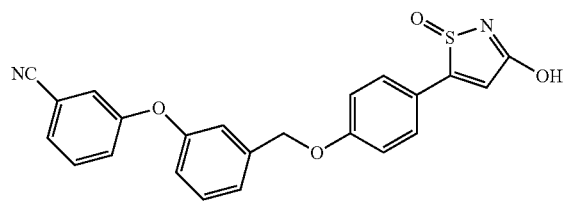
Example 69P
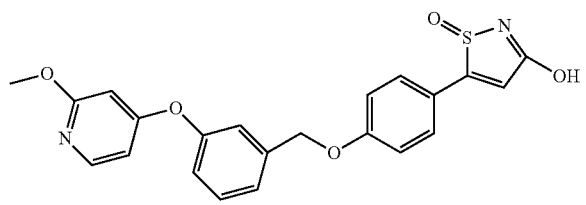
Example 70P
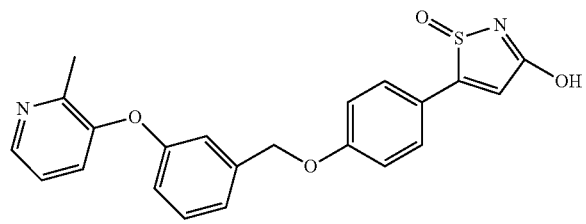
Example 71P
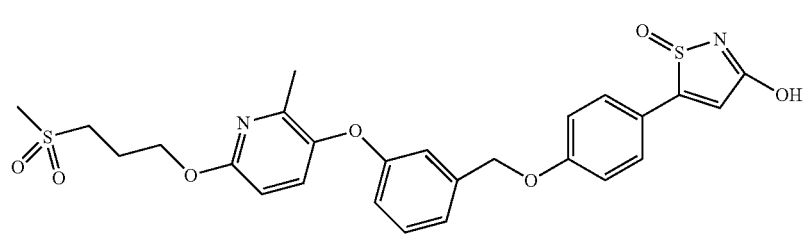
Example 72P
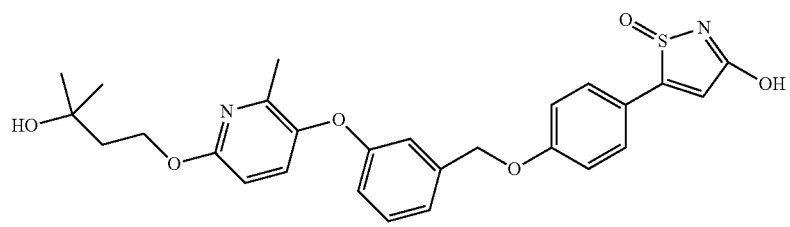

-continued
Example 73P
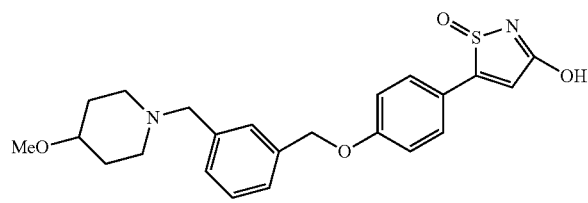
Example 74P
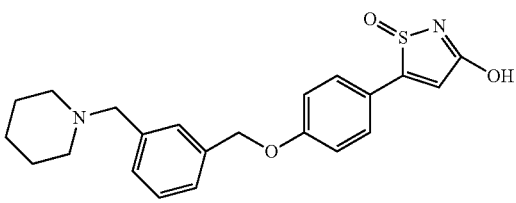
Example 75P
Structural Formula 18
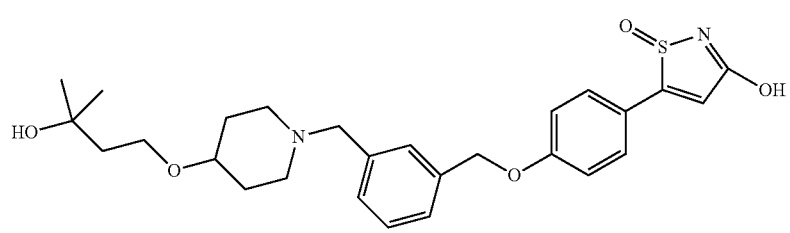
Example 76P
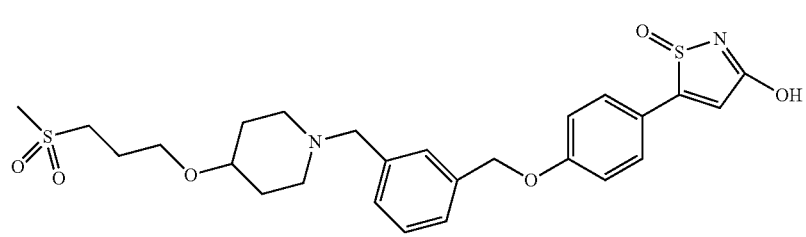
Example 77P
Example 78P
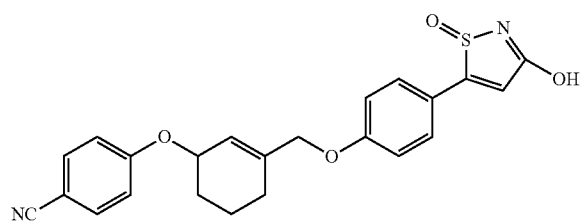
Example 79P
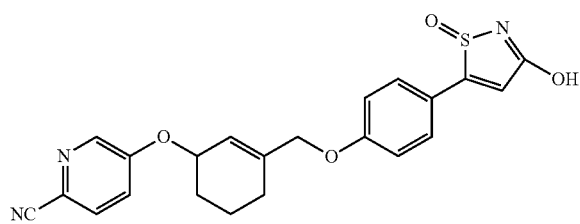
Example 80P
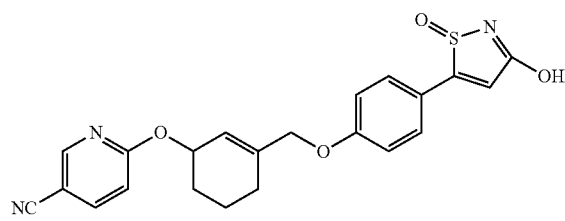
Example 81P
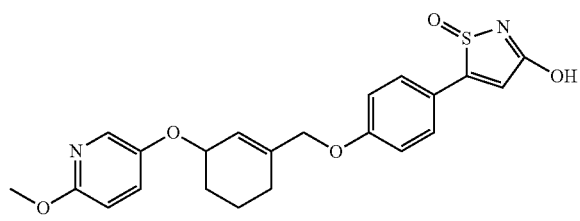

233 234
-continued
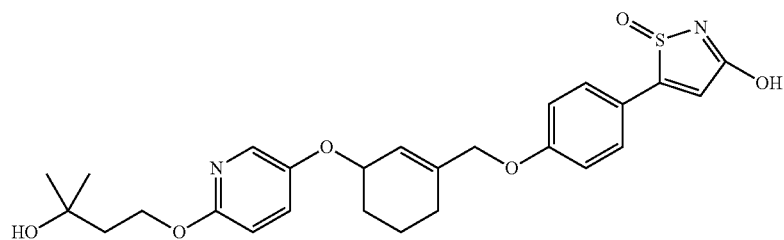
Example 82P
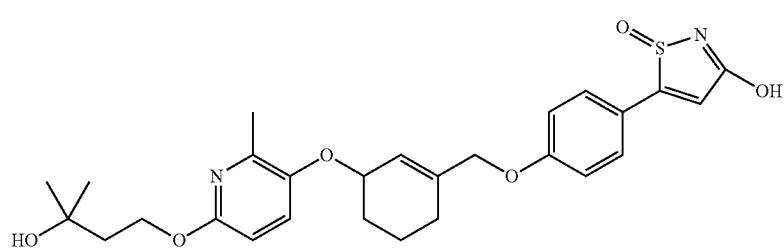
Example 83P
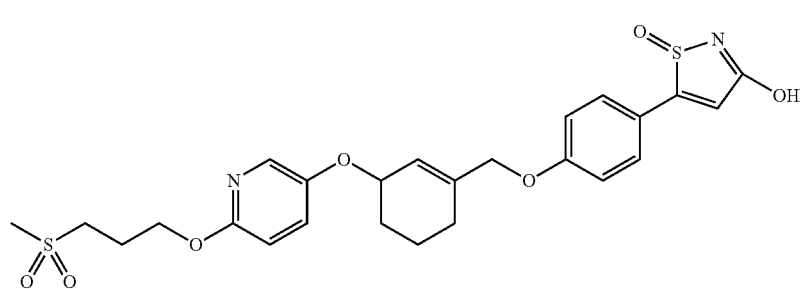
Example 84P
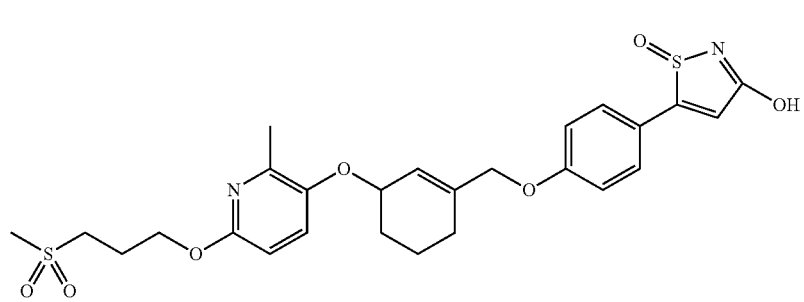
Example 85P
Example 86P    Example 87P
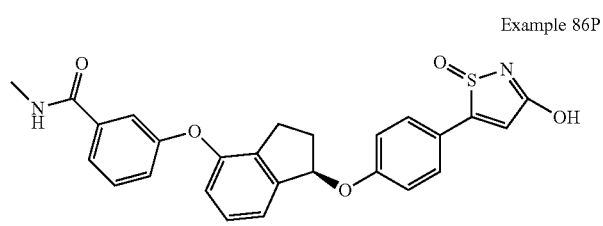    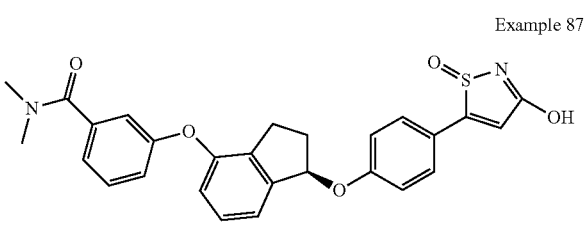
Example 88P
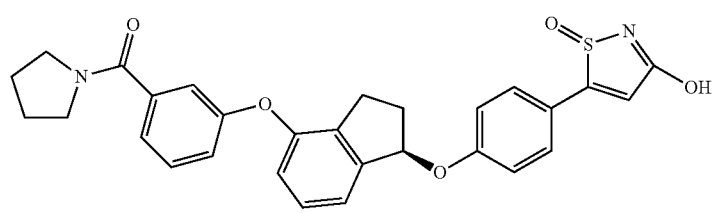

-continued
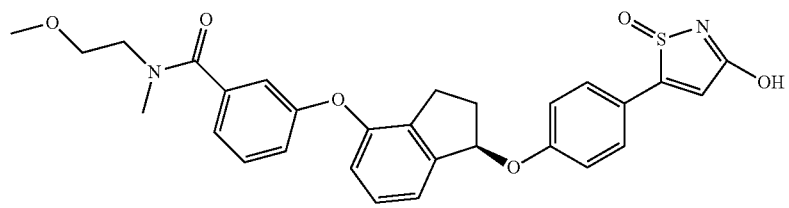
Example 89P
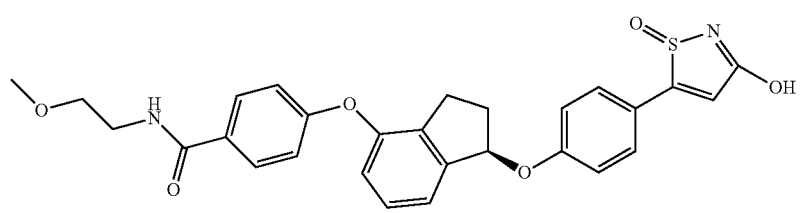
Example 90P
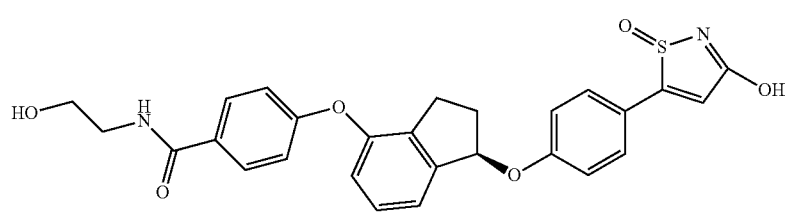
Example 91P
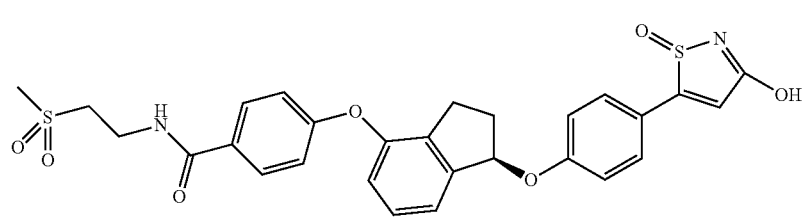
Example 92P
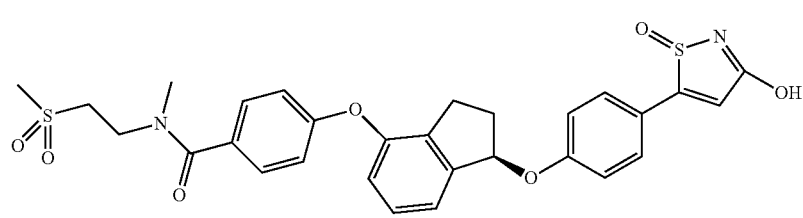
Example 93P
Structural Formula 19
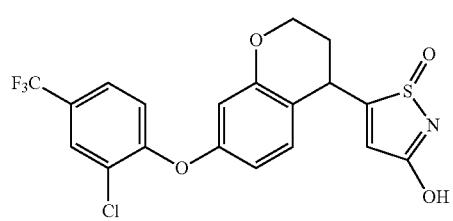
Example 94P
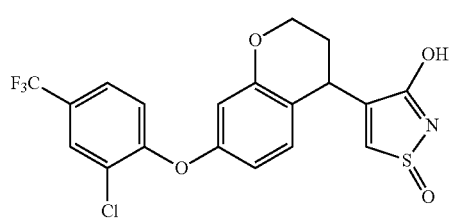
Example 95P
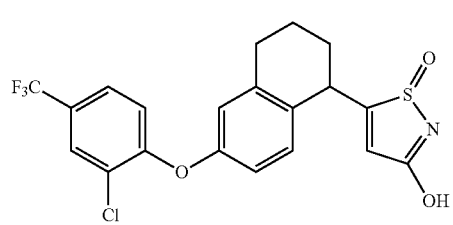
Example 96P
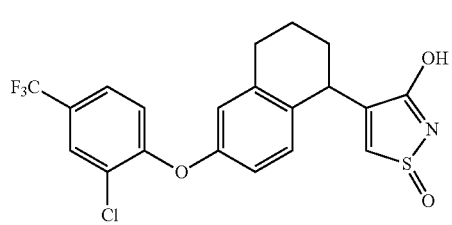
Example 97P -continued
Example 98P
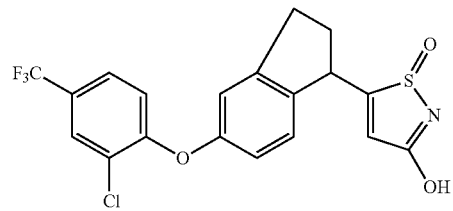
Example 99P
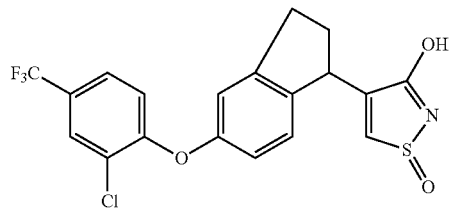
Example 100P
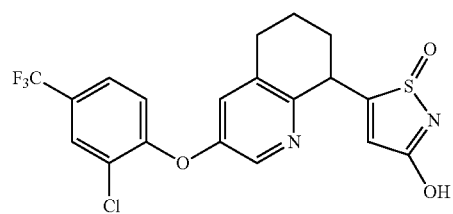
Example 101P
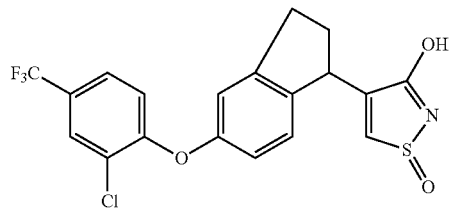
Example 102P
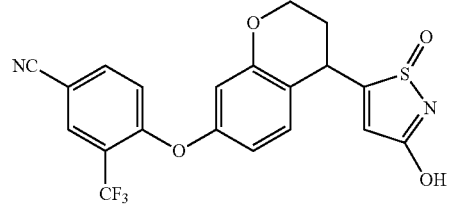
Example 103P
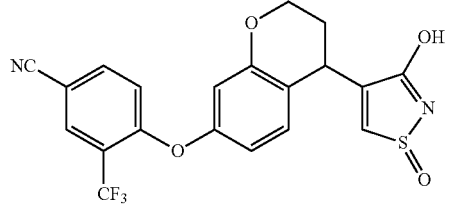
Example 104P
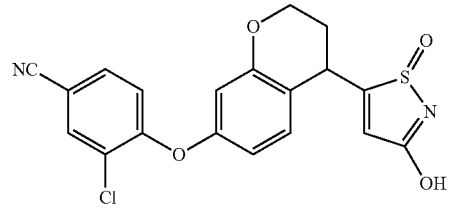
Example 105P
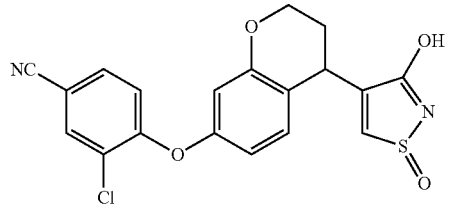
Example 106P
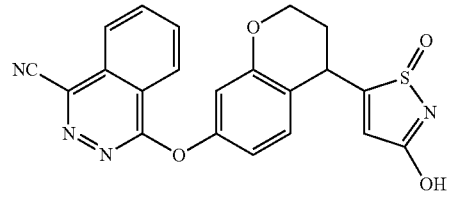
Example 107P
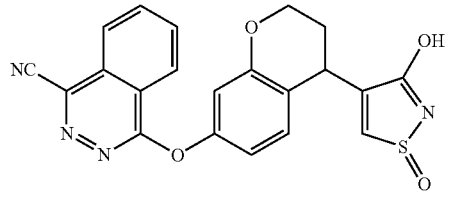
Example 108P
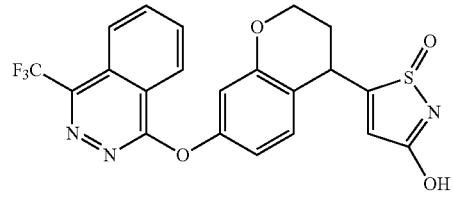
Example 109P
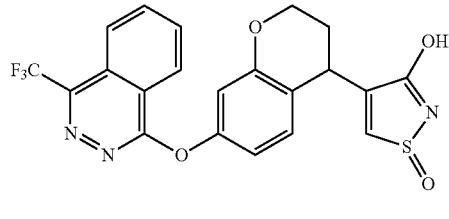
Example 110P
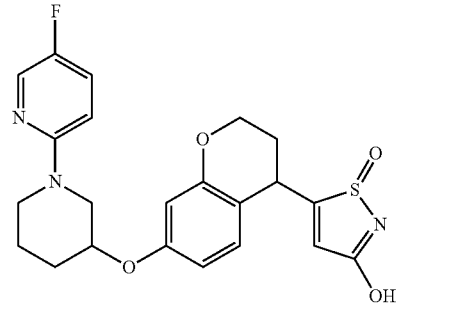
Example 111P
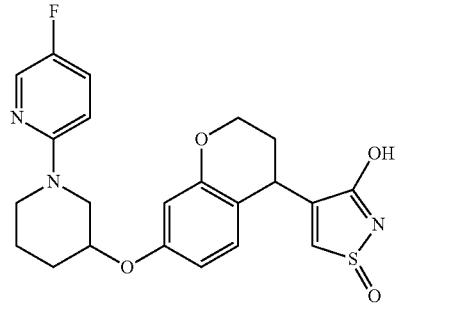

Example 112P
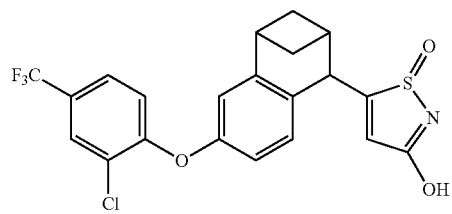
Example 113P
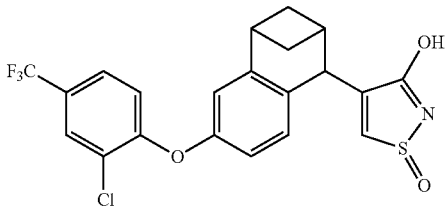
Structural Formula 20
Reference Example 1-1
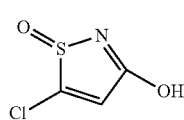
Reference Example 2
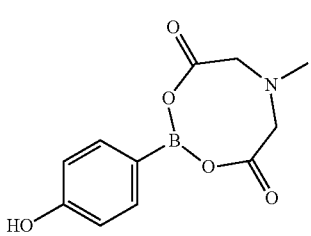
Reference Example 3-1
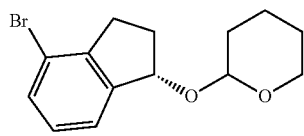
Reference Example 3-1
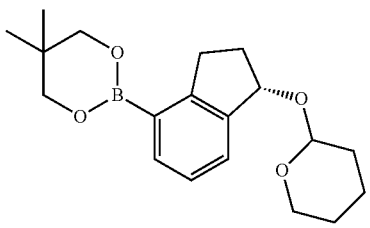
1p;1p
Reference Example 3-3
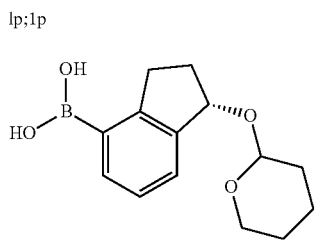
Example 1-1
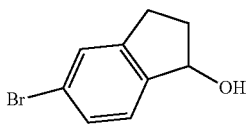
Example 1-2
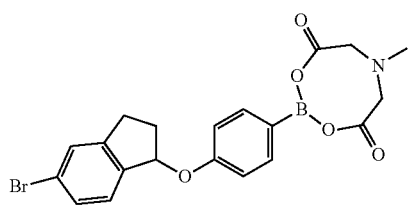
Example 2-1
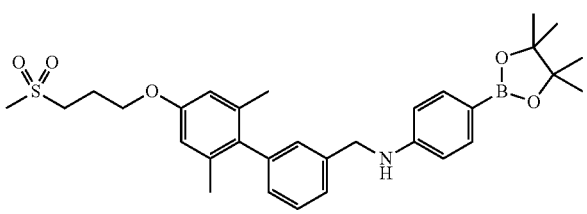
Example 3-1
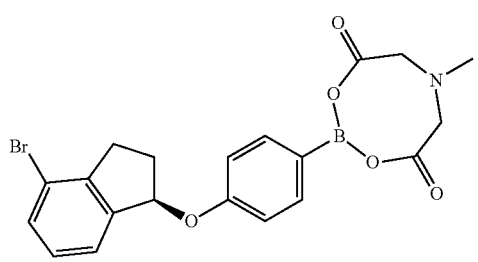
Example 83-1
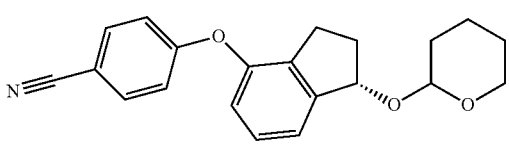

-continued
Example 83-2
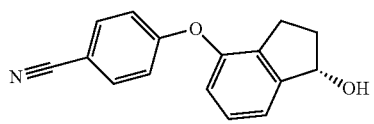
Example 83-3
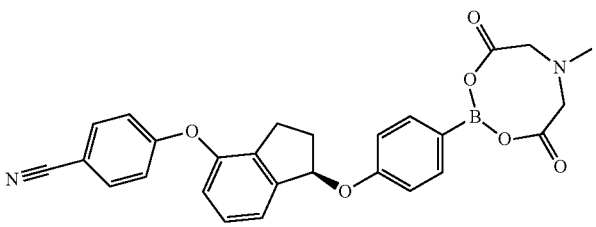
Example 90-1
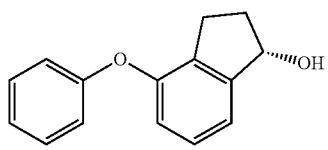
Example 90-2
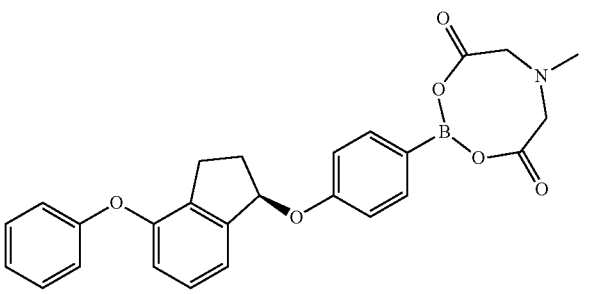
Example 96-1
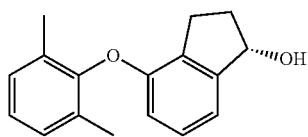
Example 96-2
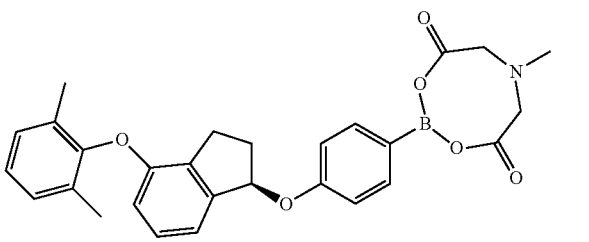
Example 99-1
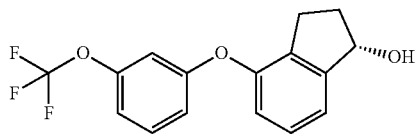
Example 99-2
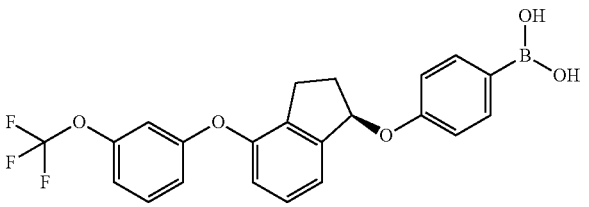
Structural Formula 21
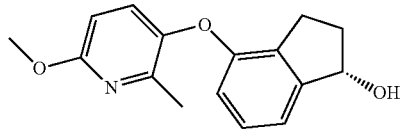
Example 106-1
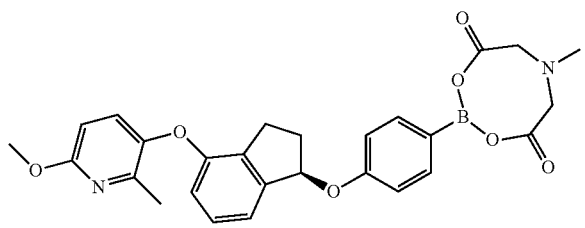
Example 106-2
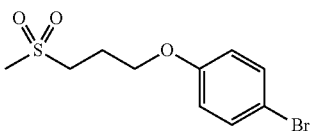
Example 115-1
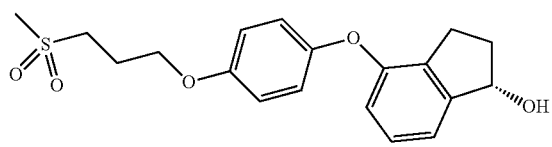
Example 115-2

Example 115-3
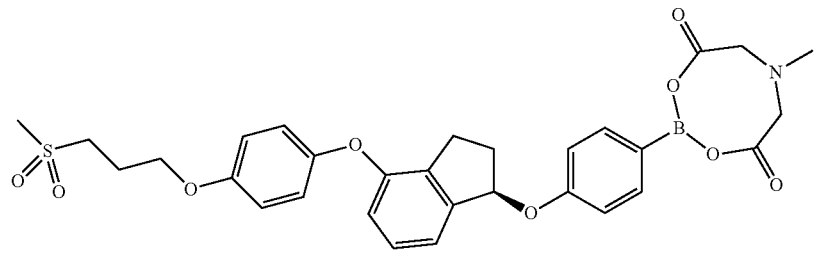
Example 118-1
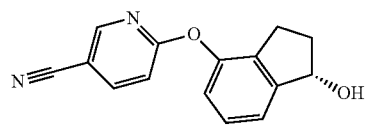
Example 118-2
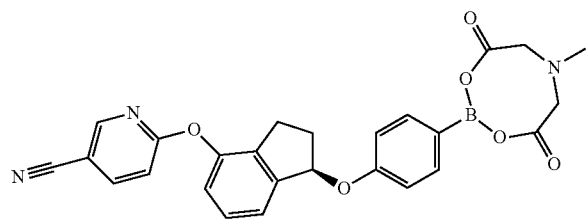
Example 120-1
Example 121-1
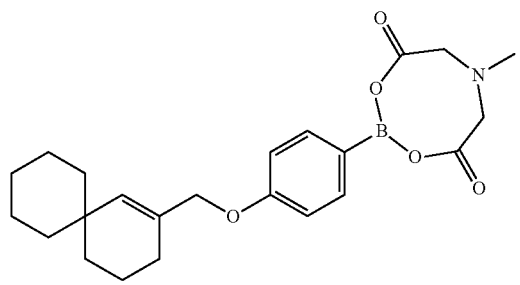
Example 121-2
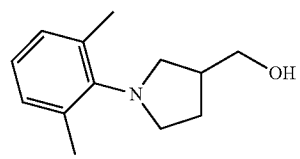
Example 122-1
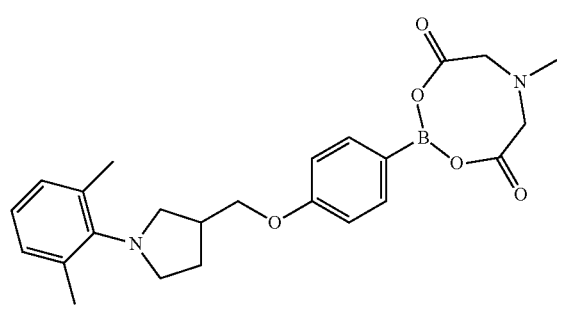
Example 123-1
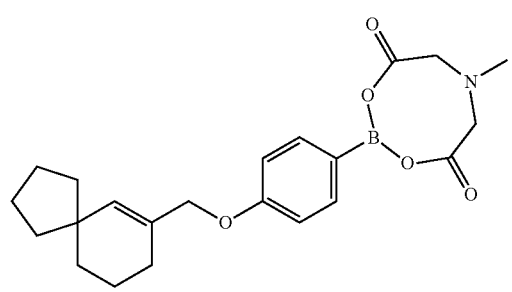
Example 124-1
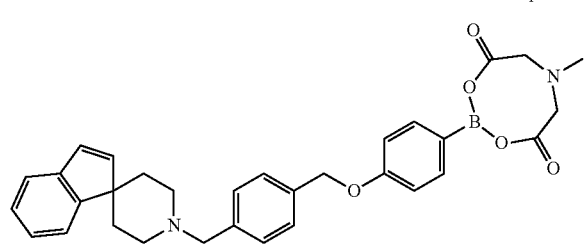
Example 124-2
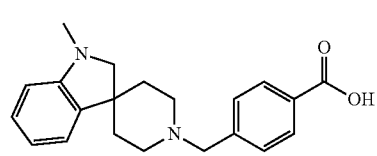
Example 124-3
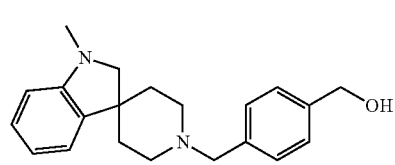
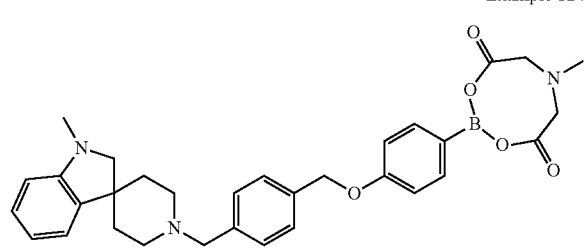

-continued
Structural Formula 22
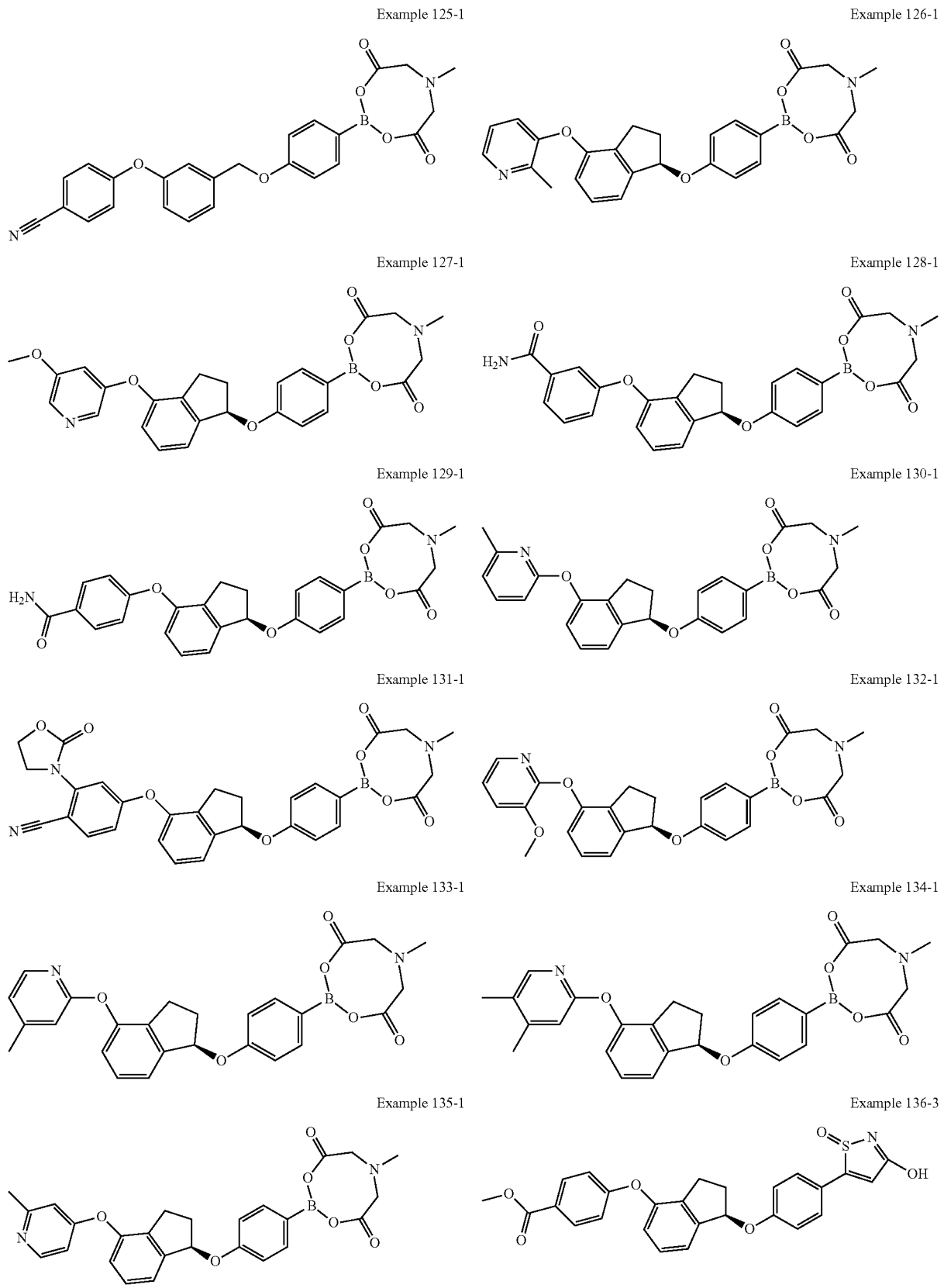

Example 136-2
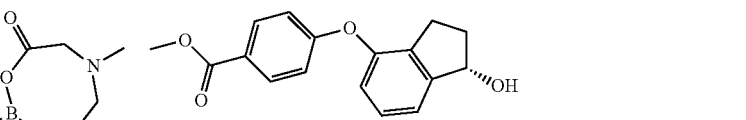
Example 136-1
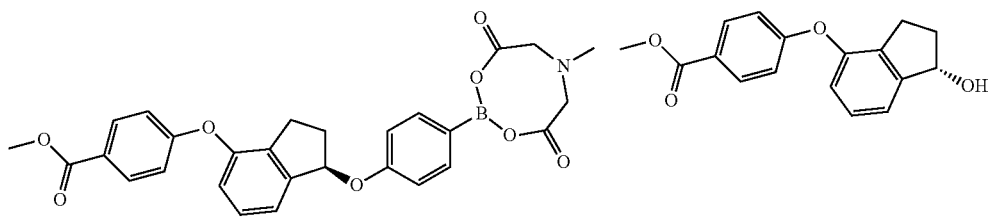
Structural Formula 23
Example 137-1
Example 137-2
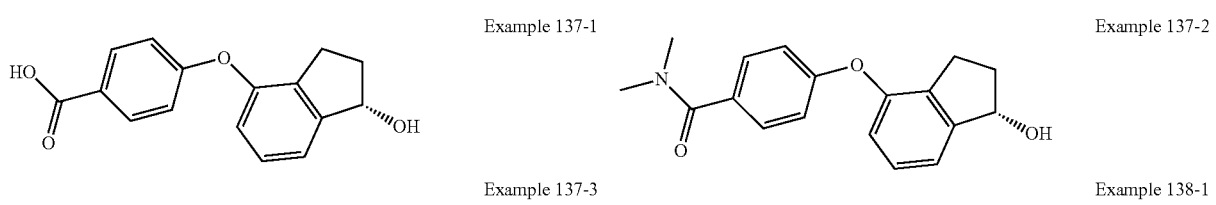
Example 137-3
Example 138-1
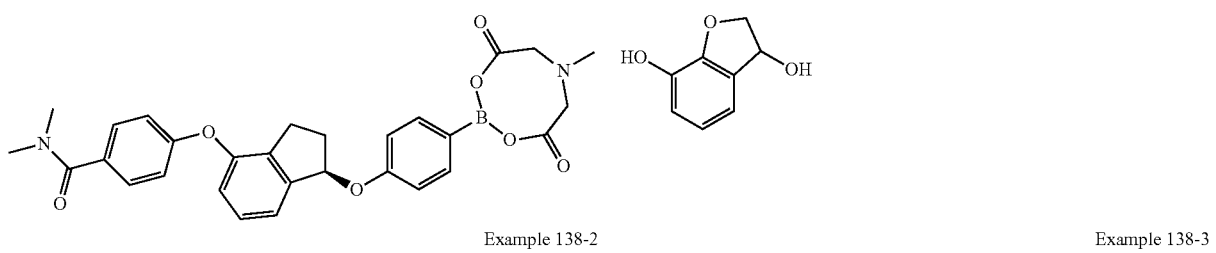
Example 138-2
Example 138-3
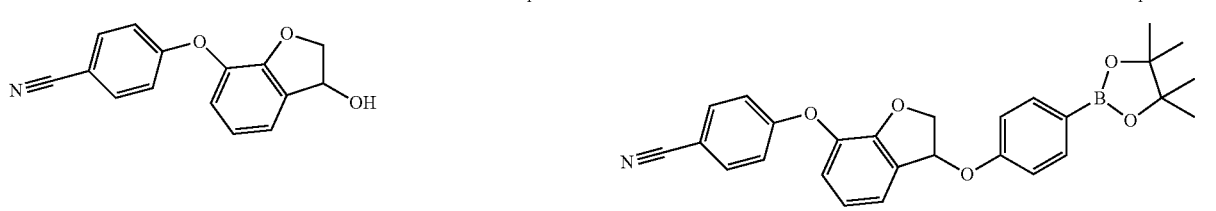
Example 139-1
Example 140-1
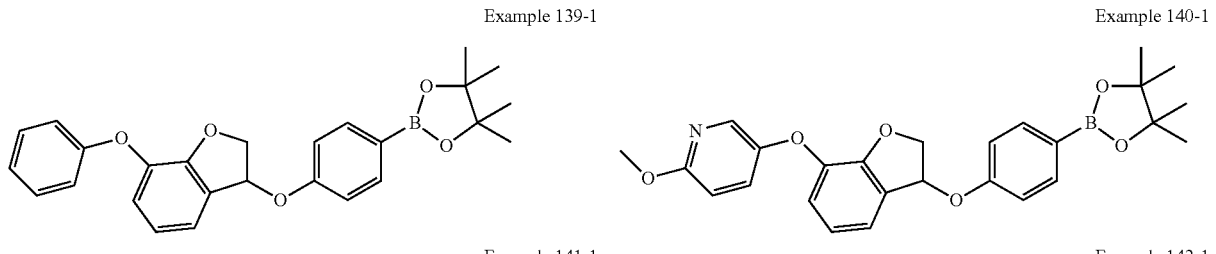
Example 141-1
Example 142-1
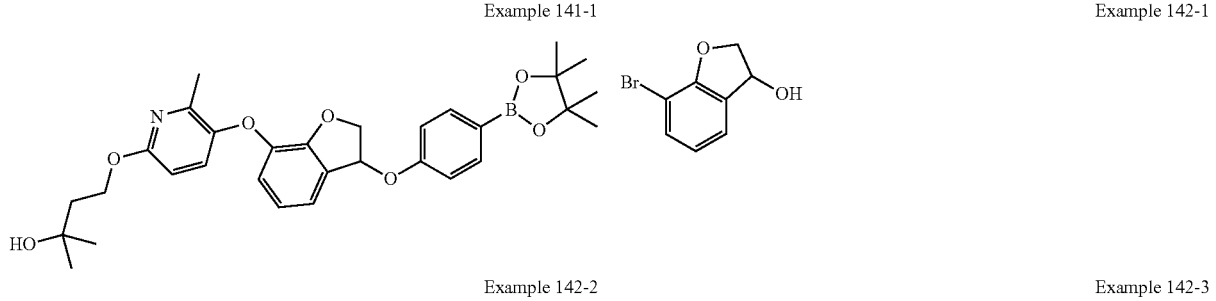
Example 142-2
Example 142-3
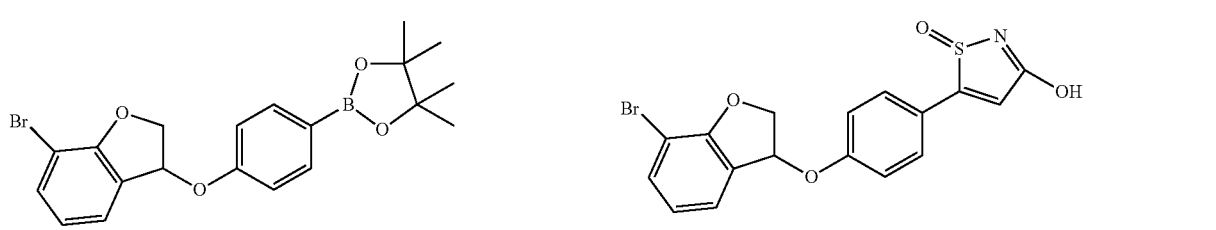

Example 146-1
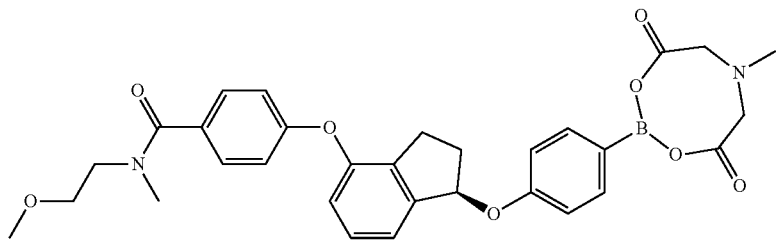
Example 147-1
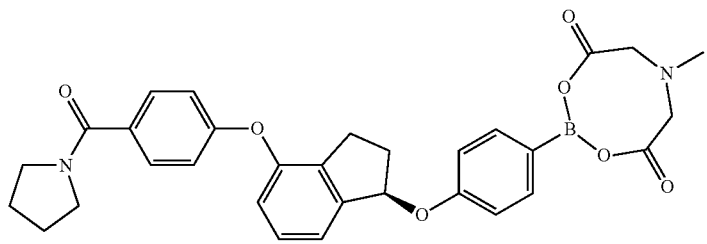
Structural Formula 24
Example 149-1
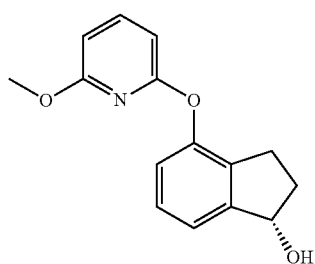
Example 149-2
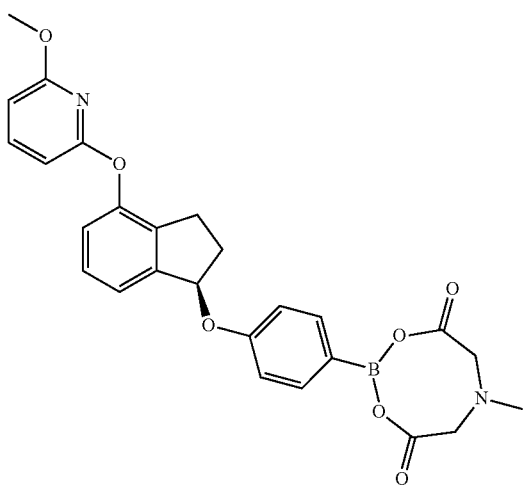
Example 150-1
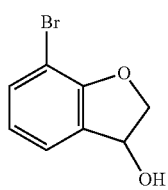
Example 150-2
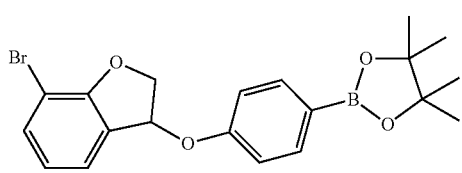
Example 151-1
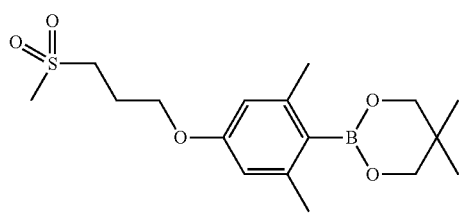
Example 155-1
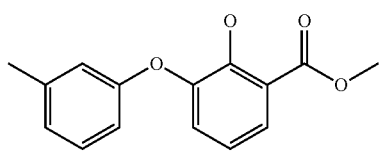

Example 155-2
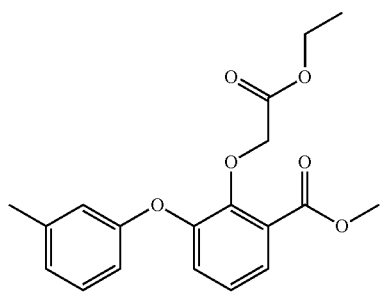
Example 155-3
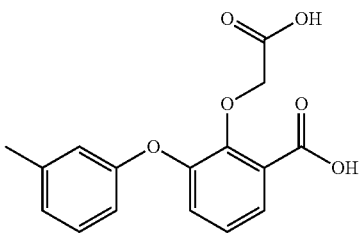
Example 155-4
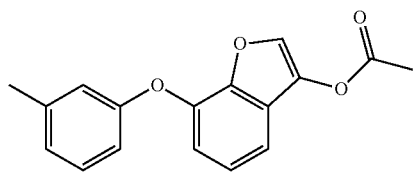
Example 155-5
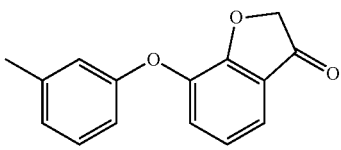
Example 155-6
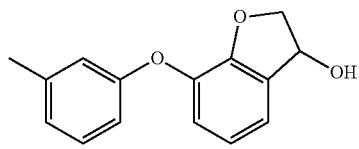
Example 155-7
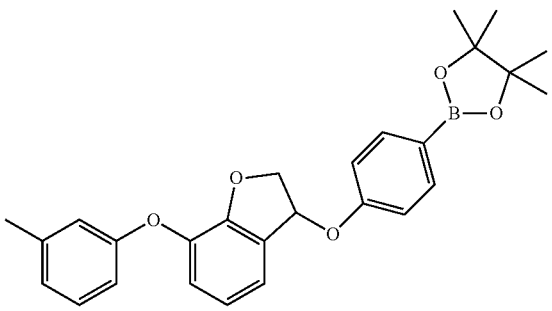
Example 159-1
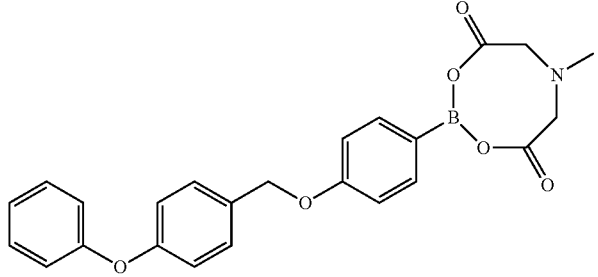
Example 161-1
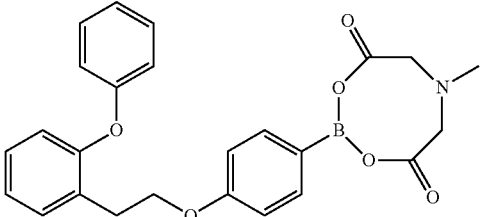
Example 162-1
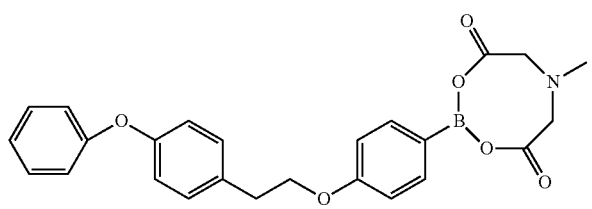
Example 163-1
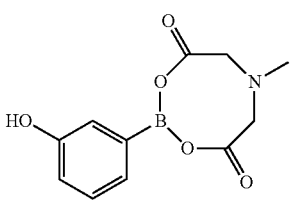
Example 163-2
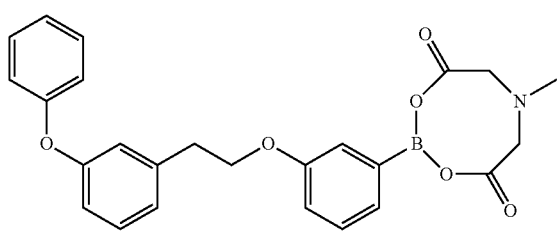

TABLE 2

| Examples | Method | MS-ESI (m/z) [M + H]⁺ | Retention time (min.) |
|---|---|---|---|
| Reference Example 3-3 | A | 285** | 5.18 |
| 3 | B | 404 | 5.95 |
| 4 | A | 464 | 6.46 |
| 5 | D | 416 | 1.30 |
| 6 | C | 436 | 1.11 |
| 7 | B | 446 | 6.22 |
| 8 | C | 436 | 1.11 |
| 9 | D | 430 | 1.34 |
| 10 | C | 436 | 1.06 |
| 11 | D | 420 | 1.25 |
| 12 | D | 438 | 1.29 |
| 13 | C | 434 | 1.11 |
| 14 | C | 466 | 1.11 |
| 15 | C | 450 | 1.13 |
| 16 | C | 454 | 1.11 |
| 17 | C | 438 | 1.02 |
| 18 | C | 480 | 1.15 |
| 19 | D | 447 | 0.99 |
| 20 | C | 430 | 1.15 |
| 21 | C | 420 | 1.04 |
| 22 | C | 444 | 1.21 |
| 23 | C | 432 | 1.01 |
| 24 | D | 416 | 1.31 |
| 25 | C | 428 | 1.11 |
| 26 | D | 444 | 1.40 |
| 27 | C | 416 | 1.07 |
| 28 | D | 458 | 1.45 |
| 29 | C | 420 | 1.04 |
| 30 | C | 432 | 1.01 |
| 31 | C | 460 | 1.11 |
| 32 | C | 446 | 1.07 |
| 33 | C | 458 | 1.23 |
| 34 | D | 444 | 1.37 |
| 35 | C | 452 | 1.13 |
| 36 | C | 430 | 1.14 |
| 37 | D | 430 | 1.11 |
| 38 | D | 434 | 1.32 |
| 39 | C | 434 | 1.08 |
| 40 | C | 446 | 1.05 |
| 41 | B | 434 | 6.22 |
| 42 | C | 508 | 1.13 |
| 43 | C | 450 | 1.12 |
| 44 | C | 464 | 1.07 |
| 45 | C | 446 | 1.06 |
| 46 | C | 438 | 1.03 |
| 47 | C | 522 | 1.20 |
| 48 | C | 466 | 1.06 |
| 49 | C | 462 | 0.99 |
| 50 | C | 466 | 1.19 |
| 51 | C | 450 | 0.81 |
| 52 | C | 466 | 1.07 |
| 53 | C | 450 | 1.01 |
| 54 | C | 462 | 0.97 |
| 55 | C | 466 | 1.08 |
| 56 | C | 450 | 1.01 |
| 57 | C | 526 | 1.15 |
| 58 | C | 480 | 1.14 |
| 59 | C | 450 | 1.00 |
| 60 | C | 480 | 1.12 |
| 61 | C | 526 | 1.15 |
| 62 | C | 526 | 1.14 |
| 63 | C | 470 | 1.11 |
| 64 | C | 470 | 1.07 |
| 65 | C | 486 | 1.09 |

TABLE 3

| Examples | Method | MS-ESI (m/z) [M + H]⁺ | Retention time (min.) |
|---|---|---|---|
| 66 | C | 488 | 1.07 |
| 67 | C | 488 | 1.10 |
| 68 | C | 504 | 1.15 |
| 69 | C | 504 | 1.36 |
| 70 | D | 480 | 1.10 |
| 71 | D | 417 | 0.84 |
| 72 | B | 417 | 4.12 |
| 73 | D | 437 | 1.16 |
| 74 | D | 437 | 1.16 |
| 75 | D | 437 | 1.12 |
| 76 | D | 479 | 1.30 |
| 77 | C | 446 | 0.68 |
| 78 | C | 473 | 1.04 |
| 79 | D | 450 | 1.15 |
| 80 | C | 492 | 1.17 |
| 81 | C | 442 | 0.83 |
| 82 | C | 408 | 1.00 |
| 83 | B | 443 | 5.70 |
| 84 | A | 508** | 6.70 |
| 85 | B | 419 | 4.80 |
| 86 | B | 443 | 5.75 |
| 87 | A | 508** | 6.65 |
| 88 | A | 462 | 5.80 |
| 90 | A | 418 | 6.38 |
| 91 | A | 448 | 6.37 |
| 92 | A | 448 | 6.32 |
| 93 | A | 432 | 6.63 |
| 94 | A | 432 | 6.58 |
| 95 | A | 454** | 6.70 |
| 96 | B | 446 | 6.38 |
| 97 | B | 521 | 5.87 |
| 98 | B | 507 | 5.88 |
| 99 | B | 502 | 6.38 |
| 100 | A | 449 | 6.07 |
| 101 | A | 535 | 6.20 |
| 102 | A | 521 | 6.37 |
| 103 | B | 502 | 6.30 |
| 104 | A | 469 | 6.17 |
| 105 | A | 463 | 6.22 |
| 106 | A | 463 | 6.28 |
| 107 | A | 496 | 5.43 |
| 108 | A | 534 | 6.22 |
| 109 | B | 504 | 5.18 |
| 110 | B | 450 | 5.42 |
| 111 | A | 424 | 6.28 |
| 112 | B | 520 | 6.02 |
| 113 | B | 520 | 6.05 |
| 114 | A | 449 | 6.07 |
| 115 | A | 554 | 5.72 |
| 116 | A | 555 | 5.52 |
| 117 | A | 569 | 5.68 |
| 118 | B | 444 | 5.37 |
| 119 | B | 444 | 5.35 |
| 120 | B | 372 | 6.47 |
| 121 | A | 397 | 6.72 |
| 122 | B | 358 | 6.33 |
| 123 | B | 497 | 4.43 |
| 124 | B | 514 | 4.27 |
| 125 | A | 417 | 5.68 |
| 126 | B | 433 | 4.38 |
| 127 | A | 449 | 5.65 |
| 128 | A | 461 | 5.37 |
| 129 | A | 461 | 5.33 |
| 130 | A | 433 | 5.80 |
| 131 | B | 550** | 5.17 |
| 132 | A | 449 | 5.32 |
| 133 | A | 433 | 5.73 |
| 134 | A | 433 | 5.75 |
| 135 | B | 433 | 3.98 |
| 136 | A | 475 | 5.57 |
| 137 | A | 489 | 5.58 |
| 138 | A | 445 | 5.55 |
| 139 | A | 442** | 5.78 |
| 140 | A | 451 | 5.57 |
| 141 | A | 537 | 5.73 |
| 142 | A | 521 | 5.82 |
| 143 | A | 556** | 6.13 |
| 144A | A | 445 | 5.68 |
| 144B | A | 445 | 5.65 |
| 145A | B | 442** | 5.62 |

TABLE 3-continued

| Examples | Method | MS-ESI (m/z) [M + H]+ | Retention time (min.) |
|---|---|---|---|
| 145B | B | 442** | 5.65 |
| 146 | B | 533 | 5.52 |
| 147 | B | 515 | 5.63 |
| 148A | A | 556** | 6.10 |
| 148B | A | 556** | 6.07 |

*[M − H]−
**[M + Na]+

TABLE 4

| Examples | Method | MS-ESI (m/z) [M + H]+ | Retention time (min.) |
|---|---|---|---|
| 149 | A | 449 | 6.10 |
| 150 | A | 428** | 5.63 |
| 151 | A | 590** | 5.65 |
| 152A | B | 451 | 5.38 |
| 152B | B | 451 | 5.38 |
| 153A | A | 537 | 5.85 |
| 153B | A | 537 | 5.85 |
| 154A | A | 521 | 5.87 |
| 154B | A | 521 | 5.85 |
| 155 | B | 456** | 5.82 |
| 156 | F | 449** | 1.12 |
| 157 | F | 428 | 1.04 |
| 158 | B | 457 | 6.35 |
| 159 | A | 390* | 6.17 |
| 160 | A | 390* | 6.17 |
| 161 | A | 406 | 6.37 |
| 162 | A | 406 | 6.30 |
| 163 | A | 406 | 6.50 |

*[M − H]−
**[M + Na]+

TABLE 5

| Examples | Method | MS-ESI (m/z) [M + H]+ | Retention time (min.) |
|---|---|---|---|
| 1-1 | A | 195# | 5.07 |
| 2-1 | A | 550 | 6.28 |
| 3-1 | A | 443* | 5.75 |
| 83-1 | A | 358** | 6.15 |
| 83-2 | A | 234# | 5.48 |
| 83-3 | A | 481* | 5.57 |
| 90-1 | A | 209# | 5.57 |
| 90-2 | A | 480** | 5.92 |
| 96-1 | A | 237# | 6.03 |
| 96-2 | A | 486 | 5.85 |
| 99-1 | A | 293# | 6.05 |
| 99-2 | A | 429* | 6.58 |
| 106-1 | A | 272 | 5.50 |
| 106-2 | A | 503 | 5.83 |
| 115-2 | A | 345# | 4.88 |
| 118-1 | A | 235# | 4.50 |
| 118-2 | A | 484 | 5.13 |
| 120-1 | A | 410* | 3.27 |
| 121-1 | A | 206 | 4.10 |

TABLE 5-continued

| Examples | Method | MS-ESI (m/z) [M + H]+ | Retention time (min.) |
|---|---|---|---|
| 121-2 | A | 437 | 6.15 |
| 122-1 | A | 420** | 6.17 |
| 123-1 | A | 537 | 3.58 |
| 124-1 | A | 337 | 3.15 |
| 124-2 | B | 323 | 3.47 |
| 124-3 | A | 554 | 3.38 |
| 125-1 | A | 457 | 5.42 |
| 126-1 | A | 473 | 5.20 |
| 127-1 | A | 489 | 5.32 |
| 128-1 | A | 501 | 5.00 |
| 129-1 | A | 501 | 5.00 |
| 130-1 | A | 473 | 5.32 |
| 131-1 | A | 568 | 5.02 |
| 132-1 | A | 489 | 4.98 |
| 133-1 | A | 473 | 5.42 |
| 134-1 | A | 473 | 5.39 |
| 135-1 | A | 473 | 3.83 |
| 136-1 | A | 267# | 5.57 |
| 136-2 | A | 516 | 5.92 |
| 136-3 | A | 476 | 6.32 |
| 137-1 | B | 253# | 5.10 |
| 137-2 | A | 298 | 4.83 |
| 137-3 | A | 529 | 5.23 |
| 138-1 | B | 135# | 1.47 |
| 138-2 | A | 254 | 4.87 |
| 138-3 | A | 478** | 6.37 |
| 139-1 | A | 453** | 6.57 |
| 140-1 | A | 462 | 6.43 |
| 141-1 | A | 548 | 6.58 |
| 142-2 | A | 439, 441** | 6.50 |
| 142-3 | A | 428, 430** | 5.57 |
| 146-1 | A | 573 | 5.27 |
| 147-1 | A | 555 | 5.40 |

*[M − H]−
**[M + Na]+
[M − H2O + H]+

TABLE 6

| Examples | Method | MS-ESI (m/z) [M + H]+ | Retention time (min.) |
|---|---|---|---|
| 149-1 | A | 280** | 5.22 |
| 149-2 | A | 489 | 5.67 |
| 150-1 | A | 215 | 4.18 |
| 150-2 | A | 439** | 6.49 |
| 155-1 | A | 257* | 6.08 |
| 155-2 | A | 367** | 5.88 |
| 155-3 | B | 325** | 5.58 |
| 155-4 | B | 283 | 6.22 |
| 155-5 | B | 241 | 5.62 |
| 155-6 | B | 265** | 5.32 |
| 155-7 | B | 467** | 6.75 |
| 159-1 | A | 454** | 5.70 |
| 161-1 | A | 468** | 5.83 |
| 162-1 | A | 468** | 5.83 |
| 163-1 | A | 250 | 2.20 |

*[M − H]−
**[M + Na]+

TABLE 7

| Examples | NMR data (δ: ppm) < *: 300 MHz > |
|---|---|
| Reference Example 1-1 | 1H-NMR (CDCl3) δ: 8.12 (1H, bs), 6.68 (1H, s) |
| Reference Example 2 | 1H-NMR (DMSO-d6) δ: 9.41 (1H, s), 7.21 (2H, d, J = 8 Hz), 6.73 (2H, d, J = 8 Hz), 4.27 (2H, d, J = 17 Hz), 4.04 (2H, d, J = 17 Hz), 2.46 (3H, s) |

TABLE 7-continued

| Examples | NMR data (δ: ppm) < *: 300 MHz > |
|---|---|
| Reference Example 3-1 | $^1$H-NMR (CDCl$_3$) δ: 7.42-7.38 (3H, m), 7.28 (1H, d, J = 8 Hz), 7.09 (2H, dt, J = 14, 6 Hz), 5.37 (1H, t, J = 6 Hz), 5.21 (1H, dd, J = 7, 5 Hz), 4.86-4.81 (2H, m), 4.03-3.93 (2H, m), 3.63-3.54 (2H, m), 3.13-3.03 (2H, m), 2.86-2.77 (2H, m), 2.49-2.38 (2H, m), 2.21-2.13 (1H, m), 2.06-1.98 (1H, m), 1.91-1.78 (2H, m), 1.78-1.68 (2H, m), 1.68-1.47 (8H, m). |
| Reference Example 3-2 | $^1$H-NMR (CDCl$_3$) δ: 7.72-7.68 (2H, m), 7.52 (1H, d, J = 7 Hz), 7.40 (1H, d, J = 8 Hz), 7.24-7.16 (2H, m), 5.29 (1H, t, J = 6 Hz), 5.13 (1H, dd, J = 7, 5 Hz), 4.87 (1H, t, J = 4 Hz), 4.83 (1H, dd, J = 5, 3 Hz), 4.08-3.94 (2H, m), 3.75 (4H, s), 3.75 (4H, s), 3.62-3.54 (2H, m), 3.33-3.22 (2H, m), 3.04-2.94 (2H, m), 2.42-2.32 (2H, m), 2.16-2.07 (1H, m), 1.75-1.52 (13H, m), 1.02 (6H, s), 1.01 (6H, s). |
| 1 | $^1$H-NMR (DMSO-d$_6$) δ: 11.27 (1H, s), 7.81 (2H, d, J = 7 Hz), 7.61-7.53 (1H, m), 7.47-7.31 (2H, m), 7.22 (2H, d, J = 7 Hz), 7.16-7.04 (1H, m), 6.04-5.89 (1H, m), 3.14-2.99 (1H, m), 2.99-2.84 (1H, m), 2.70-2.39 (1H, m), 2.15-1.95 (1H, m). |
| 2 | $^1$H-NMR (DMSO-d$_6$) δ: 11.01 (1H, s), 7.55 (2H, d, J = 9 Hz), 7.39 (1H, t, J = 8 Hz), 7.34-7.27 (2H, m), 7.07-7.02 (1H, m), 7.00-6.94 (1H, m), 6.75 (1H, s), 6.73-6.65 (4H, m), 4.43 (2H, d, J = 6 Hz), 4.07 (2H, t, J = 6 Hz), 3.30-3.21 (2H, m), 3.03 (3H, s), 2.17-2.05 (2H, m), 1.91-1.86 (6H, m). |
| 3* | $^1$H-NMR (DMSO-d$_6$) 11.28 (1H, s), 7.83 (2H, d, J = 9 Hz), 7.57 (1H, d, J = 8 Hz), 7.46-7.41 (1H, m), 7.27-7.19 (1H, m), 7.23 (2H, d, J = 9 Hz), 7.11 (1H, s), 6.10 (1H, dd, J = 7, 4 Hz), 3.11-2.97 (1H, m), 2.97-2.83 (1H, m), 2.71-2.58 (1H, m), 2.15-2.00 (1H, m) |
| 4 | $^1$H-NMR (CDCl$_3$) δ: 7.77-7.70 (2H, m), 7.43 (2H, d, J = 7 Hz), 7.36-7.27 (2H, m), 7.18-7.11 (2H, m), 7.04-6.92 (2H, m), 6.89 (1H, dd, J = 9, 5 Hz), 6.64 (1H, s), 5.90 (1H, dd, J = 7, 4 Hz), 3.97 (2H, q, J = 7 Hz), 3.07-2.96 (1H, m), 2.89-2.78 (1H, m), 2.63-2.51 (1H, m), 2.22-2.10 (1H, m), 1.27 (3H, t, J = 7 Hz). |
| 41 | $^1$H-NMR (DMSO-d$_6$) δ: 11.29 (1H, s), 7.85-7.82 (2H, m), 7.45 (1H, d, J = 7 Hz), 7.38-7.31 (2H, m), 7.28-7.23 (2H, m), 7.22-7.07 (3H, m), 7.06-6.98 (1H, m), 6.12-6.00 (1H, m), 2.90-2.52 (3H, m), 2.12-1.94 (4H, m). |
| 83* | $^1$H-NMR (DMSO-d$_6$) δ: 11.29 (1H, s), 7.90-7.78 (4H, m), 7.42-7.33 (2H, m), 7.25 (2H, d, J = 9 Hz), 7.16-7.03 (4H, m), 6.10-6.03 (1H, m), 2.90-2.56 (3H, m), 2.11-1.98 (1H, m). |
| 89 | $^1$H-NMR (CDCl$_3$) δ: 7.88 (1H, s), 7.76-7.71 (2H, m), 7.29-7.21 (3H, m), 7.16-7.11 (2H, m), 7.00-6.81 (4H, m), 6.65 (1H, s), 5.88 (1H, dd, J = 7, 4 Hz), 3.86 (2H, t, J = 6 Hz), 3.06 (1H, ddd, J = 17, 9, 5 Hz), 2.92-2.82 (3H, m), 2.67-2.56 (1H, m), 2.21 (1H, ddd, J = 18, 9, 5 Hz), 1.45 (1H, bs). |
| 96 | $^1$H-NMR (CDCl$_3$) δ: 7.77-7.71 (2H, m), 7.57 (1H, s), 7.18-7.13 (2H, m), 7.13-7.03 (5H, m), 6.65 (1H, s), 6.29 (1H, dd, J = 7, 2 Hz), 5.91 (1H, dd, J = 7, 4 Hz), 3.28 (1H, ddd, J = 17, 9, 5 Hz), 3.14-3.04 (1H, m), 2.76-2.65 (1H, m), 2.29 (1H, ddd, J = 18, 9, 5 Hz), 2.13 (6H, s). |
| 99* | $^1$H-NMR (DMSO-d$_6$) δ: 11.29 (1H, s), 7.84 (2H, d, J = 9 Hz), 7.50 (1H, t, J = 9 Hz), 7.39-7.28 (2H, m), 7.25 (2H, d, J = 9 Hz), 7.16-7.09 (1H, m), 7.12 (1H, s), 7.03 (1H, dd, J = 7, 2 Hz), 7.00-6.93 (2H, m), 6.11-6.02 (1H, m), 2.96-2.82 (1H, m), 2.81-2.55 (2H, m), 2.13-1.95 (1H, m). |
| 115 | $^1$H-NMR (CDCl$_3$) δ: 7.76-7.71 (2H, m), 7.54 (1H, br s), 7.23-7.10 (4H, m), 6.98-6.92 (2H, m), 6.89-6.83 (2H, m), 6.79 (1H, dd, J = 8, 1 Hz), 6.64 (1H, s), 5.88 (1H, dd, J = 7, 4 Hz), 4.14-4.07 (2H, m), 3.31-3.23 (2H, m), 3.15-3.03 (1H, m), 2.97 (3H, s), 2.95-2.85 (1H, m), 2.67-2.56 (1H, m), 2.40-2.30 (2H, m), 2.28-2.16 (1H, m). |
| 118* | $^1$H-NMR (DMSO-d$_6$) δ: 11.28 (1H, s), 8.65 (1H, s), 8.37-8.31 (1H, m), 7.84 (2H, d, J = 9 Hz), 7.43-7.15 (6H, m), 7.11 (1H, s), 6.11-6.04 (1H, m), 2.85-2.40 (3H, m), 2.10-1.96 (1H, m). |
| 120* | $^1$H-NMR (CDCl$_3$) δ: 7.72-7.63 (2H, m), 7.61 (1H, bs), 7.06-6.98 (2H, m), 6.61 (1H, s), 5.69 (1H, s), 4.44 (2H, s), 2.02 (2H, t, J = 6 Hz), 1.71-1.58 (2H, m), 1.54-1.22 (14H, m). |
| 121* | $^1$H-NMR (DMSO-d$_6$) δ: 11.28 (1H, s), 7.82 (2H, d, J = 9 Hz), 7.17 (2H, d, J = 9 Hz), 7.09 (1H, s), 7.04-6.91 (3H, m), 4.16 (2H, d, J = 7 Hz), 3.40-3.30 (1H, m), 3.22 (2H, t, J = 1 Hz), 3.05 (1H, dd, J = 8, 6 Hz), 2.90-2.74 (1H, m), 2.30-2.10 (1H, m), 2.24 (6H, s), 1.93-1.78 (1H, m). |
| 123 | $^1$H-NMR (CDCl$_3$) δ: 7.70 (2H, d, J = 9 Hz), 7.45-7.37 (5H, m), 7.30 (1H, d, J = 7 Hz), 7.25-7.16 (2H, m), 7.10 (2H, d, J = 9 Hz), 6.88-6.82 (1H, m), 6.77-6.72 (1H, m), 6.62 (1H, s), 5.13 (2H, s), 3.66 (2H, s), 3.03-2.95 (2H, m), 2.44-2.34 (2H, m), 2.25-2.15 (2H, m), 1.39-1.32 (2H, m). |
| 138 | $^1$H-NMR (DMSO-d$_6$) δ: 11.31 (1H, s), 7.90-7.77 (4H, m), 7.50-7.42 (1H, m), 7.30-7.19 (3H, m), 7.12-6.99 (4H, m), 6.34-6.26 (1H, m), 4.81 (1H, dd, J = 11, 6 Hz), 4.62-4.55 (1H, m). |
| 142 | $^1$H-NMR (DMSO-d$_6$) δ: 7.72 (2H, d, J = 9 Hz), 7.58-7.46 (2H, m), 7.25 (1H, d, J = 7 Hz), 7.13 (2H, d, J = 9 Hz), 7.07-6.99 (1H, m), 6.71-6.57 (2H, m), 6.30-6.16 (1H, m), 4.85-4.71 (1H, m), 4.61-4.47 (1H, m), 4.43-4.26 (3H, m), 2.28 (3H, s), 1.89-1.79 (2H, m), 1.17 (6H, s). |
| 143 | $^1$H-NMR (DMSO-d$_6$) δ: 7.79 (2H, d, J = 9 Hz), 7.48 (1H, d, J = 7 Hz), 7.19 (2H, d, J = 9 Hz), 7.11-6.97 (2H, m), 6.94 (1H, s), 6.68 (2H, s), 6.31-6.22 (1H, m), 4.80-4.67 (1H, m), 4.53-4.41 (1H, m), 4.38 (1H, S), 4.15-3.99 (2H, m), 2.05-1.90 (6H, m), 1.90-1.77 (2H, m), 1.17 (6H, s). |

TABLE 8

| Examples | NMR data (δ: ppm) < *: 300 MHz > |
|---|---|
| 150 | ¹H-NMR (CDCl₃) δ: 7.74 (2H, d, J = 9 Hz), 7.50 (1H, d, J = 8 Hz), 7.36 (1H, d, J = 7 Hz), 7.05 (2H, d, J = 9 Hz), 6.88-6.83 (1H, m), 6.66 (1H, s), 6.10-6.05 (1H, m), 4.83 (1H, dd, J = 11, 6 Hz), 4.72 (1H, dd, J = 11, 3 Hz). |
| 151* | ¹H-NMR (CDCl₃) δ: 7.74 (2H, d, J = 9 Hz), 7.45-7.41 (1H, m), 7.13-7.02 (4H, m), 6.67 (2H, s), 6.65 (1H, s), 6.08-6.04 (1H, m), 4.73-4.66 (1H, m), 4.58-4.52 (1H, m), 4.12 (2H, t, J = 6 Hz), 3.29-3.22 (2H, m), 2.96 (3H, s), 2.40-2.29 (2H, m), 2.09 (3H, s), 2.04 (3H, s). |
| 155* | ¹H-NMR (CDCl₃) δ: 7.75 (2H, d, J = 9 Hz), 7.23-7.17 (2H, m), 7.07 (2H, d, J = 9 Hz), 7.00 (1H, dd, J = 8, 1 Hz), 6.94-6.89 (2H, m), 6.86-6.78 (2H, m), 6.66 (1H, s), 6.10-6.03 (1H, m), 4.79 (1H, dd, J = 11, 7 Hz), 4.67 (1H, dd, J =11, 3 Hz), 2.33 (3H, s). |
| 158* | ¹H-NMR (CDCl₃) δ: 7.73 (2H, d, J = 9 Hz), 7.57 (1H, br s), 7.35-7.20 (3H, m), 7.14 (2H, d, J = 9 Hz), 7.03 (1H, d, J = 8 Hz), 6.94-6.86 (1H, m), 6.68-6.61 (1H, m), 6.64 (1H, s), 6.30-6.24 (1H, m), 5.87 (1H, dd, J = 7, 4 Hz), 3.58 (2H, t, J = 6 Hz), 2.97-2.92 (1H, m), 2.89 (2H, t, J = 7 Hz), 2.77-2.65 (1H, m), 2.63-2.51 (1H, m), 2.22-2.03 (3H, m). |

TABLE 9

| Examples | NMR data (δ: ppm) < *: 300 MHz > |
|---|---|
| 1-2 | ¹H-NMR (CDCl₃) δ: 7.49-7.43 (3H, m), 7.39-7.34 (1H, m), 7.30-7.25 (1H, m), 7.00 (2H, d, J = 9 Hz), 5.75-5.69 (1H, m), 3.90 (2H, d, J = 16 Hz), 3.77 (2H, d, J = 16 Hz), 3.19-3.08 (1H, m), 2.98-2.87 (1H, m), 2.64-2.52 (1H, m), 2.59 (3H, s), 2.26-2.16 (1H, m). |
| 83-1* | ¹H-NMR (CDCl₃) δ: 7.64-7.51 (2H, m), 7.42-7.22 (2H, m), 6.98-6.90 (3H, m), 5.42-5.14 (1H, m), 4.93-4.81 (1H, m), 4.09-3.90 (1H, m), 3.68-3.52 (1H, m), 3.00-2.79 (1H, m), 2.75-2.51 (1H, m), 2.51-2.35 (1H, m), 2.22-1.92 (1H, m), 1.92-1.70 (2H, m), 1.70-1.48 (4H, m). |
| 83-2* | ¹H-NMR (CDCl₃) δ: 7.62-7.55 (2H, m), 7.34-7.29 (2H, m), 6.99-6.91 (3H, m), 5.31 (1H, q, J = 6 Hz), 2.95-2.80 (1H, m), 2.70-2.42 (2H, m), 2.02-1.88 (1H, m), 1.82 (1H, d, J = 6 Hz). |
| 83-3* | ¹H-NMR (CDCl₃) δ: 7.64-7.56 (2H, m), 7.51-7.45 (2H, m), 7.34-7.30 (2H, m), 7.06-6.95 (5H, m), 5.82 (1H, dd, J = 1, 5 Hz), 3.97-3.73 (4H, m), 3.01-2.88 (1H, m), 2.82-2.68 (1H, m), 2.68-2.50 (1H, m), 2.60 (3H, s), 2.26-2.12 (1H, m). |
| 96-1 | ¹H-NMR (CDCl₃) δ: 7.12-7.02 (5H, m), 6.24-6.20 (1H, m), 5.32 (1H, dd, J = 12, 7 Hz), 3.25-3.15 (1H, m), 2.93 (1H, ddd, J = 16, 8, 6 Hz), 2.63-2.55 (1H, m), 2.11 (6H, s), 2.08-1.95 (1H, m), 1.78 (1H, d, J = 7 Hz). |
| 96-2 | ¹H-NMR (CDCl₃) δ: 7.48 (2H, d, J = 9 Hz), 7.13-7.00 (7H, m), 6.28-6.24 (1H, m), 5.87-5.82 (1H, m), 3.92 (2H, d, J = 16 Hz), 3.77 (2H, d, J = 16 Hz), 3.32-3.20 (1H, m), 3.13-2.97 (1H, m), 2.75-2.63 (1H, m), 2.60 (3H, s), 2.33-2.22 (1H, m), 2.13 (6H, s). |
| 99-1 | ¹H-NMR (CDCl₃) δ: 7.33-7.23 (3H, m), 6.95-6.87 (2H, m), 6.87-6.82 (1H, m), 6.81-6.77 (1H, m), 5.30 (1H, dt, J = 7, 5 Hz), 2.98-2.88 (1H, m), 2.72-2.61 (1H, m), 2.56-2.44 (1H, m), 2.01-1.90 (1H, m), 1.78 (1H, d, J = 7 Hz). |
| 99-2 | ¹H-NMR (CDCl₃) δ: 8.22 (2H, d, J = 9 Hz), 7.36-7.23 (3H, m), 7.14 (2H, d, J = 9 Hz), 7.01-6.81 (4H, m), 5.99-5.90 (1H, m), 3.12-2.97 (1H, m), 2.91-2.76 (1H, m), 2.73-2.56 (1H, m), 2.36-2.18 (1H, m). |
| 115-1 | ¹H-NMR (CDCl₃) δ: 7.41-7.35 (2H, m), 6.79-6.73 (2H, m), 4.08 (2H, t, J = 6 Hz), 3.28-3.21 (2H, m), 2.96 (3H, s), 2.39-2.30 (2H, m). |
| 115-2 | ¹H-NMR (CDCl₃) δ: 7.22-7.13 (2H, m), 6.95-6.89 (2H, m), 6.87-6.81 (2H, m), 6.75-6.70 (1H, m), 5.35-5.22 (1H, m), 4.15-4.05 (2H, m), 3.30-3.22 (2H, m), 3.05-2.93 (4H, m), 2.80-2.68 (1H, m), 2.56-2.45 (1H, m), 2.39-2.30 (2H, m), 2.02-1.91 (1H, m), 1.84-1.73 (1H, m). |
| 115-3 | ¹H-NMR (CDCl₃) δ: 7.50-7.44 (2H, m), 7.22-7.14 (2H, m), 7.07-7.00 (2H, m), 6.97-6.90 (2H, m), 6.88-6.82 (2H, m), 6.77 (1H, dd, J = 7, 2 Hz), 5.81 (1H, dd, J = 7, 4 Hz), 3.89 (2H, d, J = 16 Hz), 3.76 (2H, d, J = 16 Hz), 3.31-3.23 (2H, m), 3.11-3.00 (1H, m), 2.97 (3H, s), 2.92-2.80 (1H, m), 2.65-2.52 (4H, m), 2.40-2.30 (2H, m), 2.26-2.13 (1H, m). |
| 118-1 | ¹H-NMR (CDCl₃) δ: 8.43 (m, d, J = 2 Hz), 7.92 (m, dd, J = 9, 2 Hz), 7.39-7.31 (2H, m), 7.06-7.01 (2H, m), 5.36-5.25 (1H, m), 2.90-2.79 (1H, m), 2.65-2.44 (2H, m), 2.00-1.88 (1H, m), 1.85 (1H, d, J = 1 Hz). |
| 118-2 | ¹H-NMR (CDCl₃) δ: 8.45 (1H, d, J = 1 Hz), 7.93 (1H, dd, J = 9, 2 Hz), 7.47 (2H, d, J = 9 Hz), 7.40-7.30 (2H, m), 7.10-7.01 (4H, m), 5.88-5.81 (1H, m), 3.91 (2H, d, J = 16 Hz), 3.77 (2H, d, J = 16 Hz), 3.00-2.88 (1H, m), 2.76-2.54 (5H, m), 2.24-2.13 (1H, m). |
| 120-1 | ¹H-NMR (DMSO-d₆) δ: 7.31 (2H, d, J = 9 Hz), 6.91 (2H, d, J = 9 Hz), 5.69 (1H, s), 4.37 (2H, s), 4.29 (2H, d, J = 17 Hz), 4.06 (2H, d, J = 17 Hz), 2.46 (3H, s), 2.03-1.95 (2H, m), 1.64-1.53 (2H, m), 1.51-1.21 (14H, m). |
| 123-1 | ¹H-NMR (CDCl₃) δ: 7.46-7.36 (7H, m), 7.30 (1H, d, J = 1 Hz), 7.25-7.16 (2H, m), 7.01 (2H, d, J = 9 Hz), 6.85 (2H, d, J = 5 Hz), 6.73 (1H, d, J = 5 Hz), 5.07 (1H, s), 3.89 (2H, d, J = 16 Hz), 3.74 (2H, d, J = 16 Hz), 3.65 (2H, s), 3.02-2.95 (2H, m), 2.56 (3H, s), 2.42-2.33 (2H, m), 2.24-2.15 (2H, m), 1.38-1.31 (2H, m). |
| 138-1 | ¹H-NMR (DMSO-d₆) δ: 6.84-6.75 (1H, m), 6.71-6.62 (2H, m), 5.22 (1H, dd, J = 7, 3 Hz), 4.45 (1H, dd, J = 10, 7 Hz), 4.19 (1H, dd, J = 10, 3 Hz). |

TABLE 9-continued

| Examples | NMR data (δ: ppm) < *: 300 MHz > |
|---|---|
| 138-2 | $^1$H-NMR (DMSO-$d_6$) δ: 7.80 (2H, d, J = 9 Hz), 7.35-7.29 (1H, m), 7.11 (1H, dd, J = 8, 1 Hz), 7.05-6.95 (3H, m), 5.79-5.70 (1H, m), 5.37-5.27 (1H, m), 4.52 (1H, dd, J = 10, 7 Hz), 4.23 (1H, dd, J = 10, 3 Hz). |
| 138-3 | $^1$H-NMR (DMSO-$d_6$) δ: 7.82 (2H, d, J = 9 Hz), 7.63 (2H, d, J = 9 Hz), 7.44-7.39 (1H, m), 7.23 (1H, dd, J = 8, 1 Hz), 7.07-6.99 (5H, m), 6.24-6.18 (1H, m), 4.78 (1H, dd, J = 11, 6 Hz), 4.53 (1H, dd, J = 11, 2 Hz), 1.28 (12H, s). |
| 142-1 | $^1$H-NMR (DMSO-$d_6$) δ: 7.41 (1H, dd, J = 8, 1 Hz), 7.37-7.32 (1H, m), 6.84 (1H, dd, J = 8, 7 Hz), 5.76 (1H, s), 5.34 (1H, dd, J = 7, 3 Hz), 4.58 (1H, dd, J = 10, 7 Hz), 4.29 (1H, dd, J = 10, 3 Hz). |
| 142-2 | $^1$H-NMR (CDCl$_3$) δ: 7.78 (2H, d, J = 9 Hz), 7.46 (1H, dd, J = 8, 1 Hz), 7.36-7.32 (1H, m), 6.90 (2H, d, J = 9 Hz), 6.82 (1H, t, J = 8 Hz), 6.04 (1H, dd, J = 6, 3 Hz), 4.80 (1H, dd, J = 11, 6 Hz), 4.70 (1H, dd, J = 11, 3 Hz), 1.34 (12H, s). |
| 142-3 | $^1$H-NMR (CDCl$_3$) δ: 7.74 (2H, d, J = 9 Hz), 7.65 (1H, bs), 7.50 (1H, d, J = 8 Hz), 7.36 (1H, d, J = 8 Hz), 7.05 (2H, d, J = 9 Hz), 6.89-6.82 (1H, m), 6.66 (1H, s), 6.08 (1H, dd, J = 7, 3 Hz), 4.86-4.79 (1H, m), 4.75-4.68 (1H, m). |

TABLE 10

| Examples | NMR data (δ: ppm) < *: 300 MHz > |
|---|---|
| 150-1* | $^1$H-NMR (CDCl$_3$) δ: 7.44 (1H, d, J = 8 Hz), 7.36 (1H, d, J = 8 Hz), 6.84 (1H, dd, J = 8, 8 Hz), 5.50-5.42 (1H, m), 4.65 (1H, dd, J = 11, 7 Hz), 4.55 (1H, dd, J =11, 3 Hz), 1.96 (1H, d, J = 8 Hz). |
| 150-2* | $^1$H-NMR (CDCl$_3$) δ: 7.78 (2H, d, J = 9 Hz), 7.46 (1H, d, J = 7 Hz), 7.34 (1H, d, J = 8 Hz), 6.90 (2H, d, J = 9 Hz), 6.85-6.80 (1H, m), 6.08-6.00 (1H, m), 4.80 (1H, dd, J = 11, 7 Hz), 4.70 (1H, dd, J = 11, 3 Hz), 1.34 (12H, s). |
| 151-1* | $^1$H-NMR (CDCl$_3$) δ: 6.48 (2H, s), 4.07 (2H, t, J = 6 Hz), 3.77 (4H, s), 3.23 (2H, t, J = 8 Hz), 2.93 (3H, s), 2.36 (6H, s), 2.34-2.25 (2H, m), 1.09 (6H, s). |
| 155-1 | $^1$H-NMR (CDCl$_3$) δ: 10.92 (m, s), 7.66 (m, dd, J = 8, 2 Hz), 7.22-7.16 (2H, m), 6.88-6.74 (4H, m), 3.97 (3H, s), 2.32 (3H, s). |
| 155-2* | $^1$H-NMR (CDCl$_3$) δ: 7.52 (m, dd, J = 6, 3 Hz), 7.23-7.16 (1H, m), 7.10-7.08 (1H, m), 7.08-7.07 (1H, m), 6.93-6.88 (1H, m), 6.77-6.73 (2H, m), 4.72 (2H, s), 4.18 (2H, q, J = 7 Hz), 3.91 (3H, s), 2.32 (3H, s), 1.23 (3H, t, J = 7 Hz). |
| 155-3* | $^1$H-NMR (CDCl$_3$) δ: 7.86 (1H, dd, J = 8, 2 Hz), 7.21-7.15 (3H, m), 6.96 (1H, d, J = 8 Hz), 6.77-6.73 (2H, m), 4.91 (2H, s), 2.34 (3H, s). |
| 155-4* | $^1$H-NMR (CDCl$_3$) δ: 8.01 (1H, s), 7.31 (m, dd, J = 8, 1 Hz), 7.22 (1H, d, J = 8 Hz), 7.17 (1H, d, J = 8 Hz), 6.95-6.81 (4H, m), 2.38 (3H, s), 2.33 (3H, s). |
| 155-5* | $^1$H-NMR (CDCl$_3$) δ: 7.47-7.42 (1H, m), 7.24-7.20 (2H, m), 7.06-7.00 (1H, m), 6.98-6.91 (1H, m), 6.87-6.80 (2H, m), 4.69 (2H, s), 2.35 (3H, s). |
| 155-6* | $^1$H-NMR (CDCl$_3$) δ: 7.24-7.19 (1H, m), 7.17 (1H, d, J = 8 Hz), 6.97-6.86 (3H, m), 6.83-6.75 (2H, m), 5.47-5.40 (1H, m), 4.61 (1H, dd, J = 11, 6 Hz), 4.51 (1H, dd, J =11, 3 Hz), 2.32 (3H, s), 1.93 (1H, d, J = 8 Hz). |
| 155-7* | $^1$H-NMR (CDCl$_3$) δ: 7.78 (2H, d, J = 9 Hz), 7.20 (1H, d, J = 7 Hz), 7.17 (1H, d, J = 8 Hz), 6.98-6.78 (7H, m), 6.03 (1H, dd, J = 7, 3 Hz), 4.77 (1H, dd, J = 11, 7 Hz), 4.65 (1H, dd, J = 11, 3 Hz), 2.32 (3H, s), 1.34 (12H, s). |
| 163-2 | $^1$H-NMR (CDCl$_3$) δ: 7.35-7.25 (4H, m), 7.12-6.85 (9H, m), 4.18-4.12 (2H, m), 3.89 (2H, d, J = 16 Hz), 3.75 (2H, d, J = 16 Hz), 3.06 (2H, t, J = 7 Hz), 2.56 (3H, s). |

The invention claimed is:

1. A compound of Formula (II)-3a-1:

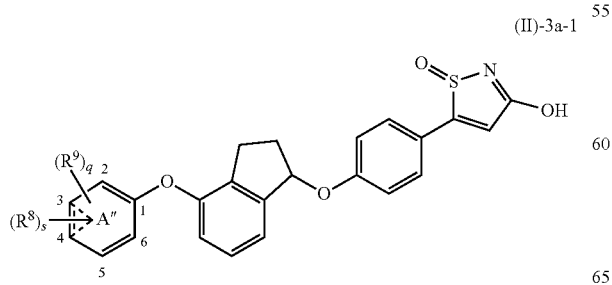

(II)-3a-1 wherein q is an integer of 0 to 4;

s is an integer of 0 to 2;

$R^8$s are independently a $C_{1-6}$ alkoxy group which is substituted with 1 to 5 substituent(s) RIII, an aralkyloxy group, a heterocyclic oxy group (the heterocyclic oxy group is optionally substituted with 1 to 3 $C_{1-6}$ alkyl group(s) or 1 to 3 oxo group(s)), or a heterocyclic group (the heterocyclic group is optionally substituted with 1 to 3 $C_{1-6}$ alkyl group(s));

the substituent RIII is a group optionally selected from —OH, a $C_{1-6}$ alkoxy group, an aryl group (the aryl group is optionally substituted with 1 to 3 halogen atom(s)), a heterocyclic group (the heterocyclic group is optionally substituted with 1 to 3 $C_{1-6}$ alkyl groups or 1 to 3 oxo groups), a —S(O)$_i$R$^a$ (i is an integer of 0 to 2) group, a —SO$_2$NR$^d$R$^e$ group, a —CONR$^d$R$^e$ group, and a —NR$^{b1}$R$^{c1}$ group;

$R^9$s are independently a group arbitrarily selected from a halogen atom, a cyano group, a $C_{1-6}$ alkyl group (the $C_{1-6}$ alkyl group is optionally and arbitrarily substituted with 1 to 5 halogen atom(s), 1 to 5 —OH or 1 to 5 $C_{1-6}$ alkoxy group(s)), a $C_{1-6}$ alkoxy group (the $C_{1-6}$ alkoxy group is optionally and arbitrarily substituted with 1 to 5 halogen atoms(s)), a $C_{2-6}$ alkenyl group, a $C_{2-7}$ alkanoyl group, a group: —S(O)$_i$R$^a$ (i is an integer of 0 to 2), a group: —CONR$^d$R$^e$ and a group: —NR$^{b1}$R$^{c1}$;

$R^a$ is a group arbitrarily selected from a $C_{1-6}$ alkyl group and a halogenated $C_{1-6}$ alkyl group;

$R^d$ and $R^e$ are independently a hydrogen atom or a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s));

$R^{b1}$ and $R^{c1}$ are independently a group arbitrarily selected from a hydrogen atom, a $C_{1-6}$ alkyl group, a $C_{2-7}$ alkanoyl group and a $C_{1-6}$ alkylsulfonyl group, or $R^{b1}$ and $R^{c1}$ optionally form together with a nitrogen atom to which $R^{b1}$ and $R^{c1}$ are bonded, a 3- to 8-membered cyclic group, where in the cyclic goup, one or two carbon atom(s) is(are) optionally substituted with an atom arbitrarily selected from an oxygen atom, a sulfur atom, and a nitrogen atom (the nitrogen atom is optionally substituted with a $C_{1-6}$ alkyl group) or with a carbonyl group;

a ring A" is a benzene ring, a pyridine ring, or a pyrimidine ring;

the broken line indicates the bonding position of $R^8$, and the numbers of "1" to "6" indicate the bonding position of the substituents (with the proviso that compounds of 3-hydroxy-5-[4-[(4-phenoxy-2,3-dihydro-1H-inden-1-yl)oxy]phenyl]isothiazole 1-oxide, 3-hydroxy-5-[4-[[4-(2-methylpyridin-3-yl)oxy-2,3-dihydro-1H-inden-1-yl]oxy]phenyl]isothiazole 1-oxide, 3-hydroxy-5-[4-[[4-(2-methoxypyridin-4-yl)oxy-2,3-dihydro-1H-inden-1-yl]oxy]phenyl]isothiazole 1-oxide, and 3-hydroxy-5-[4-[(4-pyridin-4-yl)oxy-2,3-dihydro-1H-inden-1-yl)oxy]phenyl]isothiazole 1-oxide, are excluded)), or a pharmaceutically acceptable salt of the compound, or a pharmaceutically acceptable solvate of the salt or a pharmaceutically acceptable solvate of the compound.

2. The compound according to claim 1, wherein any one of q and s is 1 or more, or a pharmaceutically acceptable salt of the compound, or a pharmaceutically acceptable solvate of the salt or a pharmaceutically acceptable solvate of the compound, 3. The compound according to claim 2, wherein any one of q and s is 1 or more and $R^9$ is a group optionally selected from a halogen atom, a cyano group, a $C_{1-6}$ alkyl group (the $C_{1-6}$ alkyl group is substituted with 1 to 5 halogen atom(s), 1 to 5 —OH, or 1 to 5 $C_{1-6}$alkoxy group(s)), a $C_{2-6}$ alkoxy group (the $C_{1-6}$ alkoxy group is substituted with 1 to 5 halogen atom(s)), a $C_{2-6}$ alkenyl group, a $C_{2-7}$ alkanoyl group, a —S(O)$_i$ R$^a$ (i is an integer of 0 to 2) group, a —CONR$^d$R$^e$ group, and a —NR$^{b1}$R$^{c1}$ group, or a pharmaceutically acceptable salt of the compound, or a pharmaceutically acceptable solvate of the salt or a pharmaceutically acceptable solvate of the compound.

4. The compound according to claim 2, wherein any one of q and s is 1 or more;

$R^8$ is a $C_{1-6}$ alkoxy group (the $C_{1-6}$ alkoxy group is substituted with 1 to 5 —OH, 1 to 5 $C_{1-6}$ alkoxy group(s), or 1 to 5 —S(O)$_i$R$^a$ (i is an integer of 0 to 2) group(s)); and $R^9$ is a group optionally selected from a halogen atom, a cyano group, a $C_{1-6}$ alkyl group (the $C_{1-6}$ alkyl group is substituted with 1 to 5 halogen atom(s) or 1 to 5 —OH), a $C_{1-6}$ alkoxy group (the $C_{1-6}$ alkoxy group is substituted with 1 to 5 halogen atom(s)), a —S(O)$_i$R$^a$ (i is an integer of 0 to 2) group, and a —NR$^{b1}$R$^{c1}$ group, or a pharmaceutically acceptable salt of the compound, or a pharmaceutically acceptable solvate of the salt or a pharmaceutically acceptable solvate of the compound.

5. The compound according to claim 1, wherein any one of q and s is 1 or more;

with the proviso that when q is 1, s is 0, and $R^9$ is a $C_{1-6}$ alkyl group or a $C_{1-6}$ alkoxy group wherein $R^9$ substituted at a 4-position, or a pharmaceutically acceptable salt of the compound, or a pharmaceutically acceptable solvate of the salt or a pharmaceutically acceptable solvate of the compound.

6. A pharmaceutical composition comprising a compound of claim 1, or a pharmaceutically acceptable salt of the compound, or a pharmaceutically acceptable solvate of the compound or a pharmaceutically acceptable solvate of the salt.

7. A pharmaceutical composition comprising a compound of claim 1, or a pharmaceutically acceptable salt of the compound, or a pharmaceutically acceptable solvate of the compound or a pharmaceutically acceptable solvate of the salt, and a compound selected from a group consisting of a PPAR gamma agonist, a biguanide agent, a sulfonylurea, a rapid-acting insulin secretagogue, an alpha-glucosidase inhibitor, insulin or an insulin derivative, GLP-1 and a GLP-1 agonist, a DPP-1V inhibitor, an alpha-2 antagonist, an SGIT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR, agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

8. The pharmaceutical composition of claim 7 wherein the DPP-IV inhibitor is selected from sitagliptin, alogliptin, saxagliptin, linagliptin, and tenegligliptin, or a pharmaceutically acceptable salt thereof.

9. The pharmaceutical composition of claim 7 wherein the DPP-IV inhibitor is sitagliptin, or a pharmaceutically acceptable salt thereof.

10. A compound of Formula (II)-3a-l:

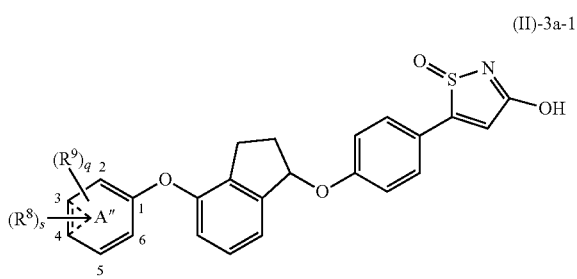

(II)-3a-l where the definitions of
q is an integer of 0 to 4;
s is an integer of 0 to 2;
wherein any one of q and s is 1 or more;
$R_8$s are independently a $C_{1-6}$ alkoxy group which is substituted with 1 to 5 substituent(s) RIII, an aralkyloxy group, a heterocyclicoxy group (the heterocyclicoxy group is optionally substituted with 1 to 3$C_{1-6}$ alkyl group(s) or 1 to 3 oxo group(s)), or a heterocyclic group (the heterocyclic group is optionally substituted with 1 to 3 $C_{1-6}$ alkyl group(s));
the substituent RIII is a group arbitrarily selected from —OH, a $C_{1-6}$ alkoxy group, an aryl group (the aryl group is optionally substituted with 1 to 3 halogen atom(s)), a heterocyclic group (the heterocyclic group is optionally substituted with 1 to 3 $C_{1-6}$ alkyl group or 1 to 3 oxo group), a —S(O)$_i$R$^a$ (i is an integer of 0 to 2) group, a —SO$_2$NR$^d$R$^e$ group, a —CONR$^d$R$^e$ group, and a —NR$^{b1}$R$^{c1}$ group;
$R^9$s are independently a group arbitrarily selected from a halogen atom, a cyano group, a $C_{1-6}$alkyl group (the $C_{1-6}$ alkyl group is substituted with 1 to 5 halogen atom(s), 1 to 5 —OH or 1 to 5 $C_{1-6}$ alkoxy group(s)), a $C_{1-6}$ alkoxy group (the $C^{1-6}$ alkoxy group is substituted with 1 to 5 halogen atom(s), a $C_{2-6}$ alkenyl group, a $C_{2-7}$ alkanoyl group, a group: —S(O)$_i$R$^a$ (i is an integer of 0 to 2), a group: —CONR$^d$R$^e$ and a group: —NR$^{b1}$R$^{c1}$;
R$^a$ is a group arbitrarily selected from a $C_{1-6}$ alkyl group and a halogenated $C_{1-6}$alkyl group;
R$^d$ and R$^e$ are independently a hydrogen atom or a $C_{1-6}$ alkyl group (the $C_{1-6}$ alkyl group is optionally substituted with 1 to 5 halogen atom(s), 1 to 5 —OH or 1 to 5 $C_{1-6}$ alkoxyl group(s)),;
R$^{b1}$R$^{c1}$ are independently a group arbitrarily selected from a hydrogen atom, a $C_{1-6}$ alkyl group, a $C_{2-7}$ alkanoyl group and a $C_{1-6}$ alkylsulfonyl group, or R$^{b1}$ and R$^{c1}$ optionally form together with a nitrogen atom to which R$^{b1}$ and $^{Rc1}$ are bonded, a 3- to 8-membered cyclic group, where in the cyclic group, one or two carbon atom(s) is(are) optionally substituted with an atom arbitrarily selected from an oxygen atom, a sulfur atom, and a nitrogen atom (the nitrogen atom is optionally substituted with a $C_{1-6}$ alkyl group) or with a carbonyl group;
the ring A" is a benzene ring, a pyridine ring, or a pyrimidine ring;
and the broken line indicates the bonding position of R$^8$, and the numbers of "1" to "6" indicate the bonding position of the substituents,
or a pharmaceutically acceptable salt of the compound, or a pharmaceutically acceptable solvate of the salt or a pharmaceutically acceptable solvate of the compound.

11. The compound according to claim 10, wherein any one of q and s is 1 or more:
R$^8$ is a $C_{1-6}$ alkoxy group (the $C_{1-6}$ alkoxy group is substituted with 1 to 5 —OH, 1 to 5 $C_{1-6}$ alkoxy group(s), or 1 to 5 —S(O)$_i$R$^a$ (i is an integer of 0 to 2) group(s)); and R$^9$ is a group arbitrarily selected from a halogen atom, a cyano group, a $C_{1-6}$ alkyl group (the $C_{1-6}$ alkyl group is substituted with 1to 5 halogen atom(s) or 1 to 5 —OH), a $C_{1-6}$ alkoxy group (the $C_{1-6}$ alkoxy group is substituted with 1 to 5 halogen atom(s)), a —S(O)$_i$R$^a$ (i is an integer of 0 to 2) group, and a —NR$^{b1}$R$^{c1}$ group,
or a pharmaceutically acceptable salt of the compound, or a pharmaceutically acceptable solvate of the salt or a pharmaceutically acceptable solvate of the compound.

12. A pharmaceutical composition comprising a compound of claim 10, or a pharmaceutically acceptable salt of the compound, or a pharmaceutically acceptable solvate of the compound or a pharmacetically acceptable solvate of the salt.

13. A pharmaceutical composition comprising a compound of claim 10, or a pharmaceutically acceptable salt of the compound, or a pharmaceutically acceptable solvate of the compound or a pharmaceutically acceptable solvate of the salt, and
a compound selected from a group consisting of a PPAR gamma agonist, a biguanide agent, a sulfonylurea, a rapid-acting, insulin secretagogue, an alpha-glucosidase inhibitor, insulin or an insulin derivative, GLP-1 and a GLP-1 agonist, a DPP-IV inhibitor, an alpha-2 antagonist, an SGLT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

14. The pharmaceutical composition of claim 13, wherein the DPP-IV inhibitor is selected from sitagliptin, vildagliptin, alogliptin, saxagliptin, linagliptin, and teneligliptin, or a pharmaceutically acceptable salt thereof.

15. The pharmaceutical composition of claim 13 wherein the DPP-IV inhibitor is sitagliptin, or a pharmaceutically acceptable salt thereof.

* * * * *